(12) United States Patent
Gaillard et al.

(10) Patent No.: US 8,614,215 B2
(45) Date of Patent: *Dec. 24, 2013

(54) QUINOXALINE INHIBITORS OF PHOSPHOINOSITIDE-3-KINASES (PI3KS)

(75) Inventors: Pascale Gaillard, Collonges Sous Saleve (FR); Vincent Pomel, Groisy (FR); Isabelle Jeanclaude-Etter, Bellevue (CH); Jerome Dorbais, Annecy (FR); Jasna Klicic, Biberach (DE); Cyril Montagne, Saint-Genis-Pouilly (FR)

(73) Assignee: Merck Serono SA, Coinsins, Vaud (CH)

( * ) Notice: Subject to any disclaimer, the term of this patent is extended or adjusted under 35 U.S.C. 154(b) by 168 days.

This patent is subject to a terminal disclaimer.

(21) Appl. No.: 12/525,095

(22) PCT Filed: Feb. 21, 2008

(86) PCT No.: PCT/EP2008/052102
§ 371 (c)(1),
(2), (4) Date: Dec. 30, 2009

(87) PCT Pub. No.: WO2008/101979
PCT Pub. Date: Aug. 28, 2008

(65) Prior Publication Data
US 2010/0137308 A1    Jun. 3, 2010

Related U.S. Application Data

(60) Provisional application No. 60/891,058, filed on Feb. 22, 2007.

(30) Foreign Application Priority Data

Feb. 22, 2007 (EP) .................... 07102873

(51) Int. Cl.
*A61K 31/495* (2006.01)
(52) U.S. Cl.
USPC ........... 514/249; 544/116; 544/356; 544/359; 546/210; 546/268.1; 548/247; 548/335.1; 549/13; 549/59; 549/356
(58) Field of Classification Search
USPC ........... 514/249; 544/116, 356, 359; 546/210, 546/268.1; 548/247, 335.1; 549/13, 59, 356
See application file for complete search history.

(56) References Cited

FOREIGN PATENT DOCUMENTS

| WO | WO 03/035075 | 5/2003 |
|----|---|---|
| WO | WO 03/051870 | 6/2003 |
| WO | WO 2004/007491 | 1/2004 |
| WO | WO 2004/056820 | 7/2004 |
| WO | WO 2004/078754 | 9/2004 |
| WO | WO 2005/021513 | 3/2005 |
| WO | WO 2005/021519 | 3/2005 |
| WO | WO 2007/023186 | 3/2007 |
| WO | WO 2007/044729 | 4/2007 |
| WO | WO 2008/021389 | 2/2008 |

OTHER PUBLICATIONS

Cantley, L.C. "The Phosphoinositide 3-Kinase Pathway" *Science*, May 31, 2002, pp. 1655-1657, vol. 296.
Fraser, J. D. et al. "Regulation of Interleukin-2 Gene Enhancer Activity by the T Cell Accessory Molecule CD28" *Science*, Jan. 18, 1991, pp. 313-316, vol. 251.
Fruman, D.A. et al, "Phosphoinositide Kinases" *Annu. Rev. Biochem.*, 1998, pp. 481-507, vol. 67.
Gerard, C. et al. "Chemokines and disease" *Nature Immunology*, Feb. 2001, pp. 108-115, vol. 2, No. 2.
Grant, S. "Targeted Therapies in Cancer—Second International Congress" *Current Drugs*, 2003, pp. 946-948, vol. 6, No. 10.
Laffargue, M. et al. "Phosphoninositide 3-Kinase γ Is an Essential Amplifier of Mast Cell Function" *Immunity*, Mar. 2002, pp. 441-451, vol. 16.
Lawlor, M. A. et al. "PKB/Akt: a key mediator of cell proliferation, survival and insulin responses?" *Journal of Cell Science*, 2001, pp. 2903-2910, vol. 114.
Parker, P. J. "PI 3-kinase puts GTP on the Rac" *Current Biology*, 1995, pp. 577-599, vol. 5, No. 6.
Stein, R. C. et al. "PI3-kinase inhibition: a target for drug development?" *Molecular Medicine Today*, Sep. 2000, pp. 347-357, vol. 6.
Thelen, M. et al. "Wortmannin binds specifically to 1-phosphatidylinositol 3-kinase while inhibiting guanine nucleotide-binding protein-coupled receptor signaling in neutrophil leukocytes" *Proc. Natl. Acad. Sci. USA*, May 1994, pp. 4960-4964, vol. 91.

(Continued)

*Primary Examiner* — Douglas M Willis
(74) *Attorney, Agent, or Firm* — Saliwanchik, Lloyd & Eisenschenk

(57) ABSTRACT

The present invention is related to quinoxaline compounds of Formula (I) in particular for the treatment of autoimmune disorders and/or inflammatory diseases, cardiovascular diseases, neurodegenerative diseases, bacterial or viral infections, kidney diseases, platelet aggregation, cancer, transplantation, graft rejection or lung injuries.

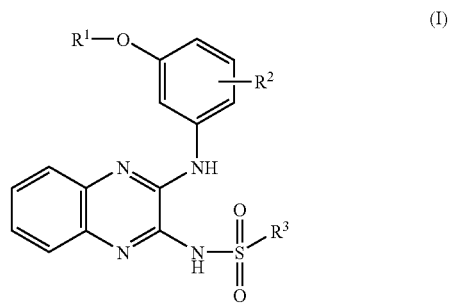

18 Claims, 2 Drawing Sheets

(56) References Cited

OTHER PUBLICATIONS

Figure 1:
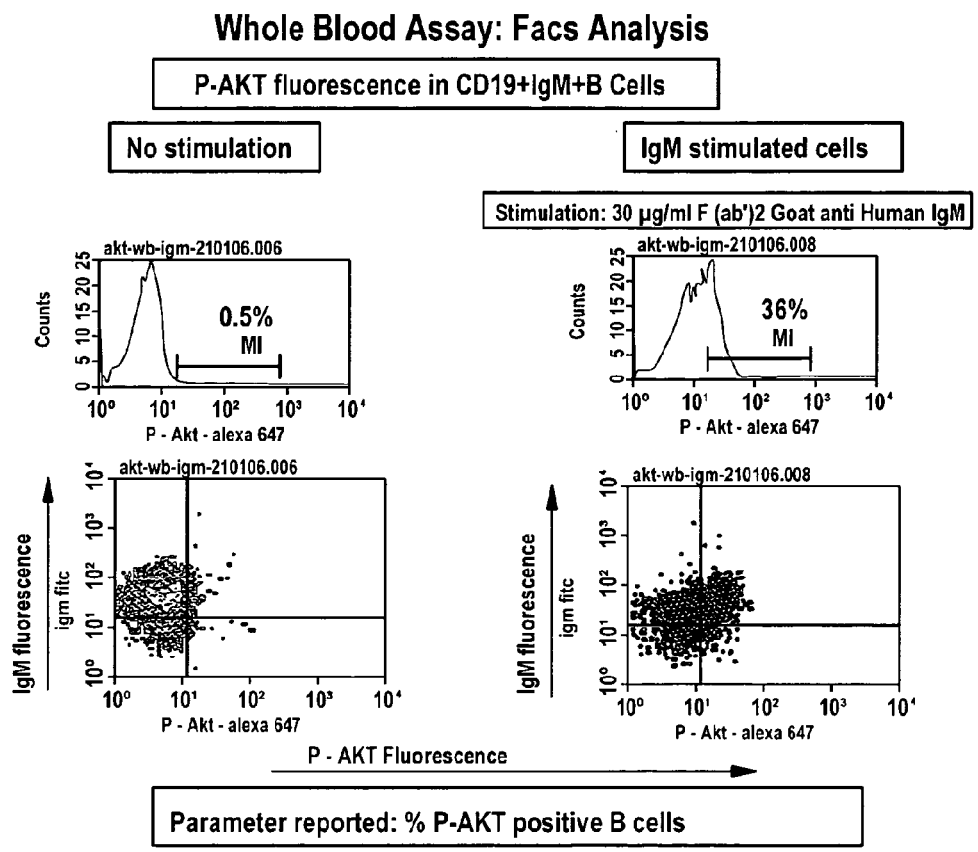

Toker, A. "Phosphoinositides and signal transduction" *Cellular and Molecular Life Sciences*, 2002, pp. 761-779, vol. 59.

Vanhaesebroeck, B. et al. "Synthesis and Function of 3-Phosphorylated Inositol Lipids" *Ann. Rev. Biochem.*, 2001, pp. 535-602, vol. 70.

Wymann, M. P. et al. "Lipids on the move: phosphoinositide 3-kinases in leukocyte function" *Immunology Today*, Jun. 2000, pp. 260-264, vol. 21, No. 6.

Yao, R. et al. "Requirement for Phosphatidylinositol-3 Kinase in the Prevention of Apoptosis by Nerve Growth Factor" *Science*, Mar. 31, 1995, pp. 2003-2005, vol. 267.

Ali, K. et al. "Essential role for the p110δ phosphoinositide 3-kinase in the allergic response" *Nature*, Oct. 21, 2004, pp. 1007-1010, vol. 431.

Glazko, A. J. et al. "The Metabolic Disposition of a Novel 5,5-Diphenylhydantoin Pro-drug" vol. 14 of the A.C.S. Symposium Series, American Chemical Society, 1975, pp. 184-195.

Han, S. et al. "Synthesis and Evaluation of Alternative Substrates for Arginase" *Bioorganic Chemistry*, 2002, pp. 81-94, vol. 30.

Imamura, S. et al. "CCR5 antagonists as anti-HIV-1 agents. Part 3: Synthesis and biological evaluation of piperidine-4-carboxamide derivatives" *Bioorganic & Medicinal Chemistry*, 2005, pp. 397-416, vol. 13.

Jou, S. et al. "Essential, Nonredundant Role for the Phosphoinositide 3-Kinase p110δ in Signaling by the B-Cell Receptor Complex" *Molecular and Cellular Biology*, Dec. 2002, pp. 8580-8591, vol. 22, No. 24.

Kocienski, P. J. "Protecting Groups" 1994, Thieme Medical Publishers, Inc., New York, pp. 1-248.

Kupchinsky, S. et al. "A novel class of achiral *seco*-analogs of CC-1065 and the duocarmycins: design, synthesis, DNA binding, and anticancer properties" *Bioorganic & Medicinal Chemistry*, 2004, pp. 6221-6236, vol. 12.

Litvinenko, S. V. et al. "Synthesis, Structure, and Chemical Properties of Some N-(3-Chloro-2-Quinoxalyl)Arylsulfonamides" *Chemistry of Heterocyclic Compounds*, 1994, pp. 340-344, vol. 30, No. 3.

Theoharides, T. C. et al. "Critical role of mast cells in inflammatory diseases and the effect of acute stress" *Journal of Neuroimmunology*, 2004, pp. 1-12, vol. 146.

Loriga, M. et al. "Quinoxaline Chemistry. Part 4. 2-(R)-Anilinoquinoxalines as Nonclassical Antifolate Agents. Synthesis, Structural Elucidation and Evaluation of In Vitro Anticancer Activity" *Farmaco*, 1995, pp. 289-301, vol. 50, No. 5, XP-002100549.

Budesinsky, Z. et al. "Sulfanilamidoquinoxalines" *Collection of Czechoslovak Chemical Communications*, 1972, pp. 887-895, vol. 37, XP-009011416.

Written Opinion in International Application No. PCT/EP2008/052102, May 15, 2008, pp. 1-9.

QUINOXALINE INHIBITORS OF PHOSPHOINOSITIDE-3-KINASES (PI3KS)

CROSS-REFERENCE TO RELATED APPLICATION

This application is the U.S. national stage application of International Patent Application No. PCT/EP2008/052102, filed Feb. 21, 2008, which claims the benefit of U.S. Provisional Patent Application No. 60/891,058, filed Feb. 22, 2007, the disclosures of which are hereby incorporated by reference in their entirety, including all figures, tables and amino acid or nucleic acid sequences.

FIELD OF THE INVENTION

This present invention is related to specific quinoxaline compounds and use thereof for the treatment of autoimmune disorders and/or inflammatory diseases, cardiovascular diseases, neurodegenerative diseases, bacterial or viral infections, allergy, asthma, pancreatitis, multi-organ failure, kidney diseases, platelet aggregation, cancer, specifically hematopoietic cancers, transplantation, sperm motility, erythrocyte deficiency, graft rejection or lung injuries. Specifically, the present invention is related to quinoxaline compounds for the modulation, notably the inhibition of the activity or function of the phosphoinositide-3-kinases, PI3Ks.

BACKGROUND OF THE INVENTION

Phosphoinositide 3-kinases (PI3Ks) have a critical signaling role in cell proliferation, cell survival, vascularization, membrane trafficking, glucose transport, neurite outgrowth, membrane ruffling, superoxide production, actin reorganization and chemotaxis (Cantley, 2000, *Science*, 296, 1655-1657).

The term PI3K is given to a family of lipid kinases which, in mammals, consists in eight identified PI3Ks that are divided into three sub-families according to their structure and their substrate specificity.

Class I group of PI3Ks consists in two sub-groups, Class IA and Class IB.

Class IA are a family of heterodimeric lipid kinases consisting in a 85 kDa regulatory unit (responsible for protein-protein interactions via the interaction of Src homology 2 (SH2) domain with phosphotyrosine residues of other proteins) and a catalytic sub-unit of 110 kDa that generate second messenger signals downstream of tyrosine kinases, thereby controlling cell metabolism, growth, proliferation, differentiation, motility and survival. Three catalytic forms (p110α, p110β and p110δ) and five regulatory isoforms (p85α, p85β, p55γ, p55α and p50α) exist for this class.

Class IB are stimulated by G protein βγ sub-units of heterodimeric G proteins. The only characterized member of Class IB is PI3Kγ (p110γ catalytic sub-unit complex with a 101-kDa regulatory protein, p101).

Class IA PI3Ks comprises α, β and δ isoforms, which are approximately of 170 kDa and characterized by the presence of a C-terminal C2 domain.

Class III PI3Ks includes the phosphatidylinositol specific 3-kinases.

The evolutionary conserved isoforms p110α and β are ubiquitously expressed, while δ and γ are more specifically expressed in the haematopoetic cell system, smooth muscle cells, myocytes and endothelial cells (Vanhaesebroeck et al., 2001, *Annu. Rev. Biochem.*, 70, 535-602). Their expression might also be regulated in an inducible manner depending on the cellular-, tissue type and stimuli as well as disease context.

PI3Ks are enzymes involved in phospholipid signaling and are activated in response to a variety of extra-cellular signals such as growth factors, mitogens, integrins (cell-cell interactions) hormones, cytokines, viruses and neurotransmitters and also by intra-cellular cross regulation by other signaling molecules (cross-talk, where the original signal can activate some parallel pathways that in a second step transmit signals to PI3Ks by intra-cellular signaling events), such as small GTPases, kinases or phosphatases for example.

Phosphatidylinositol (PtdIns) is the basic building block for the intracellular inositol lipids in eukaryotic cells, consisting of D-myo-inositol-1-phosphate (Ins1P) linked via its phosphate group to diacylglycerol. The inositol head group of PtdIns has five free hydroxy groups and three of these are found to be phosphorylated in cells in different combinations. PtdIns and its phosphorylated derivatives are collectively referred as inositol phospholipids or phosphoinositides (PIs). Eight PI species have been documented in eukaryotic cells (Vanhaesebroeck et al., 2001, above). PIs all reside in membranes and are substrates for kinases, phosphatases and lipases.

In vitro, PI3Ks phosphorylate the 3-hydroxyl group of the inositol ring in three different substrates: phosphatidylinositol (PtdIns), phosphatidylinositol-4-phosphate (PI(4)P) and phosphatidylinositol-4,5-biphosphate (PI(4,5)P$_2$), respectively generating three lipid products, namely phosphatidylinositol 3-monophosphate (PI(3)P), phosphatidylinositol 3,4-bisphosphate (PI(3,4)P$_2$) and phosphatidylinositol 3,4,5-trisphosphate (PI(3,4,5)P$_3$ (see Scheme A below).

Scheme A

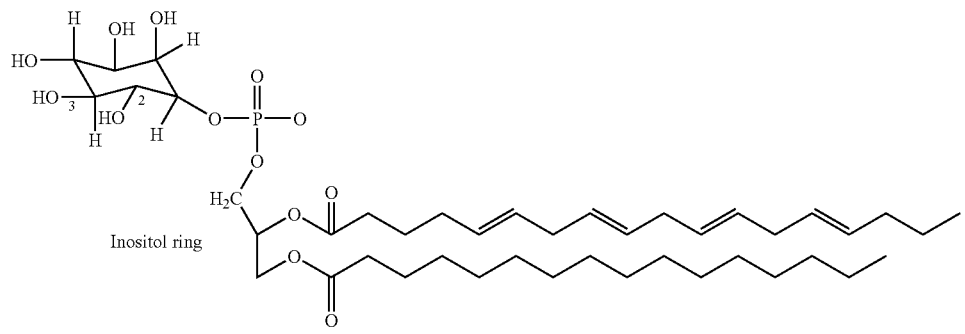

PtdIns (Phosphatidylinositol)

↓ PI3K

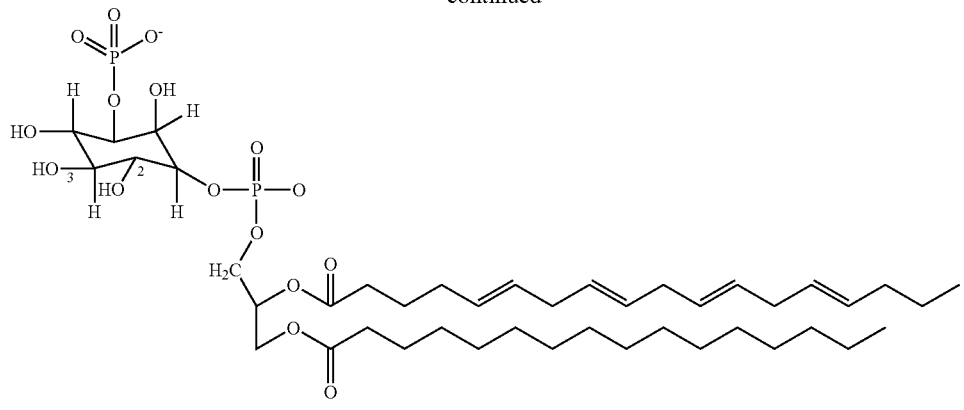

PI(3)P (Phosphatidylinositol 3-monophosphate)

The preferred substrate for Class I PI3Ks is (4,5)P$_2$. Class II PIKs have a strong preference for PtdIns as substrate over PI(4)P and PI(4,5)P$_2$ Class III PI3Ks can only use PtdIns as substrate in vivo and are likely to be responsible for the generation of most PI(3)P in cells (Vanhaesebroeck et al., 2001, above).

The phosphoinositides intracellular signaling pathway begins with the binding of a signaling molecule (extracellular ligands, stimuli, receptor dimidiation, transactivation by heterologous receptor (e.g. receptor tyrosine kinase)) to a G-protein linked transmembrane receptor integrated into the plasma membrane resulting in the activation of PI3Ks.

Once activated, PI3Ks convert the membrane phospholipid PI(4,5)P$_2$ into PI(3,4,5)P$_3$ which in turn can be further converted into another 3' phosphorylated form of phosphoinositides by 5'-specific phosphoinositide phosphatases, thus PI3K enzymatic activity results either directly or indirectly in the generation of two 3'-phosphoinositide sub-types that function as second messengers in intra-cellular signal transduction (Toker et al., 2002, Cell Mol. Life Sci. 59(5) 761-79).

The role as second messengers of phosphorylated products of PtdIns act is involved in a variety of signal transduction pathways, including those essential to cell proliferation, cell differentiation, cell growth, cell size, cell survival, apoptosis, adhesion, cell motility, cell migration, chemotaxis, invasion, cytoskeletal rearrangement, cell shape changes, vesicle trafficking and metabolic pathway (Stein, 2000, Mol. Med. Today 6(9) 347-57). Chemotaxis—the directed movement of cells toward a concentration gradient of chemical attractants, also called chemokines is involved in many important diseases such as inflammation/auto-immunity, neurodegeneration, angiogenesis, invasion/metastasis and wound healing (Wyman et al., 2000, Immunol Today 21(6) 260-4 and Gerard et al., 2001, Nat Immunol. 2(2) 108-15).

PI3-kinase activation, is therefore believed to be involved in a range of cellular responses including cell growth, differentiation, migration and apoptosis (Parker et al., 1995, Current Biology, 5, 577-99; Yao et al., 1995, Science, 267, 2003-05).

Recent biochemical studies revealed that, Class I PI3Ks (e.g. Class IB isoform PI3Kγ) are dual-specific kinase enzymes, i.e. they display both lipid kinase activity (phosphorylation of phospho-inositides) as well as protein kinase activity, as they are able to induce the phosphorylation of other protein as substrates, including auto-phosphorylation as intra-molecular regulatory mechanism.

PI3Ks appear to be involved in a number of aspects of leukocyte activation. A p85-associated PI3-kinase activity has been shown to physically associate with the cytoplasmic domain of CD28, which is an important co-stimulatory molecule for the activation of T-cells in response to antigen. These effects are linked to increases in the transcription of a number of genes including interleukin-2 (IL-2), an important T cell growth factor (Fraser et al., 1991, Science, 251, 313-16). Mutation of CD28 such that it can longer interact with PI3-kinase leads to a failure to initiate IL-2 production, suggesting a critical role for PI3-kinase in T cell activation.

Cellular processes in which PI3Ks play an essential role include suppression of apoptosis, reorganization of the actin skeleton, cardiac myocyte growth, glycogen synthase stimulation by insulin, TNFα-mediated neutrophil priming and superoxide generation, and leukocyte migration and adhesion to endothelial cells.

Recently, it has been described that PI3Kγ relays inflammatory signals through various G(i)-coupled receptors (Laffargue et al., 2002, Immunity 16(3) 441-51) and its central to mast cell function, stimuli in context of leukocytes, immunology includes cytokines, chemokines, adenosines, antibodies, integrins, aggregation factors, growth factors, viruses or hormones for example (Lawlor et al., 2001, J. Cell. Sci., 114 (Pt 16) 2903-10).

Two compounds, LY294002 and Wortmannin (cf. hereinafter), have been widely used as PI3-kinase inhibitors. These compounds are non-specific PI3K inhibitors, as they do not distinguish among the four members of Class I PI3-kinases.

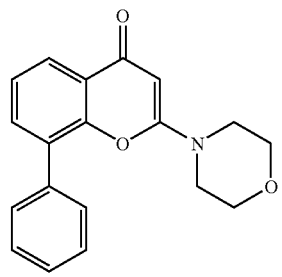

LY 294002

-continued

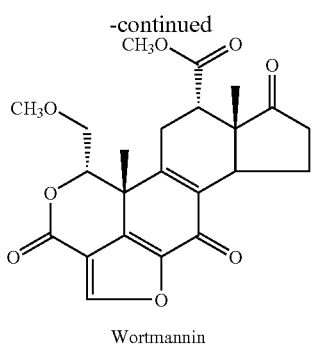

Wortmannin

IC$_{50}$ values of Wortmannin against each of the various Class I PI3-kinases are in the range of 1-10 nM and IC$_{50}$ values for LY294002 against each of these PI3-kinases are about 15-20 µM (Fruman et al., 1998, *Ann. Rev. Biochem.*, 67, 481-507), also 5-10 mM on CK2 protein kinase and some inhibitory activity on phospholipases.

Wortmannin is a fungal metabolite which irreversibly inhibits PI3K activity by binding covalently to the catalytic domain of this enzyme Inhibition of PI3K activity by Wortmannin eliminates the subsequent cellular response to the extracellular factor (Thelen et al., 1994, *Proc. Natl. Acad. Sci. USA*, 91, 4960-64). Experiments with wortmannin, show that PI3K activity in cells of hematopoietic lineage, particularly neutrophils, monocytes, and other types of leukocytes, is involved in many of the non-memory immune response associated with acute and chronic inflammation.

Based on studies using Wortmannin, there is evidence that PI3-kinase function is also required for some aspects of leukocyte signaling through G-protein coupled receptors (Thelen et al., 1994, above). Moreover, it has been shown that Wortmannin and LY294002 block neutrophil migration and superoxide release.

Some results have indicated that PI3K inhibitors, for example, LY294002, can increase the in vivo antitumor activity of certain cytotoxic agents (e.g. paclitaxel) (Grant, 2003, *Current Drugs*, 6(10), 946-948).

However, in as much as these compounds do not distinguish among the various isoforms of PI3K, it remains unclear which particular PI3K isoform or isoforms are involved in these phenomena. Specific inhibitors against individual members of a family of enzymes provide valuable tools for deciphering functions of each enzyme as depending on the disease application varying the degree of selectivity for PI3K isoforms can be of interest.

p110 δ is expressed predominantly in cells of hemopoeitic origin such as leukocytes. To assess the role of the δ isoform of the p110 catalytic subunit of PI3Ks, PI3Kδ-null mice have been recently developed (Jou et al., 2002, *Molecular and Cellular biology*, 22(4), 8580-8591) and their specific immunological phenotype has been well characterized (Vanhaesebroeck et al., 2005, *Trends in Biochemical Sciences*, 30(4), 194-204). These experiments show that the PI3Kδ-null animals are viable and that a deficiency in PI3Kδ results in a very specific loss of the function of the B-cell antigen specific receptor complex, while signaling through the cytokine receptor complexes is unaffected (Jou et al., 2002, above).

It has been also shown that the inactivation of the p110δ isoform of PI3K in mast cells leads to defective stem cell factor-mediated in vitro proliferation, adhesion and migration and to impaired allergen-IgE-induced degranulation and cytokine release. Inactivation of p110δ protects mice against anaphylactic allergic responses, suggesting p110δ as a target for therapeutic intervention in allergy and mast-cell-related pathologies (Ali. et al., 2004, *Nature*, 431, 1007-1010).

Mast cells have emerged as a unique immune cell that could participate in a variety of inflammatory diseases in the nervous system (e.g. multiple sclerosis), skin, joints as well as cardiopulmonary, intestinal and urinary systems (Theoharides et al., 2004, *J. of Neuroimmunology*, 146, 1-12).

The high relevance of the PI3K pathway in some widely spread diseases stresses the need to develop inhibitors, including selective inhibitors, of PIK isozymes, in order that the functions of each isozyme can be better characterized.

The serine-threonine protein kinase Akt (also known as protein kinase B, PKB) mediates many of the downstream effects of PI3K.

Recently, PI3K inhibitors have been developed: thiazole derivatives (WO 2005/021519; and WO 04/078754), thiazolidine derivatives (WO 2004/007491 and WO 2004/056820) and quinazolinones derivatives (WO 03/035075).

SUMMARY OF THE INVENTION

According to one aspect of the invention, are provided quinoxaline compounds.

According to another aspect of the invention, are provided quinoxaline compounds which are suitable for the treatment and/or prevention of disorders related to phosphoinositide-3-kinases, PI3Ks, such as PI3K alpha or PI3K gamma or PI3K delta or PI3K beta.

According to another aspect of the invention, are provided quinoxaline compounds, which are able to modulate, especially inhibit the activity or function of phosphoinositide-3-kinases, PI3Ks in disease states in mammals, especially in humans.

According to another aspect of the invention, are provided methods for the treatment and/or prevention of disorders selected from auto-immune, inflammatory disorders, cardiovascular diseases, neurodegenerative disorders, bacterial and viral infections, allergy, asthma, pancreatitis, multi-organ failure, kidney diseases, platelet aggregation, cancer, transplantation, sperm motility, erythrocyte deficiency, graft rejection, lung injuries, respiratory diseases and ischemic conditions.

According to another aspect of the invention, are provided pharmaceutical formulations for the treatment of and/or diseases mediated selected from auto-immune, inflammatory disorders, cardiovascular diseases, neurodegenerative disorders, bacterial and viral infections, allergy, asthma, pancreatitis, multi-organ failure, kidney diseases, platelet aggregation, cancer, transplantation, sperm motility, erythrocyte deficiency, graft rejection, lung injuries, respiratory diseases and ischemic conditions.

In a first aspect, the invention provides quinoxaline compounds of Formula (I):

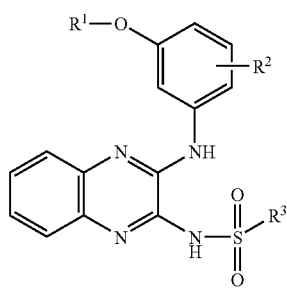

(I)

wherein R¹, R², and R³ are defined in the detailed description below.

In a second aspect, the invention provides a compound according to Formula (I) for use as a medicament.

In a third aspect, the invention provides a use of a compound according to Formula (I) for the preparation of a pharmaceutical composition for the treatment of a disorder selected from auto-immune, inflammatory disorders, cardiovascular diseases, neurodegenerative disorders, bacterial and viral infections, allergy, asthma, pancreatitis, multi-organ failure, kidney diseases, platelet aggregation, cancer, transplantation, sperm motility, erythrocyte deficiency, graft rejection, lung injuries, respiratory diseases and ischemic conditions and other disorders associated with the phosphoinositide-3-kinases, PI3Ks, comprising PI3K α, γ, δ or β.

In a fourth aspect, the invention provides a pharmaceutical composition comprising at least one compound according to Formula (I) and a pharmaceutically acceptable carrier, diluent or excipient thereof.

In a fifth aspect, the invention provides a method for treating a patient suffering from a disorder selected from auto-immune, inflammatory disorders, cardiovascular diseases, neurodegenerative disorders, bacterial and viral infections, allergy, asthma, pancreatitis, multi-organ failure, kidney diseases, platelet aggregation, cancer, transplantation, sperm motility, erythrocyte deficiency, graft rejection, lung injuries, respiratory diseases and ischemic conditions and other diseases and disorders associated with the phosphoinositide-3-kinases, PI3Ks wherein the method comprises administering a therapeutically effective amount of a compound according to Formula (I) to a subject in need thereof.

In a sixth aspect, the invention provides methods of synthesis of compounds according to Formula (I).

In a seventh aspect, the invention provides compounds according to Formula (II).

In an eighth aspect, the invention provides compounds according to Formula (XI).

DETAILED DESCRIPTION OF THE INVENTION

The following paragraphs provide definitions of the various chemical moieties that make up the compounds according to the invention and are intended to apply uniformly through-out the specification and claims unless an otherwise expressly set out definition provides a broader definition.

"$C_1$-$C_6$ alkyl" refers to alkyl groups having 1 to 6 carbon atoms. This term is exemplified by groups such as methyl, ethyl, n-propyl, isopropyl, n-butyl, isobutyl, text-butyl, n-hexyl and the like.

"Alkoxy" denotes an $C_1$-$C_6$ alkyl group attached to the rest of the molecule by an oxygen atom.

"$C_2$-$C_6$ alkenyl" refers to alkenyl groups preferably having from 2 to 6 carbon atoms and having at least 1 or 2 sites of alkenyl unsaturation.

"Aryl" or $C_6$-$C_{18}$ aryl" refers to a six membered aromatic carbocyclic group of from 6 to 18, preferably 6 to 14, carbon atoms having a single ring (e.g., phenyl).

"Heteroaryl" or "$C_6$-$C_{18}$ heteroaryl" refers to any aromatic group comprising from 6 to 18, preferably from 3 to 5 carbon atoms, and interrupted by one or several heteroatoms selected from N, O, S. It refers more specifically to a monocyclic heteroaromatic group. Particular examples of heteroaromatic groups include pyridyl and imidazolyl.

"$C_3$-$C_8$ cycloalkyl" refers to a saturated carbocyclic group of from 3 to 8 carbon atoms having a single ring (e.g., cyclohexyl) or multiple condensed rings. $C_3$-$C_8$-cycloalkyl includes cyclopropyl, cyclobutyl, cyclopentyl, cyclohexyl, norbornyl and the like.

"Heterocycloalkyl" or "$C_3$-$C_8$-heterocycloalkyl" refers to a $C_3$-$C_8$-cycloalkyl group according to the definition above, in which up to 3 carbon atoms are replaced by heteroatoms chosen from the group consisting of O, S (either S, or $SO_2$), NR, R being defined as hydrogen, methyl, acetyl, acyl ($COCH_2N(Me)_2$) or sulfone ($SO_2Me$). Heterocycloalkyl include more preferably pyrrolidine, piperidine, piperazine, morpholine, imidazolidine, pyrazolidine, tetrahydropyrane, 1,1-dioxo-tetrahydro-thiopyrane, tetrahydropyrane, tetrahydrothiopyrane, 8-methyl-8-aza-bicyclo[3.2.1]octane and the like.

"Amino" refers to the group —NRR' where each R and R' is independently hydrogen or "$C_1$-$C_6$-alkyl" or "aryl" or "heteroaryl" or "cycloalkyl", or "heterocycloalkyl", and where R and R', together with the nitrogen atom to which they are attached, can optionally form a 3-8-membered heterocycloalkyl ring as defined above.

"Amino ($C_1$-$C_6$)alkyl" refers to ($C_1$-$C_6$)alkyl groups having an amino substituent, including dimethylamino methyl, 2-(1-pyrrolidinyl)ethyl and the like.

"Halogen" refers to fluoro, chloro, bromo and iodo atoms.

"Alkoxycarbonyl" refers to the group —C(O)OR where R refers to "$C_1$-$C_6$alkyl".

"Halogenoalkyl" refers to alkyl as defined above substituted by at least one halogen atom, such as trifluoromethyl.

"Acyl" refers to the group —C(O)R where R includes H, "$C_1$-$C_6$-alkyl", "aryl", "heteroaryl", "$C_3$-$C_8$cycloalkyl", "amino $C_1$-$C_6$alkyl" or "heterocycloalkyl". Acyl group is more preferably —C(O)CH₃ or —C(O)CH₂N(CH₃)₂.

"Sulfone group" refers to the group —$SO_2$R where R includes H, "$C_1$-$C_{12}$-alkyl", preferably "$C_1$-$C_6$alkyl", "aryl", "heteroaryl", "$C_3$-$C_8$-cycloalkyl", "amino", "$C_1$-$C_6$alkylamino", "amino($C_1$-$C_6$)alkyl" or "heterocycloalkyl". Sulfone group is more preferably —$SO_2CH_3$.

"Alkyl-heteroaryl" refers to a heteroaryl substituted by an alkyl group such as 1-methyl-1H-imidazole.

"Alkyl-heterocycloalkyl-$C_1$-$C_6$alkyl" refers to a $C_1$-$C_6$alkyl group that is linked with an heterocycloalkyl substituted by alkyl group such as 1-methyl-piperidin-4-ylmethyl.

"Alkyl-sulfonyl-heterocycloalkyl-$C_1$-$C_6$alkyl" refers to a $C_1$-$C_6$alkyl group that is linked with an heterocycloalkyl substituted by a "sulfone group" wherein R is an alkyl group such as 1-methanesulfonyl-piperidin-4-ylmethyl.

"Acyl-heterocycloalkyl-$C_1$-$C_6$alkyl" refers to a $C_1$-$C_6$alkyl group that is linked with an heterocycloalkyl substituted with an acyl group such as 1-acetyl-piperidin-4-ylmethyl.

"Dialkylamino-acyl-heterocycloalkyl-C1-C6alkyl" refers to a $C_1$-$C_6$alkyl group that is linked with an heterocycloalkyl substituted with an acyl group wherein R is a dialkylamino group such as 2-dimethylamino-1-(4-methyl-piperidin-1-yl)-ethanone.

"Cycloalkyl-$C_1$-$C_6$alkyl" refers to a $C_1$-$C_6$ alkyl group that is linked with a $C_3$-$C_8$ cycloalkyl group such as methylcyclohexane or methylcyclopentane.

"Heterocycloalkyl-$C_1$-$C_6$alkyl" refers to $C_1$-$C_6$alkyl group that is linked with a heterocycloalkyl group such as 4-methyl-piperidine or 4-methyl-piperazine.

"Hydroxy-cycloalkyl-$C_1$-$C_6$ alkyl" refers to $C_1$-$C_6$alkyl group that is linked with a $C_3$-$C_8$ cycloalkyl substituted by a hydroxy group such as 4-methyl-cyclohexanol.

"Hydroxy-alkyl" refers to a $C_1$-$C_6$alkyl group that is linked with a hydroxy group such as butan-1-ol or ethanol.

"CO-alkyl-heterocycloalkyl" refers to an acyl group wherein R is a heterocycloalkyl substituted by an alkyl group such as 1-methyl-piperazine.

"Alkyl-sulfonyl-heterocycloalkyl" refers to a heterocloalkyl substituted by a sulfone group wherein R is an alkyl group such as 1-methanesulfonyl-piperidine or 1-methanesulfonyl-piperazine.

"Dimethylaminobenzyl" refers to a benzyl group bearing a dimethylamino group as follow $(Me)_2N-CH_2$-Phenyl.

"Dialkylaminobenzyl" refers to a benzyl group bearing a dialkylamino group.

"Aryl-$C_1$-$C_6$alkyl" refers to an $C_1$-$C_6$ alkyl group bearing an aryl group such as benzyl.

"$C_1$-$C_6$alkyl-Aryl" refers to an aryl group bearing an $C_1$-$C_6$ alkyl group such as toluen.

"Halogenophenyl" refers to phenyl substituted by a halogeno group such as fluorophenyl.

"Substituted or not": Unless otherwise constrained by the definition of the individual substituent, the above set out groups, like "alkyl", "alkoxy", "alkenyl", "alkynyl", "aryl", "heteroaryl", "cycloalkyl", "heterocycloalkyl" etc. groups can optionally be substituted with from 1 to 5 substituents selected from the group consisting of "halogen", "$C_1$-$C_6$alkyl", "$C_2$-$C_6$alkenyl", "$C_2$-$C_6$alkynyl", "cycloalkyl", "heterocycloalkyl", "aryl", "amino", "ammonium", "acyl", "heteroaryl", "alkoxy", "carboxy", sulfone, oxy, dioxy, halogenoalkyl, cyano, hydroxy, mercapto, nitro, and the like.

"Pharmaceutically acceptable salts or complexes" refers to salts or complexes of the below-identified compounds of Formula (I) that retain the desired biological activity. Examples of such salts include, but are not restricted to acid addition salts formed with inorganic acids (e.g., hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and poly-galacturonic acid. Said compounds can also be administered as pharmaceutically acceptable quaternary salts known by a person skilled in the art, which specifically include the quaternary ammonium salt of the formula —NR, R',R"$^+$ Z$^-$, wherein R, R', R" is independently hydrogen, alkyl, or benzyl, $C_1$-$C_6$alkyl, $C_2$-$C_6$alkenyl, $C_2$-$C_6$alkynyl, $C_1$-$C_6$alkyl aryl, $C_1$-$C_6$alkyl heteroaryl, cycloalkyl, heterocycloalkyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

Also comprised are salts formed by reaction of compounds of Formula (I) with organic or inorganic bases such as hydroxide, carbonate or bicarbonate of a metal cation such as those selected in the group consisting of alkali metals (sodium, potassium or lithium), alkaline earth metals (e.g. calcium or magnesium), or with an organic primary, secondary or tertiary alkyl amine. Amine salts derived from methyl amine, dimethylamine, trimethylamine, ethylamine, diethylamine, triethylamine, morpholine, ammonium, N-methyl-D-glucamine, N,N'-bis(phenylmethyl)-1,2-ethanediamine, tromethamine, ethanolamine, diethanolamine, ethylenediamine, N-methylmorpholine, procaine, piperidine, piperazine and the like are contemplated being within the scope of the instant invention.

"Pharmaceutically active derivative" refers to any compound that upon administration to the recipient is capable of providing directly or indirectly, the activity disclosed herein. The term "indirectly" also encompasses prodrugs which may be converted to the active form of the drug via endogenous enzymes or metabolism. The term "prodrug", as of the compounds of formula I, refers to derivative compounds that are rapidly transformed in vivo to yield the parent compound of the formula I, as for example by hydrolysis in blood. T. Higuchi and V. Stella provide a thorough discussion of the prodrug concept in "Pro-drugs as Novel Delivery Systems", Vol 14 of the A.C.S. Symposium Series, American Chemical Society (1975). Examples of esters useful as prodrugs for compounds containing carboxyl groups can be found on pages 14-21 of "Bioreversible Carriers in Drug Design: Theory and Application", edited by E. B. Roche, Pergamon Press: New York (1987). It is intended that these references, and any others cited throughout this specification, are incorporated herein by reference.

It has now been found that compounds of the present invention are modulators, in particular inhibitors, of the Phosphatoinositides 3-kinases (PI3Ks), comprising PI3K α, γ δ or β. When the phosphatoinositides 3-kinase (PI3K) enzyme is inhibited by the compounds of the present invention, PI3K is unable to exert its enzymatic, biological and/or pharmacological effects.

The compounds of the present invention are therefore useful in the treatment and prevention of autoimmune disorders and/or inflammatory diseases, cardiovascular diseases, neurodegenerative diseases, bacterial or viral infections, allergy, asthma, pancreatitis, multi-organ failure, kidney diseases, platelet aggregation, cancer, transplantation, sperm motility, erythrocyte deficiency, graft rejection or lung injuries.

General Formula (I) according to the present invention also comprises its tautomers, its geometrical isomers, its optically active forms as enantiomers, diastereomers and its racemate forms, as well as pharmaceutically acceptable salts thereof. Preferred pharmaceutically acceptable salts of the Formula (I) are base addition salts formed by reaction of compounds of formula (I) with pharmaceutically acceptable bases like sodium, potassium or calcium of hydroxides, ammonium or N-methyl-D-glucamine or acid addition salt formed by reaction of compounds of formula (I) with pharmaceutically acceptable acids like HCl or trifluoromethanesulfonic acid.

The compounds according to Formula (I) are suitable for the modulation, notably the inhibition of the activity of phosphatoinositides 3-kinases (PI3K). It is therefore believed that the compounds of the present invention are also particularly useful for the treatment and/or prevention of disorders, which are mediated by PI3Ks, particularly PI3K α and/or PI3K γ and/or PI3K β and/or PI3K δ. Said treatment involves the modulation—notably the inhibition or the down regulation—of the phosphatoinositides 3-kinases.

In particular, the inventors have surprisingly found that by using the inventive compounds it will be possible to inhibit Phosphatoinositides 3-kinases (PI3Ks) and to also modulate, and in particular inhibit, Akt action. The inventors found that by this approach one may achieve positive effects in, i.e. one may prevent or treat, the diseases referred to here; in particular one may treat thus cancers and specifically hematopoietic cancers. This will be apparent from the examples described below.

The compounds according to Formula (I) are suitable for use as a medicament, in particular for the treatment as mentioned below.

In one embodiment, the invention provides quinoxaline compounds of Formula (I):

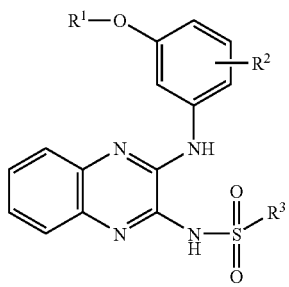

(I)

wherein:

$R^1$ is selected from H; $C_1$-$C_6$alkyl;

$R^2$ is selected from $(CH_2)m$-$R^4$, $(CH_2)m$-$CH(R^4)_2$, $CH(R^4)_2$, $CH((CH_2)_mOH)_2$, $CH((CH)_2m$-$C_1$-$C_6$ alkoxy)$_2$, CO—$R^{4'}$ and $SO_2$—$R^{4'}$ group;

$R^3$ is selected from $C_1$-$C_6$alkyl; $C_3$-$C_8$ cycloalkyl; $C_3$-$C_8$ heterocycloalkyl; $C_6$-$C_{18}$ aryl; and $C_3$-$C_{18}$ heteroaryl group; $(CH_2)m$-S—$C_1$-$C_6$alkyl; $(CH_2)m$-$SO_2$—$C_1$-$C_6$alkyl; $(CH_2)m$-$C_1$-$C_6$alkoxy;

wherein aryl and heteroaryl may also be substituted by one or more of the groups $C_1$-$C_6$alkyl; $C_1$-$C_6$alkoxy; $NH_2$, NH—($C_1$-$C_6$ alkyl), N($C_1$-$C_6$ alkyl)$_2$, $(CH_2)mNH_2$, $(CH_2)mNH$—($C_1$-$C_6$ alkyl), $(CH_2)mN(C_1$-$C_6$ alkyl)$_2$, $(CH_2)mOH$, $(CH_2)m$-($C_1$-$C_6$ alkoxy), halogen, CN, $NHCO(CH_2)mOH$, NHCO$(CH_2)m$-($C_1$-$C_6$ alkoxy), $C_3$-$C_8$ heterocycloalkyl; or $R^3$ is the following group:

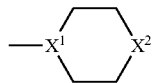

wherein
$X^1$ is CH or N,
$X^2$ denotes $CH_2$, O, S, $SO_2$, NH, NQY, CHOQY
Q is $(CH_2)p$, $(CH_2)pCO(CH_2)p'$, $(CH_2)pSO_2(CH_2)p'$,
Y denotes H, $C_1$-$C_6$ alkyl, $C_1$-$C_6$ alkoxy, NH($C_1$-$C_6$ alkyl), N($C_1$-$C_6$ alkyl)$_2$, $OCH_2$aryl, Oaryl
p and p' and independently chosen from 0, 1, 3, 4, 5 or 6,
$R^4$ is selected from a hydroxy; $C_1$-$C_6$ alkoxy; CH(OH)$(CH_2)mOH$, $N((CH_2)mOH)C_1$-$C_6$ alkyl, OCONH($C_1$-$C_6$ alkyl), $NH_2$, NH—($C_1$-$C_6$ alkyl), N($C_1$-$C_6$ alkyl)$_2$, NH—CO—($C_1$-$C_8$ alkyl), NH—$SO_2$—($C_1$-$C_8$ alkyl), NH$(CH_2)m$-OH, NH—$(CH_2)m$-($C_1$-$C_6$ alkoxy), N($C_1$-$C_6$ alkyl)$(CH_2)mOH$, N($C_1$-$C_6$ alkyl)$(CH_2)m(C_1$-$C_6$ alkoxy), $N((CH_2)mOH)C_1$-$C_6$ alkyl, $SO_2$-($C_1$-$C_6$ alkyl), $C_3$-$C_8$ cycloalkyl; $C_3$-$C_8$ heterocycloalkyl; OCOCH($NH_2$)($C_1$-$C_6$ alkyl), OCOCH($C_1$-$C_6$alkyl)$NHCOOCH_2$-(9H-fluoren-9-yl) or the following group:

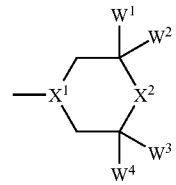

wherein
$X^1$, $X^2$, Q, Y, and p are as defined above for $R^3$ and
$W^1$, $W^2$, $W^3$, $W^4$ are H or $CH_3$, and $W^1$ and $W^3$ together may also be $CH_2CH_2$, $R^{4'}$ is selected from $C_1$-$C_6$ alkoxy; CH(OH)$(CH_2)mOH$, $N((CH_2)mOH)C_1$-$C_6$ alkyl, $NH_2$, NH—($C_1$-$C_6$ alkyl), N($C_1$-$C_6$ alkyl)$_2$, NH$(CH_2)m$-OH, NH—$(CH_2)m$-($C_1$-$C_6$ alkoxy), N($C_1$-$C_6$ alkyl)$(CH_2)mOH$, N($C_1$-$C_6$ alkyl)$(CH_2)m(C_1$-$C_6$ alkoxy), $N((CH_2)mOH)C_1$-$C_6$ alkyl, $C_3$-$C_8$ cycloalkyl; $C_3$-$C_8$ heterocycloalkyl; or the following group:

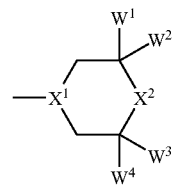

wherein
$X^1$, $X^2$, Q, Y, $W^1$, $W^2$, $W^3$, $W^4$ and p are as defined above,
m is an integer selected from 1 to 6, preferably 1, 2, and 3;
as well as its geometrical isomers, its optically active forms as enantiomers, diastereomers, tautomers and its racemate forms, as well as pharmaceutically acceptable salts thereof.

$R^1$ is preferably $C_1$-$C_6$alkyl.

$R^2$ is preferably $(CH_2)m$-$R^4$ or $(CH_2)m$-CH—$(R^4)_2$. $R^2$ is especially $CH_2R^4$. $R^2$ is preferably in para position to the group $R^1$—O.

In another specific embodiment, the invention provides quinoxaline compounds of Formula (I) wherein $R^1$ is methyl.

p and/or p' is preferably 0, 1 or 2. More preferably, one of p and p' is 0.

Generally, $R^4$ and $R^{4'}$ independently are preferably chosen from the following group:

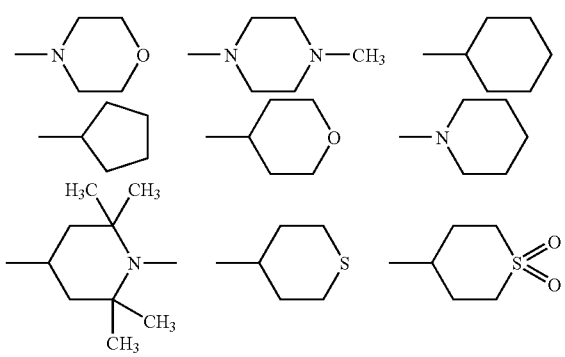

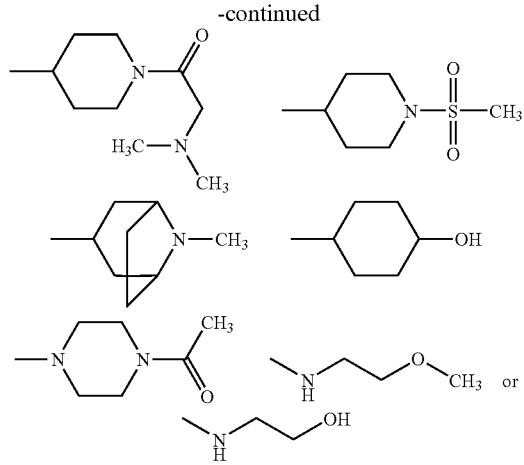
Also, R⁴ may be the following group:
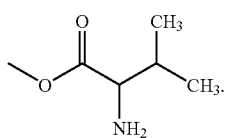
Generally, R³ is preferably chosen from the following group:
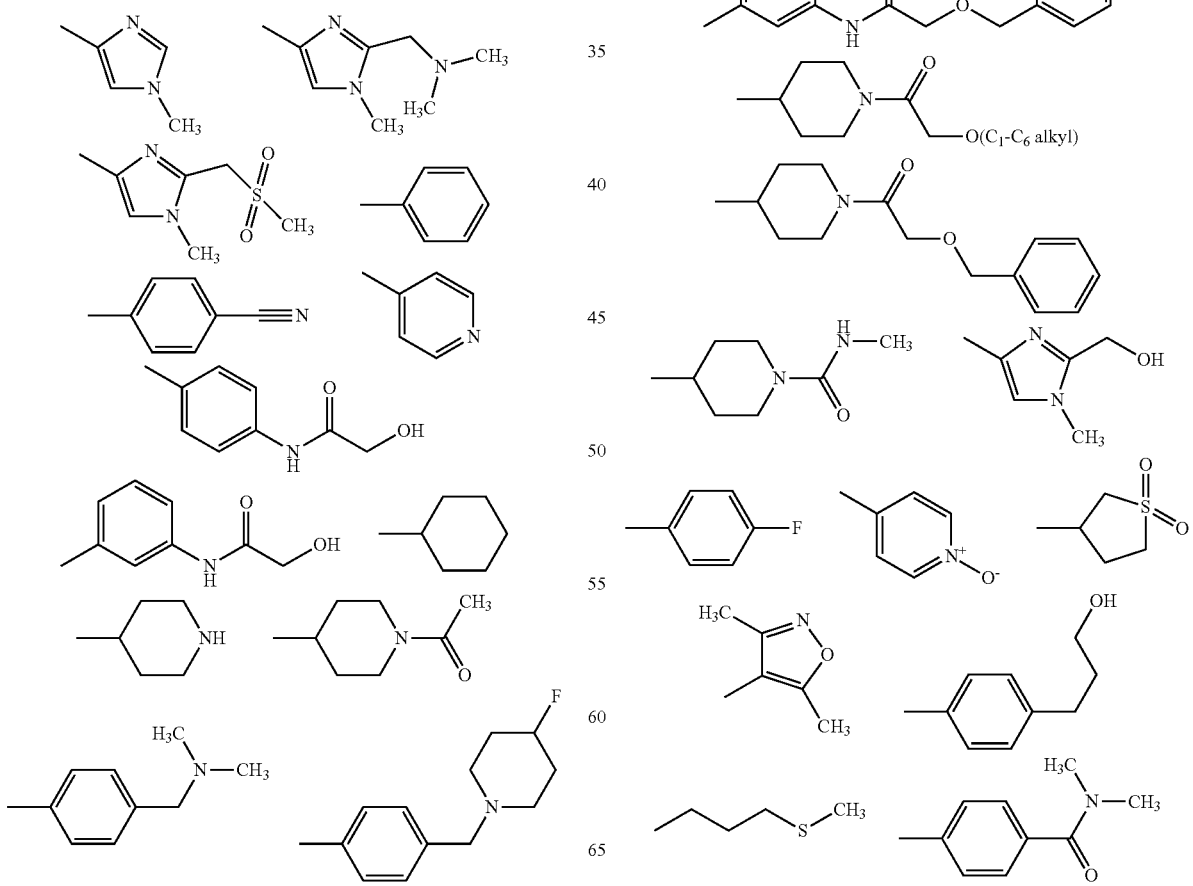
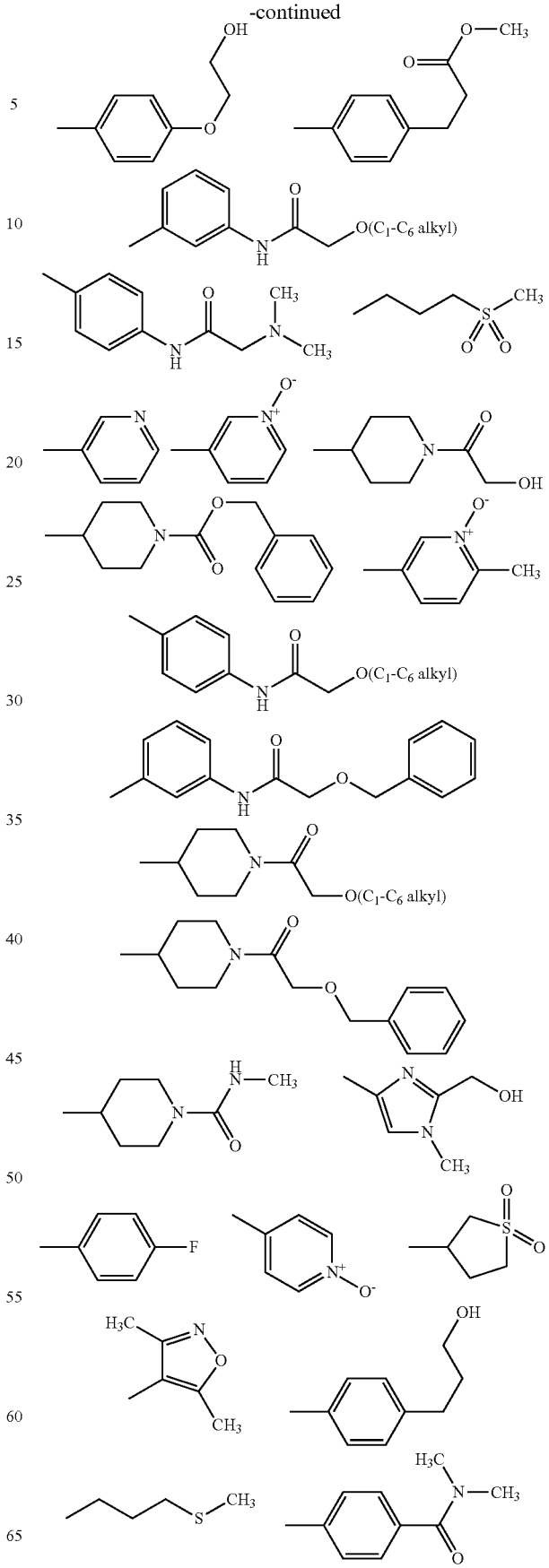

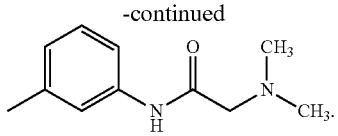

In another specific embodiment, the invention provides quinoxaline compounds of Formula (I) wherein $R^3$ is selected from $C_1$-$C_4$alkyl; phenyl; and heteroaryl group, said groups can be substituted or not, and more specifically substituted by at least one $C_1$-$C_4$alkyl group, halogen atom, amino ($C_1$-$C_6$) alkyl group.

If any of the groups such as $R^1$, $R^2$, $R^3$, $X^1$, $X^2$ Q, Y, m, p occurs more than once in a chemical compound, it is independently from one another.

When $R^3$ is $C_1$-$C_4$alkyl group, it includes more specifically methyl, ethyl, butyl, or propyl group.

When $R^3$ is a heteroaryl group, it is more preferably imidazole or pyridine, optionally substituted by $C_1$-$C_4$ alkyl group, more preferably by methyl or ethyl. Examples of heteroaryl, optionally substituted, include 1-methyl-1H-imidazol-4-yl and pyridine.

When $R^3$ is a phenyl, it can be substituted more specifically by at least one halogen atom, in particular fluor, or amino($C_1$-$C_6$)alkyl group, in particular dimethylamino methyl. Examples of substituted phenyl include 4-fluorophenyl and 4-dimethylaminomethylphenyl.

In a particular embodiment, the invention provides quinoxaline compounds of Formula (I) wherein $R^2$ is $(CH_2)m$-$R^4$, with m is 1 or 2.

In another specific embodiment, the invention provides quinoxaline compounds of Formula (I) wherein $R^2$ is $(CH_2)m$-$R^4$, wherein $R^4$ is a hydroxy, $C_3$-$C_8$ cycloalkyl or $C_3$-$C_8$ heterocycloalkyl group, more particularly with m is 1 or 2, and more specifically with m is 1.

According to this specific embodiment, when $R^4$ is a $C_3$-$C_8$ cycloalkyl group, it is preferably a cyclohexyl or cyclopentyl group, which is optionally substituted, and more specifically substituted by hydroxy, such as 4-hydroxycyclohexyl group.

According to this specific embodiment, when $R^4$ is a $C_3$-$C_8$ heterocycloalkyl group, it is preferably selected from piperazine, morpholine, tetrahydropyran, tetrahydrothiopyrane, piperidine, and 8-methyl-8-aza-bicyclo[3.2.1]octane, optionally substituted. Said substituents are more preferably at least one alkyl, acyl, sulfone or dioxy group. Examples of substituted heterocycloalkyl groups include 1-acetylpiperidin-4-yl, 1-methylpiperidin-4-yl, 4-methylpiperazin-1-yl, or 1,2,2,6,6-pentamethylpiperidin-4-yl.

In yet another specific embodiment, the invention provides quinoxaline compounds of Formula (I) wherein $R^2$ is CO—$R^{4'}$, in which $R^{4'}$ is $C_1$-$C_6$alkoxy; or $C_3$-$C_8$ heterocycloalkyl group, said groups being optionally substituted.

According to this specific embodiment, when $R^{4'}$ is a $C_1$-$C_6$alkoxy group, it is more preferably a methoxy or ethoxy group.

According to this specific embodiment, when $R^{4'}$ is a $C_3$-$C_8$ heterocycloalkyl group, it is preferably selected from piperazine, morpholine, tetrahydropyran, and piperidine, and more preferably a piperazine or morpholine group, optionally substituted by alkyl (e.g., methyl), acyl or alkylsulfonyl group. Examples of substituted heterocycloalkyl groups include 1-acetylpiperidin-4-yl, 1-methylpiperidin-4-yl, or 4-methylpiperazin-1-yl, 1-methylsulfonyl piperidine-4-yl.

In another specific embodiment, the invention provides quinoxaline compounds of Formula (I) wherein $R^1$ is methyl; $R^2$ and $R^3$ are as defined above, including any of the specific embodiments and combinations thereof.

According to preferred embodiments, the compounds according to the invention correspond to general formula (I) wherein:
—$R^1$ is methyl; and/or
—$R^2$ is $(CH_2)m$-$R^4$, wherein $R^4$ is a hydroxy, $C_3$-$C_8$ cycloalkyl or $C_3$-$C_8$ heterocycloalkyl group, more particularly with m is 1, 2 or 3, and more specifically with m is 2 or 3, and more particularly where $R^4$ is as defined above; or $R^2$ is CO—$R^{4'}$, in which $R^4$ and $R^{4'}$ is $C_1$-$C_6$alkoxy, or $C_3$-$C_8$ heterocycloalkyl group, and more particularly where $R^4$ and $R^{4'}$ are as defined above; and/or
—$R^3$ is selected from $C_1$-$C_4$ alkyl; phenyl; and heteroaryl group, and more particularly where $R^3$ is as defined above.

According to another preferred embodiment, the compounds according to the invention correspond to general formula (I) wherein:
$R^1$ and $R^3$ are as defined above in formula (I);
$R^2$ is alkyl-heterocycloalkyl-$C_1$-$C_6$ alkyl, alkyl-sulfonyl-heterocycloalkyl-$C_1$-$C_6$ alkyl, acyl-heterocycloalkyl-$C_1$-$C_6$ alkyl, dialkylamino-acyl-heterocycloalkyl-$C_1$-$C_6$ alkyl, cycloalkyl-$C_1$-$C_6$ alkyl, heterocycloalkyl-$C_1$-$C_6$ alkyl, hydroxy-cycloalkyl-$C_1$-$C_6$ alkyl, hydroxy-alkyl, carboxylic acid, COOalkyl, CO-alkyl-heterocycloalkyl, CO-heterocycloalkyl, or alkyl-sulfonyl-heterocycloalkyl,
wherein the heterocycloalkyl is preferably selected from a 5 to 8 membered, more preferably 6 or 8 membered, heterocycloalkyl bearing at least one heteroatom selected from N, S, O and wherein preferably the cycloalkyl is selected from a 5 to 6 membered cycloalkyl.

In a more preferred embodiment, $R^2$ is selected from:
—$CH_2$-methylpiperazine, —$CH_2$-tetrahydropyrane, —$CH_2$-1,1-dioxo-tetrahydrothiopyran, —$CH_2$-tetrahydrothiopyran, —COOMe, —CO-methylpiperazine, —CO-morpholino, —COOH, —$CH_2$-methylpiperidine, —$CH_2$-acetylpiperidine, hydroxyethyl, —$CH_2$-methylpiperazine, —$CH_2$-tetrahydropyrane, —$CH_2$-morpholino, —$CH_2$-cyclohexane, —$CH_2$-cyclohexanol, hydroxymethyl, —$CH_2$-1,2,2,6,6-pentamethylpiperidine, —$CH_2$-dimethylamino-acetyl-piperidine, —$CH_2$-piperidine-methanesulfonyl, —$CH_2$-(1R,5S)-8-methyl-8-aza-bicyclo[3.2.1]octyl, and —$CH_2$-cyclopentane.

In even more preferred embodiments, $R^1$ is defined as above for formula (I) and $R^2$ and $R^3$ are as following:
1. when $R^3$ is an alkyl-heteroaryl, $R^2$ is selected from COOalkyl, hydroxy-alkyl, alkyl-heterocycloalkyl-$C_1$-$C_6$ alkyl, acyl-heterocycloalkyl-$C_1$-$C_6$ alkyl, dialkylamino-acyl-heterocycloalkyl-$C_1$-$C_6$ alkyl, alkyl-sulfonyl-heterocycloalkyl-$C_1$-$C_6$ alkyl, heterocycloalkyl-$C_1$-$C_6$ alkyl, cycloalkyl-$C_1$-$C_6$ alkyl, and hydroxy-cycloalkyl-$C_1$-$C_6$ alkyl,
wherein the heterocycloalkyl is selected from 5 to 8 membered heterocycloalkyl, more preferably 6 or 8, bearing at least one heteroatom selected from N, S, O.
1.1. when $R^3$ is substituted methylimidazole, such as methylimidazole substituted by $CH_2$—$N(Me)_2$, $R^2$ is selected from COOMe, hydroxy-methyl, —$CH_2$-methylpiperidine, —$CH_2$-1,2,2,6,6-pentamethylpiperidine, —$CH_2$-acetylpiperidine, —$CH_2$-dimethylamino-acetyl-piperidine, —$CH_2$-piperidine-methanesulfonyl, —$CH_2$-tetrahydropyrane, —$CH_2$-(1R,5S)-8-methyl-8-aza-bicyclo[3.2.1]octyl, —$CH_2$-tetrahydrothiopyran, —$CH_2$-1,1-dioxo-tetrahydrothiopyran, —$CH_2$-cyclohexane, —$CH_2$-cyclohexanol, and —$CH_2$-cyclopentane.

2. when R³ is an alkyl, R² is selected from:
COOalkyl, alkyl-heterocycloalkyl-$C_1$-$C_6$alkyl, acyl-heterocycloalkyl-$C_1$-$C_6$alkyl, CO-heterocycloalkyl, heterocycloalkyl-$C_1$-$C_6$alkyl, and cycloalkyl-$C_1$-$C_6$alkyl,
wherein the heterocycloalkyl is selected from a 6 membered heterocycloalkyl bearing at least one heteroatom selected from N, O.

2.1. when R³ is methyl, R² is selected from COOMe, —CH₂-methylpiperidine, —CH₂-acetylpiperidine, —CO-morpholino, —CH₂-tetrahydropyrane, and —CH₂-cyclohexane.

3. when R³ is a heteroaryl, R² is selected from COOalkyl, CO-alkyl-heterocycloalkyl, CO-heterocycloalkyl, carboxylic acid, alkyl-heterocycloalkyl-$C_1$-$C_6$alkyl, acyl-heterocycloalkyl-$C_1$-$C_6$alkyl, hydroxy-alkyl, heterocycloalkyl $C_1$-$C_6$alkyl, cycloalkyl-$C_1$-$C_6$alkyl, and hydroxy-cycloalkyl-$C_1$-$C_6$alkyl,
wherein the heterocycloalkyl is selected from a 6 membered heterocycloalkyl bearing at least one heteroatom selected from N, O.

3.1. when R³ is pyridin, R² is selected from COOMe, CO-methylpiperazine, CO-morpholino, COOH, —CH₂-methylpiperidine, —CH₂-acetylpiperidine, hydroxy-ethyl, —CH₂-methylpiperazine, —CH₂-tetrahydropyrane, —CH₂-morpholino, —CH₂-cyclohexane, and —CH₂-cyclohexanol.

4. when R³ is a dialkylamino-benzyl, R² is selected from hydroxy-cycloalkyl-$C_1$-$C_6$alkyl, cycloalkyl $C_1$-$C_6$alkyl, and heterocycloalkyl-$C_1$-$C_6$alkyl, wherein the heterocycloalkyl is selected from a 6 membered heterocycloalkyl bearing at least one heteroatom selected from S, O.

4.1. when R³ is dimethylamino-benzyl, R² is selected from —CH₂-cyclohexanol, —CH₂-cyclohexane, —CH₂-1,1-dioxo-tetrahydro-thiopyran, —CH₂-tetrahydrothiopyran, and —CH₂-tetrahydropyrane.

5. when R³ is a halogenophenyl, R² is selected from alkyl-heterocycloalkyl-$C_1$-$C_6$alkyl, and heterocycloalkyl-$C_1$-$C_6$alkyl, wherein the heterocycloalkyl is selected from a 6 membered heterocycloalkyl bearing at least one heteroatom selected from N, O.

5.1. when R³ is fluorophenyl, R² is selected from —CH₂-methylpiperazine, and —CH₂-tetrahydropyrane.

In a more preferred embodiments R² and R³ are as above and R¹ equals methyl.

Compounds of the present invention include in particular those of the group consisting of:

methyl 4-methoxy-2-[(3-{[(1-methyl-1H-imidazol-4-yl)sulfonyl]amino}quinoxalin-2-yl)amino]benzoate methyl 4-methoxy-2-({3-[(pyridin-3-ylsulfonyl)amino]quinoxalin-2-yl}amino)benzoate methyl 4-methoxy-2-({3-[(methylsulfonyl)amino]quinoxalin-2-yl}amino)benzoate N-[3-({3-methoxy-5-[(4-methylpiperazin-1-yl)carbonyl]phenyl}amino)quinoxalin-2-yl]pyridine-3-sulfonamide N-(3-{[3-methoxy-5-(morpholin-4-ylcarbonyl)phenyl]amino}quinoxalin-2-yl)pyridine-3-sulfonamide N-(3-{[3-methoxy-5-(morpholin-4-ylcarbonyl)phenyl]amino}quinoxalin-2-yl)methanesulfonamide N-(3-{[5-methoxy-2-(tetrahydro-2H-pyran-4-ylmethyl)phenyl]amino}quinoxalin-2-yl)-1-methyl-1H-imidazole-4-sulfonamide N-(3-{[5-methoxy-2-(tetrahydro-2H-pyran-4-ylmethyl)phenyl]amino}quinoxalin-2-yl)methanesulfonamide N-(3-{[5-methoxy-2-(tetrahydro-2H-pyran-4-ylmethyl)phenyl]amino}quinoxalin-2-yl)pyridine-3-sulfonamide 4-fluoro-N-(3-{[5-methoxy-2-(tetrahydro-2H-pyran-4-ylmethyl)phenyl]amino}quinoxalin-2-yl)benzenesulfonamide N-[3-({5-methoxy-2-[(1-methylpiperidin-4-yl)methyl]phenyl}amino)quinoxalin-2-yl]-1-methyl-1H-imidazole-4-sulfonamide N-[3-({5-methoxy-2-[(1-methylpiperidin-4-yl)methyl]phenyl}amino)quinoxalin-2-yl]pyridine-3-sulfonamide N-[3-({5-methoxy-2-[(1-methylpiperidin-4-yl)methyl]phenyl}amino)quinoxalin-2-yl]methanesulfonamide N-[3-({5-methoxy-2-[(1,2,2,6,6-pentamethylpiperidin-4-yl)methyl]phenyl}amino)quinoxalin-2-yl]-1-methyl-1H-imidazole-4-sulfonamide N-{3-[(5-methoxy-2-{[(1R,5S)-8-methyl-8-azabicyclo[3.2.1]oct-3-yl]methyl}phenyl)amino]quinoxalin-2-yl}-1-methyl-1H-imidazole-4-sulfonamide N-[3-({2-[(1-acetylpiperidin-4-yl)methyl]-5-methoxyphenyl}amino)quinoxalin-2-yl]-1-methyl-1H-imidazole-4-sulfonamide N-[3-({2-[(1-acetylpiperidin-4-yl)methyl]-5-methoxyphenyl}amino)quinoxalin-2-yl]pyridine-3-sulfonamide N-[3-({2-[(1-acetylpiperidin-4-yl)methyl]-5-methoxyphenyl}amino)quinoxalin-2-yl]methanesulfonamide N-(3-{[2-(cyclohexylmethyl)-5-methoxyphenyl]amino}quinoxalin-2-yl)pyridine-3-sulfonamide N-(3-{[2-(cyclohexylmethyl)-5-methoxyphenyl]amino}quinoxalin-2-yl)-1-methyl-1H-imidazole-4-sulfonamide N-(3-{[2-(cyclohexylmethyl)-5-methoxyphenyl]amino}quinoxalin-2-yl)methanesulfonamide N-[3-({2-[(4-hydroxycyclohexyl)methyl]-5-methoxyphenyl}amino)quinoxalin-2-yl]-1-methyl-1H-imidazole-4-sulfonamide N-[3-({2-[(4-hydroxycyclohexyl)methyl]-5-methoxyphenyl}amino)quinoxalin-2-yl]pyridine-3-sulfonamide N-(3-{[2-(cyclopentylmethyl)-5-methoxyphenyl]amino}quinoxalin-2-yl)-1-methyl-1H-imidazole-4-sulfonamide N-(3-{[5-methoxy-2-(tetrahydro-2H-thiopyran-4-ylmethyl)phenyl]amino}quinoxalin-2-yl)-1-methyl-1H-imidazole-4-sulfonamide N-[3-({2-[(1,1-dioxidotetrahydro-2H-thiopyran-4-yl)methyl]-5-methoxy phenyl}amino)quinoxalin-2-yl]-1-methyl-1H-imidazole-4-sulfonamide N-(3-{[2-(2-hydroxyethyl)-5-methoxyphenyl]amino}quinoxalin-2-yl)pyridine-3-sulfonamide N-(3-{[2-(3-Hydroxypropyl)-5-methoxyphenyl]amino}quinoxalin-2-yl)-1-methyl-1H-imidazole-4-sulfonamide N-[3-({2-[2-Hydroxy-1-(hydroxymethyl)ethyl]-5-methoxyphenyl}amino)quinoxalin-2-yl]-1-methyl-1H-imidazole-4-sulfonamide N-{3-[(2-Isopropyl-5-methoxyphenyl)amino]quinoxalin-2-yl}-1-methyl-1H-imidazole-4-sulfonamide N-[3-({2-[3-(Dimethylamino)propyl]-5-methoxyphenyl}amino)quinoxalin-2-yl]-1-methyl-1H-imidazole-4-sulfonamide 4-{[(3-{[2-(2-Hydroxyethyl)-5-methoxyphenyl]amino}quinoxalin-2-yl)amino]sulfonyl}-N,N-dimethylbenzamide N-(3-{[2-(2-Hydroxyethyl)-5-methoxyphenyl]amino}quinoxalin-2-yl)-6-methylpyridine-3-sulfonamide 1-oxide 4-cyano-N-(3-{[2-(2-Hydroxyethyl)-5-methoxyphenyl]amino}quinoxalin-2-yl)benzenesulfonamide N-(3-{[2-(2-Hydroxyethyl)-5-methoxyphenyl]amino}quinoxalin-2-yl)-1-methyl-1H-imidazole-4-sulfonamide 4-Fluoro-N-(3-{[2-(2-hydroxyethyl)-5-methoxyphenyl]amino}quinoxalin-2-yl)benzenesulfonamide N-(3-{[2-(2-Hydroxyethyl)-5-methoxyphenyl]amino}quinoxalin-2-yl)methanesulfonamide N-(3-{[2-(2-Hydroxyethyl)-5-methoxyphenyl]amino}quinoxalin-2-yl)ethanesulfonamide N-(3-{[2-(2-Hydroxyethyl)-5-methoxyphenyl]amino}quinoxalin-2-yl)propane-1-sulfonamide N-[3-({5-Methoxy-2-[2-(methylsulfonyl)ethyl]phenyl}amino)quinoxalin-2-yl]-1-methyl-1H-imidazole-4-sulibnamide Methyl 3-(4-{[(3-{[2-(2-hydroxyethyl)-5-methoxyphenyl]amino}quinoxalin-2-yl)amino]sulfonyl}phenyl)propanoate N-(3-{[2-(3-Hydroxypropyl)-5-methoxyphenyl]amino}quinoxalin-2-yl)-3,5-dimethylisoxazole-4-sulfonamide N-(3-{[2-(2-Hydroxyethyl)-5-methoxyphenyl]amino}quinoxalin-2-yl)-3,5-dimethylsoxazole-4-sulfonamide N-[3-({5-Methoxy-2-[2-(methylsulfonyl)ethyl]phenyl}amino)quinoxalin-2-yl]methanesulfonamide N-(3-{[2-(2-Hydroxyethyl)-5-methoxyphenyl]amino}quinoxalin-2-yl)cyclohexanesulfonamide N-(3-{[2-(3-Hydroxypropyl)-5-methoxyphenyl]amino}quinoxalin-2-yl)methanesulfonamide 2-[(Dimethylamino)methyl]-N-(3-{[2-(3-hydroxypropyl)-5-methoxyphenyl]amino}quinoxalin-2-yl)-1-methyl-1H-imidazole-4-sulfonamide N-(3-{[2-(3-Hydroxypropyl)-5-methoxyphenyl]amino}quinoxalin-2-yl)ethanesulfonamide N-(3-{[2-(3-Hydroxypropyl)-5-methoxyphenyl]amino}quinoxalin-2-yl)propane-1-sulfonamide N-(3-{[2-(3-Hydroxypropyl)-5-methoxyphenyl]amino}quinoxalin-2-yl)propane-2-sulfonamide N-[3-({5-Methoxy-2-[2-(methylsulfonyl)ethyl]phenyl}amino)quinoxalin-2-yl]ethanesulfonamide N-[3-({5-Methoxy-2-[2-(methylsulfonyl)ethyl]phenyl}amino)quinoxalin-2-yl]propane-2-sulfonamide N-[3-({5-Methoxy-2-[2-(methylsulfonyl)ethyl]phenyl}amino)quinoxalin-2-yl]propane-1-sulfonamide N-[3-({5-Methoxy-2-[2-(methylsulfonyl)ethyl]phenyl}amino)quinoxalin-2-yl]-3,5-dimethylisoxazole-4-sulfonamide N-[3-({5-Methoxy-2-[2-(methylsulfonyl)ethyl]phenyl}amino)quinoxalin-2-yl]benzenesulfonamide N-(3-{[2-(2-Hydroxyethyl)-5-methoxyphenyl]amino}quinoxalin-2-yl)tetrahydrothiophene-3-sulfonamide 1,1-dioxide N-[3-({5-Methoxy-2-[2-(methylsulfonyl)ethyl]phenyl}amino)quinoxalin-2-yl]-3-(methylthio)propane-1-sulfonamide N-(3-{[2-(2-Hydroxyethyl)-5-methoxyphenyl]amino}quinoxalin-2-yl)-3-(methylthio)propane-1-sulfonamide N-[3-({5-Methoxy-2-[2-(methylsulfonyl)ethyl]phenyl}amino)quinoxalin-2-yl]-3-(methylsulfonyl)propane-1-sulfonamide N-(3-{[2-(3-Hydroxypropyl)-5-methoxyphenyl]amino}quinoxalin-2-yl)-3-(methylsulfonyl)propane-1-sulfonamide N-(3-{[2-(2-Hydroxyethyl)-5-methoxyphenyl]amino}quinoxalin-2-yl)-3-(methylsulfonyl)propane-1-sulfonamide N-(3-{[5-Methoxy-2-(2-methoxyethyl)phenyl]amino}quinoxalin-2-yl)-1-methyl-1H-imidazole-4-sulfonamide N-(3-{[2-(3-Hydroxypropyl)-5-methoxyphenyl]amino}quinoxalin-2-yl)tetrahydrothiophene-3-sulfonamide 1,1-dioxide N-(2-Hydroxyethyl)-4-methoxy-2-{3-({[3-(methylsulfonyl)propyl]sulfonyl}amino)quinoxalin-2-yl]amino}benzenesulfonamide 2-[(Dimethylamino)methyl]-N-[3-({5-methoxy-2-[2-(methylsulfonyl)ethyl]phenyl}amino)quinoxalin-2-yl]-1-methyl-1H-imidazole-4-sulfonamide Benzyl 4-{[(3-{[2-(3-hydroxypropyl)-5-methoxyphenyl]amino}quinoxalin-2-yl)amino]sulfonyl}piperidine-1-carboxylate N-(2-Hydroxyethyl)-3-methoxy-5-[(3-{[(1-methyl-1H-imidazol-4-yl)sulfonyl]amino}m quinoxalin-2-yl)amino]benzamide N-[3-({5-Methoxy-2-[3-(methylsulfonyl)propyl]phenyl}amino)quinoxalin-2-yl]-1-methyl-1H-imidazole-4-sulfonamide 2-Hydroxy-N-(4-{[(3-{[2-(2-hydroxyethyl)-5-methoxyphenyl]amino}quinoxalin-2-yl)amino]sulfonyl}phenyl)acetamide 2-Dimethylamino-N-(4-{[(3-{[2-(2-hydroxyethyl)-5-methoxyphenyl]amino}quinoxalin-2-yl)]sulfamoyl}phenyl)-acetamide 2-Dimethylamino-N-(4-{[(3-{[2-(3-hydroxypropyl)-5-methoxyphenyl]amino}quinoxalin-2-yl)]sulfamoyl}phenyl)-acetamide 2-(Benzyloxy)-N-(3-{[(3-{[2-(3-hydroxypropyl)-5-methoxyphenyl]amino}quinoxalin-2-yl)amino]sulfonyl}phenyl)acetamide N-(2-Hydroxyethyl)-3-methoxy-5-{[3-({[3-(methylsulfonyl)propyl]sulfonyl}amino)quinoxalin-2-yl]amino}benzamide 2-(Hydroxymethyl)-N-(3-{[2-(3-hydroxypropyl)-5-methoxyphenyl]amino}quinoxalin-2-yl)-1-methyl-1H-imidazole-4-sulfonamide 3-Methoxy-N,N-dimethyl-5-[(3-{[(1-methyl-1H-imidazol-4-yl)sulfonyl]amino}quinoxalin-2-yl)amino]benzamide N-(3-{[2-(3-Hydroxypropyl)-5-methoxyphenyl]amino}quinoxalin-2-yl)-1-methyl-2-[(methylsulfonyl)methyl]-1H-imidazole-4-sulfonamide N-[3-({2-[(2R,2S)-2,3-Dihydroxypropyl]-5-methoxyphenyl}amino)quinoxalin-2-yl]-1-methyl-1H-imidazole-4-sulfonamide.

2-Dimethylamino-N-(3-{[(3-{[2-(3-hydroxypropyl)-5-methoxyphenyl]amino}quinoxalin-2-yl)]sulfamoyl}phenyl)-acetamide N-(3-{[5-Methoxy-2-(2-methoxyethyl)phenyl]amino}quinoxalin-2-yl)-1-methyl-2-[(methylsulfonyl)methyl]-1H-imidazole-4-sulfonamide 3-Methoxy-N-(2-methoxyethyl)-5-[(3-{[(1-methyl-1H-imidazol-4-yl)sulfonyl]amino}quinoxalin-2-yl)amino]benzamide N-[3-({5-methoxy-2-[(4-methylpiperazin-1-yl)methyl]phenyl}amino)quinoxalin-2-yl]pyridine-3-sulfonamide 4-fluoro-N-[3-({5-methoxy-2-[(4-methylpiperazin-1-yl)methyl]phenyl}amino)quinoxalin-2-yl]benzenesulfonamide N-(3-{[5-methoxy-2-(morpholin-4-ylmethyl)phenyl]amino}quinoxalin-2-yl)pyridine-3-sulfonamide 4-[(dimethylamino)methyl]-N-[3-({2-[(4-hydroxycyclohexyl)methyl]-5-methoxyphenyl}amino)quinoxalin-2-yl]benzenesulfonamide 4-[(dimethylamino)methyl]-N-[3-({2-[(1,1-dioxidotetrahydro-2H-thiopyran-4-yl)methyl]-5-methoxyphenyl}amino)quinoxalin-2-yl]benzenesulfonamide 4-[(dimethylamino)methyl]-N-(3-{[5-methoxy-2-(tetrahydro-2H-pyran-4-ylmethyl)phenyl]amino}quinoxalin-2-yl)benzenesulfonamide N-(3-{[2-(cyclohexylmethyl)-5-methoxyphenyl]amino}quinoxalin-2-yl)-4-[(dimethylamino)methyl]benzenesulfonamide 4-[(dimethylamino)methyl]-N-(3-{[5-methoxy-2-(tetrahydro-2H-thiopyran-4-ylmethyl)phenyl]amino}quinoxalin-2-yl)benzenesulfonamide 4-[(Dimethylamino)methyl]-N-(3-{[2-(2-hydroxyethyl)-5-methoxyphenyl]amino}quinoxalin-2-yl)benzenesulfonamide 4-[(4-Fluoropiperidin-1-yl)methyl]-N-(3-{[2-(2-hydroxyethyl)-5-methoxyphenyl]amino}quinoxalin-2-yl)benzenesulfonamide N-(3-{[2-(hydroxymethyl)-5-methoxyphenyl]amino}quinoxalin-2-yl)-1-methyl-1H-imidazole-4-sulfonamide N-[3-({3-methoxy-5-[(4-methylpiperazin-1-yl)methyl]phenyl}amino)quinoxalin-2-yl]pyridine-3-sulfonamide N-(3-{[2-(2-Hydroxyethyl)-5-methoxyphenyl]amino}quinoxalin-2-yl)-4-(3-hydroxypropyl)benzenesulfonamide 4-(2-Hydroxyethoxy)-N-(3-{[2-(2-hydroxyethyl)-5-methoxyphenyl]amino}quinoxalin-2-yl)benzenesulfonamide N-[3-({3-[(Dimethylamino)methyl]-5-methoxyphenyl}amino)quinoxalin-2-yl]-1-methyl-1H-imidazole-4-sulfonamide N-{3-[(2-{[1-(N,N-dimethylglycyl)piperidin-4-yl]methyl}-5-methoxyphenyl)amino]quinoxalin-2-yl}-1-methyl-1H-imidazole-4-sulfonamide N-{3-[(5-methoxy-2-{[1-(methylsulfonyl)piperidin-4-yl]methyl}phenyl)amino]quinoxalin-2-yl}-1-methyl-1H-imidazole-4-sulfonamide 4-methoxy-2-({3-[(pyridin-3-ylsulfonyl)amino]quinoxalin-2-yl}amino)benzoic acid N-(3-{[2-(3-Hydroxypropyl)-5-methoxyphenyl]amino}quinoxalin-2-yl)piperidine-4-sulfonamide N-(3-{[5-Methoxy-2-(2-methoxyethyl)phenyl]amino}quinoxalin-2-yl)piperidine-4-sulfonamide 1-Acetyl-N-(3-{[5-methoxy-2-(2-methoxyethyl)phenyl]amino}quinoxalin-2-yl)piperidine-4-sulfonamide 2-Hydroxy-N-(3-{[(3-{[2-(3-hydroxypropyl)-5-methoxyphenyl]amino}quinoxalin-2-yl)amino]sulfonyl}phenyl)acetamide 2-{4-Methoxy-2-[(3-{[(1-methyl-1H-imidazol-4-yl)sulfonyl]amino}quinoxalin-2-yl)amino]phenyl}ethyl N-[(9H-fluoren-9-ylmethoxy)carbonyl]-L-valinate 2-{4-Methoxy-2-[(3-{[(1-methyl-1H-imidazol-4-yl)sulfonyl]amino}quinoxalin-2-yl)amino]phenyl}ethyl-L-valinate The compounds of the present invention are useful as medicaments. They may be used for the treatment of autoimmune disorders and/or inflammatory diseases, cardiovascular diseases, neurodegenerative diseases, bacterial or viral infections, allergy, asthma, pancreatitis, multi organ failure, kidney diseases, platelet aggregation, cancer, transplantation, sperm motility, erythrocyte deficiency, graft rejection or lung injuries.

In one embodiment, the compounds of Formula (I) are useful for the treatment of autoimmune diseases or inflammatory diseases such as multiple sclerosis, psoriasis, rheumatoid arthritis, osteoarthritis, systemic lupus erythematosis, inflammatory bowel disease, lung inflammation, thrombosis or brain infection/inflammation such as meningitis or encephalitis.

In another embodiment, the compounds of Formula (I) are useful for the treatment of neurodegenerative diseases including Alzheimer's disease, Huntington's disease, CNS trauma, stroke or ischemic conditions.

In still a further embodiment according to the invention, the compounds of Formula (I) are useful for the treatment of cardiovascular diseases such as atherosclerosis, heart hypertrophy, cardiac myocyte dysfunction, elevated blood pressure or vasoconstriction.

In still a further embodiment according to the invention, the compounds of Formula (I) are useful for the treatment of erythrocyte deficiency such as an anaemia, including haemolytic anaemia, aplastic anaemia and pure red cell anaemia.

In still a further embodiment according to the invention, the compounds of Formula (I) are useful for the treatment of cancers including non-small cell lung (NSCL) cancer, B cell malignancies, hematopoietic cancers such as lymphomas, Hodgkin- and non-Hodgkin lymphomas, T-cell lymphomas (T-CLL, T-ALL, CTCL), B-cell lymphomas (B-CLL), mantle cell lymphoma (MCL), leukemias, acute myelogenous leukemia (AML), acute lymphocytic leukemia (ALL), chronic myelogenous leukemia (CML), chronic lymphocytic leukemia (CLL), myelomas, multiple myeloma, plasmacytomas, Waldenstroem macroglobulinemia, myelodysplastic syndrome, myeloproliferative disorders, chronic myelomonocytic leukemias, juvenile myelomonocytic leukemia, pancreatic cancer, endometrial cancer, ovarian cancer, bladder cancer, seminomas, thyroid cancer, breast cancer, glioblastoma multiforme, mammary carcinoma, gastric cancers, and lymphomas, cancers of the lung, prostate, liver, colon, breast, kidney, brain, skin including malignant melanoma, testes or ovaries, or leukemias, including myelogenous and lymphocytic leukemias, myelogenousmultiple myeloma-related bone disorder, metastatic melanoma and malignant melanoma and Kaposi's sarcoma.

In still another embodiment according to the invention, the compounds of Formula (I) are useful for the treatment of chronic obstructive pulmonary disease, anaphylactic shock fibrosis, psoriasis, allergic diseases, asthma, stroke or ischemic conditions, ischemia-reperfusion, platelets aggregation/activation, skeletal muscle atrophy/hypertrophy, leukocyte recruitment in cancer tissue, angiogenesis, invasion metastisis, in particular melanoma, Karposi's sarcoma, acute and chronic bacterial and viral infections, sepsis, transplantation, graft rejection, glomerulo sclerosis, glomerulo nephritis, progressive renal fibrosis, endothelial and epithelial injuries in the lung or in general lung airways inflammation.

In yet another embodiment according to the invention, it provides for a method of prevention and/or treatment of autoimmune, inflammatory disorders, cardiovascular diseases, neurodegenerative disorders, bacterial and viral infections, allergy, asthma, pancreatitis, multi-organ failure, kidney diseases, platelet aggregation, cancer, transplantation, sperm motility, erythrocyte deficiency, graft rejection, lung injuries, respiratory diseases and ischemic conditions, preferably chronic obstructive pulmonary disease, anaphylactic shock fibrosis, psoriasis, allergic diseases, asthma, stroke or ischemic conditions, ischemia-reperfusion, platelets aggregation/activation, skeletal muscle atrophy/hypertrophy, leukocyte recruitment in cancer tissue, angiogenesis, invasion metastisis, in particular melanoma, Karposi's sarcoma, acute and chronic bacterial and viral infections, sepsis, transplantation, graft rejection, glomerulo sclerosis, glomerulo nephritis, progressive renal fibrosis, endothelial and epithelial injuries in the lung or in general lung airways inflammation, comprising administering to a subject a pharmaceutical composition which comprises a compound according to formula (I) in a suitable dosage form and in a suitable route of administration.

In yet another embodiment according to the invention, it provides for a method of prevention and/or treatment of cancer, in particular hematopoietic cancer, comprising administering to a subject a pharmaceutical composition comprising a compound according to formula (I) in a suitable dosage form and in a suitable route of administration.

Within the context of the invention, the term treatment denotes curative, symptomatic, and preventive treatment. Compounds of the invention can be used in subjects, in particular humans, with existing disease, including at early or late stages of progression of the disease. The compounds of the invention will not necessarily cure the patient who has the disease but will delay or slow the progression or prevent further progression of the disease, ameliorating thereby the patients' condition. The compounds of the invention can also be administered to those who do not have the diseases but who would normally develop the disease or be at increased risk for the disease, they will not develop the disease. Treatment also includes delaying the development of the disease in an individual who will ultimately develop the disease or would be at risk for the disease due to age, familial history, genetic or chromosomal abnormalities, and/or due to the presence of one or more biological markers for the disease, such as a known genetic mutation in tissues or fluids. By delaying the onset of the disease, compounds of the invention have prevented the individual from getting the disease during the period in which the individual would normally have gotten the disease or reduce the rate of development of the disease or some of its effects but for the administration of compounds of the invention up to the time the individual ultimately gets the disease. Treatment also includes administration of the compounds of the invention to those individuals thought to be predisposed to the disease. In treating the above diseases, the compounds of the invention are administered in a therapeutically effective amount.

In another embodiment according to the invention, is provided a process for the preparation of quinoxaline compounds according to Formula (I), comprising the step of reacting a chloro derivative of Formula (II) with an aniline of Formula (III) in an appropriate solvent such as EtOH or MeOH in absence of base, either by traditional thermic methods or using microwave technology such as those described hereinafter in the Examples:

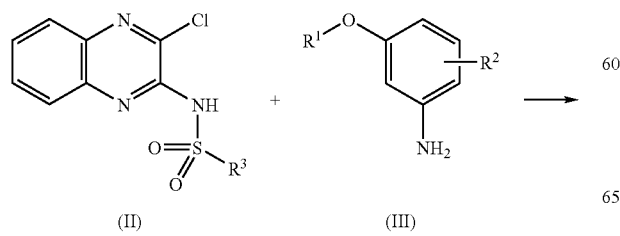

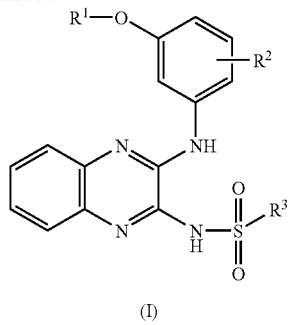

(I)

wherein $R^1$, $R^2$, and $R^3$ are as above defined.

In another embodiment according to the invention, is provided a process for the preparation of quinoxaline compound according to Formula (I) comprising the step of reacting an amino derivative of Formula (XI) and a sulfonylchloride of Formula (IX) in the presence of base such as triethylamine, isopropylamine, DIEA(diisopropylethylamine), with the optional presence of a co-solvent such as 1,2-dichlorobenzene. A preferred base is pyridine.

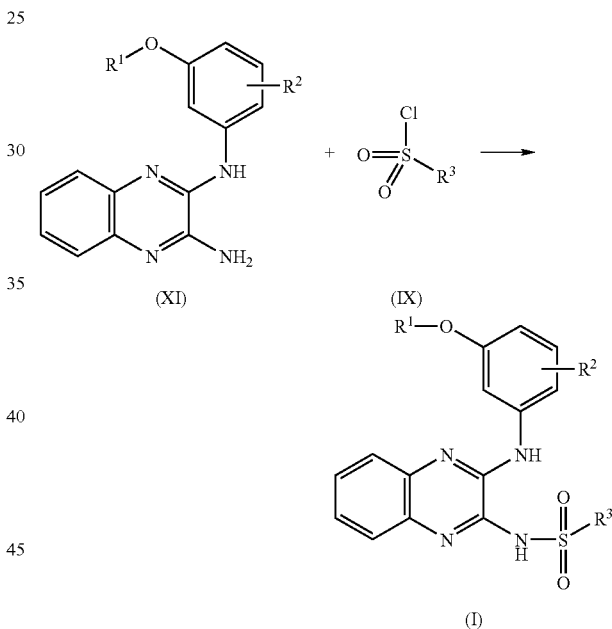

wherein $R^1$, $R^2$, and $R^3$ are as above defined.

In another embodiment according to the invention, is provided a compound of Formula (II)

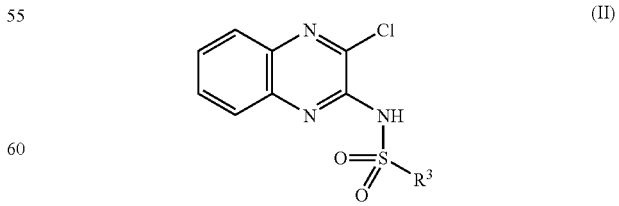

wherein $R^3$ is as defined above and more preferably wherein the compounds of Formula (II) are
4-{[(3-chloroquinoxalin-2-yl)amino]sulfonyl}-N,N-dimethylbenzamide N-(3-Chloroquinoxalin-2-yl)-4-[(4-fluoropiperidin-1-yl)carbonyl]benzenesulfonamide
N-(3-Chloro-2-quinoxalinyl)benzenesulfonamide
N-(3-chloroquinoxalin-2-yl)-4-fluorobenzenesulfonamide
N-(3-Chloroquinoxalin-2-yl)-4-cyanobenzenesulfonamide
N-(3-chloroquinoxalin-2-yl)pyridine-3-sulfonamide
N-(3-chloroquinoxalin-2-yl)-1-methyl-1H-imidazole-4-sulfonamide
N-(3-Chloroquinoxalin-2-yl)-6-methylpyridine-3-sulfonamide 1-oxide
Methyl (4-{[(3-chloroquinoxalin-2-yl)amino]sulfonyl}phenoxy)acetate
Methyl 3-(4-{[(3-chloroquinoxalin-2-yl)amino]sulfonyl}phenyl)propanoate
4-Amino-N-(3-chloroquinoxalin-2-yl)benzenesulfonamide
2-(Benzyloxy)-N-(3-{[(3-chloroquinoxalin-2-yl)amino]sulfonyl}phenyl)acetamide
N-(3-{[(3-Chloroquinoxalin-2-yl)]sulfamoyl}phenyl)-2-dimethylamino-amide
N-(3-Chloroquinoxalin-2-yl)-2-[(dimethylamino)methyl]-1-methyl-1H-imidazole-4-sulfonamide
2-({[tert-Butyl(dimethyl)silyl]oxy}methyl)-N-(3-chloroquinoxalin-2-yl)-1-methyl-1H-imidazole-4-sulfonamide
N-(3-Chloroquinoxalin-2-yl)-1-methyl-2-[(methylsulfonyl)methyl]-1H-imidazole-4-sulfonamide
N-(3-Chloroquinoxalin-2-yl)-3,5-dimethylisoxazole-4-sulfonamide
N-(3-chloroquinoxalin-2-yl)methanesulfonamide
N-(3-Chloroquinoxalin-2-yl)ethanesulfonamide
N-(3-Chloroquinoxalin-2-yl)propane-1-sulfonamide
N-(3-Chloroquinoxalin-2-yl)propane-2-sulfonamide
N-(3-Chloroquinoxalin-2-yl)cyclohexanesulfonamide
Benzyl 4-{[(3-chloroquinoxalin-2-yl)amino]sulfonyl}piperidine-1-carboxylate
N-(3-Chloroquinoxalin-2-yl)-3-(methylthio)propane-1-sulfonamide
N-(3-Chloroquinoxalin-2-yl)-3-(methylsulfonyl)propane-1-sulfonamide
N-(3-Chloroquinoxalin-2-yl)tetrahydrothiophene-3-sulfonamide 1,1-dioxide
2-[(4-{[(3-Chloroquinoxalin-2-yl)amino]sulfonyl}phenyl)amino]-2-oxoethyl acetate
N-(4-{[(3-Chloroquinoxalin-2-yl)]sulfamoyl}phenyl)-2-dimethyamino-acetamide Very much preferred are the following compounds:
N-(3-{[2-(3-hydroxypropyl)-5-methoxyphenyl]amino}quinoxalin-2-yl)-1-methyl-1H-imidazole-4-sulfonamide
N-[3-({5-methoxy-2-[(1-methylpiperidin-4-yl)methyl]phenyl}amino)quinoxalin-2-yl]-1-methyl-1H-imidazole-4-sulfonamide
2-[(dimethylamino)methyl]-N-(3-{[2-(3-hydroxypropyl)-5-methoxyphenyl]amino}quinoxalin-2-yl)-1-methyl-1H-imidazole-4-sulfonamide
N-(3-{[5-methoxy-2-(2-methoxyethyl)phenyl]amino}quinoxalin-2-yl)-1-methyl-1H-imidazole-4-sulfonamide
N-[3-({5-methoxy-2-[(4-methylpiperazin-1-yl)methyl]phenyl}amino)quinoxalin-2-yl]pyridine-3-sulfonamide In another embodiment according to the invention, is provided a compound of Formula (XI):

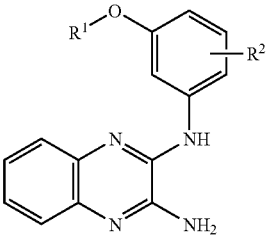

(XI)

wherein $R^1$ and $R^2$ are as defined above, including the particular embodiments as specified above.

The quinoxaline compounds exemplified in this invention may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

When employed as pharmaceuticals, the compounds of the present invention are typically administered in the form of a pharmaceutical composition. Hence, pharmaceutical compositions comprising a compound of Formula (I) and a pharmaceutically acceptable carrier, diluent or excipient, therefore are also within the scope of the present invention. A person skilled in the art is aware of a whole variety of such carrier, diluent or excipient compounds suitable to formulate a pharmaceutical composition.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

Pharmaceutical compositions containing quinoxaline compounds of this invention can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of the present invention can be administered by a variety of routes including oral, rectal, transdermal, subcutaneous, intravenous, intramuscular and intranasal. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, pre-measured ampoules or syringes of the liquid compositions or pills, tablets, capsules or the like in the case of solid compositions. In such compositions, the quinoxaline compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as pepper-mint, methyl salicylate, or orange flavoring.

Injectable compositions are typically based upon injectable sterile saline or phosphate-buffered saline or other injectable carriers known in the art. As above mentioned, the quinoxaline compounds of Formula (I) in such compositions is typically a minor component, frequently ranging between 0.05 to 10% by weight with the remainder being the injectable carrier and the like.

The components above described for orally administered or injectable compositions are merely representative. Further materials as well as processing techniques and the like are set out in Part 5 of *Remington's Pharmaceutical Sciences, 20th Edition*, 2000, Marck Publishing Company, Easton, Pa., which is incorporated herein by reference.

The compounds of this invention can also be administered in sustained release forms or from sustained release drug delivery systems. A description of representative sustained release materials can also be found in the incorporated materials in *Remington's Pharma-ceutical Sciences*.

Synthesis of Compounds of the Invention:

The quinoxaline compounds according to Formula (I) may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

The following abbreviations refer respectively to the definitions below: min (min-ute), hr (hour), g (gram), mmol (millimole), m.p. (melting point), eq. (equivalents), mL (milliliter), µL (microliters), ACN (Acetonitrile), AcOH, (acetic acid), CCl$_4$ (tetrachlorocarbone), CDCl$_3$ (deuterated chloroform), CsCO$_3$ (Cesium carbonate), mCPBA (3-chloro perbenzoic acid), CuI (Copper iodide), DCM (Dichloromethane), DCE (Dichloroethane), DIBAL-H (Diisobutyl aluminum hydride), DME (Dimethoxy ethane), DMA (Dimethylacetamide), DMF (Dimethylformamide), DMSO (Dimethyl-sulfoxide), DMSO-d$_6$ (deuterated dimethylsulfoxide), Et$_3$N (Triethylamine), EtOAc (ethyl acetate), EtOH (Ethanol), Et$_2$O (Diethyl ether), HCl (Hydrochloric acid), HPLC (High Performance Liquid Chromatography), iPrOH (isopropanol), K$_2$CO$_3$ (Potassium carbonate), MS (mass spectrometry), MgSO$_4$ (Magnesium sulfate), NaHCO$_3$ (Sodium bicarbonate), MeOH, (Methanol), NH$_4$Cl (Ammonium chloride), (NH$_4$)$_2$CO$_3$ (Ammonium carbonate), NaI (Sodium iodide), Na$_2$SO$_4$, (Sodium sulfate), NMP (N-methylpyrrolidone), NMR (Nuclear Magnetic Resonance), MeOH (methanol), PIs (Phosphoinositides), PI3Ks (Phosphoinositide 3-kinases), PI(3)P (Phosphatidylinositol 3-monophosphate), PI(3,4)P$_2$ (Phosphatidylinositol 3,4-bisphosphate), PI(3,4,5)P$_3$(Phosphatidylinositol 3,4,5-trisphosphate), PI(4)P (Phosphatidylinositol-4-phosphate), PI(4,5)P$_2$) (Phosphatidyl inositol-4,5-biphosphate), POCl$_3$ (phosphorus oxychloride), PtdIns (Phosphatidylinositol), TDB pol (7-methyl-1,5,7-triazabicyclo[4.4.0]dec-5-ene on polystyrene), TFA (Trifluoroacetic acid), THF (Tetrahydrofuran), TLC (Thin Layer Chromatography), rt (room temperature), Rt (retention time), UPLC (Ultra High Performance Liquid Chromatography).

Depending on the nature of R$^1$, R$^2$, R$^3$, and R$^4$ different synthetic strategies may be selected for the synthesis of compounds of Formula (I). In the process illustrated in the following schemes R$^1$, R$^2$, R$^3$, and R$_4$ are as above-defined in the description.

Generally, the quinoxaline sulfonamide compounds according to the general Formula (I) may be obtained by several processes using solution-phase chemistry protocols.

According to one process, quinoxaline sulfonamide compounds according to the general Formula (I), whereby the substituents R$^1$, R$^2$, R$^3$ and R$^4$ are as above defined, are prepared from the chloro compounds of Formula (II) and anilines of Formula (III), by well known solution-phase chemistry protocols, such as those shown in Scheme 1 below. In a typical procedure, the nucleophilic substitution is performed in an appropriate solvent such as EtOH or MeOH in absence of base or presence of acid such as AcOH, either by traditional thermic methods or using microwave technology such as those described hereinafter in the Examples.

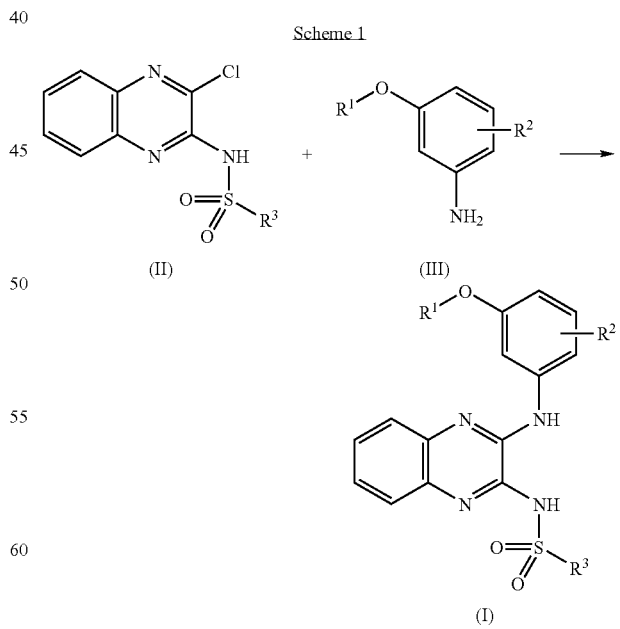

Scheme 1

The aniline compounds of Formula (III) may be obtained either from commercial sources or they may be prepared from known compounds using procedures such as those described hereinafter in the examples, or conventional procedures, known by one skilled in the art.

The chloro compounds of Formula (II), whereby the substituent $R^3$ is as above defined, are prepared from the dichloro compounds of Formula (IV) and sulfonamides of Formula (V), by well known solution-phase chemistry protocols such as shown in Scheme 2 below (Litvinenko et al., 1994, *Chemistry of heterocyclic compounds,* 30 (3), 340-344). In a typical procedure, the nucleophilic substitution is performed in an appropriate solvent such as DMF or DMA in presence of a base such as $K_2CO_3$, $Cs_2CO_3$ or TDB pol. Depending on the intrinsic reactivity of dichloro compounds of Formula (IV) and sulphonamide compounds of Formula (V), the reaction can be performed at various temperatures in the presence or absence of NaI or CuI, either by traditional thermic methods or using microwave technology such as those described hereinafter in the Examples.

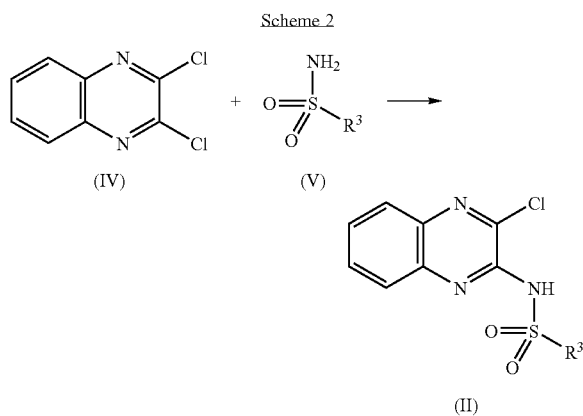

The dichloro compounds of Formula (IV) may be obtained either from commercial sources or they may be prepared from the corresponding bis amino compounds of Formula (VI) using conventional procedures, known by one skilled in the art as shown in the Scheme 3 below. In a typical procedure, the first step is performed in aqueous HCl under reflux. In a subsequent step, a dione of Formula (VIII) is treated with $POCl_3$ in the presence of an organic base such as $Et_3N$ to give the expected dichloro compounds of Formula (IV), such as those described hereinafter in the Examples.

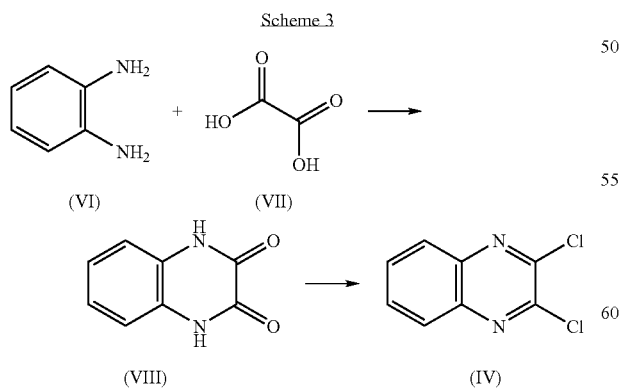

Sulfonamides of Formula (V) may be obtained either from commercial sources or they may be prepared from the corresponding sulfonylchlorides of Formula (IX) using conventional procedures known by one skilled in the art, as shown in the Scheme 4 below. In a typical procedure, the reaction is performed in the presence of ammonia of Formula (X), in a solvent such as EtOH, MeOH, dioxane or water, such as those described hereinafter in the Examples.

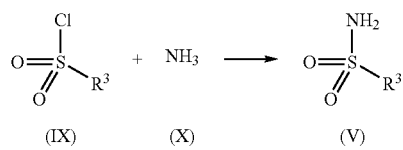

According to another process, quinoxaline sulfonamide compounds according to the general Formula (I), whereby the substituents $R^1$, $R^2$, and $R^3$ are as above defined, are prepared from the amino compounds of Formula (XI) and sulfonylchlorides of Formula (IX), by well known solution-phase chemistry protocols, as shown in Scheme 5, below. In a typical procedure, the sulfonylation is performed in the presence of pyridine, with or without a co-solvent such as 1,2-dichlorobenzene. Depending on the intrinsic reactivity of the sulfonylchlorides of Formula (IX), the reaction can be performed at various temperatures, either by traditional thermic methods or using microwave technology such as those described hereinafter in the Examples.

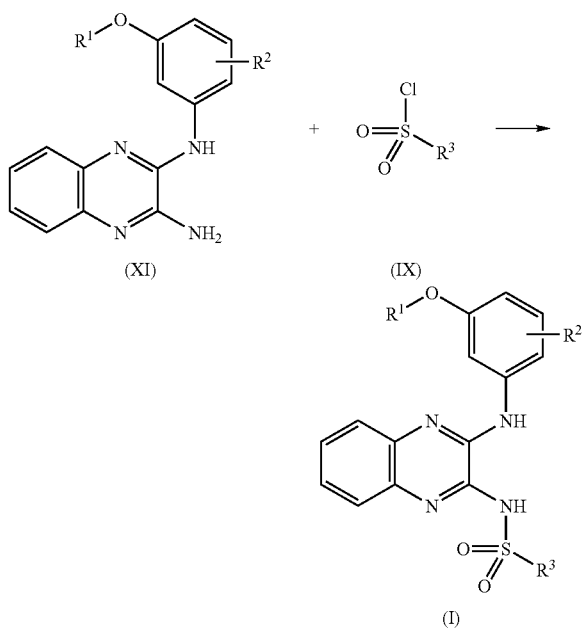

Amino compounds of Formula (XI) are prepared from the 2-amino 3-chloro compounds of Formula (XII) and anilines of Formula (III), by well-known solution-phase chemistry protocols, as shown in Scheme 6 below. In a typical procedure, the nucleophilic substitution is performed in absence of base using an appropriate solvent such as NMP, DMF or DMA, such as those described hereinafter in the Examples.

Scheme 6

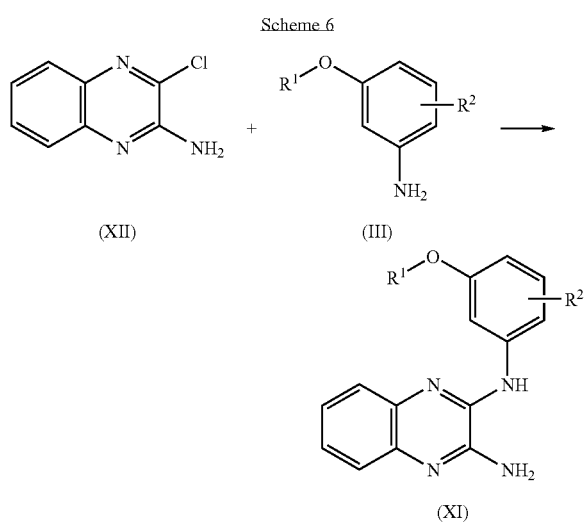

2-Amino 3-chloro compounds of Formula (XII) are prepared from the dichloro compounds of Formula (IV), by well-known solution-phase chemistry protocols, as shown in Scheme 7 below. In a typical procedure, the reaction is performed using (NH$_4$)$_2$CO$_3$ (XIII) or aqueous ammonia in an appropriate solvent such as DMF, DMA or dioxane, such as those described hereinafter in the Examples.

Scheme 7

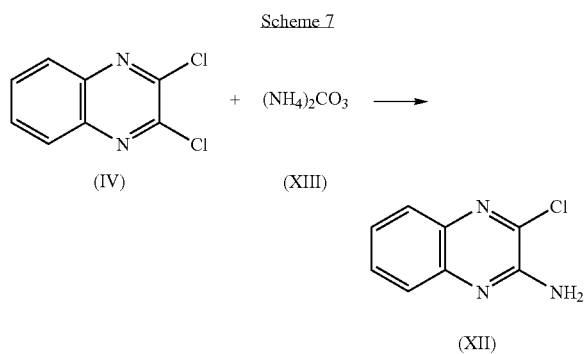

If the above set out general synthetic methods are not applicable for the obtention of compounds of Formula (I), suitable methods of preparation known by a person skilled in the art should be used.

The pharmaceutically acceptable cationic salts of compounds of the present invention are readily prepared by reacting the acid forms with an appropriate base, usually one equivalent, in a co-solvent. Typical bases are sodium hydroxide, sodium methoxide, sodium ethoxide, sodium hydride, potassium hydroxide, potassium methoxide, magnesium hydroxide, calcium hydroxide, benzathine, choline, diethanolamine, ethylenediamine, meglumine, benethamine, diethylamine, piperazine and tromethamine. The salt is isolated by concentration to dryness or by addition of a non-solvent. In some cases, salts can be prepared by mixing a solution of the acid with a solution of the cation (sodium ethylhexanoate, magnesium oleate), employing a solvent in which the desired cationic salt precipitates, or can be otherwise isolated by concentration and addition of a non-solvent.

According to a further general process, compounds of Formula (I) can be converted to alternative compounds of Formula (I), employing suitable interconversion techniques well known by a person skilled in the art.

Suitable methods of preparation for the compounds and intermediates of the invention are known by a person skilled in the art which should be used. In general, the synthesis pathways for any individual compound of Formula (I) will depend on the specific substitutents of each molecule and upon the ready availability of intermediates necessary; again such factors being appreciated by those of ordinary skill in the art. For all the protection and deprotection methods, see Philip J. Kocienski, in "*Protecting Groups*", Georg Thieme Verlag Stuttgart, New York, 1994 and, Theodora W. Greene and Peter G. M. Wuts in "*Protective Groups in Organic Synthesis*", Wiley Interscience, 3$^{rd}$ Edition 1999.

Compounds of this invention can be isolated in association with solvent molecules by crystallization from evaporation of an appropriate solvent. The pharmaceutically acceptable acid addition salts of the compounds of Formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solu-tion of compound of Formula (I) with a suitable base. Both types of salts may be formed or interconverted using ion-exchange resin techniques.

The process for the preparation of quinoxaline compounds according to Formula (I), comprising the step of reacting a chloro derivative of Formula (II) with an aniline of Formula (III) in an appropriate solvent such as EtOH, MeOH or water in absence of base, or in the presence of an acid such as AcOH either by traditional thermic methods or using microwave technology is herein described:

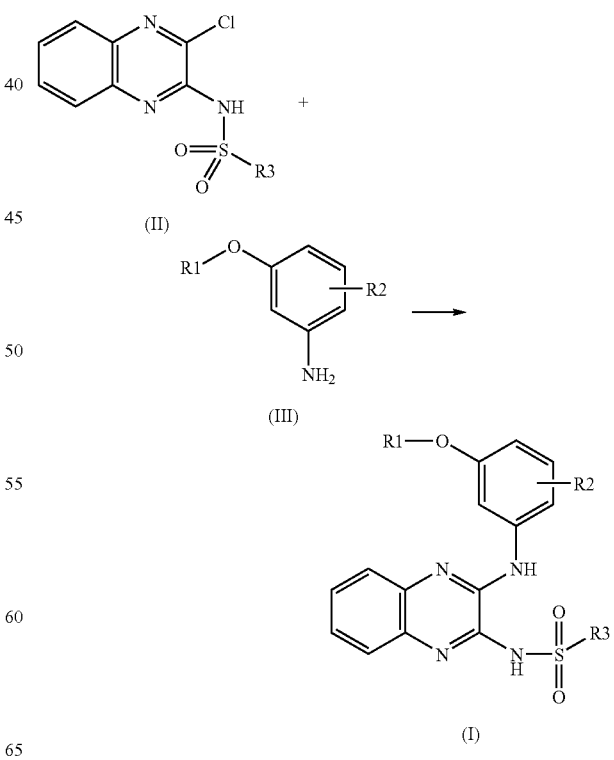

wherein R$^1$, R$^2$, R$^3$ are as above defined.

The chloro compounds of Formula (II), whereby the substituent R³ is as above defined, are prepared from the dichloro compounds of Formula (IV) and sulfonamides of Formula (V), by well known solution-phase chemistry protocols such as shown in Scheme 2 below (Litvinenko et al., 1994, *Chemistry of heterocyclic compounds*, 30 (3), 340-344). In a typical procedure, the nucleophilic substitution is performed in an appropriate solvent such as DMF or DMA in presence of a base such as $K_2CO_3$, $Cs_2CO_3$ or TDB pol. Depending on the intrinsic reactivity of dichloro compounds of Formula (IV) and sulphonamide compounds of Formula (V), the reaction can be performed at various temperatures in the presence or absence of NaI or CuI, either by traditional thermic methods or using microwave technology such as those described hereinafter in the Examples.

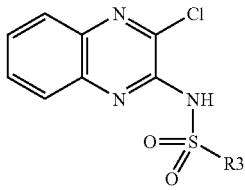

(II)

wherein R³ is as defined above is also described therein. The method for preparing the compounds of Formula (II) selected from the list below:

4-{[(3-chloroquinoxalin-2-yl)amino]sulfonyl}-N,N-dimethylbenzamide
N-(3-Chloroquinoxalin-2-yl)-4-[(4-fluoropiperidin-1-yl)carbonyl]benzenesulfonamide
N-(3-Chloro-2-quinoxalinyl)benzenesulfonamide
N-(3-chloroquinoxalin-2-yl)-4-fluorobenzenesulfonamide
N-(3-chloroquinoxalin-2-yl)-4-cyanobenzenesulfonamide
N-(3-chloroquinoxalin-2-yl)pyridine-3-sulfonamide
N-(3-chloroquinoxalin-2-yl)-1-methyl-1H-imidazole-4-sulfonamide
N-(3-Chloroquinoxalin-2-yl)-6-methylpyridine-3-sulfonamide 1-oxide
Methyl (4-{[(3-chloroquinoxalin-2-yl)amino]sulfonyl}phenoxy)acetate
Methyl 3-(4-{[(3-chloroquinoxalin-2-yl)amino]sulfonyl}phenyl)propanote
4-Amino-N-(3-chloroquinoxalin-2-yl)benzenesulfonamide
2-(Benzyloxy)-N-(3-{[(3-chloroquinoxalin-2-yl)amino]sulfonyl}phenyl)acetamide
N-(3-{[(3-Chloroquinoxalin-2-yl)]sulfamoyl}phenyl)-2-ditriethylamino-amide
N-(3-Chloroquinoxalin-2-yl)-2-[(dimethylamino)methyl]-1-methyl-1H-imidazole-4-sulfonamide
2-({[tert-Butyl(dimethyl)silyl]oxy}methyl)-N-(3-chloroquinoxalin-2-yl)-1-methyl-1H-imidazole-4-sulfonamide
N-(3-Chloroquinoxalin-2-yl)-1-methyl-2-[(methylsulfonyl)methyl]-1H-imidazole-4-sulfonamide
N-(3-Chloroquinoxalin-2-yl)-3,5-dimethylisoxazole-4-sulfonamide
N-(3-chloroquinoxalin-2-yl)methanesulfonamide
N-(3-Chloroquinoxalin-2-yl)ethanesulfonamide
N-(3-Chloroquinoxalin-2-yl)propane-1-sulfonamide
N-(3-Chloroquinoxalin-2-yl)propane-2-sulfonamide
N-(3-Chloroquinoxalin-2-yl)cyclohexanesulfonamide
Benzyl 4-{[(3-chloroquinoxalin-2-yl)amino]sulfonyl}piperidine-1-carboxylate
N-(3-Chloroquinoxalin-2-yl)-3-(methylthio)propane-1-sulfonamide
N-(3-Chloroquinoxalin-2-yl)-3-(methylsulfonyl)propane-1-sulfonamide
N-(3-Chloroquinoxalin-2-yl)tetrahydrothiophene-3-sulfonamide 1,1-dioxide
2-[(4-{[(3-Chloroquinoxalin-2-yl)amino]sulfonyl}phenyl)amino]-2-oxoethyl acetate
N-(4-{[(3-Chloroquinoxalin-2-yl)]sulfamoyl}phenyl)-2-dimethyamino-acetamide
is more particularly described in the examples.

The aniline compounds III, whereby the substituent R¹ and R² are as above defined, may be obtained either from commercial sources or they may be prepared from known compounds using conventional procedures, known by one skilled in the art. In particular, aniline compounds IIIa, may be prepared by catalytic hydrogenation of Horner-Wittig products IVa obtained from diethyl (4-methoxy-2-nitrobenzyl)phosphonate, itself obtained from an Arbuzov reaction (Bioorg. Med. Chem, 2005) on 1-(bromomethyl)-4-methoxy-2-nitrobenzene (Bioorg. Chem, 2002) as described in the scheme below. Aniline compounds IIIa can be further derivatized using conventional procedures, known by one skilled in the art. In aniline compounds IIIa, A is selected from C or heteroatoms selected from N, S, $SO_2$, O, n equals 1 or 2 and B is selected from H, OH, $C_1$-$C_6$alkyl, acyl, acetyl, or sulfone.

In particular, aniline compounds IIIb, whereby substituent A is as above defined, may be prepared by catalytic hydrogenation of nitro compounds IVb obtained using conventional procedures, known by one skilled in the art.

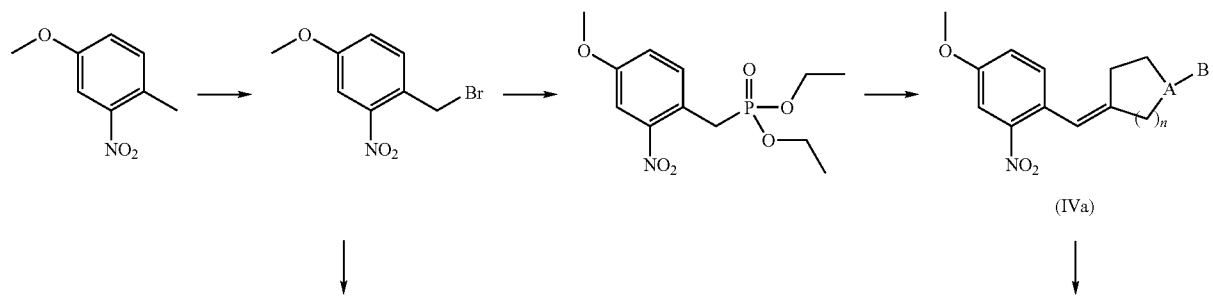

(IVa)

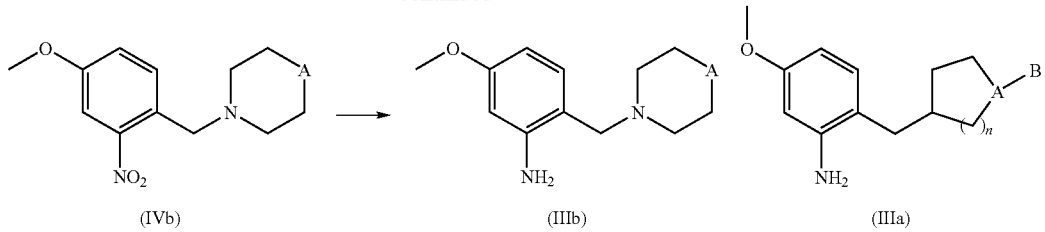

In particular, 3-(2-amino-4-methoxyphenyl)propan-1-ol may be prepared by hydrogenation of 3-(4-methoxy-2-nitrophenyl)propan-1-ol obtained by reduction of (2E)-3-(4-methoxy-2-nitrophenyl)acrylic acid, resulting from the condensation of malonic acid with 4-methoxy-2-nitrobenzaldehyde. The latter may prepared by hydrolysis of 1-(dibromomethyl)-4-methoxy-2-nitrobenzene obtained by dibromination of 4-methyl 3-nitroanisole. Similarly, 2-[3-(dimethylamino)propyl]-5-methoxyaniline may be prepared by hydrogenation of the product resulting from the reaction between dimethyl amine and 3-(4-methoxy-2-nitrophertyl)propyl methanesulfonate. The latter may be obtained by methanesulfonylation of 3-(4-methoxy-2-nitrophenyl)propan-1-ol as described in the scheme below.

In particular, 5-methoxy-2-[3-(methylsulfonyl)propyl] aniline may be prepared by oxidation of 5-methoxy-2-[3-(methylthio)propyl]aniline (via the temporary protection of the anline moiety). 5-Methoxy-2-[3-(methylthio)propyl] aniline may be prepared by hydrogenation of 4-methoxy-1-[(3-(methylthio)prop-1-enyl]-2-nitrobenzene, obtained from reaction between sodium thiomethoxide and 1-[3-bromoprop-1-enyl]-4-methoxy-2-nitrobenzene. The latter may be prepared from (2E)-3-(4-methoxy-2-nitrophenyl)prop-2-en-1-ol, obtained by selective reduction of methyl (2Z)-3-(4-methoxy-2-nitrophenyl)acrylate, prepared from the corresponding acid (2E)-3-(4-methoxy-2-nitrophenyl)acrylic acid, as described in the scheme below.

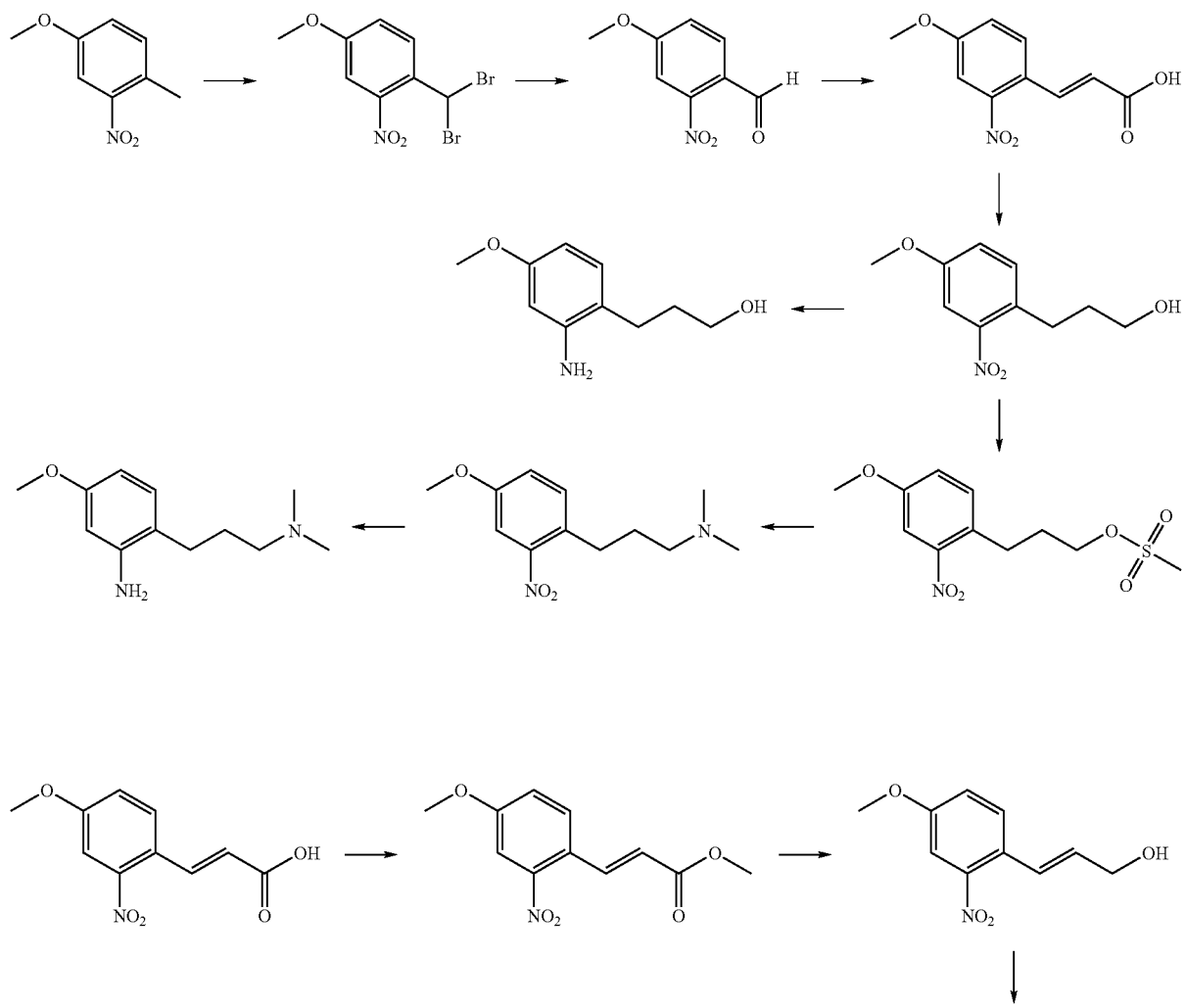

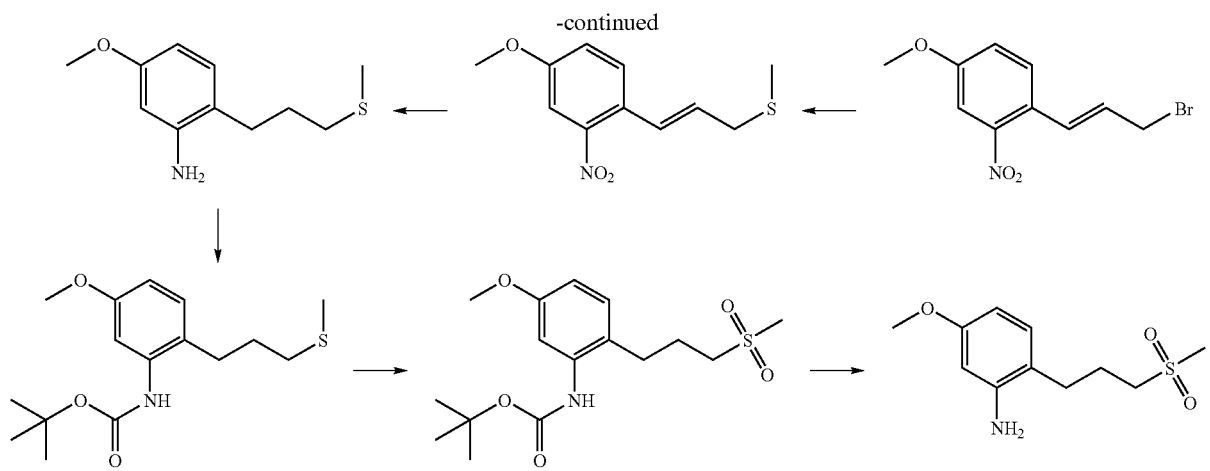

In particular, aniline compounds IIIc, whereby substituent A is as above defined, may be prepared by catalytic hydrogenation of nitro compounds IVc obtained from 3-nitro-5-benzoic acid using classical coupling conditions through the acid chloride or activated ester.

(4-methoxy-2-nitrophenyl)malonate. Also, 5-methoxy-2-(2-methoxyethyl)aniline may be prepared by reduction of the product resulting from the methylation of 2-(4-methoxy-2-nitrophenyl)ethanol. 5-Methoxy-2-[2-(methylsulfonyl)ethyl]aniline may be prepared by hydrogenation of the prod-

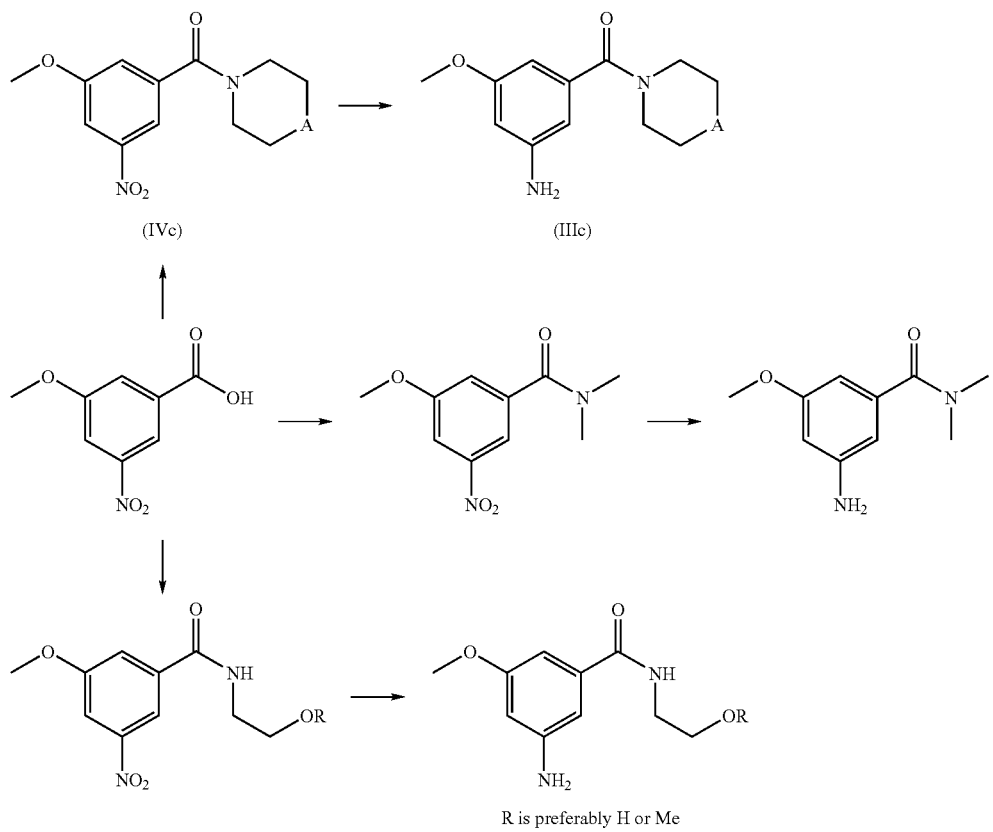

R is preferably H or Me

In particular, 2-(2-amino-4-methoxyphenyl)ethanol may be prepared from 1-chloro-4-methoxy-2-nitrobenzene using conventional procedures, known by one skilled in the art and described in the literature (Bioorg. Med. Chem, 2004). Similarly, 2-(2-amino-4-methoxyphenyl)propane-1,3-diol may be prepared by hydrogenation of 2-(4-methoxy-2-nitrophenyl)propane-1,3-diol obtained by reduction of diethyl uct resulting from the oxidation of 4-methoxy-1-[2-(methylthio)ethyl]-2-nitrobenzene. The latter may be prepared by reaction between sodium thiomethoxide and the intermediate obtained by bromo-de-hydroxylation of 2-(4-methoxy-2-nitrophenyl)ethanol as described in the scheme below.

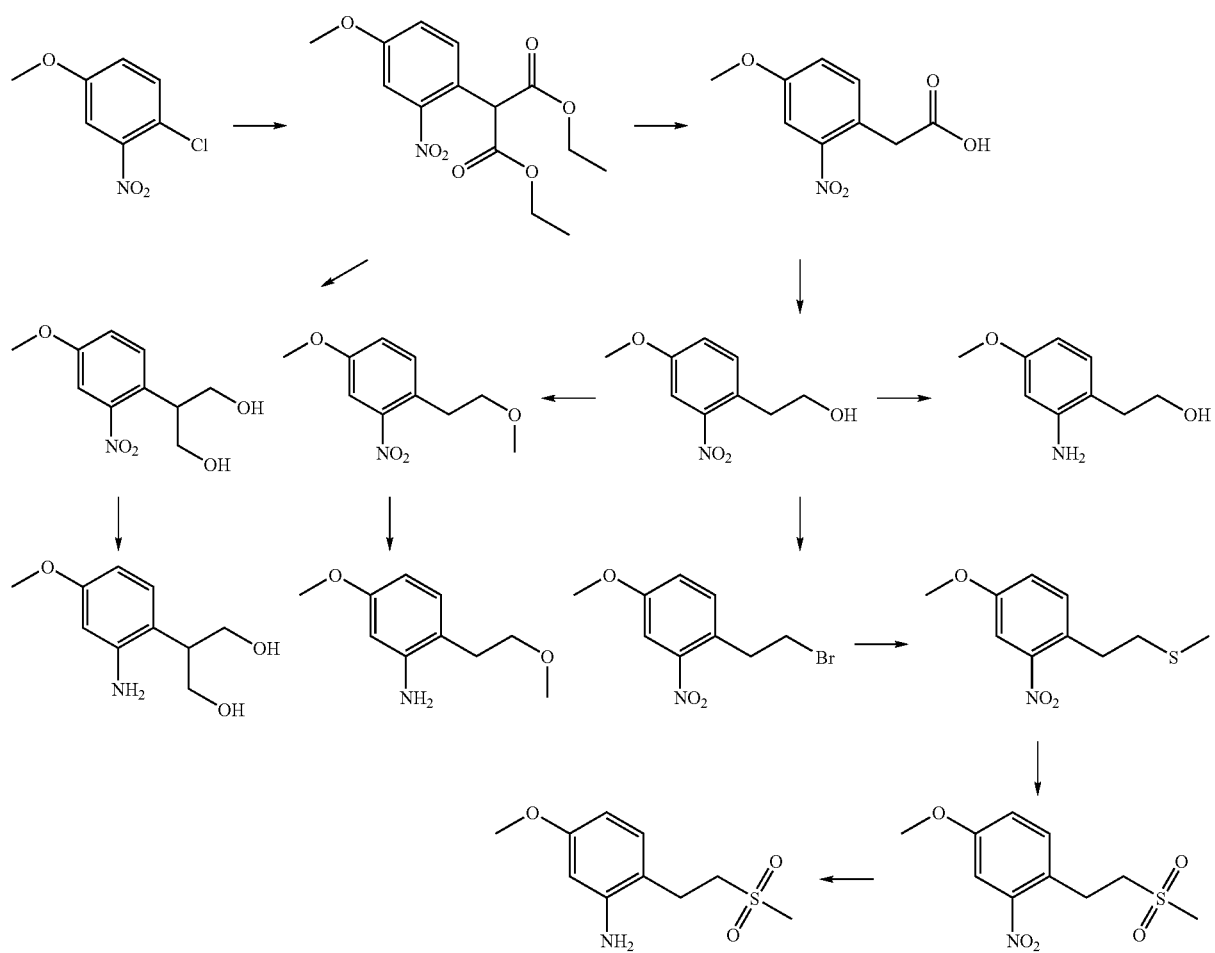

In particular, 2-{(4S,4R)-2,2-Dimethyl-(1,3)dioxolan-4-ylmethyl}-5-methoxy-phenylamine may be prepared by hydrogenation of (4S,4R)-4-(4-methoxy-2-nitrobenzyl)-2,2-dimethyl-1,3-dioxolane obtained by protection of the diol resulting from dihydroxylation of 1-allyl-4-methoxy-2-nitrobenzene. The latter may be prepared by a palladium catalyzed coupling between allyl boronic acid pinacol ester and 1-iodo-4-methoxy-2-nitrobertzene obtained by a Sandmeyer reaction starting from 4-methoxy-2-nitroaniline using conventional procedures, known by one skilled in the art.

In particular, 2-amino-N-(2-hydroxyethyl)-4-methoxybenzenesulfonamide may be prepared by hydrogenation of N-(2-hydroxyethyl)-4-methoxy-2-nitrobenzenesulfonamide obtained from 4-methoxy-2-nitrobenzenesulfonyl chloride by reaction with ethanolamine using conventional procedures, known by one skill in the art.

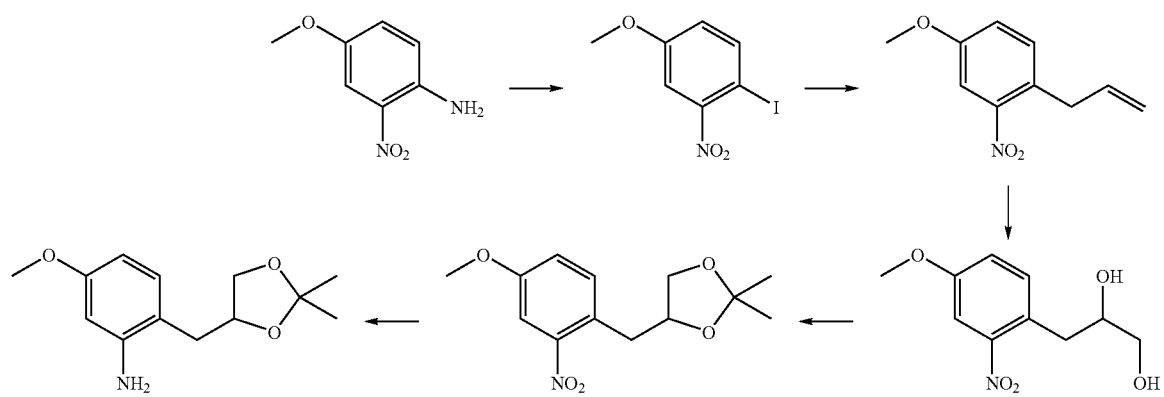

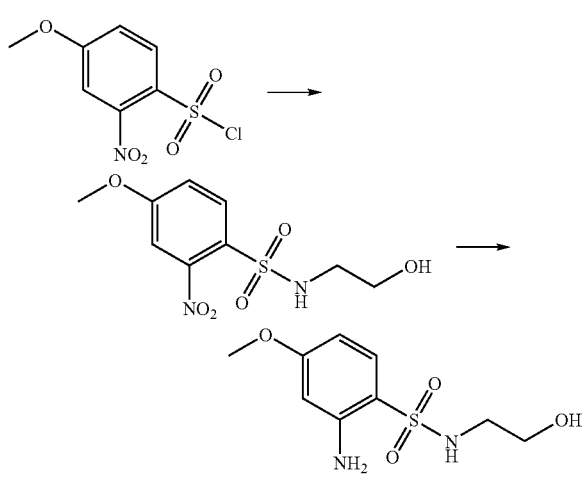

In particular, 2-isopropyl-5-methoxyaniline may be prepared by dehydration and further hydrogenation of 2-(2-amino-4-methoxyphenyl)propan-2-ol obtained by reaction between methyl magnesium bromide and 2-amino-4-methoxy-benzoic acid methyl ester using conventional procedures, known by one skilled in the art.

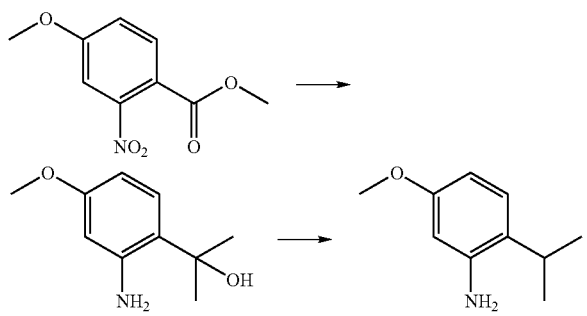

The chloro compounds II, whereby the substituent $R^3$ is as above defined, are prepared from the dichloro compound V and sulphonamides VI, by well known solution-phase chemistry protocols, such as those described in the Examples and shown in the Scheme, below.

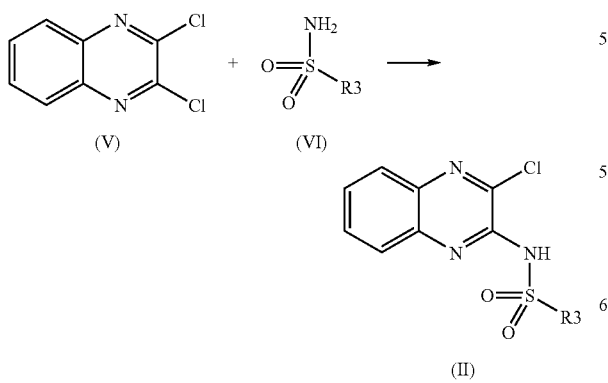

The sulphonamides VI, whereby the substituent $R^3$ is as above defined, may be obtained either from commercial sources or they may be prepared from the corresponding sulphonyl chlorides (VII) using conventional procedures, known by one skilled in the art as shown in the scheme below. The sulphonamides VI can be further substituted using conventional procedures, known by one skilled in the art, like amide bond formation.

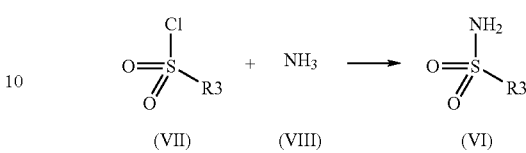

In another embodiment according to the invention, is provided a compound of Formula (VI)

wherein $R^3$ is as defined above and wherein the compounds of Formula (VI) are selected from the list below:

Pyridine-3-sulfonamide
5-(Aminosulfonyl)-2-methylpyridine-N-oxide
4-(aminosulfonyl)-N,N-dimethylbenzamide
4-[(4-Fluoropiperidin-1-yl)carbonyl]benzenesulfonamide
Propane-1-sulfonamide
Propane-2-sulfonamide
Cyclohexanesulfonamide
Tetrahydrothiophene-3-sulfonamide 1,1-dioxide
3-(Methylthio)propane-1-sulfonamide
3-(Methylsulfonyl)propane-1-sulfonamide
Benzyl 4-(aminosulfonyl)piperidine-1-carboxylate
Methyl 3-[4-(aminosulfonyl)phenyl]propanoate
N-[3-(Aminosulfonyl)phenyl]-2-(benzyloxy)acetamide
2-Dimethylamino-N-[3-(sulfamoyl)phenyl]-acetamide
Methyl[4-(aminosulfonyl)phenoxy]acetate
2-[(Dimethylamino)methyl]-1-methyl-1H-imidazole-4-sulfonamide
2-({[tert-Butyl(dimethyl)silyl]oxy}methyl)-1-methyl-1H-imidazole-4-sulfonamide
1-Methyl-2-[(methylsulfonyl)methyl]-1H-imidazole-4-sulfonamide
3,5-Dimethyisoxazole-4-sulfonamide In particular, 5-(aminosulfonyl)-2-methylpyridine-N-oxide may be prepared from 5-(aminosulfonyl)-2-methylpyridine using conventional oxidation procedures, known by one skilled in the art.

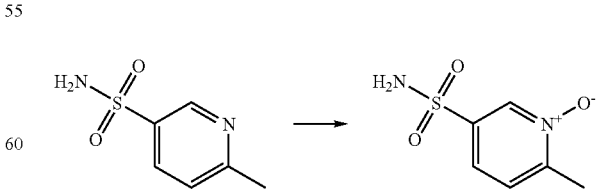

In particular, 4-[(4-fluoropiperidin-1-yl)carbonyl]benzenesulfonamide may be prepared from 4-carboxybenzenesulfonamide using classical coupling conditions through the acid chloride or activated ester.

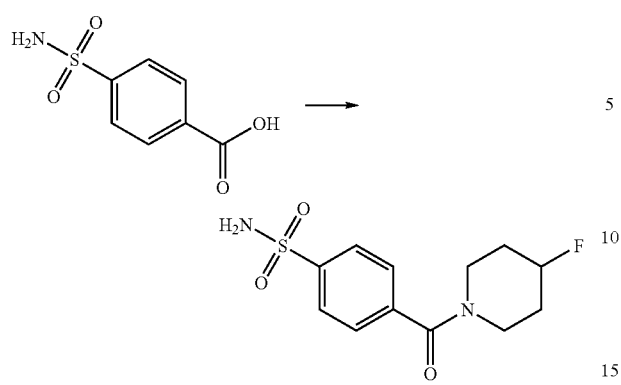

In particular, methyl[4-(aminosulfonyl)phenoxy]acetate may be prepared from 4-fluoro benzenesulfonamide and methyl glycolate using conventional procedures, known by one skilled in the art.

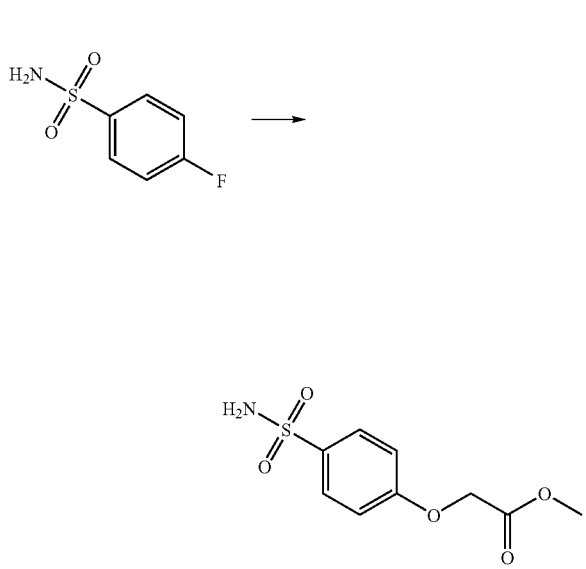

In particular, 3-(methylsulfonyl)propane-1-sulfonamide may be prepared by oxidation of 3-(methythio)propane-1-sulfonamide obtained from [1,2]oxathiolane 2,2-dioxide using conventional procedures, known by one skilled in the art such as ring opening with sodium thiomethoxide followed by sulfonyl chloride formation and further reaction with ammonia.

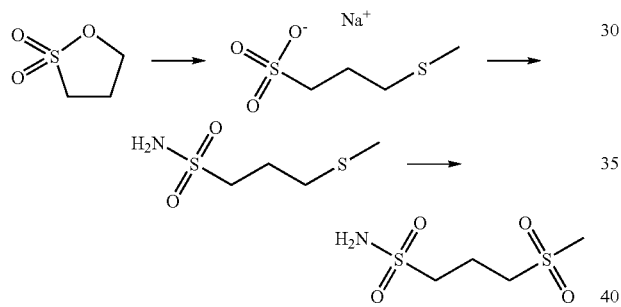

In particular, 2-[(dimethylamino)methyl]-1-methyl-1H-imidazole-4-sulfonamide may be Obtained by reaction between dimethyl amine and 2-(chloromethyl)-1-methyl-1H-imidazole-4-sulfonamide prepared from (1-methyl-1H-imidazol-2-yl)methanol by sulfonylation, followed by chlorination and further reaction with ammonia. Similarly, 2-({[tert-butyl(dimethyl)silyl]oxy}methyl)-1-methyl-1H-imidazole-4-sulfonamide may be obtained by hydrolysis of 2-(chloromethyl)-1-methyl-1H-imidazole-4-sulfonamide followed by protection of the free alcohol. Also, 1-methyl-2-[(methylsulfonyl)methyl]-1H-imidazole-4-sulfonamide may be prepared by oxidation of the intermediate obtained by reaction between 2-(chloromethyl)-1-methyl-1H-imidazole-4-sulfonamide and sodium thiomethoxide.

In particular, N-[3-(aminosulfonyl)phenyl]-2-(benzyloxy)acetamide and 2-dimethylamino-N-[3-(sulfamoyl)phenyl]-acetamide may be prepared from 1-aminobenzene-3-sulfonamide using classical coupling conditions through the acid chloride or activated ester.

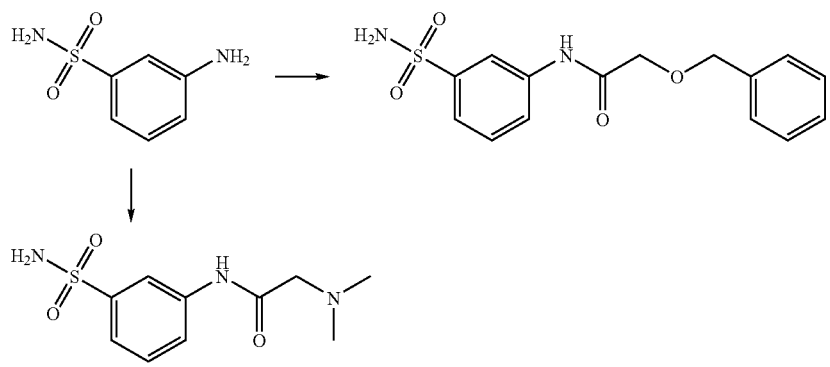

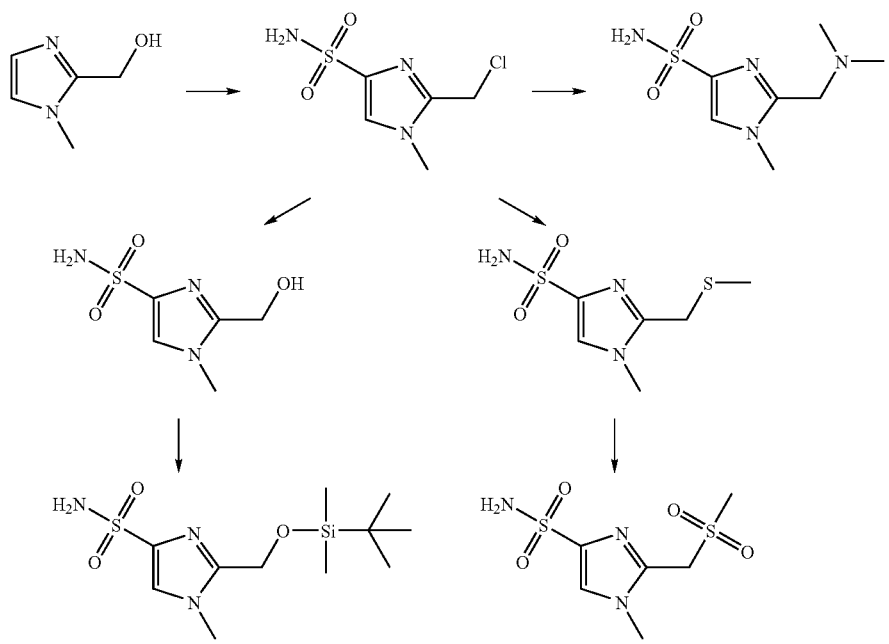

According to a further general process, compounds of Formula (I) can be converted to alternative compounds of Formula (I), employing suitable interconversion techniques well known by a person skilled in the art.

If the above set of general synthetic methods is not applicable to obtain compounds according to Formula (I) and/or necessary intermediates for the synthesis of compounds of Formula (I), suitable methods of preparation known by a person skilled in the art should be used. In general, the synthesis pathways for any individual compound of Formula (I) will depend on the specific substituents of each molecule and upon the availability of necessary intermediates; again such factors being appreciated by those of ordinary skill in the art. For all the protection and deprotection methods, see Philip J. Kocienski, in "*Protecting Groups*", Georg Thieme Verlag Stuttgart, New York, 1994 and, Theodora W. Greene and Peter G. M. Wuts in "*Protective Groups in Organic Synthesis*", Wiley Interscience, $3^{rd}$ Edition 1999.

Compounds of this invention can be isolated in association with solvent molecules by crystallization from evaporation of an appropriate solvent. The pharmaceutically acceptable acid addition salts of the compounds of Formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of Formula (I) with a suitable base. Both types of salts may be formed or interconverted using ion-exchange resin techniques.

FIG. 1 describes a typical FACS analysis as performed to measure IgM-induced Akt phosphorylation in B cells in the presence of whole blood for representative compounds of the invention (Example C).

Figure 2:
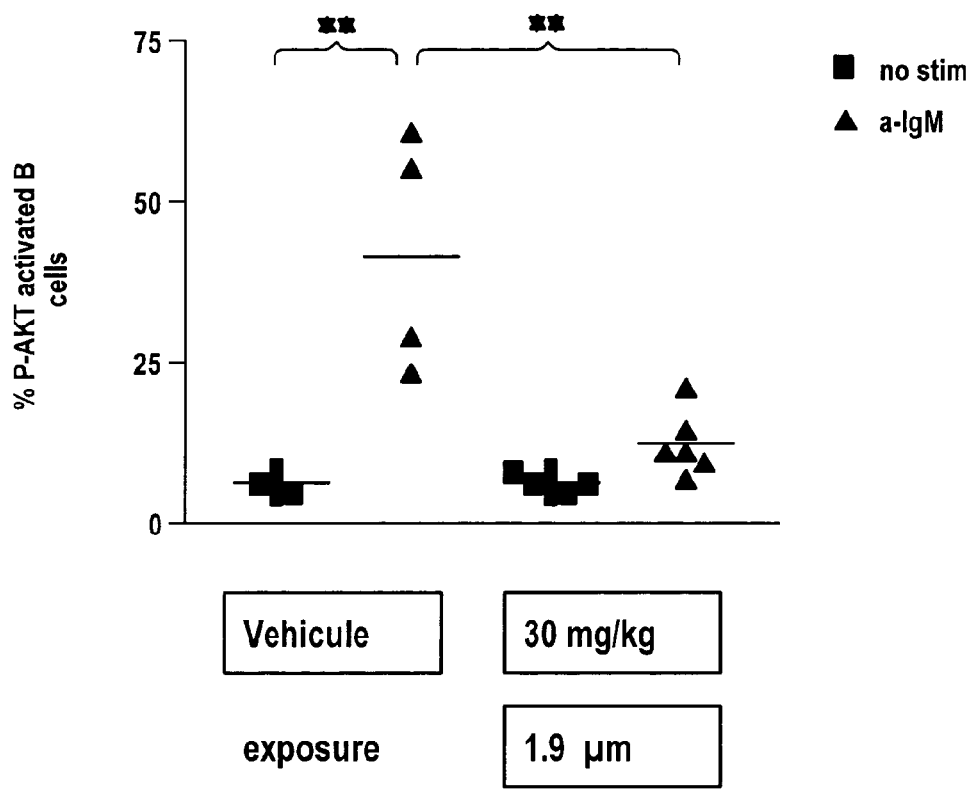

FIG. 2 describes the ex-vivo IgM-induced Akt phosphorylation in mouse after oral administration of a representative compounds of the invention (compound of example 28) (Example D).

In the following the present invention shall be illustrated by means of some examples, which are not construed to be viewed as limiting the scope of the invention.

EXAMPLES

The commercially available starting materials used in the following experimental description were preferably purchased from Aldrich, Fluka, ABCR, Impamex or Fluorochem. The HPLC, NMR and MS data provided in the examples described below are obtained as followed: HPLC: column Waters Symmetry C8 50×4.6 mm, Conditions: MeCN/H2O, 5 to 100% (8 min), max plot 230-400 nm; LC/MS spectra: Waters ZMD (ES); 1H-NMR: Bruker DPX-300 MHz unless otherwise reported. UPLC/MS: Waters Acquity, column Waters Acquity UPLC BEH C18 1.7 μm 2.1×50 mm, conditions: solvent A (10 mM ammonium acetate in water+5% ACN), solvent B (ACN), gradient 5% B to 100% B over 3 min, UV detection (PDA, 230-400 nm) and MS detection (SQ detector, positive and negative ESI modes, cone voltage 30V).

The preparative HPLC purifications are performed with HPLC Waters Prep LC 4000 System equipped with columns ®PrepMS C18 10 μm, 50×300 mm. All the purifications were performed with a gradient of ACN/H2O/TFA (0.1%).

The microwave chemistry is performed on a single mode microwave reactor Emrys™ Optimiser from Personal Chemistry.

Hydrogenation reactions are performed with H-Cube™ Continuous-flow Hydrogenation Reactor Continuous hydrogenation reactions are performed in a flow system. The hydrogen gas necessary for the reaction is generated in-situ. Reactions take place on disposable proprietary CatCarts™, packed catalyst columns modeled after conventional HPLC systems. Every aspect of the operation on the H-Cube is controlled and monitored using a touch-screen panel.

INTERMEDIATES

Intermediate 1:
1-(bromomethyl)-4-methoxy-2-nitrobenzene

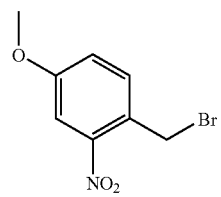

To a solution of 4-methyl-3-nitroanisole (16.53 mL; 119.64 mmol; 1 eq), in CCl$_4$ (500 mL) is added N-bromosuccinimide (21.29 g; 119.64 mmol; 1 eq) and azoisobutyronitrile (392.9 mg; 2.39 mmol; 0.02 eq). The mixture is heated at 85° C. for 20 h. The solution is cooled down to room temperature and the precipitate of succinimide is removed by filtration. The filtrate is concentrated to afford a yellow oil. The oil crystallizes after one night at −25° C. It is redissolved in EtOAc (15 mL) and petroleum ether is added. After 2 h at −25° C., the compound recrystallizes. After filtration and washing with petroleum ether, the solid is dried under vacuum to afford 17.4 g (59%) of the title compound as a liquid. $^1$H NMR (DMSO-d$_6$) δ 7.68 (d, J=8 Hz, 1H), 7.56 (d, J=3 Hz, 1H), 7.33 (dd, J=8.0, 3.0 Hz, 1H), 4.89 (s, 2H), 3.87 (s, 3H). HPLC (max plot) 99%; Rt 4.09 min.

Intermediate 2: Methyl 4-methoxy-2-nitrobenzoate

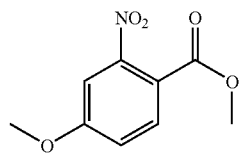

To a solution of 4-methoxy-2-nitrobenzoic acid (12 g; 61 mmol; 1 eq; commercially available from Aldrich) in MeOH (200 mL) is added thionyl chloride (13 mL, 178 mmol, 2.9 eq) and the mixture is stirred at room temperature for 15 h. The solvent is removed under vacuum and the residue is diluted with EtOAc (150 mL) and washed with a 10% aqueous solution of sodium bicarbonate, water, and then dried over MgSO$_4$. The solvent is removed under reduced pressure to afford 11 g (85%) of the title compound as a white solid. $^1$H NMR (CDCl$_3$, 400 MHz) δ 7.81-7.79 (m, 1H), 7.27-7.25 (m, 1H), 7.13-7.11 (m, 1H), 3.92 (s, 3H), 3.89 (s, 3H).

Procedure A

Intermediate 3:
1-(4-methoxy-2-nitrobenzyl)-4-methylpiperazine

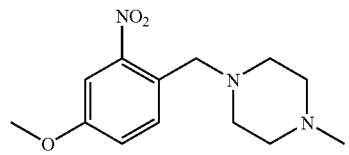

To a solution of N-methyl piperazine (5.7 g; 57 mmol; 2 eq) in dry DCM (150 mL) are added Et$_3$N (5.75 g; 57 mmol; 2 eq) and 1-(bromomethyl)-4-methoxy-2-nitrobenzene (7 g; 28.5 mmol; 1 eq). The mixture is stirred at room temperature for 8 h then diluted with water (150 mL). The organic phase is washed with brine and dried. The solvent is removed under vacuum to afford 6.5 g (86%) of the title compound as a viscous liquid. $^1$H NMR (CDCl$_3$, 400 MHz) δ 7.46-7.44 (m, 1H), 7.34 (s, 1H), 7.08-7.05 (m, 1H), 3.86 (s, 3H), 3.73 (s, 2H), 2.54-2.46 (very br s, 8H), 2.29 (s, 3H). LC/MS (ES+): 266.0.

Intermediate 4:
4-(4-Methoxy-2-nitrobenzyl)morpholine

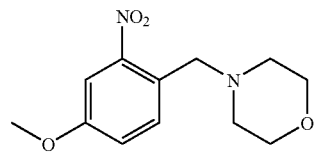 [SMILES: COc1ccc(CN2CCOCC2)c([N+](=O)[O-])c1]

Following the protocol outlined in Procedure A, intermediate 4 is obtained from morpholine (5 g; 57 mmol; 2 eq), Et$_3$N (5.75 g; 57 mmol; 2 eq) and 1-(bromomethyl)-4-methoxy-2-nitrobenzene (7 g; 28.5 mmol; 1 eq) in dry DCM (150 mL), to afford 6.5 g (84%) of the title compound as a viscous liquid. $^1$H NMR (CDCl$_3$, 400 MHz) δ 7.47-7.45 (m, 1H), 7.35 (s, 1H), 7.09-7.06 (m, 1H), 3.86 (s, 3H), 3.72 (s, 2H), 3.67-3.65 (m, 4H), 2.43-2.41 (m, 4H). LC/MS: (ES+): 252.9.

Procedure B

Intermediate 5: 5-Methoxy-2-[(4-methylpiperazin-1-yl)methyl]aniline

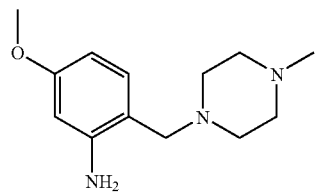 [SMILES: COc1ccc(CN2CCN(C)CC2)c(N)c1]

To a solution of 1-(4-methoxy-2-nitrobenzyl)-4-methylpiperazine (6 g; 25.5 mmol; 1 eq) in methanol (100 mL) was added palladium on charcoal (0.6 g; 10%) and the mixture is hydrogenated under atmospheric pressure of hydrogen for 3 h. The catalyst is filtered off and the filtrate is evaporated under vacuum. The crude residue is purified via column chromatography (eluent chloroform/methanol [9/1]) to afford 4.5 g (84%) of the title compound as a viscous liquid. $^1$H NMR (CDCl$_3$, 400 MHz) δ 6.90-6.88 (m, 1H), 6.24-6.22 (m, 2H), 5.32 (br s, 2H), 3.82 (s, 3H), 3.47 (s, 2H), 2.46-2.30 (m, 8H), 2.25 (s, 3H). HPLC (max plot) 99%. LC/MS(ES+): 236.0.

Intermediate 6:
5-Methoxy-2-(morpholin-4-ylmethyl)aniline

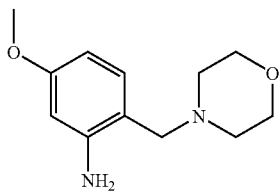 [SMILES: COc1ccc(CN2CCOCC2)c(N)c1]

Following the protocol outlined in Procedure B, intermediate 6 is obtained from 4-(4-methoxy-2-nitrobenzyl)morpholine (6 g; 23.8 mmol, 1 eq) and palladium on charcoal (0.6 g; 10%) in methanol (100 mL), to afford 2.5 g (48%) of the title compound as a viscous liquid. $^1$H NMR (CDCl$_3$, 400 MHz) δ 6.90-6.88 (m, 1H), 6.24-6.22 (m, 2H), 4.76 (br s, 2H), 3.75 (s, 3H), 3.69-3.67 (m, 4H), 3.45 (s, 2H), 2.41 (m, 4H). HPLC (max plot): 97%. LC/MS: (ES+): 222.9.

Intermediate 7: diethyl
(4-methoxy-2-nitrobenzyl)phosphonate

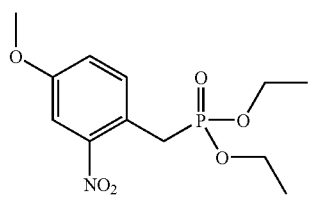

A mixture of 1-(bromomethyl)-4-methoxy-2-nitrobenzene (14.2 g; 57.71 mmol; 1 eq) and triethyl phosphite (9.49 mL; 54.82 mmol; 0.95 eq) is heated at 120° C. for 1 h. TLC analysis using cyclohexane/EtOAc [1/1] as eluent showed that the reaction is complete. The reaction mixture is cooled down to room temperature. The crude is purified by flash chromatography to afford 16.2 g (93%) of an orange oil. Storage at −25° C. allows the product to crystallize. It is then washed with petroleum ether and filtered to afford 14.4 g (82%) of the title compound. $^1$H NMR (DMSO-d$_6$) δ 7.50 (d, J=3.0 Hz, 1H), 7.45 (dd, J=9.0, 2.0 Hz, 1H), 7.28 (dd, J=9.0, 2.0 Hz, 1H), 3.98-3.89 (m, 4H), 3.84 (s, 3H), 3.64 (s, 1H), 3.57 (s, 1H), 1.14 (t, J=7.0 Hz, 6H). HPLC (max plot) 99%; Rt 3.29 min. LC/MS: (ES+): 304.3, (ES−): 302.2.

Procedure C

Intermediate 8: 4-(4-methoxy-2-nitrobenzylidene)tetrahydro-2H-pyran

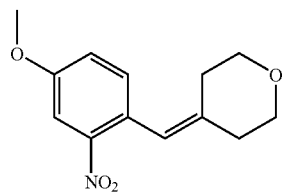 [SMILES: COc1ccc(C=C2CCOCC2)c([N+](=O)[O-])c1]

To a solution of diethyl-(4-methoxy-2-nitrobenzyl)phosphonate (3 g; 9.89 mmol; 1 eq) and 15-crown-5 (196.31 µL; 0.99 mmol; 0.1 eq) in THF (30 mL) at 0° C. is added portionwise sodium hydride (431.65 mg; 9.89 mmol; 1 eq). After 15 min, a solution of tetrahydro-2H-pyran-4-one (990.43 mg; 9.89 mmol; 1 eq) in THF (30 mL) is added dropwise at 0° C. After stirring at room temperature for 3 h, the reaction is complete. The mixture is diluted with water at 0° C. and the product is extracted with EtOAc. The organic layer is washed with saturated aqueous NaHCO$_3$ and brine then dried over MgSO$_4$. The solvent is removed under reduced pressure and the yellow residue is washed with pentane (to remove the oil from NaH) to afford 1.8 g (73%) of the title compound as an orange powder. $^1$H NMR (DMSO-d$_6$) δ 7.53 (d, J=2.3 Hz, 1H), 7.32-7.24 (m, 2H), 6.39 (s, 1H), 3.84 (s, 3H), 3.67-3.63 (m, 2H), 3.55-3.51 (m, 2H), 2.34-2.31 (m, 2H), 2.19-2.16 (m, 2H). HPLC (max plot) 87%; Rt 3.96 min.

Intermediate 9: 4-(4-methoxy-2-nitrobenzylidene)-1-methylpiperidine

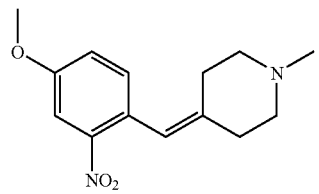 [SMILES: COc1ccc(C=C2CCN(C)CC2)c([N+](=O)[O-])c1]

Following the protocol outlined in Procedure C, Intermediate 9 is obtained from diethyl-(4-methoxy-2-nitrobenzyl)phosphonate (100 mg; 0.33 mmol; 1 eq), 15-crown-5 (6.54 µL; 0.03 mmol; 0.1 eq) and sodium hydride (14.39 mg; 0.33 mmol; 1 eq) in THF (2 mL) at 0° C. A solution of 1-methyl-4-piperidone (38.08 µL; 0.33 mmol; 1 eq) in THF (2 mL) is added and the reaction mixture is stirred overnight at room temperature to afford 74 mg (85%) of the title compound as a brown oil. $^1$H NMR (DMSO-d$_6$) δ 7.60-7.50 (m, 1H), 7.35-7.20 (m, 2H), 6.33 (s, 1H), 3.84 (s, 3H), 2.40-2.23 (m, 6H), 2.16-2.13 (m, 5H). HPLC (max plot) 98%; Rt 2.38 min. LC/MS: (ES+): 263.4.

Intermediate 10: 1-(cyclohexylidenemethyl)-4-methoxy-2-nitrobenzene

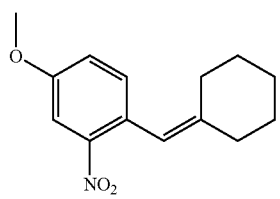 [SMILES: COc1ccc(C=C2CCCCC2)c([N+](=O)[O-])c1]

Following the protocol outlined in Procedure C, Intermediate 10 is obtained from diethyl (4-methoxy-2-nitrobenzyl) phosphonate (3.48 g; 11.48 mmol; 1 eq), 15-crown-5 (227.72 µL; 1.15 mmol; 0.1 eq) and sodium hydride (500.71 mg; 11.48 mmol; 1 eq) in THF (30 mL) at 0° C. A solution of cyclohexanone (1.42 mL; 13.77 mmol; 1.2 eq) in THF (30 mL) is added and the reaction mixture is stirred overnight at room temperature to afford 1.15 g (41%) of the title compound as a yellow solid. $^1$H NMR (DMSO-$d_6$) δ 7.50 (t, J=1.5 Hz, 1H), 7.26 (d, J=1.5 Hz, 2H), 6.26 (s, 1H), 3.84 (s, 3H), 2.24-2.20 (m, 2H), 2.07-2.03 (m, 2H), 1.57-1.55 (m, 4H), 1.46-1.44 (m, 2H). HPLC (max plot) 91%; Rt 5.42 min. LC/MS: (ES+): 248.4.

Intermediate 11: 1-acetyl-4-(4-methoxy-2-nitrobenzylidene)piperidine

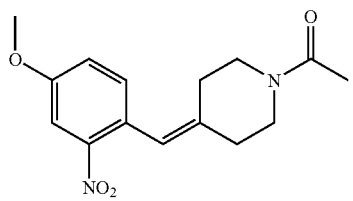 [SMILES: COc1ccc(C=C2CCN(C(C)=O)CC2)c([N+](=O)[O-])c1]

Following the protocol outlined in Procedure C, Intermediate 11 is obtained from diethyl-(4-methoxy-2-nitrobenzyl) phosphonate (10 g; 32.98 mmol; 1 eq), 15-crown-5 (654.36 µL; 3.3 mmol; 0.1 eq), sodium hydride (1.4 g; 32.98 mmol; 1 eq) in THF (100 mL) at 0° C. A solution of 1-acetyl-4-piperidone (6.07 mL; 49.46 mmol; 1.5 eq) in THF (100 mL) is added and the reaction mixture is stirred overnight at 60° C. to afford 3.9 g (41%) of the title compound as a yellow powder after crystallization in EtOAc/Cyclohexane. $^1$H NMR (DMSO-$d_6$) δ 7.59-7.50 (m, 1H), 7.35-7.23 (m, 2H), 6.50-6.40 (m, 1H), 3.85 (s, 3H), 3.55-3.20 (m, 4H), 2.45-2.32 (m, 1H), 2.30-2.15 (m, 2H), 2.14-1.97 (m, 4H). HPLC (max plot) 97%; Rt 3.48 min. LC/MS: (ES+): 291.1.

Intermediate 12: tert-butyl{[4-(4-methoxy-2-nitrobenzylidene)cyclohexyl]oxy}dimethyl silane

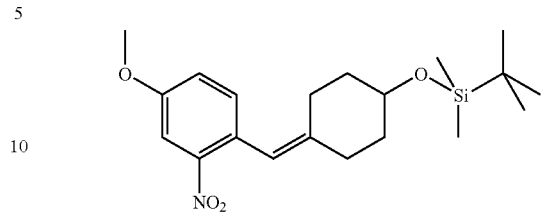

Following the protocol outlined in Procedure C, Intermediate 12 is obtained from diethyl-(4-methoxy-2-nitrobenzyl) phosphonate (5 g; 16.49 mmol; 1 eq), 15-crown-5 (0.33 mL; 1.65 mmol; 0.1 eq) and sodium hydride (0.72 g; 16.49 mmol; 1 eq) in THF (50 mL) at 0° C. A solution of 4-(tert-butyldimethylsilyloxy)cyclohexanone (4.97 mL; 19.79 mmol; 1.2 eq) in THF (50 mL) is added and the reaction mixture is stirred overnight at room temperature to afford 5.25 g (84%) of the title compound as an orange oil. HPLC (max plot) 100%; Rt 6.98 min. LC/MS: (ES+): 378.2.

Intermediate 13: 4-(4-methoxy-2-nitrobenzylidene)tetrahydro-2H-thiopyran

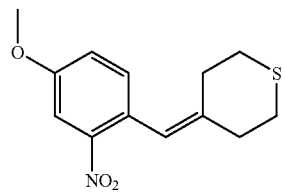 [SMILES: COc1ccc(C=C2CCSCC2)c([N+](=O)[O-])c1]

Following the protocol outlined in Procedure C, Intermediate 13 is obtained from diethyl-(4-methoxy-2-nitrobenzyl) phosphonate (500 mg; 1.65 mmol; 1 eq), 15-crown-5 (0.03 mL; 0.16 mmol; 0.1 eq) and sodium hydride (72.54 mg; 1.81 mmol; 1.1 eq) in THF (5 mL) at 0° C. A solution of tetrahydrothiopyran-4-one (249.03 mg; 2.14 mmol; 1.3 eq) in THF (2.5 mL) is added and the reaction mixture is stirred for 1.5 h at 10° C. to afford 450 mg (100%) of the title compound as an orange-yellow solid. $^1$H NMR (CDCl$_3$) δ 7.50 (br d, 1H), 7.16-7.08 (m, 2H), 6.46 (s, 1H), 3.87 (s, 3H), 2.98-2.94 (m, 1H), 2.79-2.76 (m, 2H), 2.65-2.58 (m, 4H), 2.46-2.42 (m, 2H). HPLC (max plot) 87.7%; Rt 4.82 min. LC/MS: (ES+): 266.1.

Intermediate 14: 4-(4-methoxy-2-nitrobenzylidene)-2,2,6,6-tetramethylpiperidine

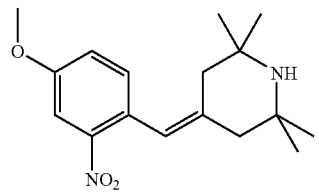 [SMILES: COc1ccc(C=C2CC(C)(C)NC(C)(C)C2)c([N+](=O)[O-])c1]

Following the protocol outlined in Procedure C, Intermediate 14 is obtained from diethyl-(4-methoxy-2-nitrobenzyl) phosphonate (5 g; 16.49 mmol; 1 eq), 15-crown-5 (6.5 mL; 32.98 mmol; 2 eq) and sodium hydride (1.44 g; 32.98 mmol; 2 eq) in THF (40 mL) at 0° C. A solution of 2,2,6,6-tetramethyl-4-piperidone (3.84 g; 24.73 mmol; 1.5 eq) in THF (40 mL) is added and the reaction mixture is stirred for 24 h at room temperature to afford 3.24 g (58%) of the title compound as a brown oil. HPLC (max plot) 99%; Rt 2.92 min. (ES+): 305.1.

Intermediate 15: (1R,3Z,5S)-3-(4-methoxy-2-nitrobenzylidene)-8-methyl-8-azabicyclo[3.2.1]octane

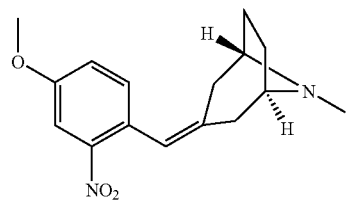 [SMILES: COc1ccc(/C=C2/C[C@H]3CC[C@@H](C2)N3C)c([N+](=O)[O-])c1]

Following the protocol outlined in Procedure C, Intermediate 15 is obtained from diethyl-(4-methoxy-2-nitrobenzyl) phosphonate (2.5 g; 8.24 mmol; 1 eq), 15-crown-5 (3.3 mL; 16.49 mmol; 2 eq) and sodium hydride (400 mg; 8.24 mmol, 1.2 Eq) in THF (10 mL) at 0° C. A solution of tropinone (1.7 g; 12.37 mmol; 1.5 eq) in THF (6 mL) is added and the reaction mixture is stirred overnight at 60° C. to afford 1.6 g (67%) of the title compound as an orange oil. HPLC (max plot) 81%; Rt 2.55 min LC/MS: (ES+): 289.1

Intermediate 16: 1-(cyclopentylidenemethyl)-4-methoxy-2-nitrobenzene

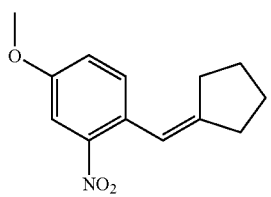 [SMILES: COc1ccc(C=C2CCCC2)c([N+](=O)[O-])c1]

Following the protocol outlined in Procedure C, Intermediate 16 is obtained from diethyl-(4-methoxy-2-nitrobenzyl) phosphonate (3 g; 9.89 mmol; 1 eq), 15-crown-5 (198.09 µL; 0.99 mmol; 0.1 eq) and sodium hydride (431.65 mg; 9.89 mmol; 1 eq) in THF (10 mL) at 0° C. A solution of cyclopentanone (1.05 mL; 11.87 mmol; 1.2 eq) in THF (20 mL) is added and the reaction mixture is stirred for 6 h at room temperature to afford 1.8 g (78%) of the title compound as a brown oil. $^1$H NMR (DMSO-d$_6$) δ 7.40-7.39 (m, 2H), 7.08 (dd, J=8.6, 3 Hz, 1H), 6.55-6.53 (m, 1H), 3.99 (s, 3H), 2.50-2.46 (m, 2H), 2.36-2.31 (m, 2H), 1.73-1.66 (m, 4H). HPLC (max plot) 91%; Rt 5.19 min.

Intermediate 17: tert-Butyl 4-(4-methoxy-2-nitrobenzylidene)piperidine-1-carboxylate

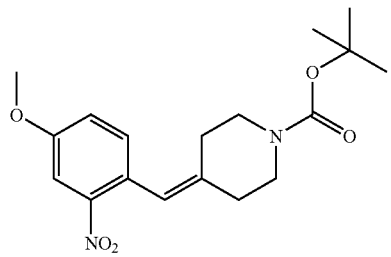 [SMILES: COc1ccc(C=C2CCN(C(=O)OC(C)(C)C)CC2)c([N+](=O)[O-])c1]

Following the protocol outlined in Procedure C, Intermediate 17 is obtained from diethyl-(4-methoxy-2-nitrobenzyl) phosphonate (12 g, 39 mmol, 1 eq), 15-crown-5 (0.78 mL, 0.0039 mol; 0.1 eq) and sodium hydride (1.89 g, 39 mmol; 1 eq) in THF (100 mL) at 0° C. A solution of N-Boc-4-piperidone (7.87 g, 39 mmol; 1 eq) in THF (50 mL) is added and the reaction mixture is stirred for 3 h at room temperature to afford 12 g (88%) of the title compound as a thick yellow liquid. $^1$H NMR (DMSO-d$_6$, 400 MHz) δ 7.53 (s, 1H), 7.32-7.30 (m, 2H), 6.43 (s, 1H), 3.83 (s, 3H), 3.41-3.39 (m, 2H), 3.29-3.27 (m, 2H), 2.28-2.25 (m, 2H), 2.13-2.11 (m, 2H), 1.40 (s, 9H). HPLC (max plot) 99%; Rt 0.6 min. LC/MS: (ES+): 348.9

Procedure D

Intermediate 18: 5-methoxy-2-(tetrahydro-2H-pyran-4-ylmethyl)aniline

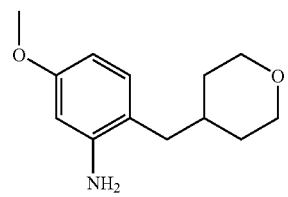 [SMILES: COc1ccc(CC2CCOCC2)c(N)c1]

4-(4-methoxy-2-nitrobenzylidene)tetrahydro-2H-pyran (1.8 g; 7.22 mmol; 1 eq) is dissolved in EtOH (100 mL) and palladium on charcoal (180 mg, 10%) is added at room temperature under argon. The solution is treated with hydrogen at atmospheric pressure. After 7 h at room temperature, the reaction is complete. The mixture is filtered through celite and the filtrate is concentrated under reduced pressure to afford 1.5 g (94%) of the title compound as an orange oil. $^1$H NMR (DMSO-d$_6$) δ 6.72 (d, J=8.3 Hz, 1H), 6.18 (d, J=2.6 Hz, 1H), 6.04 (dd, J=8.3, 2.6 Hz, 1H), 4.82 (s, 2H), 3.82-3.77 (m, 2H), 3.62 (s, 3H), 3.19 (td, J=11.7, 1.8 Hz, 2H), 2.29 (d, J=6.8 Hz, 2H), 1.72-1.61 (m, 1H), 1.51-1.46 (m, 2H), 1.24-1.10 (m, 2H). HPLC (max plot) 88%; Rt 1.83 min LC/MS: (ES+): 222.4.

Intermediate 19: 5-methoxy-2-[(1-methylpiperidin-4-yl)methyl]aniline

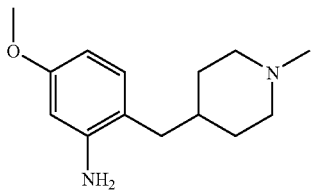 [SMILES: COc1ccc(CC2CCN(C)CC2)c(N)c1]

Following the protocol outlined in Procedure D, Intermediate 19 is obtained from 4-(4-methoxy-2-nitrobenzylidene)-1-methylpiperidine (74 mg; 0.28 mmol; 1 eq) and palladium on charcoal (7.4 mg, 10%) in EtOH (5 mL) for 2 h at room temperature to afford 58 mg (88%) of the title compound as beige crystals after recrystalisation in EtOAc. $^1$H NMR (DMSO-$d_6$) δ 6.70 (d, J=7.9 Hz, 1H), 6.17 (d. J=2.6 Hz, 1H), 6.04 (dd, J=8.3, 2.6 Hz, 1H), 4.77 (s, 2H), 3.61 (s, 3H), 3.69 (d, J=11.3 Hz, 2H), 2.26 (d, J=6.8 Hz, 2H), 2.09 (s, 2H), 1.71 (dt, J=11.6, 2.2 Hz, 2H), 1.52 (d, J=12.0 Hz, 2H), 1.41-1.33 (m, 2H), 1.14 (dq, J=12.0, 3.4 Hz, 2H). HPLC (max plot) 96%; Rt 1.16 min. LC/MS: (ES+): 235.4.

Intermediate 20: 2-(cyclohexylmethyl)-5-methoxyaniline

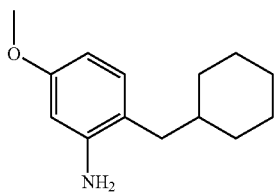 [SMILES: COc1ccc(CC2CCCCC2)c(N)c1]

Following the protocol outlined in Procedure D, Intermediate 20 is obtained from 1-(cyclohexylidenemethyl)-4-methoxy-2-nitrobenzene (1.15 g; 4.67 mmol; 1 eq) and palladium on charcoal (115 mg, 10%) in EtOH (40 mL) overnight at room temperature to afford 1.02 g (99%) of the title compound as a brown oil. $^1$H NMR (DMSO-$d_6$) δ 6.69 (d, J=8.3 Hz, 1H), 6.17 (d, J=2.6 Hz, 1H), 6.03 (dd, J=8.1, 2.4 Hz, 1H), 4.73 (br s, 2H), 3.61 (s, 3H), 2.23 (s, 1H), 2.20 (s, 1H), 1.63-1.60 (m, 5H), 1.45-1.40 (m, 1H), 1.11-1.08 (m, 3H), 0.93-0.86 (m, 2H). HPLC (max plot) 94%; Rt 3.28 min. LC/MS: (ES+): 220.5.

Intermediate 21: 2-[(1-acetylpiperidin-4-yl)methyl]-5-methoxyaniline

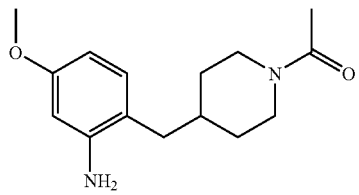 [SMILES: COc1ccc(CC2CCN(C(C)=O)CC2)c(N)c1]

Following the protocol outlined in Procedure D, Intermediate 21 is obtained from 1-acetyl-4-(4-methoxy-2-nitrobenzylidene)piperidine (1.48 g; 5.1 mmol; 1 eq) and palladium on charcoal (150 mg, 10%) in EtOH (100 mL) for 2 h at room temperature to afford 650 mg (48.5%) of the title compound as a brown oil. $^1$H NMR (DMSO-$d_6$) δ 6.72 (d, J=7.9 Hz, 1H), 6.19 (d, J=2.6 Hz, 1H), 6.04 (dd, J=7.9, 2.6 Hz, 1H), 4.83 (br s, 2H), 4.30 (br s, 1H), 3.78-3.73 (m, 1H), 3.62 (s, 3H), 3.02-2.85 (m, 1H), 2.44-2.35 (m, 1H), 2.30 (s, 1H), 2.28 (s, 1H), 1.96 (s, 3H), 1.74-1.55 (m, 3H), 0.97-0.88 (m, 2H). HPLC (max plot) 87%; Rt 1.78 min. LC/MS: (ES+): 263.5.

Intermediate 22: 2-[(4-{[tert-butyl(dimethyl)silyl]oxy}cyclohexyl)methyl]-5-methoxy aniline

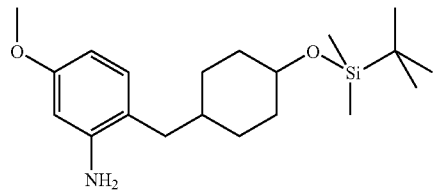 [SMILES: COc1ccc(CC2CCC(O[Si](C)(C)C(C)(C)C)CC2)c(N)c1]

Following the protocol outlined in Procedure D, Intermediate 22 is obtained from tert-butyl{[4-(4-methoxy-2-nitrobenzylidene)cyclohexyl]oxy}dimethylsilane (5.25 g; 13.91 mmol; 1 eq) and palladium on charcoal (525 mg, 10%) in EtOH (170 mL) for 7 h at room temperature to afford 4.7 g (97.5%) of the title compound as a pale yellow oil. HPLC (max plot) 66%; Rt 5.19 min. LC/MS: (ES+): 350.2.

Intermediate 23: 5-Methoxy-2-(1-boc-piperidin-4-ylmethyl)aniline

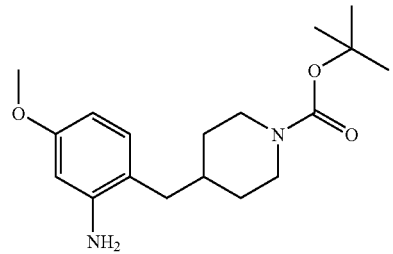 [SMILES: COc1ccc(CC2CCN(C(=O)OC(C)(C)C)CC2)c(N)c1]

Following the protocol outlined in Procedure D, Intermediate 23 is obtained from tert-butyl 4-(4-methoxy-2-nitrobenzylidene)piperidine-1-carboxylate (12 g; 37.45 mmol; 1 eq) and palladium on charcoal (800 mg, 10%) in EtOH (75 mL) for 4 h at room temperature under a pressure of 5 atmosphere, to afford (6 g, 54%) of the title compound as yellow solid. $^1$H NMR (DMSO-$d_6$, 400 MHz) δ 6.72-6.70 (m, 1H), 6.17 (s, 1H), 6.05-6.02 (m, 1H), 4.83 (br s, 2H), 4.05-4.02 (m, 2H), 3.99-3.88 (m, 2H), 3.63 (s, 3H), 2.58-2.50 (m, 2H), 2.32-2.23 (m, 2H), 1.59-1.53 (m, 2H), 1.37 (s, 9H), 1.15-1.03 (m, 2H). HPLC (max plot) 99%; Rt 3.11 min, LCMS: (ES+): 220 (BOC deprotected)

Intermediate 24: 2-(2-amino-4-methoxyphenyl)ethanol

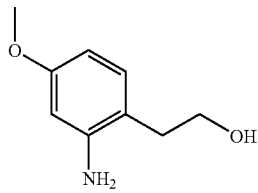

Following the protocol outlined in Procedure D, Intermediate 24 is obtained from 2-(4-methoxy-2-nitrophenyl)ethanol (100 mg; 0.5 mmol, 1 eq) and palladium on charcoal (40 mg; 10%) in EtOH (5 mL) and EtOAc (5 mL) for 3 h at room temperature under a pressure of 1 atmosphere, to afford 100 mg (90%) of the title compound as an orange oil. $^1$H NMR (CDCl$_3$) δ 6.86 (d, J=9.0 Hz, 1H), 6.33 (dd, J=9.0, 3.0 Hz, 1H), 6.16 (d, J=3.0 Hz, 1H), 3.73 (t, J=9.0 Hz, 2H), 3.65 (s, 3H), 3.40-3.20 (m, 3H), 2.60 (t, J=9.0 Hz, 2H). HPLC (max plot) 91%; Rt 1.09 min. LC/MS: (ES+): 168.

Intermediate 25: Methyl 2-amino-4-methoxybenzoate

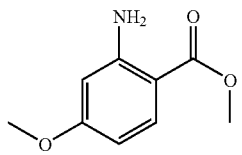

Following the protocol outlined in Procedure D, Intermediate 25 is obtained from methyl 4-methoxy-2-nitrobenzoate (11 g, 52.13 mmol, 1 eq) and palladium on charcoal (1 g, 10%) in MeOH (250 mL) for 4 h at room temperature under a pressure of 50 psi, to afford 9 g (95%) of the title compound as a solid. $^1$H NMR (DMSO-d$_6$, 400 MHz) δ 7.62-7.60 (m, 1H), 6.71 (br s, 2H), 6.26 (s, 1H), 6.14-6.11 (m, 1H), 3.73 (s, 3H), 3.71 (s, 3H). HPLC (max plot): 97%; Rt 1.12 min. LC/MS: (ES+) 182.8

Intermediate 26: 2-(2-Amino-4-methoxyphenyl)propane-1,3-diol

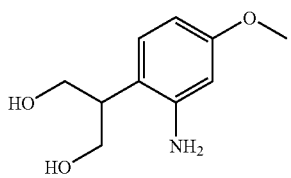

Following the protocol outlined in Procedure D, Intermediate 26 is obtained from 2-(4-methoxy-2-nitrophenyl)propane-1,3-diol (220 mg; 1 eq) and palladium on charcoal (75 mg; 10%) in EtOH (1.5 mL) and EtOAc (15 mL) for 3 h at room temperature under a pressure of 5 bars, to afford 170 mg (90%) of the title compound as a red powder. $^1$H NMR (DMSO-d$_6$) δ 6.89 (d, J=9.0 Hz, 1H), 6.28 (d, J=3.0 Hz, 1H), 6.14 (dd, J=9.0, 3.0 Hz, 1H), 5.10-4.85 (m, 2H), 3.80 (s, 3H), 3.90-3.80 (m, 2H), 3.60-3.55 (m, 2H), 4.53 (t, J=9.0, 2.0 Hz, 2H), 2.91 (q, J=9.0 Hz, 1H). HPLC (max plot) 95%; Rt 0.86 min. LC/MS: (ES+) 198.5, (ES−) 196.4.

Intermediate 27: 3-(2-Amino-4-methoxyphenyl)propan-1-ol

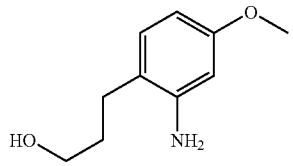

Following the protocol outlined in Procedure D. Intermediate 27 is obtained from (2Z)-3-(4-methoxy-2-nitrophenyl)prop-2-en-1-ol (12 g) and palladium on charcoal (2 g, 10%) in EtOH (150 mL) for 12 h under a pressure of 5 kg/cm$^2$, to afford 7 g (80%) of the title compound as a pale brown solid, $^1$H NMR, (DMSO-d$_6$, 400 MHz) δ 6.75-6.78 (m, 1 ED, 6.18 (s, 1.14), 6.04-6.07 (m, 1H), 4.80 (bs, 2H), 4.41-4.44 (m, 1H), 3.62 (s, 3H), 3.38-3.42 (m, 2H), 2.35-2.38 (m, 2H), 1.57-1.64 (m, 2H). LC/MS: (ES+) 182.0.

Intermediate 28: 2-[3-(Dimethylamino)propyl]-5-methoxyaniline

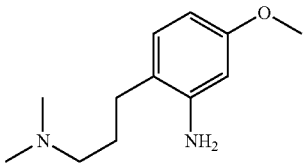

Methanesulfonylchloride (0.71 mL; 9.16 mmol; 1.5 eq) is added dropwise at CFC to a solution of 3-(4-methoxy-2-nitrophenyl)propan-1-ol (1.29 g; 6.11 mmol; 1 eq) and triethylamine (2.54 mL; 18.32 mmol; 3 eq) in DCM (50 mL) and the reaction mixture is stirred at room temperature for 16 hours. The solution is washed successively with 1 M HCl, NaHCO$_3$ water and brine, dried over MgSO$_4$ and concentrated under reduced pressure to give 1.02 g (58%) of the crude mesylate which is taken up in DMF (10 mL). To this solution is added dimethylamine (4.41 mL; 2 M; 8.81 mmol; 2.5 eq) and the reaction mixture is stirred at 65° C. for 16 hours. The solution is diluted with water (20 mL) and the product extracted with ethyl acetate (4×20 mL). The combined organic phase is washed with water, dried over MgSO$_4$ and concentrated under reduced pressure to afford 756 mg (90%) of the crude 3-(4-methoxy-2-nitrophenyl)-N,N-dimethylpropan-1-amine. Following the protocol outlined in Procedure 1), Intermediate 28 is obtained from 3-(4-methoxy-2-nitrophenyl)-N,N-dimethylpropan-1-amine (756 mg; 3.17 mmol; 1 eq) and palladium on charcoal (150 mg, 10%) in EtOH (20 mL) under a pressure of 1 atmosphere to afford 590 mg (89%) of the title compound as a brownish oil. The product was used as such in the following step. $^1$H NMR (DMSO-d$_6$) δ 6.75 (d, J=8.2 Hz, 1H), 6.17 (d, J=2.6 Hz, 1H), 6.04 (dd, J=8.2, 2.6 Hz, 1H), 4.90 (hr s, 2H), 3.60 (s, 3H), 2.35-2.30 (m, 2H), 2.16-2.09 (m, 2H), 2.09 (s, 6H), 1.61-1.52 (m, 2H). HPLC (max plot) 85%; Rt 0.95 min. LC/MS: (ES+) 210.0.

Intermediate 29: 5-Methoxy-2-[2-(methylsulfonyl)ethyl]aniline-hydrochloride salt

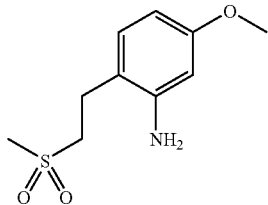

Following the protocol outlined in Procedure D, Intermediate 29 is obtained from 2-(4-methoxy-2-nitrophenyl)ethyl methyl sulfone (9 g, 0.033 mol) and palladium on charcoal (1.8 g, 10%) in EtOH (300 mL) for 12 h at 25° C. under a pressure of 2 Kg/cm$^2$, to afford 7.6 g (82%) of the title compound as pale yellow solid. $^1$H NMR (DMSO d$_6$: 400 MHz) δ 7.28-7.26 (m, 11-1), 6.85-6.83 (m, 2H), 3.75 (s, 3H), 3.47-3.42 (m, 2H), 3.02-2.98 (m, 2H), 2.88 (s, 3H). LC/MS: (ES+) 229.8

Intermediate 30: 5-Methoxy-2-(2-methoxyethyl)aniline

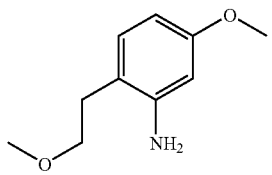

Following the protocol outlined in Procedure D, Intermediate 30 is obtained from 4-methoxy-1-(2-methoxyethyl)-2-nitrobenzene (200 mg; 0.95 mmol; 1 eq) and palladium on charcoal (50 mg; 0.05 mmol; 0.1 eq) in EtOH (15 mL) for 5 h at room temperature under a pressure of 1 atmosphere, to afford 180 mg (100%) of the title compound as a brown oil. $^1$H NMR (DMSO-d$_6$) δ 6.80 (d, J=9.0 Hz, 1H), 6.20 (d, J=3.0 Hz, 1H), 6.07 (dd, J=9.0, 3.0 Hz, 1H), 5.09-4.69 (m, 2H), 3.63 (s, 3H), 3.43 (t, J=9.0 Hz, 2H), 3.24 (s, 3H), 2.58 (t, J=9.0 Hz, 2H). HPLC (max plot) 92%; Rt 1.56 min.,

Intermediate 31: 3-Amino-N-(2-hydroxyethyl)-5-methoxybenzamide

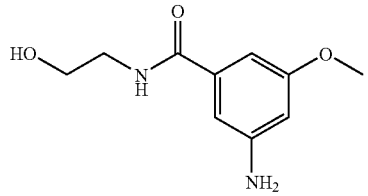

Following the protocol outlined in Procedure D, Intermediate 31 is obtained from N-(2-hydroxyethyl)-3-methoxy-5-nitrobenzamide (830 mg; 3.46 mmol; 1 eq) and palladium on charcoal (200 mg; 10%) in AcOEt (40 mL) and EtOH (10 mL) for 16 h under a pressure of 1 atmosphere, to afford 700 mg (96%) of the title compound as a brown oil. $^1$H NMR (DMSO-d$_6$) δ 8.13 (t, J=5.5 Hz, 1H), 6.63 (t, J=1.7 Hz, 1H), 6.54 (t, J=2.0 Hz, 1H), 6.24 (t, J=2.1 Hz, 1H), 5.2 (s, 2H), 4.69 (t, J=5.2 Hz, 1H), 3.69 (s, 314), 3.50-3.42 (m, 2H), 3.29-3.23 (m, 2H), HPLC (max plot) 98%; Rt 1.09 mM. LC/MS (ES+) 211.2; (ES−) 209.2.

Intermediate 32: 3-Amino-5-methoxy-N-(2-methoxyethyl)benzamide

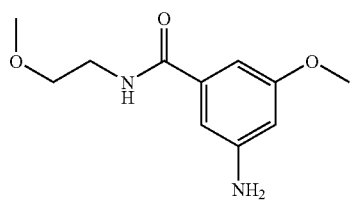

Following the protocol outlined in Procedure D, Intermediate 32 is obtained from 3-methoxy-N-(2-methoxyethyl)-5-nitrobenzamide (1.3 g; 5.11 mmol; 1 eq) and palladium on charcoal for 18 h at room temperature under a pressure of atmosphere, to afford 1.2 g (100%) of the title compound as a light pink oil. It is used in the next step without further purification. $^1$H NMR (DMSO-d$_6$) δ 8.23 (s, 1H), 6.70-6.35 (m, 2H), 6.26 (s, 1H), 5.28-5.20 (m, 2H), 3.71 s, 3H), 3.41 (t, J=9.0 Hz, 2H), 3.25 (s, 3H), 1.16-0.90 (m, 2H). HPLC (max plot) 90%; Rt 1.07 min. UPLC/MS: (ES+) 225; (ES−) 223.

Intermediate 33: 2-Amino-N-(2-hydroxyethyl)-4-methoxybenzenesulfonamide

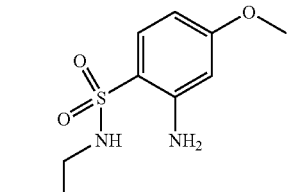

Following the protocol outlined in Procedure D, Intermediate 33 is obtained from N-(2-hydroxyethyl)-4-methoxy-2-nitrobenzenesulfonamide (2.9 g; 10.5 mmol; 1 eq) and palladium on charcoal (600 trig, 10%) in MeOH (100 mL) for 72 h under a pressure of 1 atmosphere, to afford (1.53 g, 59%) of the title compound as a yellow solid. $^1$H NMR (DMSO-d$_5$) δ 7.39 (d, J=8.7 Hz, 1H), 7.31 (br s, 1H), 6.31 (d, J=2.6 Hz, 1H), 6.21 (dd, J=8.8, 2.4 Hz, 1H), 5.9 (br s, 2H), 4.66 (br s, 1H), 3.71 (s, 3H), 3.33 (t, J=6.6 Hz, 2H), 2.70 (t, J=6.6 Hz, 2H). HPLC (max plot): 98%; Rt 1.97 min. UPLC/MS (ES+) 247.1; (ES−) 245.2.

Intermediate 34:
3-Amino-5-methoxy-N,N-dimethylbenzamide

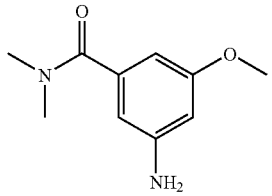

Following the protocol outlined in Procedure D, Intermediate 34 is obtained from 3-methoxy-N,N-dimethyl-5-nitrobenzamide (850 mg; 3.79 mmol; 1 eq) and palladium on charcoal (40 mg; 0.38 mmol; 0.1 eq) in EtOH (10 mL) for 1.5 days at rt under a pressure of 1 atmosphere to afford 550 mg (75%) of the title compound as a white oil. $^1$H NMR (DMSO-d$_6$) δ 6.21 (d, J=3.0 Hz, 1H), 6.16 (d, J=3.0 Hz, 1H), 6.05 (d, J=3.0 Hz, 1H), 5.39-5.19 (m, 2H), 3.78 (s, 3H), 2.95 (s, 6H). HPLC (max plot) 93.8%; Rt 1.21 min.

Intermediate 35: 2-{(4S,4R)-2,2-Dimethyl-(1,3)dioxolan-4-ylmethyl}-5-methoxy-phenylamine

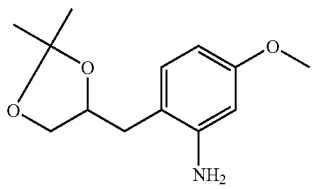

Following the protocol outlined in Procedure D, Intermediate 35 is obtained from (4S,4R)-4-(4-methoxy-2-nitrobenzyl)-2,2-dimethyl-1,3-dioxolane (1.8 g, 6.7 mmol) and palladium on charcoal (0.18 g 10%) in EtOH (300 mL) for 24 h at room temperature under a pressure of 4 Kg/cm$^2$, to afford 1.2 g (75%) of the title compound as a brown thick liquid. $^1$H NMR (DMSO-d$_6$, 400 MHz) δ 6.81-6.79 (m, 1H), 6.19 (s, 1H), 6.07-6.05 (m, 1H), 4.89 (s, 2H), 4.22-4.19 (m, 1H), 3.92-3.88 (m, 1H), 3.61 (s, 3H), 3.51-3.49 (m, 1H), 2.61-2.49 (m, 2H) 1.31 (s, 3H), 1.23 (s, 3H), LC/MS: (ES+) 238.2.
Procedure E

Intermediate 36:
2-(cyclopentylmethyl)-5-methoxyaniline

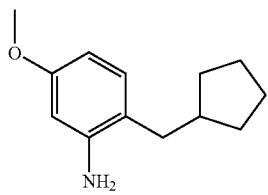

A solution of 1-(cyclopentylidenemethyl)-4-methoxy-2-nitrobenzene (1.8 g; 0.09 M, 7.72 mmol; 1 eq) in MeOH (80 mL) is pumped through the H-Cube™ flow hydrogenator fitted with a 10 mol % Pd/C catalyst cartridge (30×4 mm) heated to 25° C. at 1 bar with the full hydrogen option enabled. The flow rate is set at 1 mL/min. The catalyst is pre-saturated with hydrogen gas for 2 min before passing the substrate through. The solvent is evaporated under reduced pressure and the residue is taken up in HCl 1N and EtOAc. The organic phase is washed with brine then dried over MgSO$_4$, and the solvent is evaporated under reduced pressure to afford 1.02 g (64%) of the title compound as a brown oil. $^1$H NMR (CDCl$_3$) δ 6.94 (d, J=8.3 Hz, 1H), 6.45-6.35 (m, 2H), 4.45-3.90 (m, 2H), 3.75 (s, 3H), 2.45 (d, J=7.0 Hz, 2H), 2.12 (q, J=7.0 Hz, 1H), 1.78-1.45 (m, 6H), 1.35-1.05 (m, 2H). HPLC (max plot) 89%; Rt 2.86 min. LC/MS: (ES+): 206.1.

Intermediate 37: 5-methoxy-2-[(1,2,2,6,6-pentamethylpiperidin-4-yl)methyl]aniline

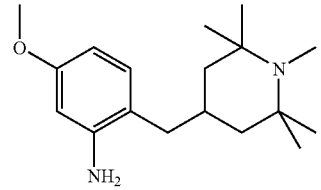 [SMILES: COc1ccc(CC2CC(C)(C)N(C)C(C)(C)C2)c(N)c1]

Following the protocol outlined in Procedure E, Intermediate 37 is obtained from a solution of 4-(4-methoxy-2-nitrobenzylidene)-1,2,2,6,6-pentamethylpiperidine (525 mg; 0.075 M; 1.65 mmol; 1 eq) in MeOH (22 mL) heated to 25° C. at 60 bars with the controlled pressure option enabled. The solvent is evaporated under vacuum to afford 394 mg (82%) of the title compound as colourless oil (no work up needed). $^1$H NMR (CDCl$_3$) δ 6.89 (d, J=8.0 Hz, 1H), 6.23 (dd, J=8.0, 2.0 Hz, 1H), 6.18 (d, J=2.0 Hz, 1H), 3.69 (s, 3H), 3.53 (br s, 2H), 2.32-2.05 (m, 5H), 2.00-1.80 (m, 1H), 1.65-1.35 (m, 4H), 1.30-0.70 (m, 12H). HPLC (max plot) 95%; Rt 1.53 min. LC/MS: (ES+): 291.2.

Intermediate 38: 5-methoxy-2-{[(1R,5S)-8-methyl-8-azabicyclo[3.2.1]oct-3-yl]methyl}aniline Mixture of Cis/Trans Isomers

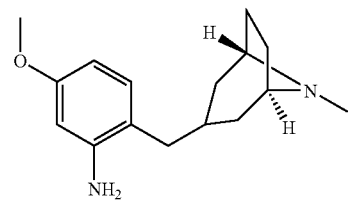 [SMILES: COc1ccc(CC2C[C@H]3CC[C@@H](C2)N3C)c(N)c1]

Following the protocol outlined in Procedure E, Intermediate 38 is obtained from a solution of (1R,3Z,5S)-3-(4-methoxy-2-nitrobenzylidene)-8-methyl-8-azabicyclo[3.2.1]octane (1.86 g; 0.065 M; 6.45 mmol; 1 eq) in MeOH (100 mL) heated to 25° C. at 50 bars with the controlled pressure option enabled (cartridge 70×4 mm). The solvent is evaporated under vacuum to afford 1.26 g (75%) of the title compound as brown oil. HPLC (max plot) 90%; Rt 1.31 min. LC/MS: (ES+): 261.2.

Intermediate 39: 5-methoxy-2-(tetrahydro-2H-thiopyran-4-ylmethyl)aniline

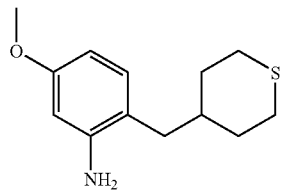 [SMILES: COc1ccc(CC2CCSCC2)c(N)c1]

Sodium borohydride (63.58 mg; 1.68 mmol; 0.07 eq) is suspended in DME (6.5 mL) at room temperature. Borane-methyl sulfide complex (39.61 mL; 2 M; 79.22 mmol; 3.3 eq) is added dropwise. After 30 min stirring at room temperature, a solution of 4-(4-methoxy-2-nitrobenzylidene)tetrahydro-2H-thiopyran (6.37 g; 24.01 mmol; 1 eq) in DME (100 mL) is added dropwise over 30 min and the orange solution is stirred at room temperature for 30 min then heated up to reflux for 3.5 days. The reaction mixture is quenched with MeOH (40 mL) upon which a yellow-brownish solution is obtained. The solution is stirred at room temperature for 1 h prior to evaporation of the solvent. The oily brownish residue obtained is taken up in MeOH (10 mL) and 5 N HCl (10 mL~2 eq) is added dropwise while cooling the solution to 0° C. with an ice bath. After addition of ⅔ of the HCl, precipitation starts. The suspension is stored at 4° C. for 30 min. The precipitate is filtered off then washed twice with cold EtOAc (10 mL) to afford 2.39 g (36%) of the title compound as a yellow powder. $^1$H NMR (DMSO-$d_6$) δ 9.61 (br s, 2H), 7.09-7.06 (m, 1H), 9.95-6.87 (m, 1H), 6.83-6.79 (m, 1H), 3.72 (s, 3H), 2.54-2.47 (m, 6H), 1.87-1.81 (m, 2H), 1.68-1.59 (m, 1H), 1.33-1.20 (m, 2H). HPLC (max plot) 95%; Rt 2.57 min. LC/MS: (ES+): 238.1; (ES−): 236.1.

Intermediate 40: 4-(4-methoxy-2-nitrobenzylidene)-1,2,2,6,6-pentamethylpiperidine

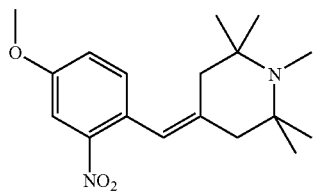 [SMILES: COc1ccc(C=C2CC(C)(C)N(C)C(C)(C)C2)c([N+](=O)[O-])c1]

4-(4-methoxy-2-nitrobenzylidene)-2,2,6,6-tetramethylpiperidine (1.1 g; 3.23 mmol; 1 eq) is dissolved in MeOH (10 mL) then formaldehyde (0.19 g; 6.45 mmol; 2 eq) and sodium cyanoborohydride (0.41 g; 6.45 mmol; 2 eq) are added. The reaction mixture is stirred at room temperature overnight. The solvents are evaporated under reduced pressure and the residue obtained is taken up in EtOAc then a saturated aqueous solution of NaHCO$_3$ is added. The organic phase is washed with brine, dried over MgSO$_4$ and the solvent is evaporated under reduced pressure to afford 320 mg (31%) of the title compound as a yellow oil. $^1$H NMR (DMSO-$d_6$) δ 7.53 (d, $J$=2.6 Hz, 1H), 7.20 (d, J=8.2 Hz, 1H), 7.10 (dd, J=8.6, 2.6 Hz, 1H), 6.49 (s, 1H), 3.87 (s, 3H), 2.22-2.15 (m, 6H), 1.20-1.10 (m, 6H), 1.00-0.90 (m, 6H). HPLC (max plot) 99.5%; Rt 2.84 min. LC/MS: (ES+): 319.1

Intermediate 41: 2,2,2-trifluoro-N-[5-methoxy-2-(tetrahydro-2H-thiopyran-4-ylmethyl)phenyl]acetamide

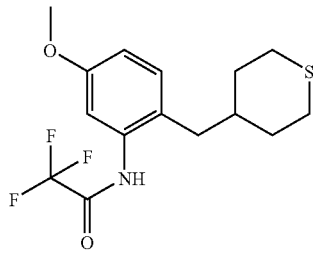 [SMILES: COc1ccc(CC2CCSCC2)c(NC(=O)C(F)(F)F)c1]

5-Methoxy-2-(tetrahydro-2H-thiopyran-4-ylmethyl)aniline (1.16 g; 4.24 mmol; 1 eq) is suspended in DCM (20 mL) at room temperature. The yellow suspension is cooled with an ice bath then triethylamine (2.07 mL; 14.85 mmol; 3.5 eq) is added dropwise followed by trifluoroacetic anhydride (1.26 mL; 8.91 mmol; 2.1 eq). The resulting brownish solution is allowed to stir overnight while warming up to room temperature. The reaction mixture is treated with water (10 mL), both layers are separated and the product is extracted from the aqueous phase with DCM (10 mL). The organic layer is dried over MgSO$_4$ and evaporated under reduced pressure to yield 1.6 g of crude material as orange-brownish oil, which solidifies upon standing. After purification on silica plug (eluent: n-heptane/EtOAc [1/1]), it affords 1.17 g (83%) of the title compound as off-white solid. $^1$H NMR (CDCl$_3$) δ 7.71 (br s, 1H), 7.43 (d, J=2.6 Hz, 1H), 7.08 (d, J=8.7 Hz, 1H), 6.78 (dd, J=8.7, 2.6 Hz, 1H), 3.80 (s, 3H), 2.62-2.58 (m, 4H), 2.44-2.42 (m, 2H), 1.97-1.94 (m, 2H), 1.48-1.32 (m, 3H). HPLC (max plot) 96%; Rt 4.49 min. LC/MS: (ES+): 334.1, (ES−): 332.1

Intermediate 42: N-{2-[(1,1-dioxidotetrahydro-2H-thiopyran-4-yl)methyl]-5-methoxyphenyl}-2,2,2-trifluoroacetamide

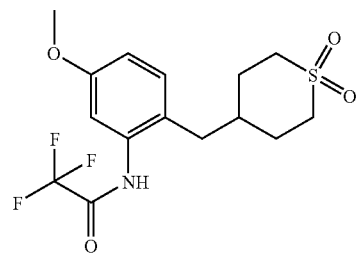 [SMILES: COc1ccc(CC2CCS(=O)(=O)CC2)c(NC(=O)C(F)(F)F)c1]

To a solution of 2,2,2-trifluoro-N-[5-methoxy-2-(tetrahydro-2H-thiopyran-4-ylmethyl)phenyl]acetamide (800 mg; 2.4 mmol; 1 eq) in DCM (8 mL) is added 3-chloro peroxybenzoic acid (869.63 mg; 5.04 mmol; 2.1 eq) in 5 portions at room temperature. After 2 min stirring, a suspension is obtained. Stirring is continued at room temperature for 10 min. The suspension is diluted with DCM (5 mL) and a saturated solution of NaHCO$_3$ (10 mL) is added. Both layers were separated, the organic phase is washed 5 times with a saturated solution of NaHCO$_3$ (10 mL). The organic phase is dried over MgSO$_4$ and evaporated under reduced pressure to give 791 mg of crude material as brownish solidified foam

Intermediate 44: 1-(3-methoxy-5-nitrobenzoyl)-4-methylpiperazine

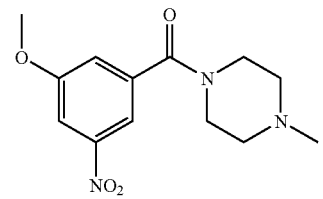

3-Nitro-5-methoxybenzoic acid (1 g; 5.07 mmol; 1 eq; commercially available IMPAMEX) is dissolved in a mixture of DCM (40 mL) and THF (10 mL) at room temperature. It is then cooled down at 0° C. and thionyl dichloride (1.1 mL; 15.22 mmol; 3 eq) is added slowly. After 30 min, triethylamine (2.11 mL; 15.22 mmol; 3 eq) and 1-methylpiperazine (1.64 mL; 15.22 mmol; 3 eq) are added at 0° C. and the reaction mixture is gently warmed up to rt and stirred for 48 h. Water is added and the solvents are evaporated. The product is extracted with EtOAc and the organic phase is washed with aqueous $Na_2CO_3$ and dried over $MgSO_4$. The solvent is concentrated under reduced pressure to afford 900 mg (63.5%) of the title compound. The next step is carried out directly on the crude material. LC/MS: (ES+): 280.3; (ES−): 278.5

Intermediate 43: 2-[(1,1-dioxidotetrahydro-2H-thiopyran-4-yl)methyl]-5-methoxyaniline

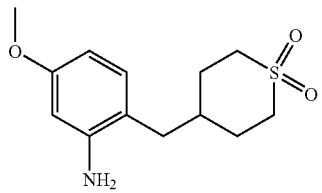 [SMILES: COc1ccc(CC2CCS(=O)(=O)CC2)c(N)c1]

N-{2-[(1,1-dioxidotetrahydro-2H-thiopyran-4-yl)methyl]-5-methoxyphenyl}-2,2,2-trifluoroacetamide (890 mg; 2.44 mmol; 1 eq) is suspended in MeOH (15 mL). To the yellow-brown suspension is added dropwise a solution of potassium carbonate (403.98 mg; 2.92 mmol; 1.2 eq) in water (4 mL). Immediately, the suspension lighted up. Stirring is continued at room temperature for 1 h. No conversion is observed. Lithium hydroxide monohydrate (112.44 mg; 2.68 mmol; 1.1 eq) is added leading to a turbid solution. Stirring is allowed to continue at room temperature overnight. No conversion is observed. Additional lithium hydroxide monohydrate (511.08 mg; 12.18 mmol; 5 eq) is added as a solution in water (5 mL). Stirring is continued at room temperature for 4 days. The suspension is cooled with an ice-bath and 5 N HCl is added until pH=1. The resulting solution is concentrated under reduced pressure until precipitation started (approx. 5 mL of solution left). n-Heptane is added as anti-solvent and the biphasic system is cooled with an ice-bath. The beige solid obtained is filtered off, rinsed twice with diethyl ether and dried under high vacuo to afford 580 mg (78%) of the title compound as an off-white solid. $^1$H NMR (DMSO-$d_6$) δ 9.80 (br s, 2H), 7.17 (d, J=8.7 Hz, 1H), 6.94 (d, J=2.6 Hz, 1H), 6.83 (dd, J=8.7 Hz, 2.6 Hz, 1H), 3.73 (s, 3H), 3.03-2.99 (m, 4H), 2.61-2.58 (m, 2H), 2.10-1.98 (m, 1H), 1.91-1.86 (m, 2H), 1.72-1.61 (m, 2H). HPLC (max plot) 95.5%; Rt 1.55 min. LC/MS: (ES+): 270.1.

Intermediate 45: 4-(3-methoxy-5-nitrobenzoyl)morpholine

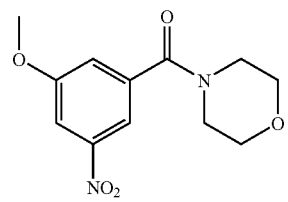

3-nitro-5-methoxybenzoic acid (900 mg; 4.57 mmol; 1 eq; commercially available IMPAMEX) is dissolved in THF (5 mL) at room temperature. 1-Ethyl-3-(3-dimethylaminopropyl)carbodiimide hydrochloride (1.05 g; 5.48 mmol; 1.2 eq) and 1-hydroxybenzotriazole hydrate (987 mg; 7.3 mmol; 1.6 eq) are added in DCM (20 mL). The reaction mixture is stirred at room temperature for 25 min before adding morpholine (795.44 mg; 9.13 mmol; 2 eq). After 3 h, the reaction mixture is quenched with water and the organic phase recovered and washed with citric acid (5%). The aqueous phase is extracted with DCM. The organic phase is dried over $MgSO_4$, and the solvent is evaporated under reduced pressure to afford 1.2 g (99%) as a yellow solid. The next step is carried out directly on the crude material. LC/MS: (ES+): 267.3; (ES−): 265.3.

Procedure F

Intermediate 46: 3-methoxy-5-[(4-methylpiperazin-1-yl)carbonyl]aniline

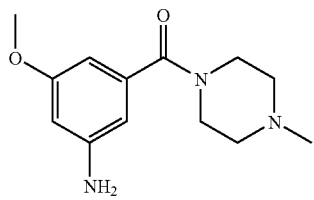 [SMILES: COc1cc(C(=O)N2CCN(C)CC2)cc([N+](=O)[O-])c1]

1-(3-Methoxy-5-nitrobenzoyl)-4-methylpiperazine (900 mg; 3.22 mmol; 1 eq) and iron powder (719.82 mg; 12.89 mmol; 4 eq) are heated for 1 h at 100° C. in a mixture of AcOH (10 mL) and EtOH (10 mL). The reaction mixture is cooled down to room temperature, concentrated under vacuum and basified with aqueous Na$_2$CO$_3$. The product is extracted with EtOAc. The organic phase is dried over MgSO$_4$ and the solvent evaporated under reduced pressure to afford 500 mg (62%) of the title compound as an orange oil. $^1$H NMR (DMSO-d$_6$) δ 6.20-6.17 (m, 1H), 6.11-6.10 (m, 1H), 6.01-5.99 (m, 1H), 5.35-5.27 (m, 2H), 3.66 (s, 3H), 3.55-3.53 (m, 4H), 2.30-2.28 (m, 4H), 2.18 (s, 3H). LC/MS: (ES+): 250.4.

Intermediate 47: 3-methoxy-5-(morpholin-4-ylcarbonyl)aniline

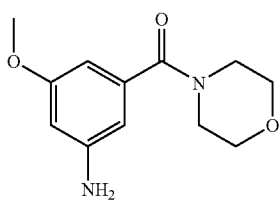 [SMILES: COc1cc(N)cc(C(=O)N2CCOCC2)c1]

Following the protocol outlined in Procedure F, Intermediate 47 is obtained from 4-(3-methoxy-5-nitrobenzoyl)morpholine (1.2 g; 4.51 mmol; 1 eq) and iron powder (1 g; 18.03 mmol; 4 eq) in a mixture of AcOH (10 mL) and EtOH (10 mL) at 85° C. for 2 h to afford 820 mg (77%) of the title compound as an orange oil. $^1$H NMR (DMSO-d$_6$) δ 6.25-6.20 (m, 1H), 6.15-6.12 (m, 1H), 6.05-5.99 (m, 1H), 5.45-5.37 (m, 2H), 3.68 (s, 3H), 3.55-3.43 (m, 4H), 2.40-2.28 (m, 4H). HPLC (max plot) 59%; Rt 1.03 min LC/MS: (ES+): 237.4.

Intermediate 48: diethyl (4-methoxy-2-nitrophenyl)malonate

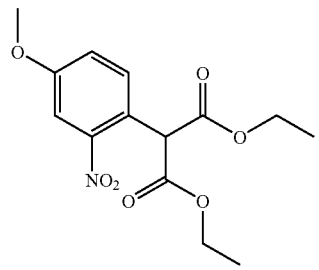 [SMILES: CCOC(=O)C(C(=O)OCC)c1ccc(OC)cc1[N+](=O)[O-]]

To a suspension of sodium hydride (2.81 g; 117.28 mmol; 2.2 eq) in DMF (35 mL) under nitrogen is added slowly at 0° C. over 20 min diethyl malonate (17.89 mL; 117.28 mmol; 2.2 eq) followed by cesium fluoride (404.91 mg; 2.67 mmol; 0.05 eq) and 1-chloro-4-methoxy-2-nitrobenzene (10 g; 53.31 mmol; 1 eq; commercially available from ACROS). The resulting reaction mixture is stirred at room temperature for 45 min then heated at 105° C. overnight. The reaction is quenched by addition of water and DMF is removed under reduced pressure. The residue obtained is taken up in EtOAc then an aqueous solution of NaHCO$_3$ is added. The organic phase is separated and dried over MgSO$_4$. The solvent is removed under reduced pressure to afford 25 g of a brown oil which is purified on silica gel (800 g) using cyclohexane/EtOAc (95/5) as eluent affording 4.7 g (28%) of the title compound as a yellow oil. HPLC (max plot) 89%; Rt 4.25 min. LC/MS: (ES+): 312.1, (ES−): 310.1.

Intermediate 49: (4-methoxy-2-nitrophenyl)acetic acid

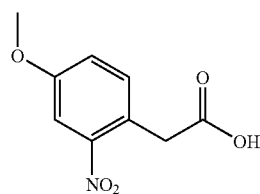

A solution of diethyl (4-methoxy-2-nitrophenyl)malonate (1.1 g; 3.53 mmol; 1 eq) in a mixture of EtOH (25 mL) and sodium hydroxide (25 mL; 1 M; 25 mmol; 7.07 eq) is heated for 1 h at 90° C. The solvents are removed under reduced pressure and the orange-yellow powder is suspended in THF (20 mL). After cooling down to 0° C., 5M HCl (20 mL) is added. The reaction mixture is refluxed at 85° C. for 1 h. After cooling down to room temperature, the 2 phases are separated and the organic phase is dried over MgSO$_4$. The aqueous phase is treated twice with EtOAc (50 mL) and the combined organic phases are dried over MgSO$_4$ then concentrated to dryness to afford 850 mg (100%) of the title compound as a brown solid. $^1$H NMR (DMSO-d$_6$) δ 8.20-8.10 (m, 1H), 7.45 (d, J=3.0 Hz, 1H), 7.05 (d, J=8.0 Hz, 1H), 6.95 (dd, J=8.0, 3.0 Hz, 1H), 3.78 (s, 2H), 3.67 (s, 3H). HPLC (max plot) 89%; Rt 2.54 min. LC/MS: (ES+): 229.0 (M+NH$_4^+$).

Intermediate 50:
2-(4-methoxy-2-nitrophenyl)ethanol

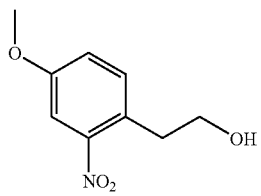

To a solution of (4-methoxy-2-nitrophenyl)acetic acid (400 mg; 1.9 mmol; 1 eq) in THF (10 mL) at 0° C. is added slowly under nitrogen borane-tetrahydrofuran complex (4.74 mL; 1 M; 4.7 mmol; 2.5 eq) and the reaction is stirred overnight at room temperature. No conversion is observed. The reaction mixture is heated at 70° C. for 2 h. The reaction is quenched by addition of water and the expected product is extracted with EtOAc. The organic phase is dried over MgSO$_4$ and the solvent removed under reduced pressure. The residue obtained is purified by the flash chromatography using cyclohexane/EtOAc (7/3) as eluent to afford 350 mg (94%) of the title compound as a yellow oil. $^1$H NMR (CDCl$_3$) δ 7.20 (d, J=3.0 Hz, 1H), 7.06 (d, J=8.0 Hz, 1H), 6.85 (dd, J=8.0, 3.0 Hz, 1H), 3.66 (t, J=9.0 Hz, 2H), 3.61 (s, 3H), 2.86 (t, J=9.0 Hz, 2H), 1.88 (br s, 1H). HPLC (max plot) 100%; Rt 2.48 min.

Intermediate 51:
4-Methoxy-1-(2-methoxyethyl)-2-nitrobenzene

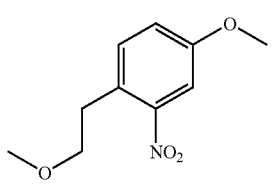

To a solution of 2-(4-methoxy-2-nitrophenyl)ethanol (1 g; 5.07 mmol; 1 eq) in THF (50 mL) is added sodium hydride (406 mg; 10.14 mmol; 2 eq) at 0° C. and the reaction mixture is stirred at 0° C. for 10 min before adding iodomethane (0.63 mL; 10.14 mmol; 2 eq). The reaction mixture is stirred overnight. It is quenched by addition of water. The product is extracted with EtOAc and the organic phase is dried over MgSO$_4$. The solvent is evaporated under reduced pressure and the residue is purified by flash chromatography using a mixture of petrol ether and EtOAc (70/30) as eluent. The solvents are evaporated to afford 680 mg (63%) of the title compound as a yellow solid. $^1$H NMR (DMSO-d$_6$) δ 7.35 (d, J=3.0 Hz, 1H), 7.21 (d, J=9.0 Hz, 1H), 6.98 (dd, J=9.0, 3.0 Hz, 1H), 3.76 (s, 3H), 3.54 (t, J=9.0 Hz, 2H), 3.24 (s, 314), 3.01 (t, J=9.0 Hz, 2H), HPLC (max plot) 94%; Rt 4.18 min.

Intermediate 52:
2-(4-Methoxy-2-nitrophenyl)propane-1-diol

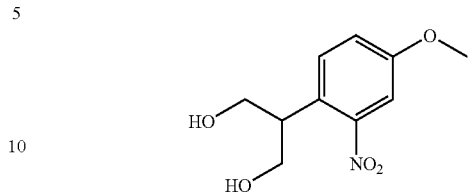

To a solution of diethyl (4-methoxy-2-nitrophenyl)malonate (1 g; 3.21 mmol; 1 eq) in THF (25 mL) is added slowly at 0° C. under an inert atmosphere diisobutylaluminum hydride (16 mL; 1.2 M; 19.3 mmol; 6 eq). The reaction mixture is stirred at 0° C. for 1 h and another 1 h at room temperature then quenched carefully with water. The product is extracted with EtOAc. The organic phase is dried over MgSO$_4$ and the solvent is removed under reduced pressure. The crude residue is purified by flash chromatography (eluent: DCM/acetone [8/2]) to give 220 mg (30%) of the title compound as a red solid. $^1$H NMR (DMSO-d$_6$) δ 7.49 (d, J=9.0 Hz, 111), 7.33 (d, J=3.0 Hz, 1H), 7.19 (dd, J=9.0, 3.0 Hz, 1H), 4.70-4.60 (m, 2H), 3.81 (s, 3H), 3.68 (m, 2H), 3.62 (m, 2H), 3.15 (q, J=9.0 Hz, 1H). HPLC (max plot) 98.5%; Rt 1.81 mM. LC/MS: (ES+): 227.1.

Intermediate 53:
1-(Dibromomethyl)-4-methoxy-2-nitrobenzene

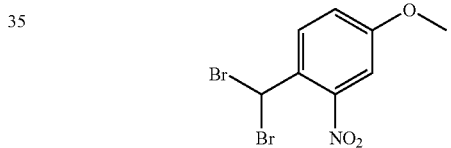

A mixture of 4-methyl 3-nitroanisole (50 g, 0.30 mol), benzoylperoxide (7.22 g, 0.030 mol) and N-bromosuccinimide (111.8 g, 0.63 mol) in CCl$_4$ (500 mL) is refluxed at 80° C. under nitrogen for 24 h. After cooling to room temperature, the reaction mixture is filtered then washed with CCl$_4$. The solvent is removed under reduced pressure and the residue is purified by chromatography using silica-gel (60-120 mesh) and petrol ether/EtOAc as eluent to give 42 g (43%) of the title compound as an orange-yellow liquid. $^1$H NMR (CDCl$_3$, 400 MHz) δ 8.15-8.13 (m, 1H), 7.44 (s, 1H), 7.38-7.39 (m, 1H), 7.24-7.25 (m, 1H), 3.80 (s, 3H).

Intermediate 54: 4-Methoxy-2-nitrobenzaldehyde

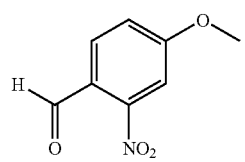

A mixture of 1-(dibromomethyl)-4-methoxy-2-nitrobenzene (42 g, 0.23 mol) and NaHCO$_3$ (3 Eq) in water (400 mL) is refluxed for 22 h. The reaction mixture is cooled to room temperature and the product is extracted with EtOAc (2×150 mL). The organic layer is washed with a solution of 1.5N HCl (2×100 mL), water (2×100 mL) and brine then dried over Na₂SO₄. The solvent is removed under reduced pressure to afford 20 g (85%) of the title compound as a brown solid. ¹H NMR (DMSO-d₆, 400 MHz) δ 10.03 (s, 1H), 7.93-7.95 (m, 1H), 7.61 (s, 1H), 7.40-7.41 (m, 1H), 3.93 (s, 3H).

Intermediate 55: (2E)-3-(4-Methoxy-2-nitrophenyl)acrylic acid

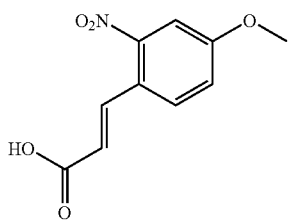 [SMILES: COc1ccc(/C=C/C(=O)O)c([N+](=O)[O-])c1]

To a mixture of 4-methoxy-2-nitrobenzaldehyde (20 g, 0.11 mol) and malonic acid (28.8 g, 0.28 mol) in pyridine (200 mL) is added piperidine (1 mL, catalytic amount) and the mixture is refluxed at 125° C. under nitrogen for 12 h. After cooling to room temperature, the solvent is removed under reduced pressure and the residue is acidified with 1.5 N HCl. The product is extracted with EtOAc and the organic layer is washed with water and brine then dried over Na₂SO₄. The solvent is removed under reduced pressure to afford 16 g (65%) of the title compound as a pale brown solid. ¹H NMR (DMSO-d₆, 400 MHz) δ 12.59 (bs, 1H), 7.91-7.93 (m, 1H), 7.68-7.72 (m, 1H), 7.56 (s, 1H), 7.31-7.33 (m, 1H), 7.46-7.50 (m, 1H), 3.87 (s, 3H).

Intermediate 56: Methyl (2E)-3-(4-methoxy-2-nitrophenyl)acrylate

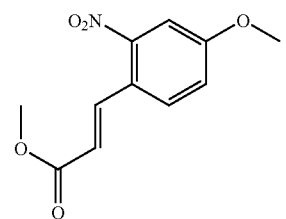 [SMILES: COC(=O)/C=C/c1ccc(OC)cc1[N+](=O)[O-]]

To a mixture of (2E)-3-(4-methoxy-2-nitrophenyl)acrylic acid (16 g, 0.067 mol) in dry MeOH (150 mL) under nitrogen is added dropwise thionyl chloride (12.3 mL, 0.169 mol) at 0° C. The reaction mixture is refluxed for 3 h then cooled to room temperature. The solvent is removed under reduced pressure and the residue is taken up in EtOAc. The organic layer is washed with 10% aqueous NaHCO₃, water and brine then dried over Na₂SO₄. The solvent is removed under reduced pressure to afford 14 g (88%) of the title compound as a yellow solid. ¹H NMR (CDCl₃, 400 MHz) δ 8.03-8.07 (m, 1H), 7.58-7.60 (m, 1H) 7.51 (s, 1H), 7.16-7.18 (m, 1H), 6.29-6.33 (m, 1H), 3.91 (s, 3H), 3.82 (s, 3H).

Intermediate 57: (2E)-3-(4-Methoxy-2-nitrophenyl)prop-2-en-1-ol

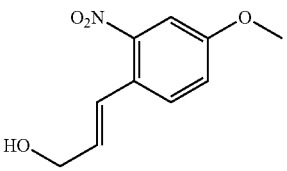

To a stirred solution of methyl (2E)-3-(4-methoxy-2-nitrophenyl)acrylate (14 g, 0.06 mol) in dry toluene (150 mL) under nitrogen is added dropwise DIBAL-H (63 mL, 0.19 mol, 3 M) at 0° C. After stirring at room temperature for 3 h, the reaction mixture is quenched with MeOH (60 mL) then 1.5 N HCl (60 mL) is added. After addition of another 100 mL of 1.5 N HCl, the product is extracted with EtOAc. The organic layer is washed with water and brine then dried over Na₂SO₄. The solvent is removed under reduced pressure to afford 10 g (81%) of the title compound as a yellow solid. ¹H NMR (CDCl₃, 400 MHz) δ 7.52-7.54 (m, 1H), 7.43 (s, 1H), 7.11-7.14 (m, 1H), 7.0-7.04 (m, 1H), 6.22-6.29 (m, 1H), 4.35-4.37 (m, 2H), 3.88 (s, 3H).

Intermediate 58: 3-(4-Methoxy-2-nitrophenyl)propan-1-ol

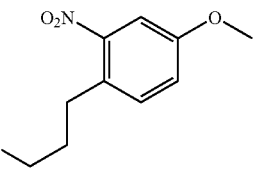

To a solution of methyl (2E)-3-(4-methoxy-2-nitrophertyl) acrylate (450 mg; 1.9 mmol; 1 eq) in THF (30 nit) is added lithium borohydride (25 mg; 1.14 mmol; 0.6 eq) at 0° C. under stirring.

The cooling bath is removed and stirring is allowed to continue at room temperature overnight. Additional lithium borohydride (10 mg; 0.47 mmol; 0.25 eq) is added at room temperature. The turbid yellow solution is cooled with an ice-bath and quenched with saturated NH₄Cl (10 mL). Water is added (pH=12) then 5 N HCl until pH=2, The product is extracted with MTBE (3×25 mol) and the combined organic layer is washed with brine (30 mL) and dried over MgSO₄ to give a brown oil. It is purified by flash chromatography (n-heptane/EtOAc=3:1, 2:1), affording 240 mg (60%) of a mixture including the title compound and the corresponding allylic alcohol as yellow-orange oil. HPLC (max plot) 99% (mixture); Rt 2.85 min.

Intermediate 59: 1-[3-Bromoprop-1-enyl]-4-methoxy-2-nitrobenzene

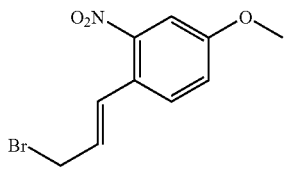

To a stirred slurry of triphenyl phosphine (16.4 g, 0.627 mol) in dry DCM (150 mL) under nitrogen at 0° C., is added dropwise a solution of bromine (3.2 mL, 0.0627 mol) in DCM (30 mL). After stirring for 15 min, a solution of (2E)-3-(4-methoxy-2-nitrophenyl)prop-2-en-1-ol (10 g, 0.044 mol) in dry DCM (100 mL) is added dropwise to the reaction mixture followed by a dropwise addition of pyridine (5.05 mL, 0.06 mol) at 0° C. After stirring at room temperature for another 4 h, the reaction mixture is quenched with ice and the product extracted with DCM. The organic layer is washed with water then brine and dried over $Na_2SO_4$. The solvent is removed under reduced pressure and the residue is purified by chromatography using silica-gel (60-120 mesh) and petrol ether/EtOAc as eluent to afford (7 g, 53%) of the title compound as a yellow solid. $^1$H NMR (CDCl$_3$, 400 MHz) δ 7.52-7.55 (m, 1H), 7.42-7.47 (m, 1H), 7.11-7.16 (m, 1H), 7.06-7.09 (m, 1H), 6.23-6.29 (m, 1H), 4.15-4.18 (m, 2H), 3.88 (s, 3H).

Intermediate 60: 4-Methoxy-1-[(3-methylthio)prop-1-enyl]-2-nitrobenzene

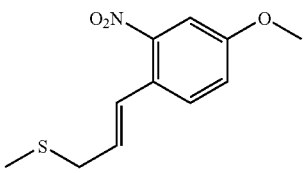

To stirred solution of 1-[3-bromoprop-1-enyl]-4-methoxy-2-nitrobenzene (5 g, 0.03 mol) in dry DCM (100 mL) under nitrogen, is added sodium thiomethoxide (2.6 g, 0.04 mol) in portions. After stirring at room temperature for 12 h, the reaction mixture is diluted with DCM (100 mL) and the organic phase is washed with water then brine, dried over $Na_2SO_4$ and concentrated under vacuum to afford (4 g, 97%) of the title compound as a brown liquid.

$^1$H NMR (CDCl$_3$, 400 MHz) δ 7.52-7.55 (m, 1H), 7.44-7.45 (m, 1H), 7.06-7.10 (m, 1H), 6.85-6.90 (m, 1H), 6.06-6.10 (m, 1H), 3.88 (s, 3H), 3.27-3.30 (m, 2H), 2.09 (s, 3H).

Intermediate 61: 5-Methoxy-2-[3-(methylthio)propyl]aniline

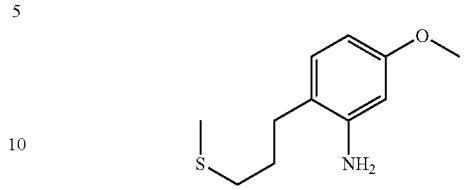

To a solution of 4-methoxy-1-[(3-(methylthio)prop-1-enyl]-2-nitrobenzene (5 g) in dry EtOH (300 mL), is added palladium on charcoal (5 g, 10%) and the mixture is hydrogenated under a pressure of 7 Kg/cm$^2$ of hydrogen for 12 h. The catalyst is removed by filtration and the filtrate is concentrated under reduced pressure. The residue is purified by chromatography using silica gel (60-120 mesh) and petrol ether/EtOAc as eluent to afford (3 g, 66%) of the title compound as a yellow thick liquid. $^1$H NMR (DMSO-d$_6$, 400 MHz) δ 6.74-6.77 (m, 1H), 6.17 (s, 1H), 6.03-6.06 (m, 1H), 4.83 (br s, 2H), 3.61 (s, 3H), 2.38-2.48 (m, 4H), 2.02 (s, 3H), 1.66-1.71 (m, 2H).

Intermediate 62: tert-Butyl 5-methoxy-2-[3-(methylthio)propyl]phenylcarbamate

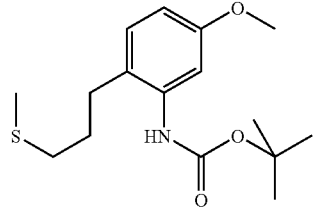 [SMILES: COc1ccc(CCCSC)c(NC(=O)OC(C)(C)C)c1]

To a stirred solution of 5-methoxy-2-[3-(methylthio)propyl]aniline (5 g, 0.02 mol) in dry THF (100 mL) is added di-terbutyl dicarbonate (5.1 g, 0.03 mol) and the reaction mixture is heated up to reflux for 4 h under nitrogen. The solvent is removed under reduced pressure to yield (7 g, 90%) of the title compound as brown liquid. $^1$H NMR (DMSO-d$_6$, 400 MHz) δ 8.48 (s, 1H), 7.05-7.07 (m, 1H), 6.87 (s, 1H), 6.65-6.67 (m, 1H), 3.69 (s, 3H), 2.49-2.50 (m, 2H), 2.39-2.43 (m, 2H), 2.02 (s, 3H), 1.68-1.71 (m, 2H), 1.45 (s, 9H).

Intermediate 63: tert-Butyl 5-methoxy-2-[3-(methylsulfonyl)propyl]phenylcarbamate

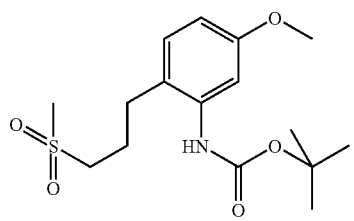 [SMILES: COc1ccc(CCCS(C)(=O)=O)c(NC(=O)OC(C)(C)C)c1]

To a stirred solution of tert-butyl 5-methoxy-2-[3-(methylthio)propyl]phenylcarbamate (7 g, 0.02 mol) in dry DCM (200 mL) at 0° C. is added m-CPBA (15.91 g, 0.09 mol) in one portion and the reaction mixture is stirred for 12 h at room temperature. The reaction mixture is filtered off and the filtrate is washed with 2% aqueous NaOH and dried over $Na_2SO_4$. The solvent is removed under reduced pressure to yield (6 g, 77%) of the title compound as yellow solid. $^1$H NMR (DMSO-$d_6$, 400 MHz) δ 8.54 (s, 1H), 7.07-7.10 (m, 1H), 6.91 (s, 1H), 6.67-6.69 (m, 1H), 3.69 (s, 3H), 3.00-3.04 (m, 214), 2.93 (s, 3H), 2.59-2.62 (m, 2H), 1.87-1.91 (m, 2H), 1.45 (s, 9H).

Intermediate 64:
5-Methoxy-2-[3-(methylsulfonyl)propyl]aniline-HCl salt

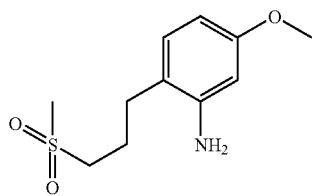 [SMILES: COc1ccc(CCCS(C)(=O)=O)c(N)c1]

To a stirred solution of tert-butyl 5-methoxy-2-[3-(methylthio)propyl]phenylcarbamate (6.5 g, 0.02 mol) in dioxane (10 mL) is added 3 M HCl in dioxane (150 mL) at 0° C. and the reaction mixture is stirred for 12 h at room temperature. The reaction mixture is concentrated under reduced pressure affording a brown solid. The solid is taken up in acetonitrile (30 mL) and the resulting suspension is filtered. The solid is dried under vacuum to afford 2.1 g, (45%) of the title compound as pale brown solid. $^1$H NMR (DMSO-$d_6$, 400 MHz) δ 9.50-10.2 (m, 3H), 7.19-7.21 (m, 1H), 6.84 (s, 1H), 6.78-6.80 (m, 1H), 3.80 (s, 3H), 3.08-3.12 (m, 2H), 2.96 (s, 3H), 2.63-2.67 (m, 2H), 1.93-1.96 (m, 2H). HPLC (max plot) 93%, Rt (min) 4.98. LC/MS: (ES+): 244.

Intermediate 65:
1-(2-Bromoethyl)-4-methoxy-2-nitrobenzene

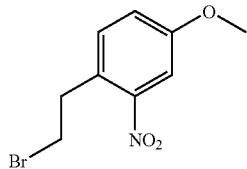

A suspension of triphenylphosphine (26 g, 1 mol) in DCM (100 mL) under nitrogen atmosphere at 25-26° C. is cooled down to 0-5° C. A solution of bromine (15.9 g, 0.1 mol) in DCM (150 mL) is added over 30 min at the same temperature. The reaction mixture is stirred for 15 min at 0-5° C. A solution of 2-(4-methoxy-2-nitrophenyl)ethanol (14 g, 0.07 mol) and pyridine (7.8 g, 0.1 mol) in DCM (100 mL) is added to the above reaction mixture over 30 min at 0-5° C. The resulting reaction mixture is warmed up to 25-26° C. and stirred for 3 h. The reaction is quenched by addition of cold water (250 mL). The crude product is extracted with DCM (2×200 mL). The organic layer is washed with water and brine (200 mL each), dried over $Na_2SO_4$ and concentrated to dryness. The crude residue obtained is purified by column chromatography (60-120 mesh silica gel, eluent: 5% EtOAc in petrol ether) to give 14.7 g (79%) of the title compound as a yellow solid. $^1$H NMR (DMSO-$d_6$, 400 MHz) δ 7.51-7.49 (m, 2H), 7.30-7.27 (m, 1H), 3.83 (s, 3H), 3.82-3.68 (m, 2H), 3.32-3.27 (m, 2H).

Intermediate 66:
4-Methoxy-1-[2-(methylthio)ethyl]-2-nitrobenzene

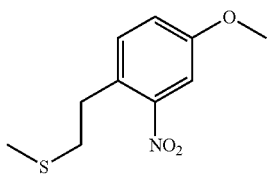

A suspension of 1-(2-bromoethyl)-4-methoxy-2-nitrobenzene (14.7 g, 0.06 mol) in EtOH (150 mL) is stirred at 25-26° C. under a nitrogen atmosphere. Sodium thiomethoxide (7.9 g, 0.1 mol) is added in one portion at 25-26° C. and the reaction mixture is heated to reflux for 12 h. The solvent is removed under reduced pressure and the brown residue is taken up in cold water (100 mL). The crude product is extracted with EtOAc (2×200 mL). The organic layer is washed with water and brine (200 mL, each), then dried over $Na_2SO_4$ and the solvent is removed under reduced pressure to afford a brown oil. The crude product is purified by column chromatography (60-120 mesh silica gel, eluent 2% EtaAc in petrol ether) to give 8.3 g (67%) of the title compound as light brown liquid. $^1$H NMR (DMSO-$d_6$, 400 MHz) δ 7.47-7.45 (m, 2H), 7.20-724(m 1H,), 3.81 (s, 3H), 3.01-2.97 (m, 2H), 2.69-2.66 (m, 2H), 2.05 (s, 3H). LC/MS: (ES+) 227.9.

Intermediate 67: 2-(4-Methoxy-2-nitrophenyl)ethyl methyl sulfone

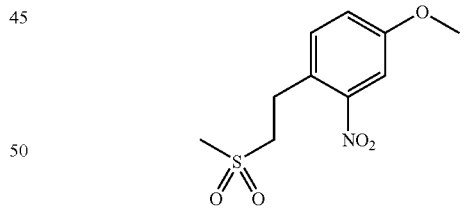

4-Methoxy-1-[2-(methylthio)ethyl]-2-nitrobenzene (5 g, 22 mmol) is taken up in DCM (120 mL) at 25-26° C. under nitrogen then cooled to –10° C. m-CPBA (8.7 g, 35 mmol) is added in one portion and stirred for 3 h at –10° C. The reaction is quenched by addition of cold water (150 mL). The crude product is extracted with DCM (2×250 mL). The organic layer is washed with a solution of sodium bicarbonate, water and brine (150 mL each) then dried over $Na_2SO_4$ and the solvent is removed under reduced pressure, affording 4.6 g (78%) of the title compound as light yellow solid. $^1$H NMR (DMSO-$d_6$, 400 MHz) δ 7.53-7.50 (m, 2H), 7.31-7.28 (m, 1H), 3.82 (s, 3H), 3.41-3.32 (m, 2H), 3.18-3.14 (m, 2H), 3.00 (s, 3H).

Intermediate 68: 1-Iodo-4-methoxy-2-nitrobenzene

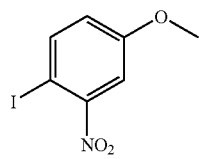

A mixture of 4-methoxy-2-nitroaniline (20 g, 0.12 mol) and concentrated HCl (30 mL) in water (30 mL) is refluxed for 15 min. The reaction mixture is cooled down to 0° C. in an ice bath. A solution of sodium nitrite (10 g, 0.14 mol) in water (30 mL) is added dropwise over 30 min. The resulting solution is stirred at 0° C. for 30 min then added dropwise to a cold solution of potassium iodide (30 g, 0.18 mol) in water (30 mL). The reaction mixture is heated to reflux for 2 h, cooled down to room temperature and diluted with EtOH (200 mL). The organic phase is washed with 3 N (100 mL) then water and dried over $Na_2SO_4$. The solvent is removed under reduced pressure and the crude product is purified by column chromatography using hexane as eluent affording 16 g (88%) of the title compound as a yellow crystalline $^1$H NMR (DMSO-$d_6$, 400 MHz) δ 7.93-7.91 (m, 1H), 7.54 (s, 1H), 7.04-7.01 (m, 1H), 3.82 (s, 3H).

Intermediate 69: 1-Allyl-4-methoxy-2-nitrobenzene

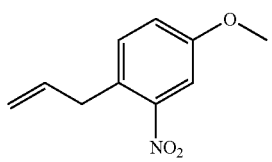

To a solution of 1-iodo-4-methoxy-2-nitrobenzene (5 g, 18 mmol) in THF (500 mL) are added cesium fluoride (11 g, 72 mmol) and Pd(PPh$_3$)$_4$ (0.56 g, 48 mmol). The resulting mixture is stirred for 30 min at room temperature. A solution of allylboronic acid pinacol ester (5.6 mL, 33 mmol) in THF (15 mL) is added dropwise. The resulting mixture is refluxed for 24 h then diluted with hexane (100 mL) followed by water (100 mL). The product is extracted with hexane (2×100 mL). The combined organic layers are washed with water (150 mL) then brine (150 mL) and dried over $Na_2SO_4$. The solvent is removed under reduced pressure and the residue is purified by column chromatography using hexane as eluent affording 1.8 g (48%) of the title compound as a brown liquid. $^1$H NMR (DMSO-$d_6$, 400 MHz) δ 7.93-7.91 (m, 1), 7.59-7.50 (m, 1H), 7.04-7.01 (m, 1H), 5.0-4.9 (m, 2H), 3.89-3.85 (m, 1H), 3.81 (s, 3H), 3.53-3.51 (m, 2H).

Intermediate 70: (2S,2R)-3-(4-Methoxy-2-nitrophenyl)propane-1,2-diol

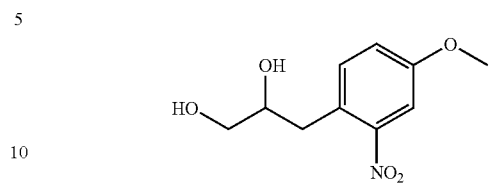

To a stirred solution of AD-Mix-alpha (5 g) and methane sulfonamide (500 mg, 5 mmol) in a mixture of tert-butanol (30 mL) and water (30 mL) at 0° C. is added 1-allyl-4-methoxy-2-nitrobenzene (1 g, 5 mmol). The reaction mixture is stirred at 0° C. for 5 h then at room temperature for 14 h. Sodium sulfite (5 g) is added and the mixture is stirred for an additional 2 h. The mixture is diluted with EtOAc (50 mL), washed with water (2×30 mL) then brine (2×20 mL) and dried over $Na_2SO_4$. The solvent is removed under reduced pressure and the crude product is purified by column chromatography using hexane: EtOAc (8:2) as eluent to afford 0.3 g (40%) of the title compound as a brown $^1$H NMR (DMSO-$d_6$, 400 MHz) δ 7.62-7.60 (m, 1H), 7.33-7.60 (m, 1H), 7.26-7.23 (m, 1H), 5.50-5.40 (m, 1H), 4.87-4.84 (m, 1H), 4.64-4.63 (m, 1H), 3.81 (s, 3H), 3.72-3.69 (m, 2H).

Intermediate 71: (4S,4R)-4-(4-Methoxy-2-nitrobenzyl)-2,2-dimethyl-1,3-dioxolane

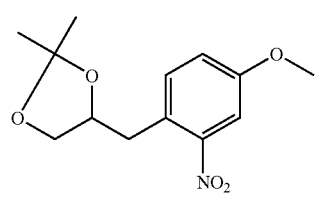 [SMILES: COc1ccc(CC2COC(C)(C)O2)c([N+](=O)[O-])c1]

To a stirred solution of (2S,2R)-3-(4-methoxy-2-nitrophenyl) propane-1,2-diol (3 g, 13.2 mmol) in 2,2-dimethoxypropane (30 mL) is added pyridinium p-toluene sulfonate (300 mg, 1.2 mmol). The reaction mixture is stirred for 6 h and the solid formed is filtered off. The filtrate is concentrated under reduced pressure then taken up in EtOAc. The organic phase is washed with water and dried over $Na_2SO_4$. The solvent is removed under reduced pressure to afford 2.2 g (62%) of the title compound as a thick brown liquid. $^1$H NMR (DMSO-$d_6$, 400 MHz) δ 7.44-742 (m, 2H), 7.25-7.22 (m, 1H), 4.22-4.19 (m, 1H), 3.99-3.95 (m, 1H), 3.81 (s, 3H), 3.56-3.52 (m, 1H), 3.08-2.9 (m, 2H), 2.42 (s, 6H).

Intermediate 72: N-(2-Hydroxyethyl)-4-methoxy-2-nitrobenzenesulfonamide

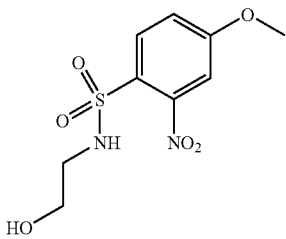 [SMILES: COc1ccc(S(=O)(=O)NCCO)c([N+](=O)[O-])c1]

4-Methoxy-2-nitrobenzenesulfonyl chloride (3.1 g; 12.3 mmol; 1 eq) is dissolved in DCM (60 mL) in the presence of triethylamine (1.7 mL; 12.3 mmol; 1 eq) at 0° C. Ethanolamine (0.6 mL; 13.6 mmol; 1.1 eq) is then added and the reaction mixture is stirred at room temperature for 16 h. Water is added to the reaction mixture then aqueous $Na_2CO_3$. The organic phase is dried over $MgSO_4$ and the solvent is evaporated under reduced pressure to give 2.9 g (85%) of the title compound as an orange oil, $^1$H NMR (DMSO-$d_6$) δ 7.92 (d, J=3.2 Hz, 1H), 7.85-7.78 (m, 1H), 7.56 (d, J=2.5 Hz, 1H), 7.37 (dd, J=8.9, 2.6 Hz, 1H), 4.79-4.71 (m, 1H), 3.90 (s, 3H), 3.42-3.46 (m, 2H), 2.92-2.87 (m, 2H). HPLC (max plot) 52.3%; Rt 220 min. UPLCIMS: (ES+) 277.2, (ES−) 275.2.

Intermediate 73: N-(2-Hydroxyethyl)-3-methoxy-5-nitrobenzamide

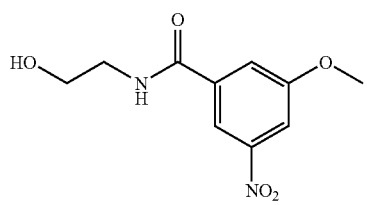

Oxalyl chloride (6.4 g; 50.7 mmol; 5 eq) is added to a suspension of 3-nitro-5-methoxy benzoic acid (2 g; 10 mmol; 1 eq) and DMF (cat.) in DCM (50 mL) and the resulting mixture is stirred at room temperature for 1 h then evaporated to dryness. The residue is taken up in THF (20 mL) and added to a solution of ethanolamine (3.1 g; 50.7 mmol; 5 eq) and DIEA (6.6 g; 50.7 mmol; 5 eq) in THF (40 mL). The resulting mixture is stirred at room temperature for 2 h. The solution is evaporated to dryness and the residue partitioned between EtOAc and 0.5 M HCl. The aqueous phase is extracted with EtOAc (3×) and the combined organic layer is washed successively with 0.5 M HCl (2×) then brine (2×). After drying over $MgSO_4$, the solution is concentrated in vacuo to afford a yellow solid. Trituration in a mixture of EtOAc and $Et_2O$ followed by filtration afforded 1.35 g (55%) of the title compound as an off-white solid. $^1$H NMR (DMSO-$d_6$) δ 8.84 (t, J=5.6 Hz, 1H), 8.29 (t, J=1.7 Hz, 1H), 7.86 (d, J=1.7 Hz, 2H), 4.77 (t, J=5.6 Hz, 1H), 3.93 (s, 3H), 3.54 (q, J=5.8 Hz, 2H), 3.35 (q, J=5.6 Hz, 2H), HPLC (max plot) 99%; Rt 1.73 mm.

Intermediate 74: 3-Methoxy-N-(2-methoxyethyl)-5-nitrobenzamide

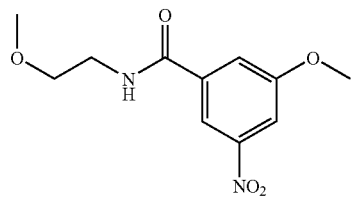 [SMILES: COCCNC(=O)c1cc(OC)cc([N+](=O)[O-])c1]

To a solution of 3-methoxy-5-nitrobenzoic acid (1 g; 5.1 mmol; 1 eq) DCM (40 mL) is added N-(3-dimethylaminopropyl)-N'-ethylcarbodiimide hydrochloride (972 mg; 5.1 mmol; 1 eq). After 5 min, 2-methoxyethylamine (381 mg; 5.1 mmol; 1 eq) is added and the reaction mixture is stirred at room temperature for 2 h. The reaction mixture is then quenched with water and the expected product extracted with EtOAc. The organic phase is washed with an aqueous solution of $Na_2CO_3$ then dried over $MgSO_4$. The solvent is evaporated to dryness to afford (1.3 g (100%) of the title compound as an orange oil. HPLC (max plot) 73.0%; Rt 2.98 min.

Intermediate 75: 3-Methoxy-N,N-dimethyl-5-nitrobenzamide

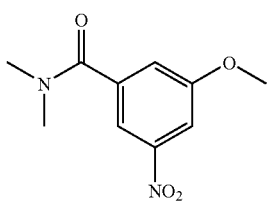

3-Methoxy-5-nitrobenzoic acid (1 g; 5.1 mmol; 1 eq) is preactivated with n-(3-dimethyl aminopropyl)-n'-ethylcarbodiimide hydrochloride (1.2 g; 6.1 mmol; 1.2 eq) in DCM (30 mL) for 10 mM. Dimethylamine (343 mg; 7.6 mmol; 1.5 eq) is then added and the reaction mixture stirred overnight. After quenching the reaction mixture with water, the organic phase is washed with water and citric acid (5%) and dried over $MgSO_4$. The solvent is evaporated to dryness according 1.1 g (97%) of the title compound as a red oil. $^1$H NMR (DMSO-$d_5$) δ 7.83-7.77 (m, 1H), 7.74-7.68 (m, 1H), 7.27-7.21 (m, 1H), 3.87 (s, 3H), 3.08 (s, 3H), 2.96 (s, 3H). HPLC (max plot) 91.9%; Rt 2.52 min.

Intermediate 76: 2-(2-Amino-4-methoxyphenyl)propan-2-ol

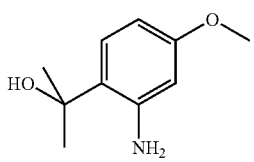

Methylmagnesium bromide (9.2 mL; 27.6 mmol; 5 eq) is diluted in THF (30 mL) at 0° C. and degassed with nitrogen for 10 min. A solution of 2-amino-4-methoxy-benzoic acid methyl ester (1 g; 5.5 mmol; 1 eq) in THF (10 mL) is added slowly at 0° C. and reaction mixture is stirred at room temperature overnight. Water (1 mL) is added slowly and the expected compound is extracted with EtOAc. The organic phase is dried over MgSO$_4$ and the solvent is removed under reduced pressure affording 1.1 g of a crude residue. It is purified on silica gel using cyclohexane/EtOAc (80/20) as eluent to afford 700 mg (70%) of the title compound as a white solid. $^1$H NMR (DMSO-d$_6$) δ 6.89 (d, J=9.0 Hz, 1H), 6.18 (d, J=3.0 Hz, 1H), 6.05 (dd, J=9.0, 3.0 Hz, 1H), 5.46-5.40 (m, 2H), 5.10-5.05 (m, 1H), 3.63 (s, 3H), 1.45 (s, 6H). HPLC (max plot) 100%; Rt 1.49 min.

Intermediate 77: 2-Isopropyl-5-methoxyaniline

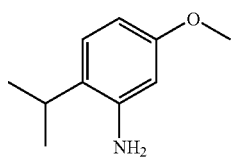

To a solution of 2-(2-amino-4-methoxyphenyl)propan-2-ol (210 mg; 1.2 mmol; 1 eq) in a mixture of EtOH (10 mL), EtOAc (3 mL) and 5 N (1 mL) under nitrogen atmosphere is added palladium on charcoal (130 mg; 10%) and the reaction mixture is hydrogenated for 1 week at room temperature at 1 atmosphere. The catalyst is filtered through celite and the organic solvents are removed under vacuum. The residue is taken up in EtOAc. The organic phase is washed with a saturated aqueous solution of Na$_2$CO$_3$ and dried over MgSO$_4$. The solvent is evaporated under reduced pressure to afford 160 mg (84%) of the title compound as a red oil. The compound is used in the next step without further purification. $^1$H NMR (DMSO-d$_6$) δ 6.89 (d, J=9.0 Hz, 1H), 6.18 (d, J=3.0 Hz, 1H), 6.05 (dd, J=9.0, 3.0 Hz, 1H), 5.45-5.39 (m, 2H), 3.85 (s, 3H), 3.30-3.11 (m, 1H), 1.97 (s, 6H). HPLC (max plot) 70%; Rt 1.88 min.

Intermediate 78: Pyridine-3-sulfonamide

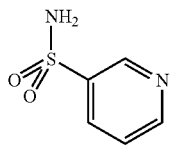

To a solution of pyridine-3-sulphonyl chloride (1 g, 5.6 mmol, 1 eq, commercially available from Davos) in THF (5 mL) is added ammonia in dioxane (23.9 mL, 2 M, 47.9 mmol, 8.5 eq). The resulting suspension is stirred at room temperature for 1 h. The solvent is removed and the residue is taken up in DCM. The organic phase is washed with a saturated aqueous solution of NH$_4$Cl then brine and the DCM is removed under reduced pressure to afford, after drying under vacuum at 40° C., 637 mg (71%) of the title compound as a yellowish powder. $^1$H NMR (DMSO-d$_6$) δ 9.20-8.90 (m, 1H), 8.85-8.75 (m, 1H), 8.40-8.05 (m, 1H), 7.80-7.40 (m, 3H).

Intermediate 79: 5-(Aminosulfonyl)-2-methylpyridine-N-oxide

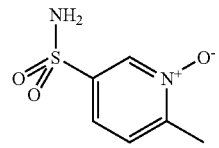

To a solution of 6-methylpyridine-3-sulfonamide (0.5 g, 3 mmol) in chloroform (40 mL) is added mCPBA (1.5 g; 8.7 mmol) and the reaction mixture is stirred overnight under nitrogen. The solvent is evaporated under reduced pressure. The residue is taken up in ACN and the precipitate is filtered off then dried under vacuum to afford 0.4 g (73%) of the title compound as an off white solid. $^1$H NMR (DMSO-d$_6$, 400 MHz) δ 8.53 (s, 1H), 7.74 (s, 2H), 7.69-7.64 (m, 1H), 7.59-7.52 (m, 1H), 2.4 (s, 3H).

Intermediate 80: 4-(aminosulfonyl)-N,N-dimethylbenzamide

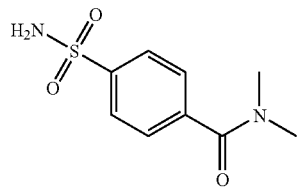

To a solution of 4-carboxybenzenesulfonamide (5 g; 24.8 mmol; 1 eq) in THF (75 mL) at 0° C. is added in one portion 1,1'-carbonyl diimidazole (4.8 g; 29.8 mmol; 1.2 eq) and the reaction mixture is stirred for 3 h at room temperature. A solution of dimethylamine (37.3 mL; 2 M; 74.6 mmol; 3 eq) in THF is added dropwise over 20 min and the reaction mixture is stirred at room temperature for 1 h. The solvent is removed under reduced pressure and the residue is diluted with EtOAc (100 mL) and the organic phase is washed with a 10% solution of NaHCO$_3$ (30 mL). The white precipitate formed in the aqueous phase is filtered off, washed with water and dried under vacuum to afford 4.1 g (72%) of the title compound as a white solid. $^1$H NMR (DMSO-d$_6$) δ 7.86 (d, J=8.3 Hz, 2H), 7.58 (d, J=8.3 Hz, 2H), 7.45 (s, 2H), 3.00 (s, 3H), 2.88 (s, 3H). HPLC (max plot) 99%; Rt 1.07 min. LC/MS: (ES+): 229.0.

Intermediate 81: 4-[(4-Fluoropiperidin-1-yl)carbonyl]benzenesulfonamide

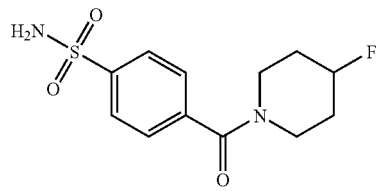 [SMILES: NS(=O)(=O)c1ccc(C(=O)N2CCC(F)CC2)cc1]

To a solution of 4-carboxybenzenesulfonamide (2 g; 9.9 mmol; 1 eq) in THF 30 mL) at 0° C. is added 1,1'-carbonyldiimidazole (1.9 g; 11.9 mmol; 1.2 eq) in one portion and the mixture is stirred for 3 h at room temperature. 4-Fluoropiperidine (3.1 g; 29.8 mmol; 3 eq) in THF (3 mL) and DMF (10 mL) is added dropwise and the mixture is stirred at room temperature for 2 h. The solvent is removed under reduced pressure and a saturated solution of $NaHCO_3$ is added to the colourless oil which precipitates. The solid is filtered off, washed with water and dried under vacuum to afford 2.6 g (91%) of the title compound as a white solid. $^1$H NMR (DMSO-$d_6$) δ 7.87 (d, J=8.3, 2H), 7.58 (d, J=8.3, 2H), 7.37 (br s, 2H), 4.92 (d, J=48.2, 1H), 3.67 (br s, 2H), 3.25 (br s, 2H), 1.87 (m, HPLC (max plot) 99%; Rt 1.77 min. LC/MS: (ES+) 287.0; (ES−) 285.0

Intermediate 82: Propane-1-sulfonamide

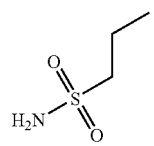

Diethylether (20 mL) is saturated with ammonia and the solution is cooled to 0° C. then 1-propanesulfonyl chloride (0.8 mL; 7 mmol; 1 eq) is added dropwise to the solution and ammonia is bubbled through for 10 min at 0° C. The solvent is evaporated and the residue is suspended in DCM. After sonication, the solid is filtered off and the filtrate is evaporated to give 878 mg (100%) of the title compound as a colourless liquid. 1H NMR (DMSO-$d_6$) δ 4.64 (br s, 2H), 3.13-3.08 (m, 2H), 1.94-1.87 (m, 2H), 1.08 (t, J=7.4 Hz, 3H).

Intermediate 83: Propane-2-sulfonamide

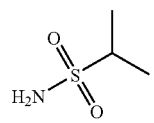

Anhydrous diethylether (20 mL) is saturated with ammonia then isopropyisulfonyl chloride (0.8 mL; 7 mmol; 1 eq) is added dropwise at 0° C. to the solution. Ammonia is bubbled through the solution for an additional 30 min, then stirred at room temperature for 2 days. The solvent is evaporated and the residue suspended in DCM. The $NH_4Cl$ formed is filtered off and the filtrate is concentrated under reduced pressure to give a solid residue. It is purified using a SPE $NH_2$ (2 g) column using DCM as eluent affording, after evaporation of the solvent and drying, 750 mg (87%) of the title compound as an off white solid. $^1$H NMR (DMSO-$d_6$) δ 4.66 (br s, 2H), 3.22 (sept., J=6.8 Hz, 1H), 1.41 (d, J=6.8 Hz, 6H).

Intermediate 84: Cyclohexanesulfonamide

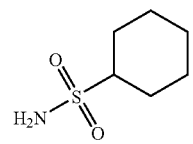

Diethylether (20 mL) is saturated with ammonia then cyclohexanesulfonyl chloride (909 mg; 5 mmol; 1 eq) is added dropwise to the reaction mixture at 0° C. Ammonia is bubbled through the solution for 10 additional min. The resulting solution is stirred at room temperature overnight. The solvent is evaporated and the residue is triturated in DCM. The $NH_4Cl$ formed is filtered off and the filtrate is concentrated. The residue obtained is dried and purified using a silica plug. The product is eluted with DCM lien the solvent is removed under reduced pressure to afford 743 mg (91%) of the title compound as a white solid. $^1$H NMR (DMSO-$d_6$) δ 4.39 (br s, 2H), 2.92 (tt, J=11.9, 3.5 Hz, 1H), 2.28-2.23 (m, 2H), 1.95-1.89 (m, 2H), 1.76-1.70 (m, 1H), 1.57-1.45 (m, 2H), 1.38-1.14 (m, 3H).

Intermediate 85: Tetrahydrothiophene-3-sulfonamide 1,1-dioxide

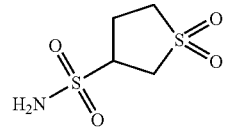

Dioxane (30 mL) is saturated with ammonia and cooled down to 0° C. A solution of tetrahydrothiophene-3-sulfonyl chloride 1,1-dioxide (0.5 g; 2.3 mmol; 1 eq) in dioxane (5 mL) is then added dropwise over 10 min. The reaction mixture is allowed to return to room temperature and stirred for 3 h while keeping ammonia bubbling. The suspension is filtered through a short plug of silica using dioxane as eluent, and the resulting solution is concentrated in vacuo to give a slightly yellow oil. The oil is taken up in MeOH and the solvent is evaporated to dryness to afford 0.37 g (81%) of the title compound as a beige solid. $^1$H NMR (DMSO-$d_6$) δ 7.25 (s, 2H), 3.98 (quint., J=8.3 Hz, 1H), 3.49 (dd, J=14.0, 9.1 Hz, 1H), 3.38-3.14 (m, 3H), 2.50-2.24 (m, 2H).

Intermediate 86: 3-(Methylthio)propane-1-sulfonic acid-sodium salt

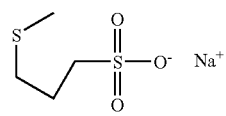

To a suspension of sodium thiomethoxide (22.95 g, 0.38 mol) in dry MeOH (250 mL) under nitrogen is added dropwise at 0° C. a solution of 1,3-propane sulfone (20 g, 0.16 mol) MeOH. A white solid precipitates out and after stirring at room temperature for 3 h, the reaction mixture is concen-

Intermediate 87: 3-(Methylthio)propane-1-sulfonamide

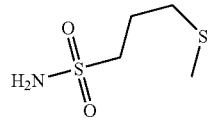

To a stirred suspension of sodium 3-(methylthio)propane-1-sulfonate (20 g) in dry DCM (200 mL), is added dropwise oxalyl chloride (80 mL) at 0° C. After stirring at room temperature for 3 h, the reaction mixture is concentrated under reduced pressure and ice (100 g) is added. The product is extracted with DCM (2×200 mL) and the organic phase is washed with brine then dried over $Na_2SO_4$. The solvent is removed under reduced pressure to afford 12 g of 3-(Methylthio)propane-1-sulfonyl chloride as colorless liquid. A solution of 3-(methylthio)propane-1-sulfonyl chloride (12 g) in dry THF (100 mL) is added dropwise to a solution of ammonia in dry THF (250 mL) at −78° C. After stirring at room temperature for 3 h, the reaction mixture is concentrated under reduced pressure. The residue is purified by chromatography using silica gel (60-120 mesh) and $CHCl_3$/MeOH as eluent to afford 9 g (84%) of the title compound as pale a yellow solid. $^1$H NMR (DMSO-$d_6$, 400 MHz) δ 6.80 (br s, 2H), 3.02-3.06 (m, 2H), 2.55-2.59 (m, 2H), 2.03 (s, 3H), 1.89-1.92 (m, 2H).

Intermediate 88: 3-(Methylsulfonyl)propane-1-sulfonamide

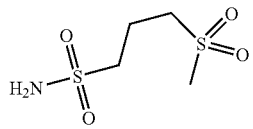

To a stirred solution of 3-(methylthio)propane-1-sulfonamide (7 g, 0.04 mol) AcOH (70 mL) is added a solution of hydrogen peroxide 30% (21 mL, 0.21 mol) at 0° C. After stirring at 80° C. for 12 h, the reaction mixture is concentrated under reduced pressure to afford 6 g (72%) of the title compound as a white solid. $^1$H NMR (DMSO-$d_6$, 400 MHz) δ 6.90 (br s, 2H), 3.24-3.28 (m, 2H), 3.09-3.13 (m, 2H), 2.98 (s, 3H), 2.08-2.12 (m, 2H).

Intermediate 89: Benzyl 4-(aminosulfonyl)piperidine-1-carboxylate

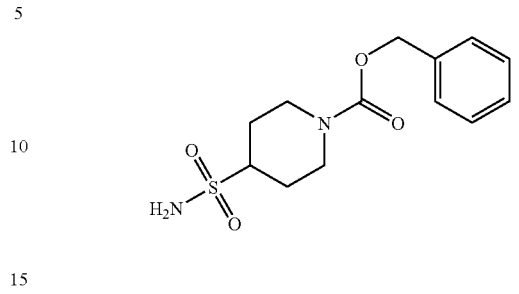

Dioxane (250 mL) is saturated with ammonia and cooled down to 0° C. A solution of benzyl-4-(chlorosulfonyl)piperidine-1-carboxylate (10 g; 31.5 mmol; 1 eq) in dioxane (25 mL) is added dropwise over 10 min. The reaction mixture is stirred at room temperature for 3 h while keeping ammonia bubbling. The suspension is filtered through a short plug of silica using dioxane as eluent and the resulting solution is concentrated in vacuo to give a colourless oil. The oil is taken up in MeOH and concentrated in vacuo to give a white foam which is crystallised from EtOAc and $Et_2O$ to afford 8.1 g (86%) of the title compound as a white solid. $^1$H NMR (DMSO-$d_6$) δ 7.40-7.29 (m, 5H), 6.79 (s, 2H), 5.08 (s, 2H), 4.10 (br d, J=13.3 Hz, 2H), 3.05 (tt, J=11.9, 3.6 Hz, 1H), 2.95-2.75 (m, 2H), 2.0 (dd, J=1.8, 11.5 Hz, 2H), 1.46 (dq, J=12.5, 4.4 Hz, 2H). HPLC (max plot) 82%; Rt 3.55 min.

Intermediate 90: Methyl 3-[4-(aminosulfonyl)phenyl]propanoate

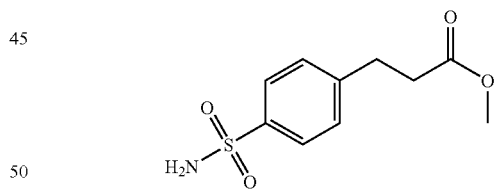

To a solution of methyl-3-(4-chlorosulphonyl)phenylpropionate (2 g; 7.6 mmol; 1 eq) in THF (5 mL) is added ammonia in MeOH (19 mL; 2M; 38 mmol; 5 eq). The resulting suspension is stirred overnight at room temperature. The solvent is removed under reduced pressure and the residue is taken up in DCM. The organic phase is washed with a saturated aqueous solution of $NH_4Cl$ then brine and the DCM is removed under reduced pressure affording, after drying under vacuum at 40° C., 1.5 g (82%) of the title compound as an off white powder. It is used as such in the next experiment. HPLC (max plot) 93%; Rt 2.07 min. LC/MS: (ES−) 241.9.

(Previous section continued at top:) trated under reduced pressure to afford 40 g (55%) of the title compound as a white hygroscopic solid. $^1$H NMR ($D_2O$, 400 MHz) δ 2.86-2.9 (m, 2H), 2.51-2.54 (m, 2H), 2.16 (s, 3H), 1.88-1.94 (m, 2H).

Intermediate 91:
N-[3-(Aminosulfonyl)phenyl]-2-(benzyloxy)acetamide

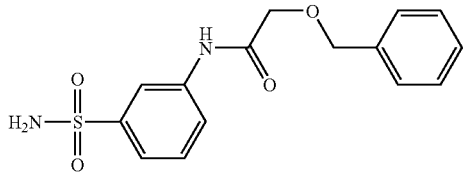 [SMILES: NS(=O)(=O)c1cccc(NC(=O)COCc2ccccc2)c1]

A suspension of 1-aminobenzene-3-sulfonamide (1 g; 5.8 mmol; 1 eq) in a mixture of acetone (10 mL) and water (10 mL) is stirred at room temperature until complete dissolution. Benzyloxyacetyl chloride (1.4 mL; 8.7 mmol; 1.5 eq) is added at 0° C. followed by the addition of NaHCO$_3$ (1.4 g) over 15 min. After 30 min, the reaction mixture is allowed to stir at room temperature for 2 h. The reaction mixture is then filtered off and the solid residue is washed with MeOH and ACN. The filtrate is concentrated to dryness, affording 1.8 g (97%) of the title compound as a brown foam. $^1$H NMR (DMSO-d$_6$) δ 8.25 (br s, 1H), 7.81-7.75 (m, 1H), 7.55-7.48 (m, 2H), 7.42-7.28 (m, 8H), 4.62 (s, 2H), 4.13 (s, 2H). HPLC (max plot) 91%; Rt 2.53 min. UPLC/MS: (ES+) 321.2; (ES−) 319.2.

Intermediate 92:
2-Dimethylamino-N-[3-sulfamoyl)phenyl]-acetamide

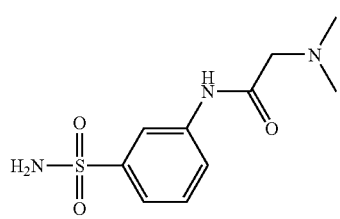 [SMILES: CN(C)CC(=O)Nc1cccc(S(N)(=O)=O)c1]

A solution of 1-aminobenzene-3-sulfonamide (1.5 g; 8.7 mmol; 1 eq) in a mixture of acetone (10 mL) and water (10 mL) is stirred at room temperature. Dimethylaminoacetyl chloride hydrochloride (2.1 g; 13.1 mmol; 1.5 eq) is added at 0° C. followed by the addition of NaHCO$_3$ (2.2 g) over 15 min. After 30 min, the reaction mixture is stirred at room temperature for 15 h. The reaction is completed by addition of dimethylaminoacetyl chloride hydrochloride (1.9 g; 12.02 mmol; 1.4 eq). The reaction mixture is then filtered and the solid is washed with MeOH and ACN. The filtrate is concentrated to dryness and purified by chromatography using MeOH as eluent, affording 1.9 g (85%) of the title compound as a yellow solid. $^1$H NMR (DMSO-d$_6$) δ 10.19 (s, 1H), 8.28-8.24 (m, 1H), 7.80-7.75 (m, 1H), 7.52-7.45 (m, 2H), 7.33 (s, 2H), 3.09 (s, 2H), 2.28 (s, 6H). HPLC (max plot) 68%; Rt 1.56 min. UPLC/MS: (ES+): 258.1, (ES−): 256.2.

Intermediate 93:
Methyl[4-(aminosulfonyl)phenoxy]acetate

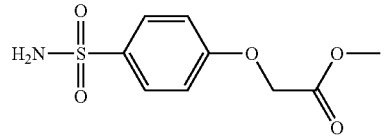

To a stirred suspension of NaH (2.8 g, 0.07 mol, 50% in mineral oil) in DMF (50 mL) is added dropwise methyl glycolate (5.5 g, 0.06 mol) over a period of 10 min. The mixture is heated up to 50° C. for 3 h and cooled down to room temperature. 4-Fluorobenzenesulfonamide g, 0.0114 mol) is added portionwise. After stirring at 50° C. for 10 h, the reaction mixture is cooled down and poured into ice-water containing HCl. The product is extracted with DCM (2×100 mL). The combined organic phase is washed with water and dried over Na$_2$SO$_4$. The solvent is evaporated under reduced pressure and the residue is purified by chromatography (silica gel, 60-120 mesh) with chloroform/methanol (9/1) as eluent to afford 900 mg (32%) of the title compound as a solid. $^1$H NMR (CDCl$_3$, 400 MHz) δ 7.68-721 (m, 2H), 7.10-7.12 (m, 2H), 6.45 (br s, 2H), 4.51 (s, 2H), 3.86 (s, 3H).

Intermediate 94: 2-(Chloromethyl)-1-methyl-1H-imidazole-4-sulfonamide

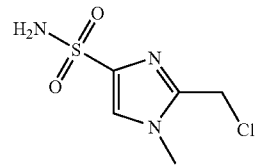

Chlorosulphonic acid (104 g, 0.9 mol) is added to (1-methyl-1H-imidazol-2-yl)methanol (10 g, 0.09 mol) at 0-5° C. under nitrogen atmosphere. The reaction mixture is heated to 150° C. then stirred for 3 h at the same temperature. The reaction mixture is cooled down to room temperature then to 0-5° C. and thionyl chloride (105 g, 0.9 mol) is added slowly. The reaction mixture is heated up to 100° C. for 3 h. The reaction mixture is cooled down to room temperature and poured into cold water (150 mL). The crude sulfonyl chloride is extracted with EtOAc (3×200 mL). The organic layer is dried over Na$_2$SO$_4$ and concentrated under reduced pressure to get the crude sulfonyl chloride as a brown oil (7.8 g). The crude intermediate is cooled down to 0-5° C. and cold aqueous ammonia (20 mL) is added dropwise over 10 min and the reaction mixture is stirred for 1 h at the same temperature. The precipitate is filtered off, washed with cold water then dried to afford 2.5 g (12.5%) of the title compound as a brown solid. $^1$H NMR (DMSO-d$_6$, 400 MHz) δ 7.69 (s, 1H), 7.20 (s, 2H), 4.88 (s, 2H), 3.71 (s, 3H). LC/MS: (ES+) 209.7.

Intermediate 95: 2-[(Dimethylamino)methyl]-1-methyl-1H-imidazole-4-sulfonamide

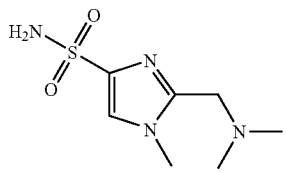

To a suspension of 2-chloromethyl-1-methyl-1H-imidazole-4-sulfonic sulfonamide (2.9 g; 13.9 mmol; 1 eq) in THF (80 mL) is added a solution of dimethylamine (139.2 mL; 2 M; 278.5 mmol; 20 eq) and the resulting suspension is stirred at room temperature overnight. The solvent is removed under reduced pressure and the residue taken up in DCM, warmed up to reflux and the remaining insoluble material is filtered off then washed with hot DCM (×3) according 2.4 g (79%) of the title compound as a beige powder. $^1$H NMR (DMSO-$d_6$) δ 7.60 (s, 1H), 7.09 (s, 2H), 3.68 (s, 3H), 3.45 (s, 2H), 2.15 (s, 6H). CHN analysis: [C7H14N4O2S-0.015 CH2Cl2] Calculated: C38.38%, H6.44%, N25.52%; Found: C38.73%, H6.41%, N25.25%.

Intermediate 96: 2-(Hydroxymethyl)-1-methyl-1H-imidazole-4-sulfonamide

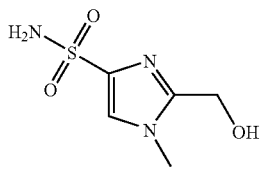

To a stirred suspension of 2-(chloromethyl)-1-methyl-1H-imidazole-4-sulfonamide (300 mg; 1.4 mmol; 1 eq) in water (5 mL) is added potassium carbonate (300 mg; 2.2 mmol; 1.5 eq) in portions and the reaction mixture is stirred at room temperature for 2 h. THF (5 mL) is added and reaction mixture is heated up to 60° C. for 3 h. The reaction mixture is cooled down and the THF is removed under reduced pressure. The resulting suspension is freeze dried to give 320 mg (contaminated with potassium salts) of the title compound as a white solid. $^1$H NMR (DMSO-$d_6$) δ 7.58 (s, 1H), 7.10-6.40 (m, 2H), 4.18 (s, 2H), 3.68 (s, 3H). HPLC (max plot) 68%; Rt 0.96 min. LC/MS (ES+) 191.8; (ES−) 189.9.

Intermediate 97: 2-({[tert-Butyl(dimethyl)silyl]oxy}methyl)-1-methyl-1H-imidazole-4-sulfonamide

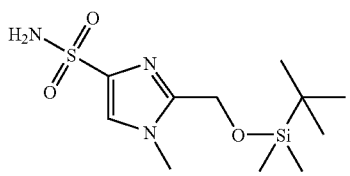 [SMILES: Cn1cc(S(N)(=O)=O)nc1CO[Si](C)(C)C(C)(C)C]

2-(Hydroxymethyl)-1-methyl-1H-imidazole-4-sulfonamide (250 mg; 1.3 mmol; 1 eq), tert-butyldimethylehlorosilane (394 mg; 2.6 mmol; 2 eq) and triethylamine (0.36 mL; 2.6 mmol; 2 eq) are stirred at room temperature for 18 h in THF (5 mL). EtOAc is added (50 mL) followed by water (5 mL). The product is extracted with EtOAc and the organic phase is dried with MgSO$_4$. The solvent is evaporated to dryness to give 160 mg (40%) of the title compound as a white powder. $^1$H NMR (DMSO-$d_6$) δ 7.50 (s, 1H), 7.10-7.0 (m, 2H), 4.61 (s, 2H), 3.61 (s, 3H), 0.80 (s, 9H), 0.10 (s, 6H). HPLC (max plot) 84%; Rt 3.57 min. LC/MS: (ES+) 305.9; (ES−) 304.5.

Intermediate 98: 1-Methyl-2-[(methylthio)methyl]-1-imidazole-4-sulfonamide

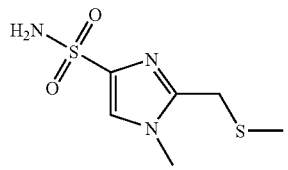

To a solution of 2-(chloromethyl)-1-methyl-1H-imidazole-4-sulfonamide (7.3 g, 0.03 mol) in DCM (500 mL) is added sodium thiomethoxide (3.7 g, 52 mmol) in portions at room temperature. The resulting suspension is stirred until completion of the reaction. The mixture is diluted with DCM (100 mL), the organic phase is washed with water (50 mL) then dried over Na$_2$SO$_4$. The solvent is evaporated to afford 6 g (78%) of the title compound as a brown solid. $^1$H NMR (CDCl$_3$, 400 MHz) δ 7.59 (s, 1H), 7.10 (br s, 2H), 3.79 (s, 2H), 3.65 (s, 3H), 2.03 (s, 3H).

Intermediate 99: 1-Methyl-2-[(methylsulfonyl)methyl]-1H-imidazole-4-sulfonamide

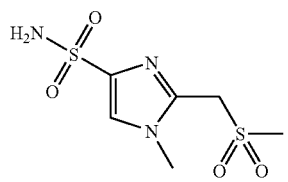

To a solution of 1-methyl-2-[(methylthio)methyl]-1H-imidazole-4-sulfonamide (6.1 g, 30 mmol) in DCM (500 mL) is added mCPBA (18.9 g, 110 mmol) in portions at room temperature. The resulting suspension is stirred for 5 h. The precipitate is filtered off and the filtrate is washed with 5% aqueous NaOH (2×100 mL) then water and dried over Na$_2$SO$_4$. The solvent is evaporated to afford 3 g (43%) of the title compound as a brown solid. NMR (CDCl$_3$, 400 MHz) δ 7.71 (s, 1H), 7.21 (br s, 2H), 1.78 (s, 2H), 3.68 (s, 3H), 3.06 (s, 3H).

Intermediate 100: 3,5-Dimethylisoxazole-4-sulfonamide

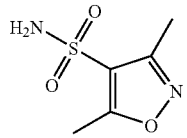

3,5-Dimethylisoxazole-4-sulfonyl chloride (4.3 g; 21.8 mmol; 1 eq) is dissolved in THF (10 mL), ammonia in MeOH (55 mL; 2 M; 109 mmol; 5 eq) is added and the reaction is stirred for 1 h at room temperature. The reaction mixture is concentrated under reduced pressure and the residue is taken up in 100 mL of EtOAc. The organic phase is washed with a saturated aqueous solution of NH$_4$Cl (100 mL) then dried over MgSO$_4$. The solvent is removed under reduced pressure, affording 2.6 g (67%) of the title compound as a white solid. $^1$H NMR (DMSO-d$_6$) δ 7.59 (s, 2H), 2.56 (s, 3H), 2.34 (s, 3H). HPLC (max plot) 96.5%; Rt 1.22 min.

Procedure G

Intermediate 101: 4-{[(3-chloroquinoxalin-2-yl)amino]sulfonyl}-N,N-dimethylbenzamide

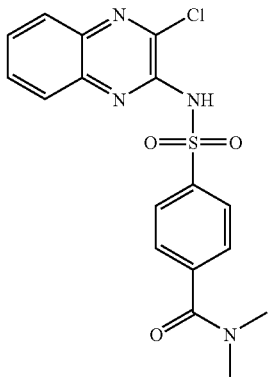 [SMILES: CN(C)C(=O)c1ccc(S(=O)(=O)Nc2nc3ccccc3nc2Cl)cc1]

2,3-Dichloroquinoxaline (3.5 g; 17.6 mmol; 1 eq), 4-(aminosulfonyl)-N,N-dimethylbenzamide (4 g; 17.6 mmol; 1 eq) and anhydrous K$_2$CO$_3$ (2.4 g; 17.6 mmol; 1 eq) are taken up in DMA (35 mL) and the resulting suspension is heated at 135° C. for 1 h. After evaporation of the DMA under reduced pressure, the reaction is stopped by addition of water (20 mL) then the suspension is acidified with a 25% aqueous solution of citric acid (70 mL). After overnight standing at 4° C., the yellow precipitate is filtered off, washed several times with water until pH=6 and dried under vacuum at 40° C. overnight affording 5.73 g of a yellow solid. It is taken up in EtOH (25 mL) and the suspension is heated for a few minutes. The precipitate is filtered off and washed twice with EtOH (10 mL) then dried under vacuum at 40° C. overnight to afford 3.96 g (57.6%) of the title compound as a yellow solid. $^1$H NMR (DMSO-d$_6$) δ 8.27-8.24 (d, J=8.3 Hz, 2H), 7.91 (t, J=7.2 Hz, 2H), 7.79-7.74 (m, 2H), 7.73-7.66 (m, 3H), 3.02 (s, 3H), 2.88 (s, 3H). HPLC (max plot) 95%; Rt 3.18 min. LC/MS: (ES+): 391.3, (ES−): 389.2.

Intermediate 102: N-(3-Chloroquinoxalin-2-yl)-4-[(4-fluoropiperidin-1-yl)carbonyl]benzenesulfonamide

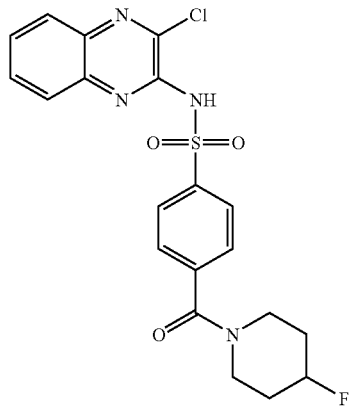 [SMILES: O=C(c1ccc(S(=O)(=O)Nc2nc3ccccc3nc2Cl)cc1)N1CCC(F)CC1]

Following the protocol outlined in Procedure G, intermediate 102 is obtained from 2,3-dichloroquinoxaline (2.1 g; 10.6 mmol; 1 eq), 4-[(4-fluoropiperidin-1-yl)carbonyl]benzene sulfonamide (3 g; 10.6 mmol; 1 eq) in the presence of K$_2$CO$_3$ (1.5 g; 10.6 mmol; 1 eq) in DMA (21 mL) under microwave conditions at 170° C. for 30 min, to afford 2.2 g (47%) of the title compound as a yellow solid. $^1$H NMR (DMSO-d$_6$) δ 8.22 (d, J=8.3 Hz, 2H), 7.87 (t, J=8.3 Hz, 2H), 7.79-7.73 (m, 1H), 7.69-7.62 (m, 3H), 5.0-4.81 (m, 1H), 3.72-3.57 (m, 3H), 3.42-3.28 (m, 1H), 3.25-3.12 (m, 1H), 1.99-1.60 (m, 4H). HPLC (max plot) 96%; Rt 3.64 min. LC/MS: (ES+) 449.2, (ES−) 447.2.

Intermediate 103: N-(3-Chloro-2-quinoxalinyl)benzenesulfonamide

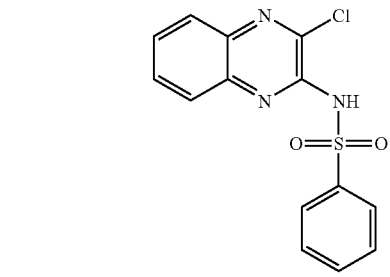 [SMILES: O=S(=O)(Nc1nc2ccccc2nc1Cl)c1ccccc1]

Following the protocol outlined in Procedure G, Intermediate 103 is obtained from 2,3-dichloroquinoxaline (1 g, 5 mmol, 1 eq) and benzenesulfonamide (790 mg, 5 mmol; 1 eq) in the presence of K$_2$CO$_3$ (694.4 mg, 5 mmol; 1 eq.) in DMA (10 mL) under microwave conditions at 170° C. for 30 min, to afford 1.3 g (80%) of the title compound as a yellow powder. $^1$H NMR (DMSO-d$_6$) δ 10.80 (br s, 1H), 8.25-8.08 (m, 2H), 7.95-7.50 (m, 7H). HPLC (max plot) 90%; Rt 3.54 min, LC/MS: (ES+) 320.0, (ES−) 318.0.

Intermediate 104: N-(3-chloroquinoxalin-2-yl)-4-fluorobenzenesulfonamide

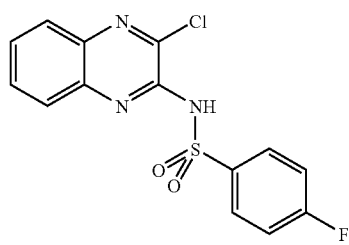 [SMILES: O=S(=O)(Nc1nc2ccccc2nc1Cl)c1ccc(F)cc1]

Following the protocol outlined in Procedure G, Intermediate 104 is obtained from 2,3-dichloroquinoxaline (1 g, 5 mmol, 1 eq) and 4-fluorobenzenesulfonamide (880.1 mg, 5 mmol, 1 eq) in the presence of $K_2CO_3$ (694.3 mg, 5 mmol, 1 eq) in DMA (5 mL) under microwave conditions at 170° C. for 30 min, to afford 540 mg (32%) of the title compound as a yellow solid. $^1$H NMR (DMSO-$d_6$) δ 8.24 (dd, J=9.1, 5.3 Hz, 2H), 7.88 (br dd, 2H), 7.79-7.74 (m, 1H), 7.69-7.64 (m, 1H), 7.49-7.43 (m, 2H). HPLC (max plot) 89%; Rt 3.87 min. LC/MS: (ES+): 338.1, (ES−):336.1.

Intermediate 105: N-(3-Chloroquinoxalin-2-yl)-4-cyanobenzenesulfonamide

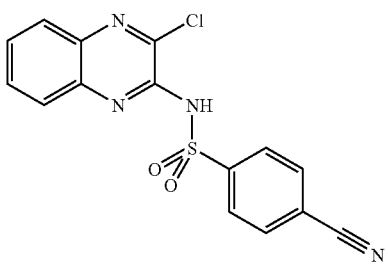 [SMILES: N#Cc1ccc(S(=O)(=O)Nc2nc3ccccc3nc2Cl)cc1]

Following the protocol outlined in Procedure G, Intermediate 104 is obtained from 2,3-dichloroquinoxaline (1 g; 5 mmol; 1 eq), 4-cyanobenzenesulphonamide (915.4 mg; 5 mmol; 1 eq) in the presence of $K_2CO_3$ (694.4 mg; 5 mmol; 1 eq) in DMA (10 mL) under microwave conditions at 170° C. for 30 min, to afford 1.37 g (79%) of the title compound as an off white powder. $^1$H NMR (DMSO-$d_6$) δ 8.29 (dd, J=8.6, 1.9 Hz, 2H), 8.09 (dd, J=8.6, 1.9 Hz, 2H), 7.90-7.79 (m, 2H), 7.74 (dt, J=7.2, 1.5 Hz, 1H), 7.68-7.59 (m, HPLC (max plot) 94%; Rt 3.60 min. LC/MS: (ES+) 345.17, (ES−) 343.20.

Intermediate 106: N-(3-chloroquinoxalin-2-yl)pyridine-3-sulfonamide

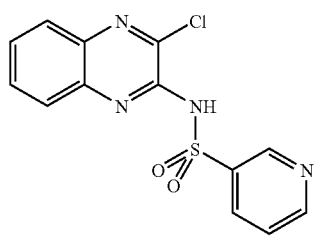 [SMILES: O=S(=O)(Nc1nc2ccccc2nc1Cl)c1cccnc1]

Following the protocol outlined in Procedure G, Intermediate 106 is obtained from 2,3-dichloroquinoxaline (165 mg, 0.8 mmol, 1 eq) and pyridine-3-sulfonamide (131 mg, 0.8 mmol, 1 eq) in the presence of $K_2CO_3$ (114.6 mg, 0.8 mmol, 1 eq) in DMA (1.6 mL), to afford 200 mg (75%) of the title compound as an orange powder. $^1$H NMR (DMSO-$d_6$) δ 9.28 (s, 1H), 8.80 (d, J=4.1 Hz, 1H), 8.57 (d, J=8.0 Hz, 1H), 7.95.-7.55 (m, 5H). HPLC (max plot) 91%; Rt 2.54 min. LC/MS: (ES+):321.2, (ES−): 319.1.

Intermediate 107

N-(3-chloroquinoxalin-2-yl)-1-methyl-1H-imidazole-4-sulfonamide

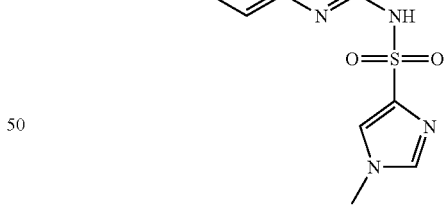

Following the protocol outlined in procedure G, intermediate 107 is obtained from 2,3-dichloroquinoxaline (500 mg; 2.5 mmol; 1 eq) and 1-methyl-1H-imidazole-4-sulfonamide (404.9 mg; 2.5 mmol; 1 eq) in the presence of $K_2CO_3$ (347.2 mg; 2.5 mmol; 1 eq) in DMA (5 mL), to afford 3.5 g (65.5%) of the title compound. $^1$H NMR (DMSO-$d_6$) δ 8.15 (s, 1H), 7.91-7.86 (m, 3H), 7.79-7.71 (m, 1H), 7.65-7.58 (m, 1H), 3.73 (s, 3H). HPLC (max plot) 92%; Rt 2.41 min. LC/MS: (ES+): 324.0, (ES−): 321.9.

Intermediate 108: N-(3-Chloroquinoxalin-2-yl)-6-methylpyridine-3-sulfonamide 1-oxide

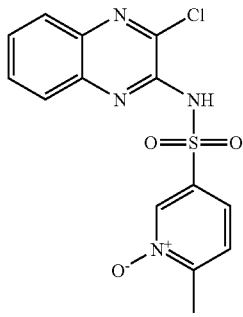 [SMILES: Cc1ccc(S(=O)(=O)Nc2nc3ccccc3nc2Cl)c[n+]1[O-]]

Following the protocol outlined in Procedure G, Intermediate 108 is obtained from 2,3-dichloroquinoxaline (500 mg; 2.5 mmol; 1 eq) and 6-methylpyridine-3-sulfonamide 1-oxide (473 mg; 2.5 mmol; 1 eq) in the presence of $K_2CO_3$ (347 mg; 2.5 mmol; 1 eq) in DMA (6 mL), to afford 460 mg (52%) of the title compound as a light brown powder. $^1$H NMR (DMSO-$d_6$) δ 8.84 (s, 1H), 8.05-7.52 (m, 7H), 2.38 (s, 3H). HPLC (max plot) 89%; Rt 2.44 min. LC/MS: (ES+) 350.9, (ES−) 348.9

Intermediate 109: Methyl (4-{[(3-chloroquinoxalin-2-yl)amino]sulfonyl}phenoxy)acetate

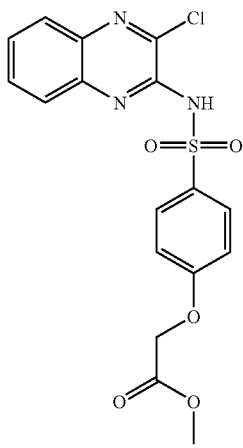 [SMILES: COC(=O)COc1ccc(S(=O)(=O)Nc2nc3ccccc3nc2Cl)cc1]

Following the protocol outlined in Procedure G, Intermediate 109 is obtained from 2,3-dichloroquinoxaline (1 g; 5 mmol; 1 eq) and (4-sulfamoyl-phenoxy)-acetic acid methyl ester (1.3 g; 5.3 mmol; 1.05 eq) in the presence of $K_2CO_3$ (694.4 mg; 5 mmol; 1 eq) in DMF (10 mL) under microwave conditions at 170° C. for 30 min, to afford 1.4 g (68%) of the title compound as a yellow powder. HPLC (max plot) 68.5%; Rt 3.23 mM. LC/MS: (ES+) 407.8, (ES−) 405.8.

Intermediate 110: Methyl 3-(4-{[3-chloroquinoxalin-2-yl)amino]sulfonyl}phenyl)propanoate

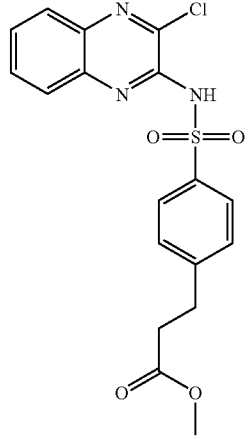 [SMILES: COC(=O)CCc1ccc(S(=O)(=O)Nc2nc3ccccc3nc2Cl)cc1]

Following the protocol outlined in Procedure G, Intermediate 110 is obtained from 2,3-dichloroquinoxaline (1 g; 5 mmol; 1 eq) and methyl 3-[4-(aminosulfonyl)phenyl]propanoate (1.2 g; 5.02 mmol; 1 eq) in the presence of $K_2CO_3$ (694.4 mg; 5 mmol; 1 eq) in DMF (12 mL) under microwave conditions at 170° C. for 30 mm, to afford 1 g (51%) of the title compound as a light yellow powder. $^1$H NMR (DMSO-$d_6$) δ 11.32 (br s, 1H), 8.10-8.00 (m, 3H), 7.78-7.66 (m, 2H), 7.64-7.53 (m, 1H), 7.37-7.28 (m, 2H), 3.53 (s, 3H), 2.95-2.84 (m, 2H), 2.64-2.54 (m, 2H). HPLC (max plot) 94.0%; Rt 4.04 min UPLC/MS: (ES+) 406.2, (ES−) 404.2.

Intermediate 111: 4-Amino-N-(3-chloroquinoxalin-2-yl)benzenesulfonamide

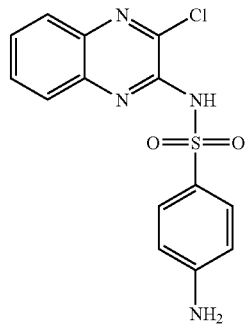 [SMILES: Nc1ccc(S(=O)(=O)Nc2nc3ccccc3nc2Cl)cc1]

Following the protocol outlined in Procedure C, Intermediate 111 is obtained from 2,3-dichloroquinoxaline (5 g; 25 mmol; 1 eq) and sulfanilamide (4.3 g; 25 mmol; 1 eq) in the presence of $K_2CO_3$ (3.5 g; 25 mmol; 1 eq) in DMA (150 mL) under microwave conditions at 170° C. for 30 min, to afford 5 g (59%) of the title compound as a yellow powder. HPLC (max plot) 75.2%; Rt 3.11 min. UPLC/MS: (ES+) 335.1, (ES−) 333.2

Intermediate 112: 2-(Benzyloxy)-N-(3-{[(3-chloro-quinoxalin-2-yl)amino]sulfonyl}phenyl)acetamide

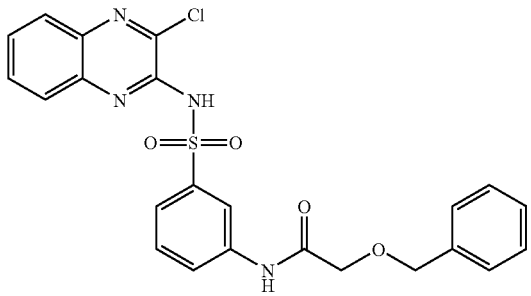 [SMILES: O=C(COCc1ccccc1)Nc1cccc(S(=O)(=O)Nc2nc3ccccc3nc2Cl)c1]

Following the protocol outlined in Procedure G, Intermediate 112 is obtained from 2,3-dichloroquinoxaline (500 mg; 2.5 mmol; 1 eq) and N-[3-(aminosulfonyl)phenyl]-2-(benzyloxy)acetamide (885 mg; 2.8 mmol; 1.1 eq) in the presence of $K_2CO_3$ (347 mg; 2.5 mmol; 1 eq) in DMA (12 mL) under microwave conditions at 170° C. for 30 min, to afford 776 mg (64%) of the title compound as a yellow oil. HPLC (max plot) 55%; Rt 4.60 min. UPLC/MS: (ES+) 483.2, (ES−) 481.3.

Intermediate 113: N-(3-{[(-Chloroquinoxalin-2-yl)]sulfamoyl}phenyl)-2-dimethylamino-amide

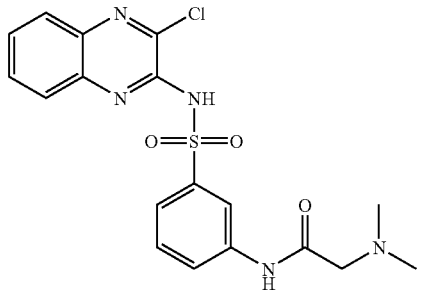 [SMILES: CN(C)CC(=O)Nc1cccc(S(=O)(=O)Nc2nc3ccccc3nc2Cl)c1]

Following the protocol outlined in Procedure G, intermediate 113 is obtained from 2,3-dichloroquinoxaline (420 mg; 2.1 mmol; 1 eq) and 2-dimethylamino-N-[3-(sulfamoyl)phenyl]-acetamide (597.3 mg; 2.3 mmol; 1.1 eq) in the presence of $K_2CO_3$ (291.6 mg; 2.1 mmol; 1 eq) in DMA (12 mL) under microwave conditions at 170° C. for 30 min, to afford 880 mg (99%) of the title compound as a yellow solid. HPLC (max plot) 91%; Rt 2.79 min. UPLC/MS: (ES+) 420.1, (ES−) 418.2.

Intermediate 114: N-(3-Chloroquinoxalin-2-yl)-2-[(dimethylamino)methyl]-1-methyl-1H-imidazole-4-sulfonamide

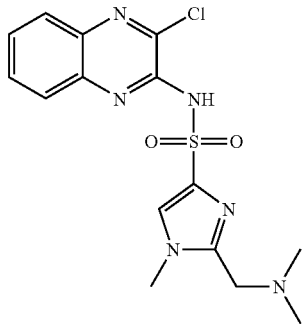 [SMILES: CN(C)Cc1nc(S(=O)(=O)Nc2nc3ccccc3nc2Cl)cn1C]

Following the protocol outlined in Procedure G, Intermediate 114 is obtained from 2,3-dichloro quinoxaline (1.2 g; 6 mmol; 1 eq) and 2-[(dimethylamino)methyl]-1-methyl-1H-imidazole-4-sulfonamide (1.5 g; 6.6 mmol; 1.1 eq) in the presence of $K_2CO_3$ (833 mg; 6 mmol; 1 eq) in DMA (18 mL) under microwave conditions at 170° C. for 30 min, to afford 1.2 g (53%) of the title compound as a beige powder. $^1$H NMR (DMSO-$d_6$) δ 10.26 (hr s, 1H), 7.84 (s, 1H), 7.70-7.40 (m, 3H), 7.35-7.15 (m, 1H), 4.22 (s, 2H), 3.69 (s, 3H), 2.65 (s, 6H). HPLC (max plot) 94%; Rt 1.97 min. UPLC/MS (ES+) 381.1; (ES−) 379.2,

Intermediate 115: 2-({[tert-Butyl(dimethyl)silyl]oxy}methyl)-N-(3-chloroquinoxalin-2-yl)-1-methyl-1H-imidazole-4-sulfonamide

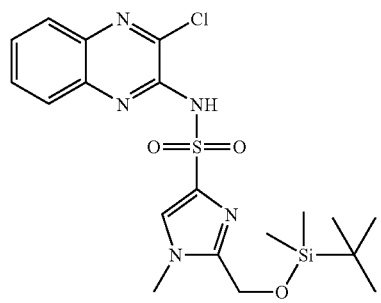 [SMILES: Cn1cc(S(=O)(=O)Nc2nc3ccccc3nc2Cl)nc1CO[Si](C)(C)C(C)(C)C]

Following the protocol outlined in Procedure G, Intermediate 115 is obtained from 2,3-dichloroquinoxaline (150 mg; 0.75 mmol; 1 eq) and 2-({[tert-butyl(dimethyl)silyl]oxy}methyl)-1-methyl-1H-imidazole-4-sulfonamide (299.3 mg; 0.98 mmol; 1.3 eq) in the presence of $K_2CO_3$ (104.2 mg; 0.75 mmol; 1 eq) in DMF (4 mL) at 100° C. for 2 h to afford 115 mg (33%) of the title compound as a yellow powder. $^1$H NMR (DMSO-$d_6$) δ 8.20 (s, 1H), 8.18-7.61 (m, 4H), 7.10 (s, 1H), 4.68 (s, 2H), 3.71 (s, 3H), 0.86 (s, 9H), 0.05 (s, 6H), HPLC (max plot) 72%; Rt 5.16 min. UPLC/MS (ES+) 468.2, (ES−) 466.3.

Intermediate 116: N-(3-Chloroquinoxalin-2-yl)-1-methyl-2-[(methylsulfonyl)methyl]-1H-imidazole-4-sulfonamide

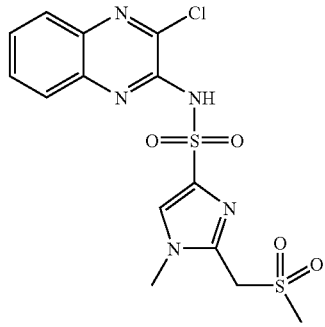 [SMILES: Cn1cc(S(=O)(=O)Nc2nc3ccccc3nc2Cl)nc1CS(C)(=O)=O]

Following the protocol outlined in Procedure G, Intermediate 116 is obtained from 2,3-dichloro quinoxaline (400 mg; 2 mmol; 1 eq) and 2-methanesulfanylmethyl-1-methyl-1H-imidazole-4-sulfonic acid amide (610.9 mg; 2.4 mmol; 1.2 eq) in the presence of $K_2CO_3$ (277.7 mg; 2 mmol; 1 eq) in DMA (5 mL) 150° C. for 20 min to afford 500 mg (60%) of the title compound as a grey powder. $^1$H NMR (DMSO-$d_6$) δ 8.25 (s, 1H), 7.98-7.62 (m, 4H), 4.81 (s, 2H), 3.79 (s, 3H), 2.97 (s, 3H). HPLC (max plot) 95.5%; Rt 2.62 min. LC/MS: (ES+) 416.1. UPLC/MS (ES+) 416.1, (ES−) 413.9.

Intermediate 117: N-(3-Chloroquinoxalin-2-yl)-3,5-dimethylisoxazole-4-sulfonamide

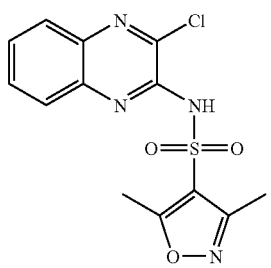 [SMILES: Cc1noc(C)c1S(=O)(=O)Nc1nc2ccccc2nc1Cl]

Following the protocol outlined in Procedure G, Intermediate 117 is obtained from 2,3-dichloroquinoxaline (2.66 g; 13.4 mmol; 1 eq) and 3,5-dimethylisoxazole-4-sulfonamide (2.6 g; 14.7 mmol; 1.1 eq) in the presence of $K_2CO_3$ (1.8 g; 13.4 mmol; 1 eq) in DMA (26 mL) under microwave conditions at 160° C. for 20 min, to afford 3.8 g (85%) of the title compound as a white powder. $^1$H NMR (DMSO-$d_6$) δ 11.90 (br s, 1H), 7.94-7.86 (d, J=8.0 Hz, 1H), 7.82-7.72 (m, 1H), 7.72-7.61 (m, 1H), 7.15-7.05 (m, 1H), 2.81 (s, 3H), 2.47 (s, 3H). HPLC (max plot) 90.5%; Rt 3.69 min. UPLC/MS: (ES+) 339.5, (ES−) 337.8

Intermediate 118: N-(3-chloroquinoxalin-2-yl)methanesulfonamide

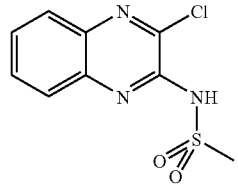 [SMILES: CS(=O)(=O)Nc1nc2ccccc2nc1Cl]

Following the protocol outlined in Procedure G, Intermediate 118 is obtained from 2,3-dichloro quinoxaline (300 mg, 1.5 mmol, 1 eq) and methanesulfonamide (143.4 mg, 1.5 mmol; 1 eq; commercially available from Aldrich) in the presence of $K_2CO_3$ (208.3 mg, 1.5 mmol, 1 eq) in DMA (3 mL), to afford 234.2 mg (60%) of the title compound as a yellow powder. $^1$H NMR (DMSO-$d_6$) δ 11.05 (br s, 1H), 8.04-7.88 (m, 2H), 7.85-7.61 (m, 2H), 3.49 (s, 3H). HPLC (max plot) 90% Rt 2.35 min. LC/MS: (ES+): 258.0, (ES−): 256.0.

Intermediate 119: N-(3-Chloroquinoxalin-2-yl)ethanesulfonamide

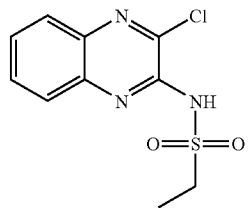 [SMILES: CCS(=O)(=O)Nc1nc2ccccc2nc1Cl]

Following the protocol outlined in Procedure G, Intermediate 119 is obtained from 2,3-dichloro quinoxaline (2 g; 10 mmol; 1 eq) and ethanesulfonamide (1.15 g; 10.6 mmol; 1.05 eq) in the presence of $K_2CO_3$ (1.4 g; 10.1 mmol; 1 eq) DMF (40 mL) under microwave conditions at 170° C. for 30 min, to afford 1.2 g (78%) of the title compound as a yellow solid. $^1$H NMR (DMSO-$d_6$) δ 8.01-7.98 (m, 2H), 7.88-7.83 (m, 1H), 7.79-7.74 (m, 1H), 3.75 (br s, 2H), 1.36 (t, J=7.4 Hz, 3H). HPLC (max plot) 78%; Rt 2.53 min. LC/MS: (ES+) 271.8, (ES−) 269.9.

Intermediate 120: N-(3-Chloroquinoxalin-2-yl)-propane-1-sulfonamide

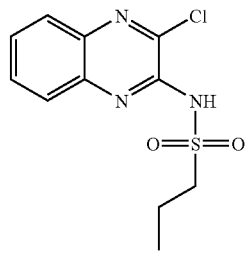 [SMILES: CCCS(=O)(=O)Nc1nc2ccccc2nc1Cl]

Following the protocol outlined in Procedure G, Intermediate 120 is obtained from 2,3-dichloro quinoxaline (1.90 g;

9.6 mmol; 1 eq) and propane-1-sulfonamide (1.23 g; 10 mmol; 1.05 eq) in the presence of $K_2CO_3$ (1.3 g; 9.6 mmol; 1 eq) in DMF (40 mL) under microwave conditions at 170° C. for 30 min, to afford 2.06 g (75%) of the title compound as a yellow solid, $^1$H NMR (DMSO-$d_6$) δ 11.19 (br s, 1H), 8.02-7.99 (m, 2H), 7.89-7.73 (m, 2H), 1.94-1.81 (m, 2H), 1.79 (br s, 2H), 1.08 (t, J=7.4 Hz, 3H). HPLC (max plot) 81%; Rt 3.43 min.

Intermediate 130:
N-(3-Chloroquinoxalin-2-yl)propane-2-sulfonamide

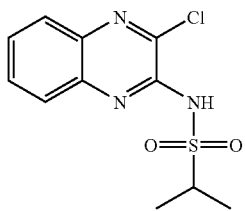 [SMILES: CC(C)S(=O)(=O)Nc1nc2ccccc2nc1Cl]

Following the protocol outlined in Procedure G, Intermediate 130 is obtained from 2,3-dichloro quinoxaline (2 g; 10 mmol; 1 eq) and propane-2-sulfonamide (1.4 g; 10.6 mmol; 1.05 eq) in the presence of $K_2CO_3$ (1.4 g; 10.1 mmol; 1 eq) in DMF (40 mL) under microwave conditions at 170° C. for 45 min, to afford 1.73 g (60%) of the title compound as a yellow solid. HPLC (max plot) 84%; Rt 3.33 min. UPLC/MS; (ES+) 286.1, (ES−) 284.2

Intermediate 131:
N-(3-Chloroquinoxalin-2-yl)-cyclohexanesulfonamide

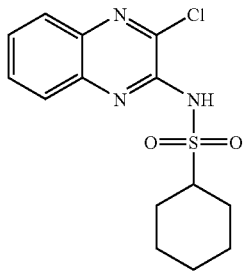 [SMILES: O=S(=O)(Nc1nc2ccccc2nc1Cl)C1CCCCC1]

Following the protocol outlined in Procedure G, Intermediate 131 is obtained from 2,3-dichloro quinoxaline (650 mg; 3.3 mmol; 1 eq) and cyclohexanesulfonamide (560 mg; 3.4 mmol; 1.05 eq) in the presence of $K_2CO_3$ (451.3 mg; 3.3 mmol; 1 eq) in DMF (8 mL), to afford 527 mg (50%) of the title compound as a yellow solid. $^1$H NMR (DMSO-$d_6$) δ 11.05 (br s, 1H), 8.02-7.36 (m, 4H), 3.98 (br s, 1H), 2.22-2.18 (m, 2H), 1.89-1.85 (m 2H), 1.71-1.24 (m, 6H). HPLC (max plot) 84%; Rt 4.09 min. UPLC/MS: (ES−) 324.2

Intermediate 132: Benzyl 4-{[(3-chloroquinoxalin-2-yl)amino]sulfonyl}piperidine-1-carboxylate

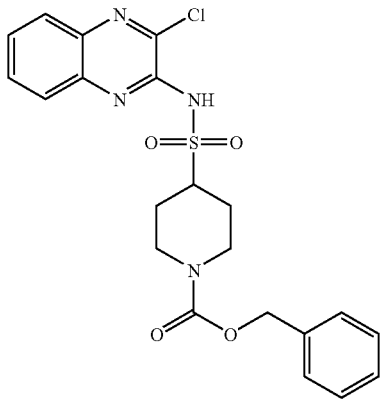 [SMILES: O=C(OCc1ccccc1)N1CCC(S(=O)(=O)Nc2nc3ccccc3nc2Cl)CC1]

Following the protocol outlined in Procedure G, Intermediate 132 is obtained from 2,3-dichloro quinoxaline (1.5 g; 7.5 mmol; 1 eq), benzyl 4-(aminosulfonyl)piperidine-1-carboxylate (2.5 g; 8.3 mmol; 1.1 eq) in the presence of $K_2CO_3$ (1 g; 7.5 mmol; 1 eq) in a iPrOH (12 mL) under microwave conditions at 160° C. for 25 min, to afford 2.2 g (63%) of the title compound as a pale yellow solid. $^1$H NMR (DMSO-$d_6$) δ 11.22 (br s, 1H), 8.12-7.84 (m, 2H), 7.78-7.71 (m, 1H), 7.65-7.55 (m, 1H), 7.40-7.29 (m, 5H), 5.09 (s, 2H), 4.20-405 (m, 3H), 3.0-2.8 (m, 2H), 2.15-1.93 (m, 2H), 1.70-1.43 (m, 2H). HPLC (max plot) 82%; Rt 4.38 min, UPLC/MS (ES+) 461.1, (ES−) 459.2

Intermediate 133: N-(3-Chloroquinoxalin-2-yl)-3-(methylthio)propane-1-sulfonamide

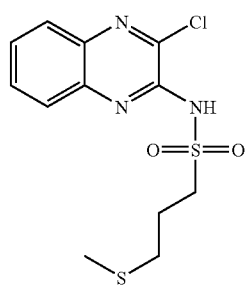 [SMILES: CSCCCS(=O)(=O)Nc1nc2ccccc2nc1Cl]

Following the protocol outlined in Procedure G, Intermediate 133 is obtained from 2,3-dichloro quinoxaline (2 g; 10 mmol; 1 eq) and 3-(methylthio)propane-1-sulfonamide (1.8 g; 10.5 mmol; 1.05 eq) in the presence of $K_2CO_3$ (1.4 g; 10 mmol; 1 eq) in DMF (15 mL) under microwave conditions at 170° C. for 30 min, to afford 957 mg (29%) of the title compound as a yellow solid. $^1$H NMR (DMSO-$d_6$) δ 11.17 (s, 1H), 8.05-7.91 (m, 2H), 7.82 (t, J=8.1 Hz, 1H), 7.72 (t, J=7.5 Hz, 1H), 3.80 (s, 2H), 2.64 (t, J=7.2 Hz, 2H), 2.06 (quint., J=7.2 Hz, 2H), 2.00 (s, 3H). HPLC (max plot) 99%; Rt 3.67 min. UPLC/MS: (ES+) 332.1 (ES−) 330.2.

Intermediate 134: N-(3-Chloroquinoxalin-2-yl)-3-(methylsulfonyl)propane-1-sulfonamide

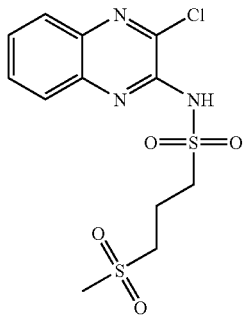 [SMILES: CS(=O)(=O)CCCS(=O)(=O)Nc1nc2ccccc2nc1Cl]

Following the protocol outlined in Procedure G, intermediate 134 is obtained from 2,3-dichloro quinoxaline (250 mg; 1.2 mmol; 1 eq) and 3-(methylsulfonyl)propane-1-sulfonamide (265.4 mg; 1.3 mmol; 1.05 eq) in the presence of $K_2CO_3$ (174 mg; 1.2 mmol; 1 eq) in DMA (2.5 mL) under microwave conditions at 160° C. for 30 min, to afford 250 mg (55%) of the title compound as a yellow solid. $^1$H NMR (DMSO-d$_6$) δ 7.97-7.93 (m, 2H), 7.84-7.66 (m, 2H), 3.88-3.82 (m, 2H), 3.37-3.32 (m, 4H), 2.98 (s, 3H), 2.28-2.18 (m, 2H). HPLC (max plot) 91%; Rt 2.75 min. UPLC/MS: (ES+) 364.1, (ES−) 362.2.

Intermediate 135: N-(3-Chloroquinoxalin-2-yl)tetrahydrothiophene-3-sulfonamide 1,1-dioxide

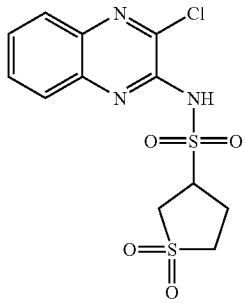 [SMILES: O=S1(=O)CCC(S(=O)(=O)Nc2nc3ccccc3nc2Cl)C1]

Following the protocol outlined in Procedure G, Intermediate 135 is obtained from 2,3-dichloro quinoxaline (340 mg; 1.7 mmol; 1 eq) and tetrahydrothiophene-3-sulfonamide 1,1-dioxide (357.4 mg; 1.8 mmol; 1.05 eq) in the presence of $K_2CO_3$ (236 mg; 1.7 mmol; 1 eq) in DMF (4 mL) under microwave conditions at 170° C. for 30 min, to afford 148 mg (24%) of the title compound as a yellow solid. $^1$H NMR (DMSO-d$_6$) δ 7.97 (d, J=8.3 Hz, 1H), 7.91 (d, J=7.9 Hz, 1H), 7.78 (t, J=7.5 Hz, 1H), 7.66 (t, J=7.8 Hz, 1H), 4.74 (br s, 1H), 3.64 (dd, J=13.9, 9.2 Hz, 1H), 3.50-3.21 (m, 3H), 2.56 (sept, J=7.7 Hz, 2H). HPLC (max plot) 92.5%; Rt 2.62 min. UPLC/MS (ES+) 362.2, (ES−) 360.2.

Intermediate 136: 2-[(4-{[(3-Chloroquinoxalin-2-yl)amino]sulfonyl}phenyl)amino]-2-oxoethyl acetate

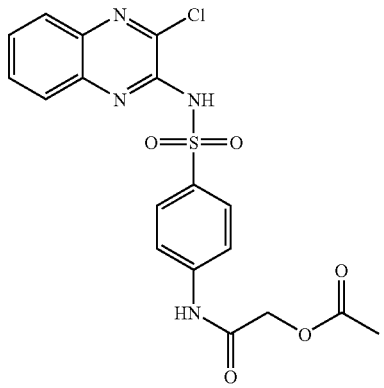 [SMILES: CC(=O)OCC(=O)Nc1ccc(S(=O)(=O)Nc2nc3ccccc3nc2Cl)cc1]

To a suspension of 4-amino-N-(3-chloroquinoxalin-2-yl)benzenesulfonamide (2 g; 4.49 mmol; 1 eq) in DCM (100 mL) is added acetoxyacetyl chloride (1.23 mL; 9 mmol; 2 eq) and N-ethyldiisopropylamine (2.3 mL; 13.5 mmol; 3 eq) and the reaction mixture is stirred at room temperature for 30 min. DCM is removed under reduced pressure and the crude residue is dissolved in EtOAc. The organic phase is washed twice with 10% citric acid then brine. The solvent is evaporated and the residue is taken up in iPrOH then refluxed and left at room temperature until precipitation. The precipitate is filtered off then dried under reduced pressure to afford 1.9 g (95%) of the title compound as a yellow powder. $^1$H NMR (DMSO-d$_6$) δ 10.70 (s, 1H), 8.25 (m, 2H), 8.09 (m, 4H), 7.88 (m, 2H), 4.71 (s, 2H), 2.13 (s, 3H). HPLC (max plot) 98%; Rt 4.03 min. UPLC/MS (ES+) 435.2.

Intermediate 137: N-(4-{[(3-Chloroquinoxalin-2-yl)]sulfamoyl}phenyl)-2-dimethyamino-acetamide

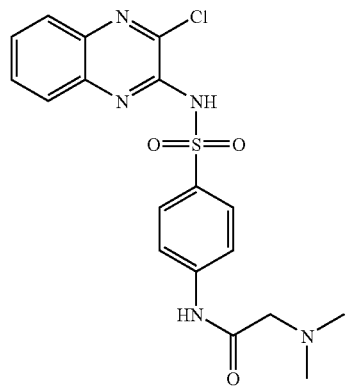 [SMILES: CN(C)CC(=O)Nc1ccc(S(=O)(=O)Nc2nc3ccccc3nc2Cl)cc1]

To a suspension of 4-amino-N-(3-chloroquinoxalin-2-yl)benzenesulfonamide (2 g; 4.5 mmol; 1 eq) in DCM (100 mL) is added dimethylaminoacetyl chloride hydrochloride (710 mg; 4.5 mmol; 1 eq) and N-ethyldiisopropylamine (2.3 mL; 13.5 mmol; 3 eq) and the reaction mixture is stirred at room temperature overnight. To complete the reaction, dimethylaminoacetyl chloride hydrochloride (1.06 g; 6.74 mmol; 1.5 eq) is added and the reaction mixture is allowed to stir another 2 days. The precipitate formed is filtered off and the filtrate is treated with a solution of citric acid. The precipitate in the organic phase is filtered and the aqueous phase is basified with $Na_2CO_3$. The product is extracted with DCM and the organic phase is concentrated to near dryness to afford 1.5 g (80%) of the title compound as a yellow powder. HPLC (max plot) 85%; Rt 2.37 min. UPLC/MS (ES+) 420.2, (ES−) 418.3.

Procedure H

Intermediate 138: N-(3-{[5-methoxy-2-(piperidin-4-ylmethyl)phenyl]amino}quinoxalin-2-yl)-1-methyl-1H-imidazole-4-sulfonamide

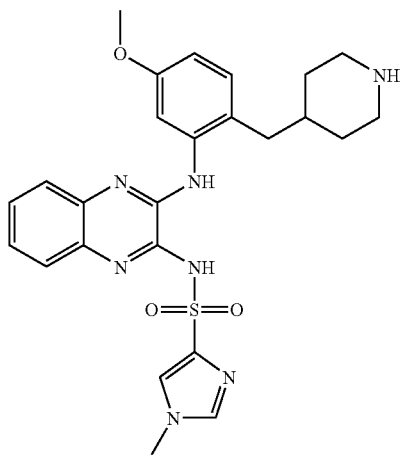 [SMILES: COc1ccc(CC2CCNCC2)c(Nc2nc3ccccc3nc2NS(=O)(=O)c2cn(C)cn2)c1]

N-(3-chloroquinoxalin-2-yl)-1-methyl-1H-imidazole-4-sulfonamide (1 g; 3.1 mmol; 1 eq) and 4-(2-amino-4-methoxy-benzyl)-piperidine-1-carboxylic acid tert-butyl ester (1.1 g; 3.4 mmol; 1.1 eq) are suspended in water (12.5 mL) and EtOH (12.5 mL) then AcOH (2.5 mL) is added. The resulting suspension is heated up to 90° C. for 3 days. Boc deprotection occurs during the reaction. The solvents are evaporated under reduced pressure and the resulting oily brown residue is taken up in water. An excess triethylamine is added until pH=8 to trap the HCl formed during the reaction. The precipitate is filtered off then washed thoroughly with water until neutral. It is dried under vacuum at 40° C. for 2 days, affording 544 mg (35%) of the title compound as a grey solid. $^1$H NMR (DMSO-$d_6$) δ 9.35 (s, 1H), 8.70 (d, J=2.4 Hz, 1H), 7.69 (s, 1H), 7.50-7.30 (m, 3H), 7.35-6.97 (m, 3H), 6.48 (dd, J=8.3, 2.7 Hz, 1H), 3.89 (s, 2H), 3.78 (s, 3H), 3.63 (s, 3H), 3.45-3.15 (m, 2H), 2.97-2.78 (m, 2H), 2.65-2.53 (m, 2H), 2.05-1.80 (m, 2H), 1.56-1.32 (m, 2H). HPLC (max plot) 89%; Rt 3.08 min. LC/MS: (ES+) 508.1, (ES−) 506.1.

Intermediate 139: 4-{[(3-{[2-(cyclohexylmethyl)-5-methoxyphenyl]amino}quinoxalin-2-yl)amino]sulfonyl}-N,N-dimethylbenzamide

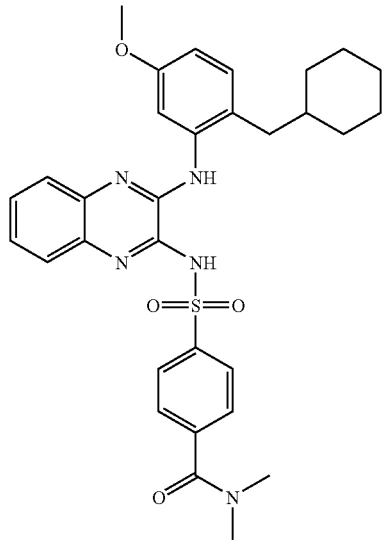 [SMILES: COc1ccc(CC2CCCCC2)c(Nc2nc3ccccc3nc2NS(=O)(=O)c2ccc(C(=O)N(C)C)cc2)c1]

Following the protocol outlined in procedure H, intermediate 139 is obtained from 4-{[(3-chloroquinoxalin-2-yl)amino]sulfonyl}-N,N-dimethylbenzamide (500 mg; 1.3 mmol; 1 eq) and 2-(cyclohexylmethyl)-5-methoxyaniline (364.7 mg; 1.7 mmol; 1.3 eq) in EtOH (3 mL), water (0.6 mL) and AcOH (1.5 mL) at 150° C. in the microwave for 13 min to afford 615 mg (55%) of the title compound as a yellow powder. HPLC (max plot) 63%; Rt 5.50 min. LC/MS: (ES+): 574.5, (ES−): 572.5.

Intermediate 140: 4-({[3-({2-[(4-hydroxycyclohexyl)methyl]-5-methoxyphenyl}amino)quinoxalin-2-yl]amino}sulfonyl)-N,N-dimethylbenzamide

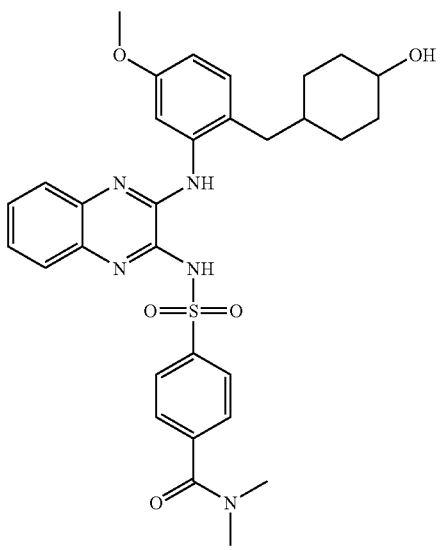 [SMILES: COc1ccc(CC2CCC(O)CC2)c(Nc2nc3ccccc3nc2NS(=O)(=O)c2ccc(C(=O)N(C)C)cc2)c1]

Following the protocol outlined in procedure H, intermediate 140 is obtained from 4-{[(3-chloro quinoxalin-2-yl)

amino]sulfonyl}-N,N-dimethylbenzamide (600 mg; 1.5 mmol; 1 eq) and 2-[(4-{[tert-butyl(dimethyl)silyl]oxy}cyclohexyl)methyl]-5-methoxyaniline (590.3 mg; 1.7 mmol; 1.1 eq) in EtOH (15 mL), water (15 mL) and AcOH (3 mL) at 90° C. overnight to afford 248 mg (27%) of the title compound as a yellow powder (TBDMS protection lost during the reaction). $^1$H NMR (DMSO-$d_6$) δ 12.51 (s, 1H), 8.72 (s, 1H), 8.34 (s, 1H), 8.10 (d, J=8.3 Hz, 2H), 7.97 (s, 1H), 7.62-7.56 (m, 3H), 7.41-7.36 (m, 2H), 7.07-7.04 (m, 1H), 6.64-6.60 (m, 1H), 3.78 (s, 3H), 3.68-3.63 (m, 1H), 2.99 (s, 3H), 2.88 (s, 3H), 2.37-2.35 (m, 2H), 1.65-0.85 (m, 10H). HPLC (max plot) 86%; Rt 4.28 min. LC/MS: (ES+): 590.1, (ES−): 588.0

Intermediate 141: 4-{[(3-{[5-methoxy-2-(tetrahydro-2H-thiopyran-4-ylmethyl)phenyl]amino}quinoxalin-2-yl)amino]sulfonyl}-N,N-dimethylbenzamide

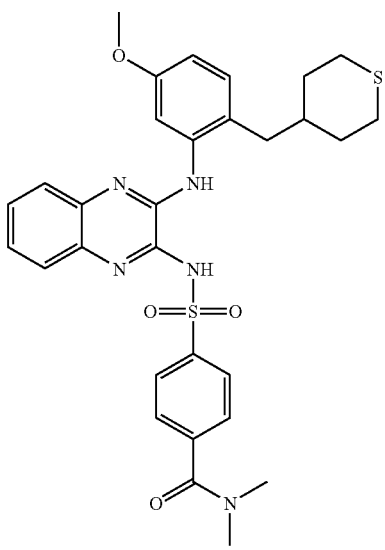 [SMILES: COc1ccc(CC2CCSCC2)c(Nc2nc3ccccc3nc2NS(=O)(=O)c2ccc(C(=O)N(C)C)cc2)c1]

Following the protocol outlined in procedure H, intermediate 141 is obtained from 4-{[(3-chloro quinoxalin-2-yl)amino]sulfonyl}-N,N-dimethylbenzamide (600 mg; 1.5 mmol; 1 eq) and 5-methoxy-2-(tetrahydro-2H-thiopyran-4-ylmethyl)aniline (420.4 mg; 1.5 mmol; 1 eq) in EtOH (8 mL), water (8 mL) and AcOH (1.5 mL) at 90° C. overnight to afford 220 mg (24%) of the title compound as a yellow powder. HPLC (max plot) 72%; Rt 3.99 min. LC/MS: (ES+): 592.1, (ES−): 590.1.

Intermediate 142: 4-({[3-({2-[(1,1-dioxidotetrahydro-2H-thiopyran-4-yl)methyl]-5-methoxyphenyl}amino)amino)quinoxalin-2-yl]amino}sulfonyl)-N,N-dimethylbenzamide

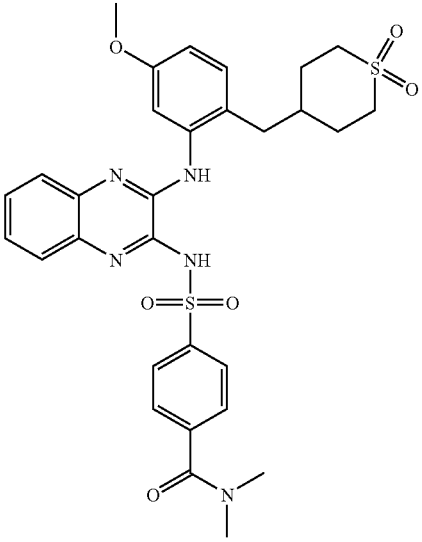 [SMILES: COc1ccc(CC2CCS(=O)(=O)CC2)c(Nc2nc3ccccc3nc2NS(=O)(=O)c2ccc(C(=O)N(C)C)cc2)c1]

Following the protocol outlined in procedure H, intermediate 142 is obtained from 4-{[(3-chloro quinoxalin-2-yl)amino]sulfonyl}-N,N-dimethylbenzamide (250 mg; 0.64 mmol; 1 eq) and 2-[(1,1-dioxidotetrahydro-2H-thiopyran-4-yl)methyl]-5-methoxyaniline (195.62 mg; 0.64 mmol; 1 eq) in EtOH (8 mL), water (8 mL) and AcOH (1.5 mL) at 90° C. overnight to afford 191.5 mg (48%) of the title compound as a yellow powder. HPLC (max plot) 79%; Rt 4.02 min. LC/MS: (ES+): 624.0, (ES−): 622.0.

Intermediate 143: 4-{[(3-{[5-methoxy-2-(tetrahydro-2H-pyran-4-ylmethyl)phenyl]amino}quinoxalin-2-yl)amino]sulfonyl}-N,N-dimethylbenzamide

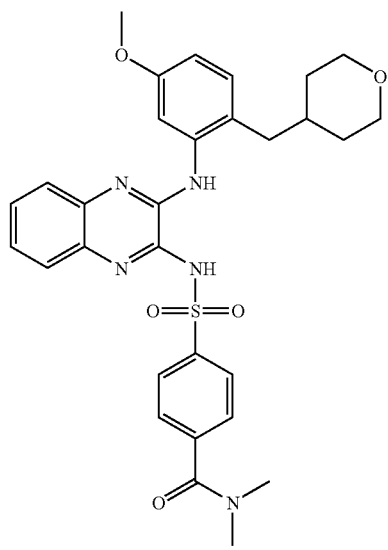 [SMILES: COc1ccc(CC2CCOCC2)c(Nc2nc3ccccc3nc2NS(=O)(=O)c2ccc(C(=O)N(C)C)cc2)c1]

Following the protocol outlined in procedure H, intermediate 143 is obtained from 4-{[(3-chloro quinoxalin-2-yl)amino]sulfonyl}-N,N-dimethylbenzamide (660 mg; 1.7 mmol; 1 eq) and 5-methoxy-2-(tetrahydro-2H-pyran-4-ylmethyl)aniline (448.43 mg; 2 mmol; 1.2 eq) in EtOH (10 mL), water (1.5 mL) and AcOH (4 mL) at 90° C. overnight to afford 220 mg (23%) of the title compound. $^1$H NMR (DMSO-$d_6$) δ 8.80-8.70 (m, 1H), 8.37-8.30 (m, 1H), 8.10 (d, J=9.0 Hz, 2H), 8.02-7.81 (m, 1H), 7.62-7.56 (m, 3H), 7.40-7.30 (m, 2H), 7.08 (d, J=9.0 Hz, 1H), 6.63 (dd, J=9.0, 3.0 Hz, 1H), 3.78 (s, 3H), 3.70-3.62 (m, 2H), 3.33 (s, 6H), 3.05-2.94 (m, 4H), 1.59-1.54 (m, 1H), 1.32-1.20 (m, 2H), 1.15-0.93 (m, 2H). HPLC (max plot) 89%; Rt 4.46 min. LC/MS: (ES+): 576.4, (ES−): 574.4.

Intermediate 144: 4[(4-Fluoropiperidin-1-yl)carbonyl]-N-(3-{[2-2-hydroxyethyl)-5-methoxyphenyl]amino}quinoxalin-2-yl)benzenesulfonamide

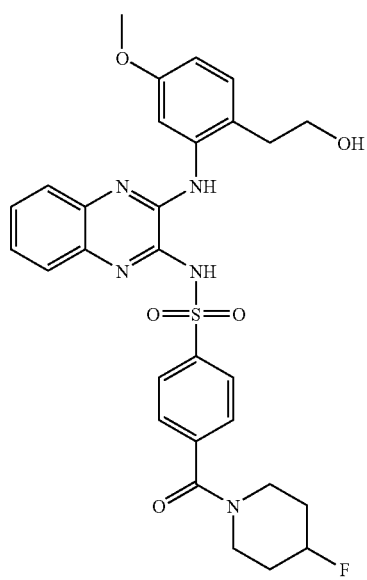 [SMILES: COc1ccc(CCO)c(Nc2nc3ccccc3nc2NS(=O)(=O)c2ccc(C(=O)N3CCC(F)CC3)cc2)c1]

Following the protocol outlined in procedure H, intermediate 144 is obtained from N-(3-chloro quinoxalin-2-yl)-4-[(4-fluoropiperidin-1-yl)carbonyl] (400 mg; 0.9 mmol; 1 eq) and 2-(2-amino-4-methoxy-phenyl)-ethanol (164 mg; 1 mmol; 1.1 eq) in EtOH (4 mL) and AcOH (153 µL; 2.7 mmol; 3 eq) at 165° C. for 15 min in the microwave to afford 190 mg (37%) of the title compound as a yellow powder. HPLC (max plot) 83%; Rt 4.06 min. LC/MS: (ES+) 580.2, (ES−) 577.7.

Intermediate 145: Methyl(4-{[(3-{[2-(2-hydroxyethyl)-5-methoxyphenyl]amino}quinoxalin-2-yl)amino]sulfonyl}phenoxy)acetate

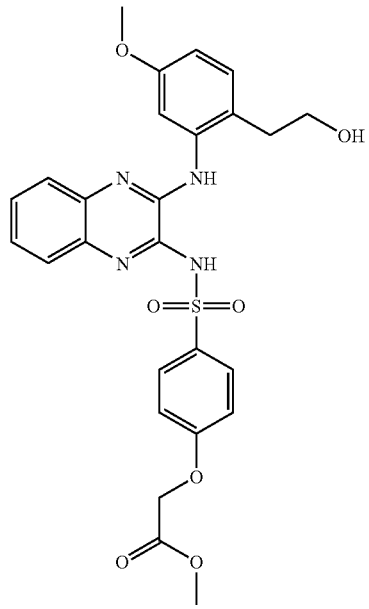

Following the protocol outlined in procedure H, intermediate 145 is obtained from methyl (4-{[(3-chloroquinoxalin-2-yl)amino]sulfonyl}phenoxy)acetate (300 mg; 0.7 mmol; 1 eq) and 2-(2-amino-4-methoxy-phenyl)-ethanol (135.3 mg; 0.8 mmol; 1.1 eq) in MeOH (4 mL) and AcOH (97 µL; 2.2 mmol; 3 eq) at 80° C. for 9 h to afford 75 mg (19%) of the title compound as a yellow powder. It was used in the next step without further purification. HPLC (max plot) 72%; Rt 4.31 min. UPLC/MS (ES+) 539.2, (ES−) 537.3.

Intermediate 146: Benzyl 4-{[(3-{[2-(3-hydroxypropyl)-5-methoxyphenyl]amino}quinoxalin-2-yl)amino]sulfonyl}piperidine-1-carboxylate

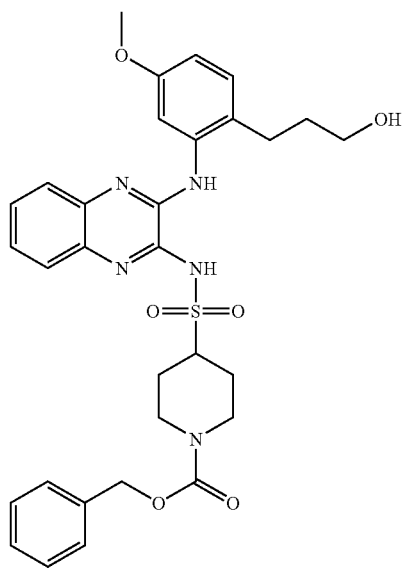 [SMILES: COc1ccc(CCCO)c(Nc2nc3ccccc3nc2NS(=O)(=O)C2CCN(C(=O)OCc3ccccc3)CC2)c1]

Following the protocol outlined in procedure H, intermediate 146 is obtained from benzyl 4-{[(3-chloroquinoxalin-2-yl)amino]sulfonyl}piperidine-1-carboxylate (300 mg; 0.65 mmol; 1 eq) and 3-(2-amino-4-methoxy-phenyl)-propan-1-ol (124 mg; 0.7 mmol; 1.05 eq) in EtOH (2 mL) at 160° C. for 15 min in the microwave to afford 245 mg (62%) of the title compound as a yellow solid, $^1$H NMR (DMSO-d$_6$) δ 12.29 (br s, 1H), 8.92 (br s, 1H), 8.27 (br s, 1H), 7.70 (br s, 1H), 7.50-7.47 (m, 1H), 7.36-7.27 (m, 7H), 7.13 (d, J=8.3 Hz, 1H), 6.63 (br d, J=7.3 Hz, 1H), 5.08 (s, 2H), 4.48 (br s, 1H), 4.13 (br d, J=12.6 Hz, 2H), 3.78 (s, 3H), 3.62-3.54 (m, 1H), 3.42-3.40 (m, 1H), 2.86 (m, 2H), 2.62 (t, J=7.4 Hz, 2H), 2.12-2.04 (m, 2H), 1.76-1.56 (m, 4H). HPLC (max plot) 97%; Rt 5.32 min. LC/MS: (ES+) 606.1, (ES−) 604.2.

Intermediate 147: Benzyl 4-{[(3-{[5-methoxy-2-(2-methoxyethyl)phenyl]amino}quinoxalin-2-yl)amino]sulfonyl}piperidine-1-carboxylate

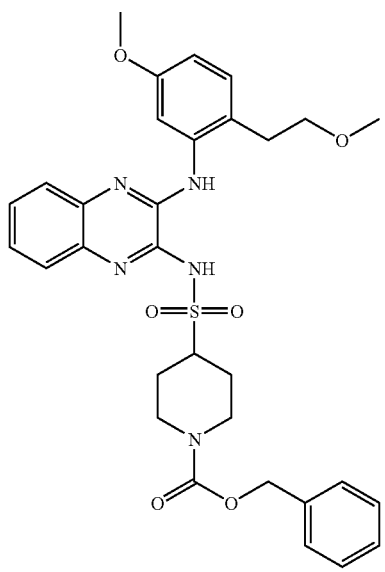 [SMILES: COCCc1ccc(OC)cc1Nc1nc2ccccc2nc1NS(=O)(=O)C1CCN(C(=O)OCc2ccccc2)CC1]

Following the protocol outlined in procedure intermediate 147 is obtained from benzyl 4-{[(3-chloroquinoxalin-2-yl)amino]sulfonyl}piperidine-1-carboxylate (700 mg; 1.5 mmol; 1 eq) and 5-methoxy-2-(2-methoxy-ethyl)-phenylamine (303 mg; 1.7 mmol; 1.1 eq) in iPrOH (7 mL) at 160° C. for 20 min in the microwave to afford 158 mg (17%) of the title compound as a yellow oil. HPLC (max plot) 76.5%; Rt 5.21 min. UPLC/MS (ES+) 472.2, (ES−) 470.3.

Intermediate 148: 3-[4-Methoxy-2-({3-[(piperidin-4-ylsulfonyl)amino]quinoxalin-2-yl}amino)phenyl] propyl trifluoroacetate TFA Salt

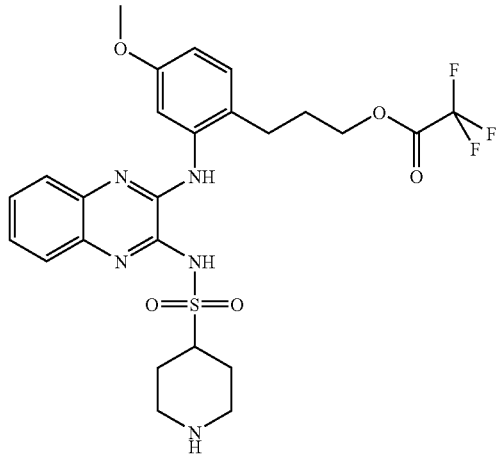 [SMILES: COc1ccc(CCCOC(=O)C(F)(F)F)c(Nc2nc3ccccc3nc2NS(=O)(=O)C2CCNCC2)c1]

To a solution of benzyl 4-{[(3-{[2-(3-hydroxypropyl)-5-methoxyphenyl]amino}quinoxalin-2-yl)amino]sulfonyl}piperidine-1-carboxylate (220 mg; 0.4 mmol; 1 eq) in DCM (30 mL) is added dropwise trifluoroacetic acid (2 mL) and the resulting solution is stirred at 0° C. then heated at 50° C. The solvents are removed under reduced pressure affording 245 mg (100%) of the title compound as a brown oil.

EXAMPLES

Procedure I

Example 1 methyl 4-methoxy-2-[(3-{[(1-methyl-1H-imidazol-4-yl)sulfonyl]amino}quinoxalin-2-yl)amino]benzoate

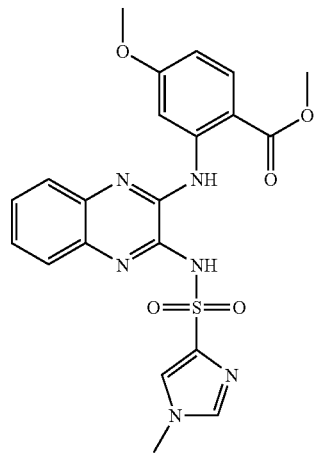 [SMILES: COC(=O)c1ccc(OC)cc1Nc1nc2ccccc2nc1NS(=O)(=O)c1cn(C)cn1]

N-(3-chloroquinoxalin-2-yl)-1-methyl-1H-imidazole-4-sulfonamide (2 g; 6.2 mmol; 1 eq) and methyl 2-amino-4- methoxybenzoate (1.2 g; 6.8 mmol; 1.1 eq) are taken up in water (60 mL) and acetic acid (160 μL; 3.65 mmol; 0.6 eq) is added. The suspension is heated up to 170° C. in the microwave under normal absorption for 20 min. The reaction is stopped by filtration of the solid and washing with water until neutral. The orange powder obtained is dried under vacuum at 40° C. overnight then taken up in DCM. Triethylamine (1.72 mL) is added. After sonication, the solvents are removed under reduced pressure and the residue obtained is washed with water then dried under vacuum at 40° C. overnight. The powder is taken up in MeOH and refluxed then the suspension is left at 4° C. for 1 h. The precipitate is filtered and washed with MeOH then dried under vacuum at 40° C. for 2 days, to afford 1.68 g (58%) of the title compound as a yellow powder. $^1$H NMR (DMSO-$d_6$) δ 11.77 (s, 1H), 9.05 (d, J=2.3 Hz, 1H), 8.10-7.95 (m, 2H), 7.90 (s, 1H), 7.85-7.76 (m, 1H), 7.73-7.60 (m, 1H), 7.55-7.35 (m, 2H), 6.73 (dd, J=8.6, 2.2 Hz, 1H), 3.91 (s, 6H), 3.72 (s, 3H). HPLC (max plot) 100%; Rt 4.12 min. LC/MS: (ES+): 469.0, (ES−): 467.1.

Example 2 methyl 4-methoxy-2-({3-[pyridin-3-ylsulfonyl)amino]quinoxalin-2-yl}amino)benzoate

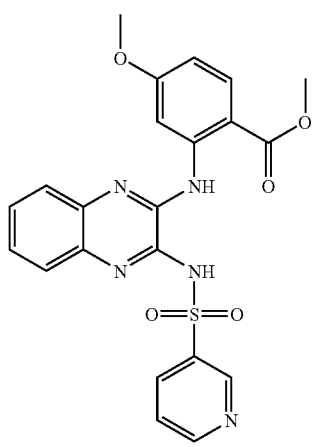 [SMILES: COC(=O)c1ccc(OC)cc1Nc1nc2ccccc2nc1NS(=O)(=O)c1cccnc1]

Following the protocol outlined in Procedure I, Example 2 is obtained from N-(3-chloro uinoxalin-2-yl)pyrimidine-3-sulfonamide (4 g; 12.5 mmol; 1 eq) and methyl 2-amino-4-methoxybenzoate (2.7 g; 15 mmol; 1.2 eq) in water (100 mL), EtOH (100 mL) and acetic acid (40 mL) at 90° C. overnight to afford 2.5 g (44%) of the title compound as a yellow green powder. $^1$H NMR (DMSO-$d_6$) δ 12.67 (bs, 1H), 11.96 (s, 1H), 9.24 (d, J=2.2 Hz, 1H), 9.04 (d, J=2.6 Hz, 1H), 8.82 (dd, J=4.9, 1.5 Hz, 1H), 8.47 (dt, J=7.9, 1.5 Hz, 1H), 7.97-7.93 (m, 2H), 7.68-7.63 (m, 2H), 7.44-7.41 (m, 2H), 6.70 (dd, J=9.0, 2.6 Hz, 1H), 3.90 (s, 3H), 3.79 (s, 3H), HPLC (max plot) 100%; Rt 4.48 min. LC/MS: (ES+): 466.4, (ES−): 464.3.

Example 3 methyl 4-methoxy-2-({3-[(methylsulfonyl)amino]quinoxalin-2-yl}amino)benzoate

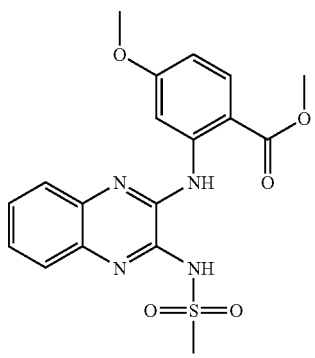 [SMILES: COC(=O)c1ccc(OC)cc1Nc1nc2ccccc2nc1NS(C)(=O)=O]

Following the protocol outlined in Procedure I, Example 3 is obtained from N-(3-chloro quinoxalin-2-yl)methanesulfonamide (979 mg; 3.8 mmol; 1 eq) and methyl 2-amino-4-methoxybenzoate (757.2 mg; 4.2 mmol; 1.1 eq) in water (20 mL), EtOH (100 mL) and acetic acid (500 μl, 11.4 mmol, 3 Eq) at 90° C. overnight to afford 1 g (67%) of the title compound as a green powder. $^1$H NMR (DMSO-$d_6$) δ 12.31 (br s, 1H), 12.01 (s, 1H), 9.06 (d, J=2.2 Hz, 1H), 8.01 (d, J=9.0 Hz, 1H), 7.91-7.88 (m, 1H), 7.66-7.64 (m, 1H), 7.42-7.37 (m, 2H), 6.73 (dd, J=9.0, 2.6 Hz, 1H), 3.92 (s, 3H), 3.90 (s, 3H), 3.24 (s, 3H). HPLC (max plot) 94%; Rt 4.49 min. LC/MS: (ES+): 403.3, (ES−): 401.3.

Example 4

N-[3-({3-methoxy-5-[(4-methylpiperazin-1-yl)carbonyl]phenyl}amino)quinoxalin-2-yl]pyridine-3-sulfonamide

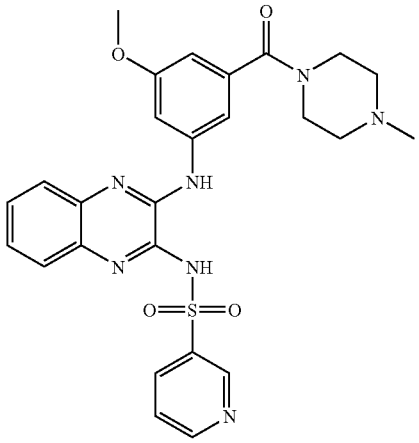 [SMILES: COc1cc(Nc2nc3ccccc3nc2NS(=O)(=O)c2cccnc2)cc(C(=O)N2CCN(C)CC2)c1]

Following the protocol outlined in Procedure I, Example 4 is obtained from N-(3-chloro quinoxalin-2-yl)pyridine-3-sulfonamide (50 mg; 0.16 mmol; 1 eq) and 3-methoxy-5-[(4-methyl piperazin-1-yl)carbonyl]aniline (38.9 mg; 0.16 mmol; 1 eq) in EtOH (1 mL) at 150° C. in the microwave for 30 min to afford 27 mg (32.5%) of the title compound as a yellow powder. $^1$H NMR (DMSO-d$_6$) δ 10.10 (br s, 1H), 9.25 (d, J=3.0 Hz, 1H), 9.20-9.10 (m, 1H), 8.80-8.75 (m, 1H), 8.50-8.44 (m, 1H), 7.90 (s, 1H), 7.70-7.50 (m, 4H), 7.40-7.32 (m, 2H), 6.70 (s, 1H), 3.82 (s, 3H), 3.40-3.10 (m, 8H), 2.82 (s, 3H). HPLC (max plot) 97%; Rt 2.65 min. LC/MS: MS (ES+): 534.3, (ES−): 532.2

Example 5

N-(3-{[3-methoxy-5-(morpholin-4-ylcarbonyl)phenyl]amino}quinoxalin-2-yl)pyridine-3-sulfonamide

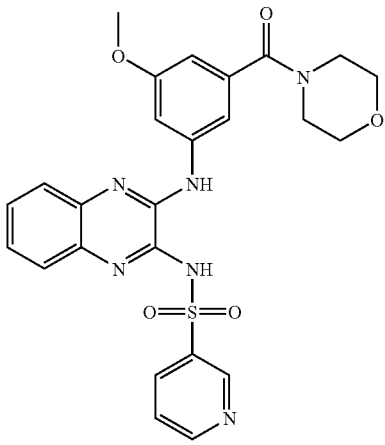 [SMILES: COc1cc(Nc2nc3ccccc3nc2NS(=O)(=O)c2cccnc2)cc(C(=O)N2CCOCC2)c1]

Following the protocol outlined in Procedure I, Example 5 is obtained from N-(3-chloro quinoxalin-2-yl)pyridine-3-sulfonamide (115 mg; 0.36 mmol; 1 eq) and 3-methoxy-5-(morpholin-4-ylcarbonyl)aniline (254.1 mg; 1.08 mmol; 3 eq) in EtOH (5 mL) at 160° C. in the microwave for 50 min to afford 120 mg (64%) of the title compound as a yellow powder. $^1$H NMR (DMSO-d$_6$) δ 9.30-9.21 (m, 1H), 9.14 (s, 1H), 8.79-8.76 (m, 1H), 8.49-8.45 (m, 1H), 7.90-7.82 (m, 2H), 7.63-7.51 (m, 3H), 7.40-7.35 (m, 2H), 6.66-6.65 (m, 1H), 3.81 (s, 3H), 3.68-3.55 (m, 4H), 3.48-3.25 (m, 4H). HPLC (max plot) 95%; Rt 3.34 min. LC/MS: (ES+): 521.2, (ES−): 519.2.

Example 6

N-(3-{[3-methoxy-5-(morpholin-4-ylcarbonyl)phenyl]amino}quinoxalin-2-yl)methanesulfonamide

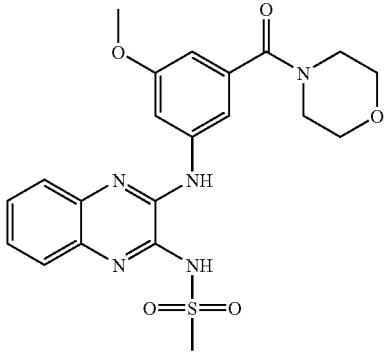 [SMILES: COc1cc(Nc2nc3ccccc3nc2NS(C)(=O)=O)cc(C(=O)N2CCOCC2)c1]

Following the protocol outlined in Procedure I, Example 6 is obtained from N-(3-chloro quinoxalin-2-yl)methanesulfonamide (212.7 mg; 0.83 mmol; 1.5 eq) and 3-methoxy-5-(morpholin-4-ylcarbonyl)aniline (130 mg; 0.55 mmol; 1 eq) in EtOH (1 mL) at 150° C. in the microwave for 1 h to afford 100 mg (40%) of the title compound as a yellow powder. $^1$H NMR (DMSO-d$_6$) δ 12.16 (br s, 1H), 9.30-9.10 (m, 1H), 7.94-7.80 (m, 2H), 7.66-7.54 (m, 2H), 7.45-7.26 (m, 2H), 6.68 (s, 1H), 3.83 (s, 3H), 3.78-3.55 (m, 8H), 3.25 (s, 3H). HPLC (max plot) 98%; Rt 3.19 min. LC/MS: (ES+): 458.4, (ES−): 456.4.

Example 7

N-(3-{[5-methoxy-2-(tetrahydro-2H-pyran-4-ylmethyl)phenyl]amino}quinoxalin-2-yl)-1-methyl-1H-imidazole-4-sulfonamide

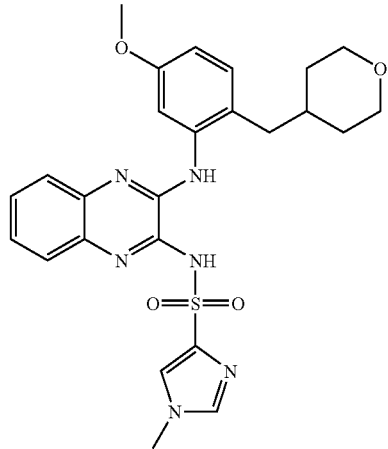 [SMILES: COc1ccc(CC2CCOCC2)c(Nc2nc3ccccc3nc2NS(=O)(=O)c2cn(C)cn2)c1]

Following the protocol outlined in Procedure I, Example 7 is obtained from N-(3-chloro quinoxalin-2-yl)-1-methyl-1H-imidazole-4-sulfonamide (20 mg; 0.06 mmol; 1 eq) and 5-methoxy-2-(tetrahydro-2H-pyran-4-ylmethyl)aniline (16.4 mg; 0.07 mmol; 1.2 eq) in EtOH (0.5 mL), water (0.5 mL) and AcOH (0.2 mL) at 90° C. overnight to afford 5.6 mg (18%) of the title compound as a yellow powder. $^1$H NMR (DMSO-d$_6$) δ 8.83 (s, 1H), 8.34 (br s, 1H), 7.95 (s, 1H), 7.88-7.83 (m, 2H), 7.62-7.58 (m, 1H), 7.43-7.38 (m, 2H), 7.11 (d, J=8.7 Hz, 1H), 6.64 (dd, J=8.3, 2.6 Hz, 1H), 3.79-3.72 (m, 8H), 3.15-3.07 (m, 2H), 2.47 (br s, 2H), 1.65 (br s, 1H), 1.48-1.43 (m, 2H), 1.22-1.10 (m, 2H). HPLC (max plot) 96%; Rt 4.11 min. LC/MS: (ES+): 509.3, (ES−): 507.2

Example 8

N-(3-{[5-methoxy-2-(tetrahydro-2H-pyran-4-ylmethyl)phenyl]amino}quinoxalin-2-yl)methanesulfonamide Potassium Salt

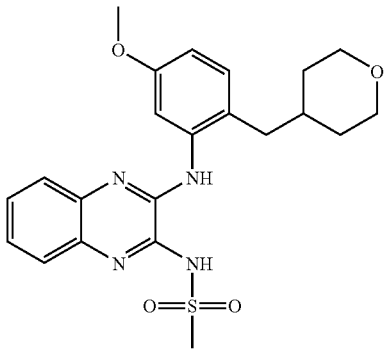 [SMILES: COc1ccc(CC2CCOCC2)c(Nc2nc3ccccc3nc2NS(C)(=O)=O)c1]

Following the protocol outlined in Procedure I, Example 8 is obtained from N-(3-chloro quinoxalin-2-yl)methanesulfonamide (100 mg; 0.39 mmol; 1 eq) and 5-methoxy-2-(tetrahydro-2H-pyran-4-ylmethyl)aniline (103 mg; 0.47 mmol; 1.2 eq) in EtOH (2.5 mL), water (2.5 mL) and AcOH (1 mL) at 90° C. overnight to afford 84 mg (49%) of the title compound as a parent. Treatment of the parent (82.5 mg; 0.19 mmol; 1 eq) with an aqueous solution of potassium hydroxide (372.85 μL; 0.5 M; 0.19 mmol; 1 eq) in water (10 mL) affords 89 mg (99%) of the title compound as a yellow powder. $^1$H NMR (DMSO-d$_6$) δ 9.26 (s, 1H), 8.72 (d, J=2.6 Hz, 1H), 7.45 (dd, J=7.5, 1.9 Hz, 1H), 7.37 (dd, J=7.9, 1.5 Hz, 1H), 7.21-7.12 (m, 2H), 7.04-7.01 (m, 1H), 6.49 (dd, J=8.3, 2.6 Hz, 1H), 3.80 (s, 5H), 3.21 (t, J=11.1 Hz, 2H), 3.05 (s, 3H), 2.56-2.54 (m, 2H), 1.83 (br s, 1H), 1.71-1.67 (m, 2H), 1.30-1.20 (m, 2H). HPLC (max plot) 97%; Rt 4.32 min. LC/MS: (ES+): 443.3, (ES−): 441.2.

Example 9

N-(3-{[5-methoxy-2-(tetrahydro-2H-pyran-4-ylmethyl)phenyl]amino}quinoxalin-2-yl)pyridine-3-sulfonamide Potassium Salt

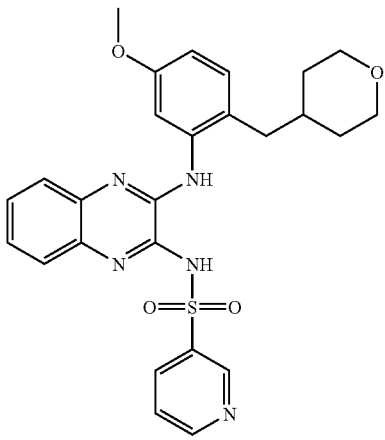 [SMILES: COc1ccc(CC2CCOCC2)c(Nc2nc3ccccc3nc2NS(=O)(=O)c2cccnc2)c1]

Following the protocol outlined in Procedure I, Example 9 is obtained from N-(3-chloro quinoxalin-2-yl)pyridine-3-sulfonamide (200 mg; 0.62 mmol; 1 eq) and 5-methoxy-2-(tetrahydro-2H-pyran-4-ylmethyl)aniline (165.6 mg; 0.75 mmol; 1.2 eq) in EtOH (5 mL), water (5 mL) and AcOH (1 mL) at 90° C. overnight to afford 122 mg (39%) of the title compound as a parent. Treatment of the parent (120 mg; 0.24 mmol; 1. eq) with an aqueous solution of potassium hydroxide (474.7 μL; 0.5 M; 0.24 mmol; 1 eq) in water (3 mL) affords 126 mg (97.5%) of the title compound as a yellow powder. $^1$H NMR (DMSO-d$_6$) δ 9.18 (s, 1H), 9.14 (d, J=1.9 Hz, 1H), 8.67 (d, J=2.6 Hz, 1H), 8.54 (dd, J=4.9, 1.5 Hz, 1H), 8.37-8.34 (m, 1H), 7.46-7.29 (m, 2H), 7.33-7.29 (m, 1H), 7.19-7.12 (m, 2H), 7.04 (d, J=8.3 Hz, 1H), 6.49 (dd, J=8.3, 2.6 Hz, 1H), 3.85-3.81 (m, 2H), 3.78 (s, 3H), 3.27-3.19 (m, 2H), 2.59 (s, 1H), 2.57 (s, 1H), 1.88-1.73 (m, 1H), 1.72-1.68 (m, 2H), 1.35-1.23 (m, 2H). HPLC (max plot) 99%; Rt 4.28 min. LC/MS: (ES+): 506.4, (ES−): 504.4.

Example 10

4-fluoro-N-(3-{[5-methoxy-2-(tetrahydro-2H-pyran-4-ylmethyl)phenyl]amino}quinoxalin-2-yl)benzenesulfonamide Potassium Salt

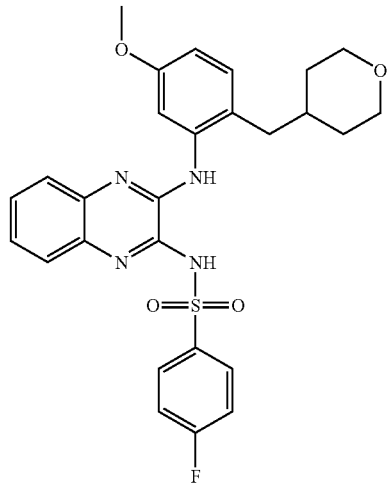 [SMILES: COc1ccc(CC2CCOCC2)c(Nc2nc3ccccc3nc2NS(=O)(=O)c2ccc(F)cc2)c1]

Following the protocol outlined in Procedure I, Example 10 is obtained from N-(3-chloro quinoxalin-2-yl)-4-fluorobenzenesulfonamide (200 mg; 0.59 mmol; 1 eq) and 5-methoxy-2-(tetrahydro-2H-pyran-4-ylmethyl)aniline (157.3 mg; 0.71 mmol; 1.2 eq) in EtOH (5 mL), water (5 mL) and AcOH (1 mL) at 90° C. overnight to afford 122 mg (39%) of the title compound as a parent. Treatment of the parent (126 mg; 0.24 mmol; 1 eq) with an aqueous solution of potassium hydroxide (482.2 μL; 0.5 M; 0.24 mmol; 1 eq) in water (3 mL) affords 138 mg (100%) of the title compound as a yellow powder. $^1$H NMR (DMSO-d$_6$) δ 8.44 (d, J=2.6 Hz, 1H), 8.07-7.98 (m, 2H), 7.68-7.65 (m, 1H), 7.41-7.27 (m, 3H), 7.22-7.17 (m, 2H), 7.00 (d, J=8.3 Hz, 1H), 6.59 (dd, J=8.3, 2.6 Hz, 1H), 3.85 (s, 3H), 3.81-3.80 (m, 2H), 3.19-3.12 (m, 2H), 2.48 (s, 1H), 2.45 (s, 1H), 1.63-1.50 (m, 1H), 1.43-1.39 (m, 2H), 1.27-1.20 (m, 2H). HPLC (max plot) 99.5%; Rt 5.22 min. LC/MS: (ES+): 523.4, (ES−): 521.4. CHN analysis: [C$_{27}$H$_{26}$N$_4$O$_4$SF—K-4.0  H20] Corrected: C51.17%, H5.41%, N8.84%; Found: C50.83%, H5.03%, N8.50%.

Example 11

N-[3-({5-methoxy-2-[(1-methylpiperidin-4-yl)methyl]phenyl}amino)quinoxalin-2-yl]-1-methyl-1H-imidazole-4-sulfonamide TFA Salt

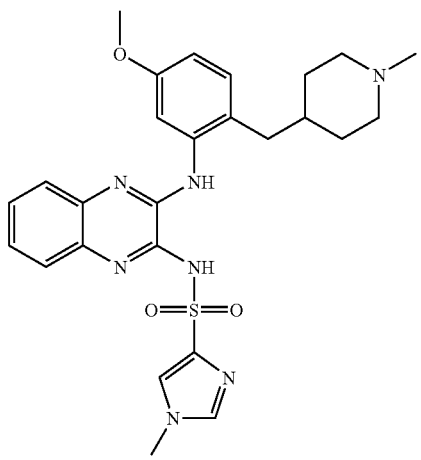 [SMILES: COc1ccc(CC2CCN(C)CC2)c(Nc2nc3ccccc3nc2NS(=O)(=O)c2cn(C)cn2)c1]

Following the protocol outlined in Procedure I, Example 11 is obtained from N-(3-chloro quinoxalin-2-yl)-1-methyl-1H-imidazole-4-sulfonamide (200 mg; 0.62 mmol; 1 eq) and 5-methoxy-2-[(1-methylpiperidin-4-yl)methyl]aniline (173.7 mg; 0.74 mmol; 1.2 eq) in EtOH (5 mL), water (5 mL) and AcOH (2 mL) at 90° C. for 2 days to afford 95 mg (20.5%) of the title compound as a yellow powder after purification by preparative HPLC in the presence of 0.1% TFA. $^1$H NMR (DMSO-d$_6$) δ 8.13 (br s, 1H), 7.90 (br s, 1H), 7.83 (s, 1H), 7.72-7.69 (m, 1H), 7.57-7.54 (m, 1H), 7.41-7.39 (m, 2H), 7.12 (d, J=8.3 Hz, 1H), 6.66 (dd, J=8.3, 2.6 Hz, 1H), 3.74 (s, 3H), 3.67 (s, 3H), 3.48-3.40 (m, 1H), 3.33-3.29 (m, 2H), 3.14-3.07 (m, 1H), 2.79-2.71 (m, 2H), 2.65 (s, 3H), 1.79-1.60 (m, 3H), 1.46-1.28 (m, 2H). HPLC (max plot) 97%; Rt 3.19 min. LC/MS: (ES+): 522.4, (ES−): 520.4.

Example 12

N-[3-({5-methoxy-2-[(1-methylpiperidin-4-yl)methyl]phenyl}amino)quinoxalin-2-yl]pyridine-3-sulfonamide HCl Salt

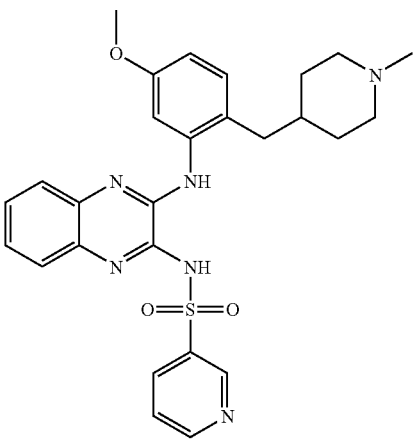 [SMILES: COc1ccc(CC2CCN(C)CC2)c(Nc2nc3ccccc3nc2NS(=O)(=O)c2cccnc2)c1]

Following the protocol outlined in Procedure I, Example 12 is obtained from N-(3-chloro quinoxalin-2-yl)pyridine-3-sulfonamide (324 mg; 1 mmol; 1 eq) and 5-methoxy-2-[(1-methylpiperidin-4-yl)methyl]aniline (236.7 mg; 1 mmol; 1 eq) in water (7 mL) and AcOH (0.02 mL; 0.46 mmol; 0.45 eq) at 170° C. in the microwave for 20 min to afford 71 mg (9.4%) of the title compound as TFA salt after purification by preparative HPLC in the presence of 0.1% TFA. Treatment of the TFA salt (71 mg, 0.11 mmol, 1 Eq) with HCl in MeOH (400 µL; 1.25 M; 0.5 mmol; 5 eq) in MeOH (0.5 mL) affords 24 mg (4%) of the title compound as a yellow powder. $^1$H NMR (DMSO-d$_6$) δ 12.64 (s, 1H), 9.49 (s, 1H), 9.26 (d, J=2.3 Hz, 1H), 8.84 (dd, J=4.9, 1.5 Hz, 1H), 8.77-8.70 (m, 1H), 8.47 (dt, J=8.3, 1.9 Hz, 1H), 8.14-8.08 (m, 1H), 7.98-7.92 (m, 1H), 7.69-7.65 (m, 1H), 7.57-7.54 (m, 1H), 7.41-7.34 (m, 2H), 7.11 (d, J=8.3 Hz, 1H), 6.69-6.65 (m, 1H), 3.77 (s, 3H), 3.29-3.25 (m, 2H), 2.71-2.64 (m, 5H), 2.43-2.41 (m, 2H), 1.56-1.44 (m, 3H), 1.36-1.23 (m, 2H). HPLC (max plot) 100%; Rt 3.13 min LC/MS: (ES+): 519.1, (ES−): 517.1.

Example 13

N-[3-({5-methoxy-2-[(1-methylpiperidin-4-yl)methyl]phenyl}amino)quinoxalin-2-yl]methanesulfonamide TFA Salt

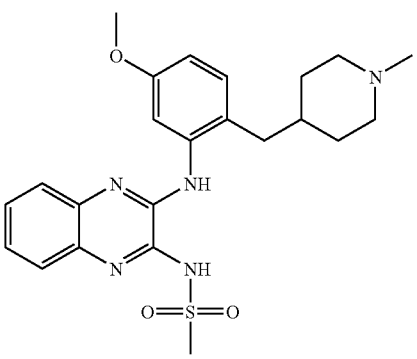 [SMILES: COc1ccc(CC2CCN(C)CC2)c(Nc2nc3ccccc3nc2NS(C)(=O)=O)c1]

Following the protocol outlined in Procedure I, Example 13 is obtained from N-(3-chloro quinoxalin-2-yl)methanesulfonamide (200 mg; 0.8 mmol; 1 eq) and 5-methoxy-2-[(1-methyl piperidin-4-yl)methyl]aniline (218.3 mg; 0.9 mmol; 1.2 eq) in EtOH (5 mL), water (5 mL) and AcOH (2 mL) at 90° C. for 2 days to afford 64.7 mg (15%) of the title compound as a yellow powder, after purification by preparative HPLC in the presence of 0.1% TFA. $^1$H NMR (DMSO-$d_6$) δ 12.28 (br s, 1H), 9.30 (br s, 1H), 8.82 (s, 1H), 8.22 (br s, 1H), 7.91-7.88 (m, 1H), 7.58-7.55 (m, 1H), 7.40-7.33 (m, 2H), 7.16 (d, J=8.3 Hz, 1H), 6.69 (dd, J=8.3, 2.6 Hz, 1H), 3.80 (s, 3H), 3.39-3.35 (m, 2H), 3.26 (s, 3H), 2.89-2.79 (m, 2H), 2.70 (d, J=6 Hz, 3H), 2.61-2.59 (m, 2H), 1.85-1.75 (m, 3H), 1.46-1.37 (m, 2H). HPLC (max plot) 99%; Rt 3.01 min LC/MS: (ES+): 456.5, (ES−): 454.4.

Example 14

N-[3-({5-methoxy-2-[(1,2,2,6,6-pentamethylpiperidin-4-yl)methyl]phenyl}amino)quinoxalin-2-yl]-1-methyl-1H-imidazole-4-sulfonamide HCl Salt

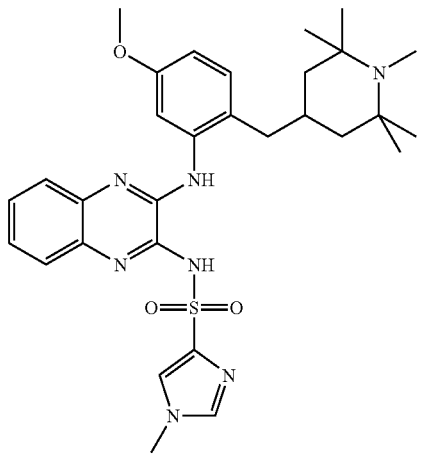 [SMILES: COc1ccc(CC2CC(C)(C)N(C)C(C)(C)C2)c(Nc2nc3ccccc3nc2NS(=O)(=O)c2cn(C)cn2)c1]

Following the protocol outlined in Procedure I, Example 14 is obtained from N-(3-chloro quinoxalin-2-yl)-1-methyl-1H-imidazole-4-sulfonamide (323.8 mg; 1 mmol; 1 eq) and 5-methoxy-2-[(1,2,2,6,6-pentamethylpiperidin-4-yl)methyl] aniline (290.5 mg; 1 mmol; 1 eq) in EtOH (8 mL), water (8 mL) and AcOH (1.5 mL) at 90° C. overnight to afford 62 mg (9%) of the title compound as a yellow powder, after purification by preparative HPLC in the presence of 0.1% TFA. Treatment of the TFA salt (62 mg; 0.11 mmol; 1 eq) with HCl in diethylether (110 µL; 0.11 mmol; 1 eq) in DCM (8 mL) affords 48.8 mg (72%) of the title compound as a yellow powder. $^1$H NMR (DMSO-$d_6$) δ 8.86 (m, 2H), 8.10 (br s, 1H), 7.99 (s, 1H), 7.94 (s, 1H), 7.83-7.76 (m, 1H), 7.58-7.54 (m, 1H), 7.40-7.37 (m, 2H), 7.17 (d, J=8.3 Hz, 1H), 6.70 (dd, J=8.3, 2.6 Hz, 1H), 3.79 (s, 3H), 3.73 (s, 3H), 2.62-2.61 (m, 3H), 2.53-2.51 (m, 2H), 2.17-2.01 (m, 1H), 1.81-1.77 (m, 2H), 1.54-1.46 (m, 2H), 1.35 (s, 6H), 1.14 (s, 6H). HPLC (max plot) 100%; Rt 3.41 min. LC/MS: (ES+): 578.1, (ES−): 576.1.

Example 15

N-{3-[(5-methoxy-2-{[(1R,5S)-8-methyl-8-azabicyclo[3.2.1]oct-3-yl]methyl}phenyl)amino]quinoxalin-2-yl}-1-methyl-1H-imidazole-4-sulfonamide (HCl Salt)

Mixture of Cis/Trans Isomers

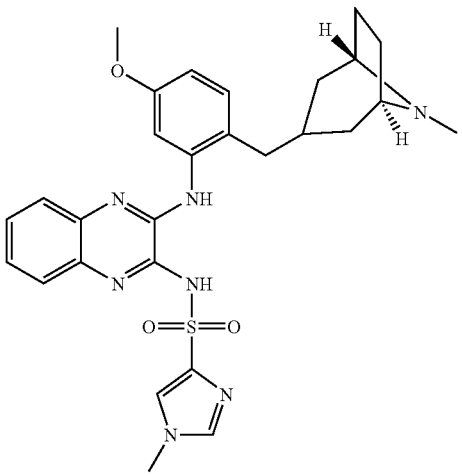 [SMILES: COc1ccc(CC2C[C@H]3CC[C@@H](C2)N3C)c(Nc2nc3ccccc3nc2NS(=O)(=O)c2cn(C)cn2)c1]

Following the protocol outlined in Procedure I, Example 15 is obtained from N-(3-chloro quinoxalin-2-yl)-1-methyl-1H-imidazole-4-sulfonamide (323.8 mg; 1 mmol; 1 eq) and 5-methoxy-2-{[(1R,5S)-8-methyl-8-azabicyclo[3.2.1]oct-3-yl]methyl}aniline (260.4 mg; 1 mmol; 1 eq) in EtOH (8 mL), water (8 mL) and AcOH (1.5 mL) at 90° C. overnight to afford 21.7 mg of the title compound as a TFA salt after purification by preparative HPLC in the presence of 0.1% TFA. The TFA salt is treated with HCl in diethylether (44 µl, 1M, 1.1 eq) in DCM (1.5 mL) to afford 22.1 mg (4%) of the title compound as a yellow powder. $^1$H NMR (DMSO-$d_6$) δ 9.63 (br s, 1H), 8.82 (br s, 1H), 8.20 (br s, 1H), 7.98 (s, 1H), 7.93 (s, 1H), 7.86-7.82 (m, 1H), 7.60-7.57 (m, 1H), 7.42-7.39 (m, 2H), 7.09 (d, J=8.3 Hz, 1H), 6.67 (dd, J=8.7, 2.6 Hz, 1H), 3.77-3.73

(m, 9H), 3.45 (br s, 2H), 2.59 (d, J=4.9 Hz, 3H), 2.05-2.02 (m, 3H), 1.68-1.65 (m, 6H). HPLC (max plot) 98%; Rt 3.17 min. LC/MS: (ES+): 548.1, (ES−): 546.1.

Example 16

N-[3-({2-[(1-acetylpiperidin-4-yl)methyl]-5-methoxyphenyl}amino)quinoxalin-2-yl]-1-methyl-1H-imidazole-4-sulfonamide (Potassium Salt)

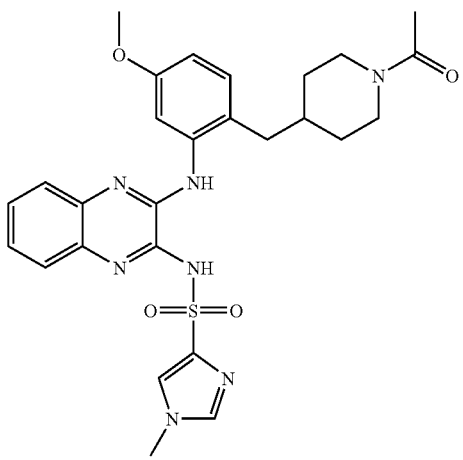 [SMILES: COc1ccc(CC2CCN(C(C)=O)CC2)c(Nc2nc3ccccc3nc2NS(=O)(=O)c2cn(C)cn2)c1]

Following the protocol outlined in Procedure I, Example 16 is obtained from N-(3-chloro quinoxalin-2-yl)-1-methyl-1H-imidazole-4-sulfonamide (325 mg; 1 mmol; 1 eq) and 2-[(1-acetylpiperidin-4-yl)methyl]-5-methoxyaniline (289.7 mg; 1.1 mmol; 1.1 eq) in EtOH (8 mL), water (8 mL) and AcOH (1.5 mL) at 90° C. for 5 h to afford 115.9 mg (21%) of the title compound as a parent. Treatment of the parent (112.4 mg; 0.2 mmol; 1 eq) with an aqueous solution of potassium hydroxide (409 µL; 0.5 M; 0.2 mmol; 1 eq) in water (3 mL) affords 122 mg (100%) of the title compound as a light yellow powder. $^1$H NMR (DMSO-d$_6$) δ 8.70 (d, J=2.3 Hz, 1H), 7.60 (s, 1H), 7.43 (s, 1H), 7.41 (dd, J=7.7, 1.7 Hz, 1H), 7.34 (d, J=7.5 Hz, 1H), 7.18-7.09 (m, 2H), 7.02 (d, J=8.3 Hz, 1H), 6.48 (dd, J=8.3, 2.6 Hz, 1H), 4.34-4.30 (m, 1H), 3.78 (s, 3H), 3.72 (br s, 1H), 3.63 (s, 3H), 2.98-2.90 (m, 1H), 2.45-2.39 (m, 3H), 1.97 (s, 3H), 1.79-1.67 (m, 3H), 1.19-1.12 (m, 1H), 0.97-0.83 (m, 2H). HPLC (max plot) 97%; Rt 3.80 min. LC/MS: (ES+): 550.5, (ES−): 548.4.

Example 17

N-[3-({2-[1-acetylpiperidin-4-yl)methyl]-5-methoxyphenyl}amino)quinoxalin-2-yl]pyridine-3-sulfonamide (Potassium Salt)

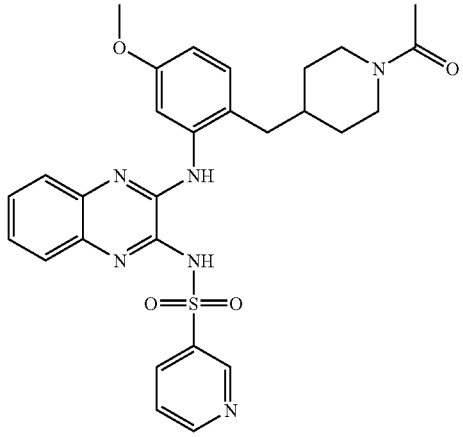 [SMILES: COc1ccc(CC2CCN(C(C)=O)CC2)c(Nc2nc3ccccc3nc2NS(=O)(=O)c2cccnc2)c1]

Following the protocol outlined in Procedure I, Example 17 is obtained from N-(3-chloro quinoxalin-2-yl)pyridine-3-sulfonamide (400 mg; 1.25 mmol; 1 eq) and 2-[(1-acetylpiperidin-4-yl)methyl]-5-methoxyaniline (359.9 mg; 1.4 mmol; 1.1 eq) in EtOH (10 mL), water (10 mL) and AcOH (2 mL) at 90° C. overnight to afford 88 mg (13%) of the title compound as a parent. Treatment of the parent (116 mg; 0.2 mmol; 1 eq) with an aqueous solution of potassium hydroxide (424.4 µL; 0.5 M; 0.2 mmol; 1 eq) in water (2 mL) affords 120 mg (98%) of the title compound as a pale yellow powder. $^1$H NMR (DMSO-d6) δ 9.18-9.14 (m, 2H), 8.68 (d, J=3.0 Hz, 1H), 8.54 (dd, J=4.9, 3.0 Hz, 1H), 8.35 (dt, J=7.9, 1.9 Hz, 1H), 7.46-7.41 (m, 2H), 7.32-7.29 (m, 1H), 7.20-7.11 (m, 2H), 7.04 (d, J=8.3 Hz, 1H), 6.49 (dd, J=8.3, 2.6 Hz, 1H), 4.40-4.35 (m, 1H), 3.85-3.80 (m, 1H), 3.78 (s, 3H), 3.00-2.92 (m, 1H), 2.59-2.57 (m, 2H), 2.48-2.40 (m, 1H), 1.99 (s, 3H), 1.89-1.76 (m, 3H), 1.27-1.00 (m, 2H). HPLC (max plot) 99%; Rt 3.90 min. LC/MS: (ES+): 547.0, (ES−): 545.0.

Example 18

N-[3-({2-[1-acetylpiperidin-4-yl)methyl]-5-methoxyphenyl}amino)quinoxalin-2-yl]methanesulfonamide Potassium Salt

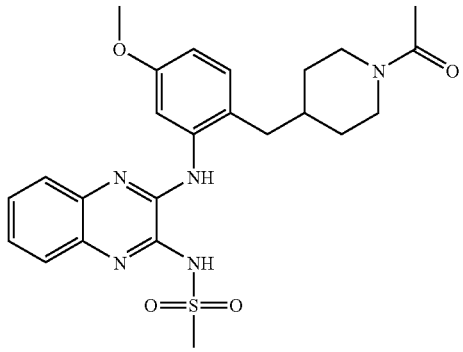 [SMILES: COc1ccc(CC2CCN(C(C)=O)CC2)c(Nc2nc3ccccc3nc2NS(C)(=O)=O)c1]

Following the protocol outlined in Procedure I, Example 18 is obtained from N-(3-chloro quinoxalin-2-yl)methanesulfonamide (350 mg; 1.4 mmol; 1 eq) and 2-[(1-acetylpiperidin-4-yl)methyl]-5-methoxyaniline (392 mg; 1.5 mmol; 1.1 eq) in EtOH (8 mL), water (8 mL) and AcOH (1.5 mL) at 90° C. overnight to afford 160 mg (24%) of the title compound as a parent. Treatment of the parent (156 mg; 0.32 mmol; 1 eq) with an aqueous solution of potassium hydroxide (644.8 µL; 0.5 M; 0.32 mmol; 1 eq) in water (10 mL) affords 162.7 mg (97%) of the title compound as a yellow powder. $^1$H NMR (DMSO-d$_6$) δ 12.24 (br s, 1H), 8.89 (br s, 1H), 8.35 (br s, 1H), 7.83 (br s, 1H), 7.55-7.53 (m, 1H), 7.39-7.26 (m, 2H), 7.12 (d, J=8.3 Hz, 1H), 6.64 (d, J=6.8 Hz, 1H), 4.35-4.30 (m, 1H), 3.80 (s, 3H), 3.74 (m, 1H), 3.19 (s, 3H), 2.96-2.88 (m, 1H), 2.58-2.56 (m, 2H), 2.45-2.37 (m, 1H), 1.95 (s, 3H), 1.97-1.73 (m, 1H), 1.72-1.62 (m, 2H), 1.19-1.01 (m, 2H). HPLC (max plot) 99%; Rt 3.92 min. LC/MS: (ES+): 484.1; (ES−): 482.2.

Example 19

N-(3-{[2-(cyclohexylmethyl)-5-methoxyphenyl]amino}quinoxalin-2-yl)pyridine-3-sulfonamide Potassium Salt

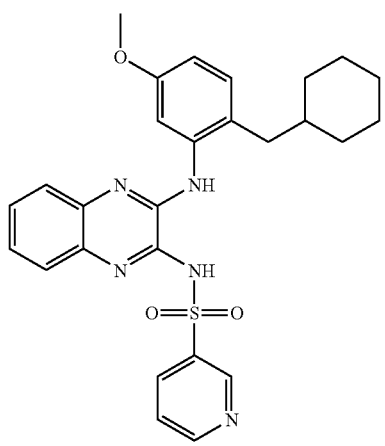 [SMILES: COc1ccc(CC2CCCCC2)c(Nc2nc3ccccc3nc2NS(=O)(=O)c2cccnc2)c1]

Following the protocol outlined in Procedure I, Example 19 is obtained from N-(3-chloro quinoxalin-2-yl)pyridine-3-sulfonamide (200 mg; 0.62 mmol; 1 eq) and 2-(cyclohexylmethyl)-5-methoxyaniline (150.4 mg; 0.7 mmol; 1.1 eq) in EtOH (1.5 mL), water (0.3 mL) and AcOH (0.75 mL) at 150° C. in the microwave for 10 min to afford 66.2 mg (21%) of the title compound as a parent. Treatment of the parent (118.2 mg; 0.23 mmol; 1 eq) with an aqueous solution of potassium hydroxide (470 µL; 0.5 M; 0.23 mmol; 1 eq) in water (20 mL) affords 119 mg (94%) of the title compound as a yellow powder. $^1$H NMR (DMSO-d$_6$) δ 9.14-9.13 (m, 2H), 8.64 (d, J=3.0 Hz, 1H), 8.55-8.52 (m, 1H), 8.38-8.34 (m, 1H), 7.45-7.39 (m, 2H), 7.32-7.29 (m, 1H), 7.19-7.10 (m, 2H), 7.01 (d, J=8.3 Hz, 1H), 6.49 (dd, J=8.3, 2.6 Hz, 1H), 3.78 (s, 3H), 1.82-1.76 (m, 2H), 1.66-1.51 (m, 4H), 1.23-0.96 (m, 6H), 0.88-0.70 (m, 1H). HPLC (max plot) 98%; Rt 5.47 min. LC/MS: (ES+): 504.5, (ES−): 502.4.

Example 20

N-(3-{[2-(cyclohexylmethyl)-5-methoxyphenyl]amino}quinoxalin-2-yl)-1-methyl-1H-imidazole-4-sulfonamide Potassium Salt

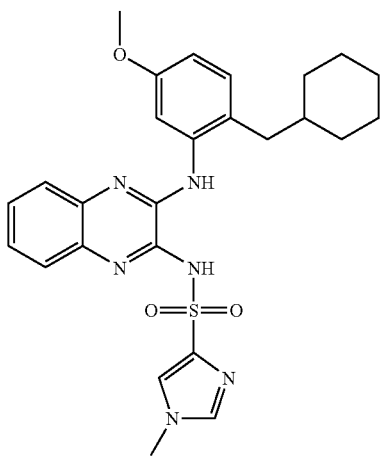 [SMILES: COc1ccc(CC2CCCCC2)c(Nc2nc3ccccc3nc2NS(=O)(=O)c2cn(C)cn2)c1]

Following the protocol outlined in Procedure I, Example 20 is obtained from N-(3-chloro quinoxalin-2-yl)-1-methyl-1H-imidazole-4-sulfonamide (280 mg; 0.86 mmol; 1 eq) and 2-(cyclohexylmethyl)-5-methoxyaniline (208.65 mg; 0.95 mmol; 1.1 eq) in EtOH (1.5 mL), water (0.3 mL) and AcOH (0.75 mL) at 150° C. in the microwave for 10 min to afford 109 mg (25%) of the title compound as a parent. Treatment of the parent (109 mg; 0.22 mmol; 1 eq) with an aqueous solution of potassium hydroxide (430 µL; 0.5 M; 0.22 mmol; 1 eq) in water (20 mL) affords 117.4 mg (100%) of the title compound as a yellow powder. $^1$H NMR (DMSO-d$_6$) δ 9.22 (s, 1H), 8.71 (d, J=2.6 Hz, 1H), 7.63-7.55 (m, 1H), 7.47 (s, 1H), 7.41-7.31 (2H), 7.17-7.07 (m, 2H), 7.00 (d, J=8.3 Hz, 1H), 6.47 (dd, J=8.3, 2.6 Hz, 1H), 3.77 (s, 3H), 3.63 (s, 3H), 2.49-2.46 (m, 2H), 1.70-1.52 (m, 6H), 1.20-0.89 (m, 5H). HPLC (max plot) 99%; Rt 5.35 min. LC/MS: (ES+): 507.5, (ES−): 505.4.

Example 21

N-(3-{[2-(cyclohexylmethyl)-5-methoxyphenyl]amino}quinoxalin-2-yl)methanesulfonamide Potassium Salt

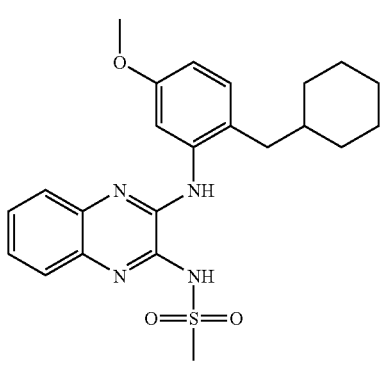 [SMILES: COc1ccc(CC2CCCCC2)c(Nc2nc3ccccc3nc2NS(C)(=O)=O)c1]

Following the protocol outlined in Procedure I, Example 21 is obtained from N-(3-chloro quinoxalin-2-yl)methanesulfonamide (100 mg; 0.4 mmol; 1 eq) and 2-(cyclohexylmethyl)-5-methoxyaniline (110.6 mg; 0.5 mmol; 1.3 eq) in EtOH (1 mL), water (0.3 mL) and AcOH (0.75 mL) at 150° C. in the microwave for 13 min to afford 226 mg (26%) of the title compound as a parent. Treatment of the parent (198 mg; 0.45 mmol; 1 eq) with an aqueous solution of potassium hydroxide (900 μL; 0.5 M; 0.45 mmol; 1 eq) in water (30 mL) affords 211.3 mg (98%) of the title compound as a yellow powder. $^1$H NMR (DMSO-$d_6$) δ 9.20 (s, 1H), 8.71 (d, J=2.6 Hz, 1H), 7.45-7.34 (m, 2H), 7.21-7.10 (m, 2H), 7.00 (d, J=8.3 Hz, 1H), 6.48 (dd, J=8.3, 2.6 Hz, 1H), 3.79 (s, 3H), 3.04 (s, 3H), 1.80-1.76 (m, 2H), 1.68-1.52 (m, 4H), 1.22-0.92 (m, 5H). HPLC (max plot) 98%; Rt 5.59 min. LC/MS: (ES+): 441.5, (ES−): 439.4.

Example 22

N-[3-({2-[(4-hydroxycyclohexyl)methyl]-5-methoxyphenyl}amino) quinoxalin-2-yl]-1-methyl-1H-imidazole-4-sulfonamide

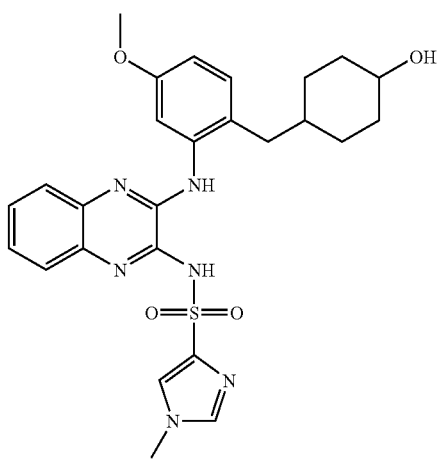 [SMILES: COc1ccc(CC2CCC(O)CC2)c(Nc2nc3ccccc3nc2NS(=O)(=O)c2cn(C)cn2)c1]

Following the protocol outlined in Procedure I, Example 22 is obtained from N-(3-chloro quinoxalin-2-yl)-1-methyl-1H-imidazole-4-sulfonamide (647.5 mg; 2 mmol; 1 eq) and 2-[(4-{[tert-butyl(dimethyl)silyl]oxy}cyclohexyl)methyl]-5-methoxyaniline (769 mg; 2.2 mmol; 1.1 eq) in EtOH (16 mL), water (16 mL) and AcOH (3 mL) at 90° C. overnight to afford 68.7 mg (6.5%) of the title compound as a yellow powder. $^1$H NMR (DMSO-$d_6$) δ 8.80 (br s, 1H), 8.33 (br s, 1H), 7.95-7.81 (m, 3H), 7.61-7.58 (m, 1H), 7.43-7.36 (m, 2H), 7.08 (d, J=8.3 Hz, 1H), 6.63 (dd, J=8.3, 2.6 Hz, 1H), 4.23 (br s, 1H), 3.79 (s, 3H), 3.72 (s, 4H), 3.48 (br s, 1H), 2.46-2.44 (m, 2H), 1.55-1.52 (m, 3H), 1.35-1.22 (m, 6H). HPLC (max plot) 98%; Rt 3.94 min. LC/MS: (ES+): 523.1, (ES−): 521.1.

Example 23

N-[3-({2-[(4-hydroxycyclohexyl)methyl]-5-methoxyphenyl}amino)quinoxalin-2-yl]pyridine-3-sulfonamide

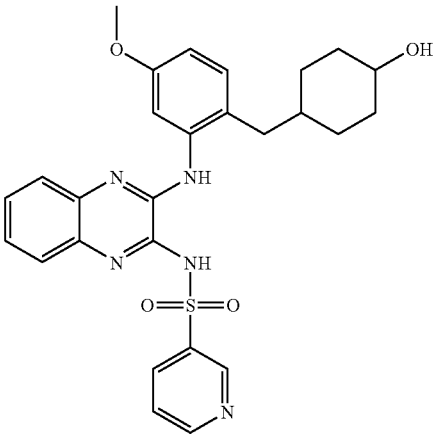 [SMILES: COc1ccc(CC2CCC(O)CC2)c(Nc2nc3ccccc3nc2NS(=O)(=O)c2cccnc2)c1]

Following the protocol outlined in Procedure I, Example 23 is obtained from N-(3-chloro quinoxalin-2-yl)pyridine-3-sulfonamide (320 mg; 1 mmol; 1 eq) and 2-[(4-{[tert-butyl(dimethyl)silyl]oxy}cyclohexyl)methyl]-5-methoxyaniline (472.8 mg; 1.35 mmol; 1.35 eq) in EtOH (8 mL), water (8 mL) and AcOH (1.5 mL) at 90° C. overnight to afford, after purification on flash chromatography, 105 mg (20%) of the title compound as a yellow powder. $^1$H NMR (DMSO-$d_6$) δ 12.58 (br s, 1H), 9.21 (d, J=1.9 Hz, 1H), 8.82 (dd, J=4.9, 1.5 Hz, 1H), 8.69 (s, 1H), 8.46-8.42 (m, 1H), 8.28 (s, 1H), 7.95 (br d, 1H), 7.67-7.63 (m, 1H), 7.59-7.56 (m, 1H), 7.43-7.34 (m, 2H), 7.06 (d, J=8.3 Hz, 1H), 6.63 (dd, J=8.3, 2.6 Hz, 1H), 3.78 (s, 3H), 3.65 (br s, 1H), 2.35 (br d, 2H), 1.48-1.08 (m, 9H). HPLC (max plot) 100%; Rt 4.11 min. LC/MS: (ES+): 520.1, (ES−): 518.1.

Example 24

N-(3-{[2-(cyclopentylmethyl)-5-methoxyphenyl]amino}quinoxalin-2-yl)-1-methyl-1H-imidazole-4-sulfonamide Potassium Salt

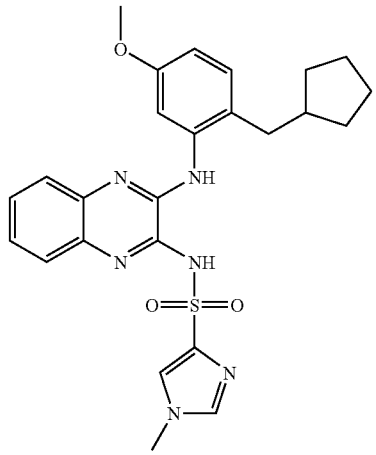 [SMILES: COc1ccc(CC2CCCC2)c(Nc2nc3ccccc3nc2NS(=O)(=O)c2cn(C)cn2)c1]

Following the protocol outlined in Procedure I, Example 24 is obtained from N-(3-chloro quinoxalin-2-yl)-1-methyl-1H-imidazole-4-sulfonamide (150 mg; 0.46 mmol; 1 eq) and 2-(cyclopentylmethyl)-5-methoxyaniline (95.1 mg; 0.46 mmol; 1 eq) in EtOH (8 mL), water (8 mL) and AcOH (1.5 mL) at 90° C. overnight to afford 73 mg (32%) of the title compound as a parent. Treatment of the parent (70 mg; 0.14 mmol; 1 eq) with an aqueous solution of potassium hydroxide (285.8 μL; 0.5 M; 0.14 mmol; 1 eq) in water (10 mL) affords 37.5 mg (49%) of the title compound as a yellow powder. $^1$H NMR (DMSO-$d_6$) δ 9.21 (br s, 1H), 8.68 (br s, 1H), 7.62 (br s, 1H), 7.47 (s, 1H), 7.42-7.39 (m, 1H), 7.37-7.28 (m, 1H), 7.18-7.08 (m, 2H), 7.06 (d, J=8.3 Hz, 1H), 6.49 (dd, J=8.3, 2.3 Hz, 1H), 3.78 (s, 3H), 3.64 (s, 3H), 2.59 (d, J=7.2 Hz, 2H), 2.21-2.08 (m, 1H), 1.73-1.44 (m, 6H), 1.23-1.11 (m, 2H). HPLC (max plot) 99%; Rt 4.99 min. LC/MS: (ES+): 493.1, (ES−): 491.1.

Example 25

N-(3-{[5-methoxy-2-(tetrahydro-2H-thiopyran-4-ylmethyl)phenyl]amino}quinoxalin-2-yl)-1-methyl-1H-imidazole-4-sulfonamide Potassium Salt

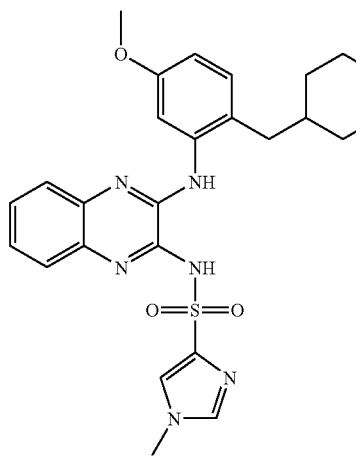

Following the protocol outlined in Procedure I, Example 25 is obtained from N-(3-chloro quinoxalin-2-yl)-1-methyl-1H-imidazole-4-sulfonamide (323.8 mg; 1 mmol; 1 eq) and 5-methoxy-2-(tetrahydro-2H-thiopyran-4-ylmethyl)aniline (273.8 mg; 1 mmol; 1 eq) in EtOH (8 mL), water (8 mL) and AcOH (1.5 mL) at 90° C. overnight to afford 102 mg (19%) of the title compound as a parent. Treatment of the parent (100 mg; 0.19 mmol; 1 eq) with an aqueous solution of potassium hydroxide (381.2 μL; 0.5 M; 0.19 mmol; 1 eq) in water (10 mL) affords 114.5 mg (100%) of the title compound as a yellow powder. $^1$H NMR (DMSO-$d_6$) δ 9.24 (br s, 1H), 8.72 (d, J=2.6 Hz, 1H), 7.61 (d, J=1.1 Hz, 1H), 7.47 (d, J=1.1 Hz, 1H), 7.40 (dd, J=7.7, 1.7 Hz, 1H), 7.33 (dd, J=7.7, 1.7 Hz, 1H), 7.17-7.08 (m, 2H), 7.01 (d, J=8.3 Hz, 1H), 6.47 (dd, J=8.3, 2.6 Hz, 1H), 3.79 (s, 3H), 3.64 (s, 3H), 3.32-3.30 (m, 2H), 2.61-2.51 (m, 4H), 2.05-2.02 (m, 2H), 1.72-1.57 (m, 1H), 1.33-1.18 (m, 2H). HPLC (max plot) 99%; Rt 4.77 min. LC/MS: (ES+): 525.1, (ES−): 523.1. CHN analysis: [$C_{25}H_{27}N_6O_3S_2$—K-5.4 $H_2O$] Corrected: C45.42%, H5.76%, N12.71%; Found: C45.78%, H5.41%, N12.43%.

Example 26

N-[3-({2-[(1,1-dioxidotetrahydro-2H-thiopyran-4-yl)methyl]-5-methoxy phenyl}amino)auinoxalin-2-yl]-1-methyl-1H-imidazole-4-sulfonamide Potassium Salt

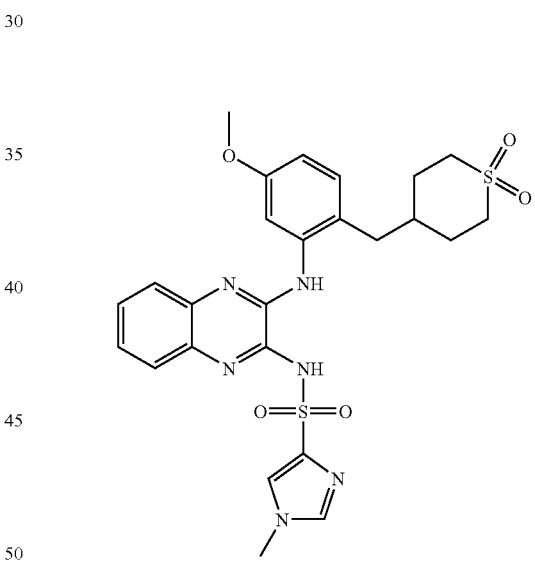

Following the protocol outlined in Procedure I, Example 26 is obtained from N-(3-chloro quinoxalin-2-yl)-1-methyl-1H-imidazole-4-sulfonamide (150 mg; 0.46 mmol; 1 eq) and 2-[(1,1-dioxidotetrahydro-2H-thiopyran-4-yl)methyl]-5-methoxyaniline (141.7 mg; 0.46 mmol; 1 eq) in EtOH (8 mL), water (8 mL) and AcOH (1.5 mL) at 90° C. overnight to afford 66 mg (26%) of the title compound as a parent. Treatment of the parent (64.6 mg; 0.12 mmol; 1 eq) with an aqueous solution of potassium hydroxide (232 μL; 0.5 M; 0.12 mmol; 1 eq) in water (10 mL) affords 31 mg (45%) of the title compound as a yellow powder. $^1$H NMR (DMSO-$d_6$) δ 9.35 (br s, 1H), 8.73 (d, J=2.6 Hz, 1H), 7.63-7.61 (m, 1H), 7.44-7.40 (m, 2H), 7.34 (dd, J=7.9, 1.5 Hz, 1H), 7.18-7.09 (m, 2H), 7.05 (d, J=8.3 Hz, 1H), 6.48 (dd, J=8.1, 2.8 Hz, 1H), 3.79 (s, 3H), 3.62 (s, 3H), 3.26-3.16 (m, 2H), 2.93-2.89 (m, 2H), 2.62-2.60 (m, 2H), 2.15-2.11 (m, 3H), 1.67-1.63 (m, 2H). HPLC (max plot) 99%; Rt 3.73 min. LC/MS: (ES+): 557.0, (ES−): 555.0.

Example 27

N-(3-{[2-(2-hydroxyethyl)-5-methoxyphenyl]amino}quinoxalin-2-yl)pyridine-3-sulfonamide Potassium Salt

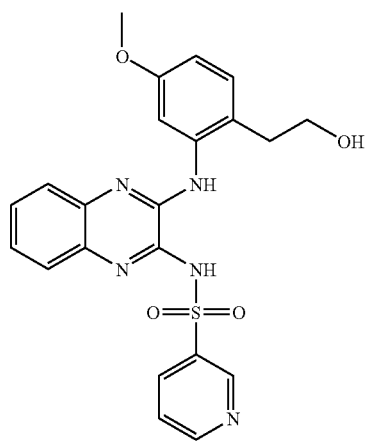 [SMILES: COc1ccc(CCO)c(Nc2nc3ccccc3nc2NS(=O)(=O)c2cccnc2)c1]

Following the protocol outlined in Procedure I, Example 27 is obtained from N-(3-chloro quinoxalin-2-yl)pyridine-3-sulfonamide (250 mg; 0.8 mmol; 1 eq) and 2-(2-amino-4-methoxyphenyl)ethanol (143.4 mg; 0.86 mmol; 1.1 eq) in EtOH (1.5 mL), water (8 mL) and AcOH (1.5 mL) at 160° C. in the microwave for 15 min to afford 180 mg (40%) of the title compound as a parent. Treatment of the parent (180 mg; 0.4 mmol; 1 eq) with an aqueous solution of potassium hydroxide (0.8 mL; 0.5 M; 0.4 mmol; 1 eq) in water (1 mL) affords 190 mg (97%) of the title compound as a pale yellow powder. $^1$H NMR (DMSO-$d_6$) δ 9.11 (d, J=3.0 Hz, 1H), 8.98-8.94 (m, 1H), 8.52 (dd, J=6.0, 3.0 Hz, 1H), 8.44-8.27 (m, 2H), 7.38-7.32 (m, 2H), 7.20-7.18 (m, 1H), 7.10-7.07 (m, 3H), 6.52 (dd, J=9.0, 3.0 Hz, 1H), 4.62 (br s, 1H), 3.73 (s, 3H), 3.67 (t, J=9.0 Hz, 2H), 2.74 (t, J=9.0 Hz, 2H). HPLC (max plot) 97%; Rt 3.45 min. LC/MS: (ES+): 452.1, (ES−): 450.0.

Example 28

N-(3-{[2-(3-Hydroxypropyl)-5-methoxyphenyl]amino}quinoxalin-2-yl)-1-methyl-1H-imidazole-4-sulfonamide Potassium Salt

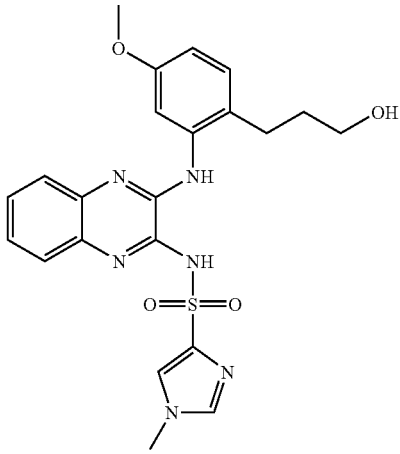 [SMILES: COc1ccc(CCCO)c(Nc2nc3ccccc3nc2NS(=O)(=O)c2cn(C)cn2)c1]

Following the protocol outlined in Procedure 1, Example 28 is obtained from 1-methyl-1H-imidazole-4-sulfonic acid (3-chloro-quinoxalin-2-yl)-amide (3 g; 9.3 mmol; 1 eq) and 3-(2-amino-4-methoxy-phenyl)-propan-1-ol (1.9 g; 10.2 mmol; 1.1 eq) in EtOH (60 mL) at 170° C. in the microwave for 20 min to afford 1.99 g (46%) of the title compound as a parent. Treatment of the parent (1.5 g; 3.1 mmol; 1 eq) with an aqueous solution of potassium hydroxide (6.3 mL; 0.5 M; 3.1 mmol; 1 eq) in water (40 mL) affords 144 g (91%) of the title compound as an off-white powder, $^1$H NMR (DMSO-$d_6$) δ 9.19 (s, 1H), 8.68-8.60 (m, 1H), 7.68-7.58 (m, 1H), 7.52-7.46 (m, 1H), 7.44-7.28 (m, 2H), 7.24-7.02 (m, 3H), 6.50 (dd, J=8.1, 2.5 Hz, 1H), 4.58-4.48 (m, 1H), 3.79 (s, 3H), 3.65 (s, 3H), 3.57-3.45 (m, 2H), 2.70-2.58 (m, 2H), 1.83-1.68 (m, 2H). HPLC (max plot) 100%; Rt 3.52 min. LC/MS: (ES+) 469.0, (ES−) 467.0. CHIN analysis: [C22H23N6O4S—K-0.02 C2H3N-1.2 H20] Corrected: C49.94%, H4.84%, N15.91%; Found: C49.64%, H4.65%, N15.91%.

Example 29

N-[3-({2-[2-Hydroxy-1-(hydroxymethyl)ethyl]-5-methoxyphenyl}amino)quinoxalin-2-yl]-1-methyl-1H-imidazole-4-sulfonamide Potassium Salt

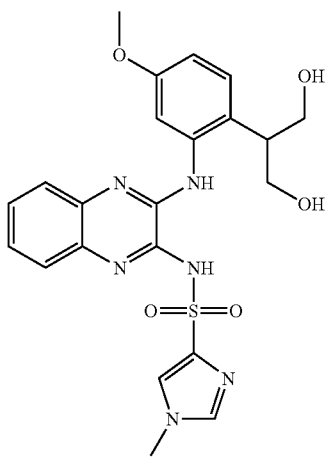 [SMILES: COc1ccc(C(CO)CO)c(Nc2nc3ccccc3nc2NS(=O)(=O)c2cn(C)cn2)c1]

Following the protocol outlined in Procedure I, Example 29 is obtained from N-(3-chloro quinoxalin-2-yl)-1-methyl-1H-imidazole-4-sulfonamide (50 mg; 0.15 mmol; 1 eq) and 2-(2-amino-4-methoxyphenyl)propane-1,3-diol (33.5 mg; 0.17 mmol; 1.1 eq) in EtOH (0.5 mL) and AcOH (0.01 mL) at 160° C. in the microwave for 20 min to afford 44 mg (59%) of the title compound as a parent. Treatment of the parent (36 mg; 0.07 mmol; 1 eq) with an aqueous solution of potassium hydroxide (0.15 mL; 0.5 M; 0.07 mmol; 1 eq) in water (2 mL) affords 30 mg (77%) of the title compound as a yellow powder. $^1$H NMR (DMSO-$d_6$) δ 9.30-9.22 (m, 1H), 8.28 (s, 1H), 7.67 (s, 1H), 7.54 (s, 1H), 7.36-7.30 (m, 2H), 7.20-7.05 (m, 3H), 6.58 (d, J=8.0 Hz, 1H), 4.87 (m, 2H), 3.77 (s, 3H), 3.66 (s, 3H), 3.65-3.60 (m, 3H), 3.09-3.05 (m, 2H). HPLC (max plot) 97%; Rt 2.79 min. LC/MS: (ES+) 485.4, (ES−) 483.4.

Example 30

N-{3-[(2-Isopropyl-5-methoxyphenyl)amino]quinoxalin-2-yl}-1-methyl-1H-imidazole-4-sulfonamide Potassium Salt

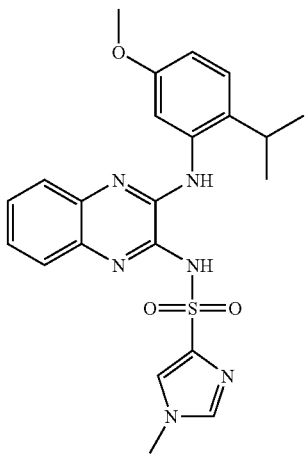 [SMILES: COc1ccc(C(C)C)c(Nc2nc3ccccc3nc2NS(=O)(=O)c2cn(C)cn2)c1]

Following the protocol outlined in Procedure I, Example 30 is obtained from N-(3-chloro quinoxalin-2-yl)-1-methyl-1H-imidazole-4-sulfonamide (35 mg; 0.11 mmol; 1 eq) and 2-isopropyl-5-methoxyaniline (20 mg; 0.13 mmol; 1.2 eq) in EtOH (1 mL) and AcOH (0.02 mL) at 90° C. overnight to afford 20 mg (41%) of the title compound as a parent. Treatment of the parent (20 mg; 0.04 mmol; 1 eq) with an aqueous solution of potassium hydroxide (0.09 mL; 0.5 M; 0.04 mmol; 1 eq) in water (2 mL) affords 20 mg (92%) of the title compound as a red powder. $^1$H NMR (DMSO-$d_6$) δ 7.99-7.95 (m, 2H), 7.29 (d, J=9.0 Hz, 1H), 7.03-6.90 (m, 5H), 6.62 (dd, J=9.0, 3.0 Hz, 1H), 6.45 (d, J=3.0 Hz, 1H), 3.75 (s, 3H), 3.68 (s, 3H), 3.38-3.30 (m, 1H), 1.19 (d, J=9.0 Hz, 3H), 0.96 (d, J=9.0 Hz, 3H). HPLC (max plot) 94%; Rt 3.33 min. LC/MS: (ES+) 453.5.

Example 31

N-[3-({2-[3-(Dimethylamino)propyl]-5-methoxyphenyl}amino)quinoxalin-2-yl]-1-methyl-1H-imidazole-4-sulfonamide HCl Salt

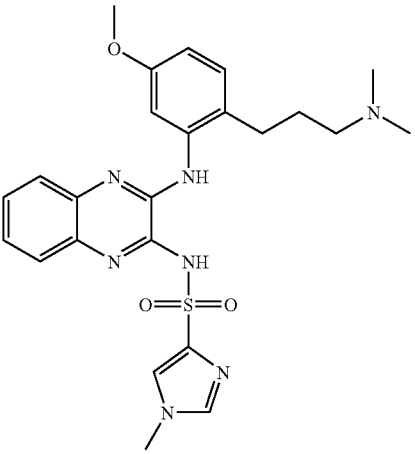 [SMILES: COc1ccc(CCCN(C)C)c(Nc2nc3ccccc3nc2NS(=O)(=O)c2cn(C)cn2)c1]

Following the protocol outlined in Procedure I, Example 31 is obtained from N-(3-chloro quinoxalin-2-yl)-1-methyl-1H-imidazole-4-sulfonamide (300 mg; 0.93 mmol; 1 eq) and 2-[3-(dimethylamino)propyl]-5-methoxyaniline (231.6 mg; 1.1 mmol; 1.2 eq) in EtOH (8 mL), water (8 mL) and AcOH (0.75 mL) at 90° C. for 2 days to afford 169 mg (37%) of the title compound as a parent. Treatment of the parent (169 mg; 0.34 mmol; 1 eq) with hydrogen chloride in diethyl ether (0.78 mL; 1 M; 0.78 mmol; 1.5 eq) in EtOH (5 mL) affords 125 mg (27%) of the title compound as a yellow solid. $^1$H NMR (DMSO-$d_6$) δ 10.07 (br s, 1H), 8.83 (s, 1H), 8.02 (br s, 1H), 7.97 (br s, 2H), 7.85-7.82 (m, 1H), 7.57-7.54 (m, 1H), 7.40-7.37 (m, 2H), 7.22 (d, J=8.7 Hz, 1H), 6.72 (dd, J=8.3, 2.6 Hz, 1H), 3.78 (s, 3H), 3.74 (s, 3H), 3.11-3.04 (m, 2H), 2.73 (s, 3H), 2.72 (s, 3H), 2.61-2.56 (m, 2H), 1.97-1.86 (m, 2H), HPLC (max plot) 99.1%; Rt 2.95 min. LC/MS: (ES+) 496.1, (ES−) 494.1.

Example 32

4-{[(3-{[2-(2-Hydroxyethyl)-5-methoxyphenyl] amino}quinoxalin-2-yl)amino]sulfonyl}-N,N-dimethylbenzamide

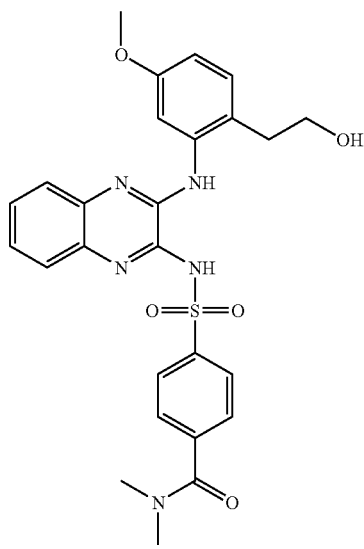 [SMILES: COc1ccc(CCO)c(Nc2nc3ccccc3nc2NS(=O)(=O)c2ccc(C(=O)N(C)C)cc2)c1]

Following the protocol outlined in Procedure I, Example 32 is obtained from 4-{[(3-chloro quinoxalin-2-yl)amino] sulfonyl}-N,N-dimethylbenzamide (210 mg; 0.54 mmol; 1 eq) and 2-(2-amino-4-methoxyphenyl)ethanol (98.8 mg; 0.6 mmol; 1.1 eq.) in EtOH (2 mL) and AcOH (0.1 mL) at 165° C. for 15 min in the microwave to afford 200 mg (71%) of the title compound as a yellow powder. $^1$H NMR (DMSO-$d_6$) δ 12.49 (s, 1H), 9.33 (s, 1H), 8.14 (d, J=9.0 Hz, 2H), 8.01-7.90 (m, 2H), 7.59 (d, J=9.0 Hz, 2H), 7.45-7.42 (m, 1H), 7.40-7.30 (m, 2H), 7.15 (d, J=9.0 Hz, 1H), 6.68 (dd, J=9.0, 3.0 Hz, 1H), 4.94 (s, 1H), 3.76 (s, 3H), 3.56 (t, J=9.0 Hz, 2H), 3.0 (s, 3H), 2.89 (s, 3H), 2.59 (t, J=9.0 Hz, 2H). HPLC (max plot) 95%; Rt 3.80 min. LC/MS: MS: (ES+) 522.1, (ES−) 520.1.

Example 33

N-(3-{[2-(2-Hydroxyethyl)-5-methoxyphenyl] amino}quinoxalin-2-yl)-6-methylpyridine-3-sulfonamide 1-oxide

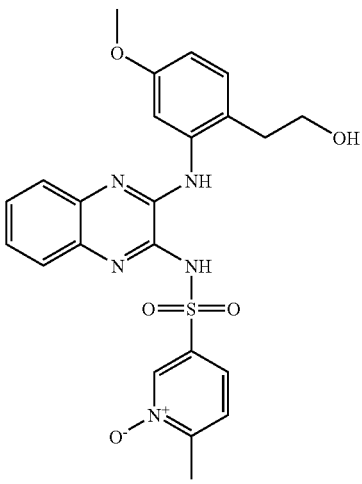 [SMILES: COc1ccc(CCO)c(Nc2nc3ccccc3nc2NS(=O)(=O)c2ccc(C)[n+]([O-])c2)c1]

Following the protocol outlined in Procedure I, Example 33 is obtained from N-(3-chloro quinoxalin-2-yl)-6-methylpyridine-3-sulfonamide 1-oxide (200 mg; 0.57 mmol; 1 eq) and 2-(2-amino-4-methoxy-phenyl)-ethanol (104.9 mg; 0.63 mmol; 1.1 eq) in EtOH (3 mL) and acetic acid (75 µL; 1.7 mmol; 3 eq) at 90° C. overnight to afford 31 mg (11%) of the title compound as a yellow powder. $^1$H NMR (DMSO-$d_6$) δ 12.37 (br s, 1H), 9.34 (s, 1H), 8.75 (s, 1H), 8.00-7.45 (m, 4H), 7.44-6.85 (m, 4H), 6.70-6.45 (m, 1H), 3.64 (s, 3H), 3.55-3.25 (m, 3H), 2.60-2.15 (m, 5H). HPLC (max plot) 97%; Rt 3.20 mm. LC/MS: (ES+) 482.2; (ES−) 479.9.

Example 34

4-cyano-N-(3-{[2-2-Hydroxyethyl)-5-methoxyphenyl]amino}quinoxalin-2-yl)benzenesulfonamide

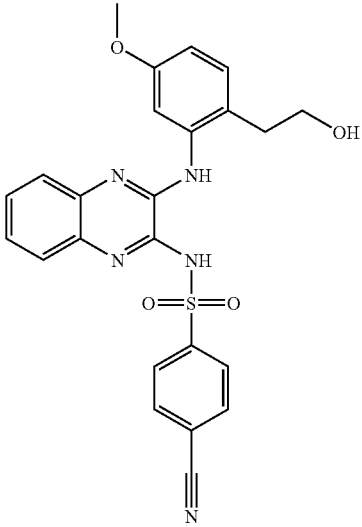 [SMILES: COc1ccc(CCO)c(Nc2nc3ccccc3nc2NS(=O)(=O)c2ccc(C#N)cc2)c1]

Following the protocol outlined in Procedure I, Example 34 is obtained from N-(3-chloro-quinoxalin-2-yl-4-cyano-benzenesulfonamide (300 mg; 0.87 mmol; 1 eq) and 2-(2- amino-4-methoxy-phenyl)-ethanol (160 mg; 0.96 mmol; 1.1 eq.) in EtOH (3 mL) and AcOH (0.16 mL) at 165° C. for 15 min in the microwave to afford 48 mg (12%) of the title compound as a yellow powder. ¹H NMR (DMSO-d₆) δ 12.61 (br s, 1H), 9.35 (s, 1H), 8.24 (d, J=8.3 Hz, 2H), 8.07 (d, J=8.3 Hz, 2H), 7.92-7.90 (m, 1H), 7.82 (s, 1H), 7.50-7.45 (m, 1H), 7.39-7.32 (m, 2H), 7.15 (d, J=8.3 Hz, 2H), 6.71-6.68 (m, 1H), 3.76 (s, 3H), 3.56-3.50 (m, 2H), 2.60-2.56 (m, 2H). HPLC (max plot) 98%; Rt 4.22 min. LC/MS: (ES+) 475.8, (ES−) 474.0.

Example 35

N-(3-{[2-(2-Hydroxyethyl)-5-methoxyphenyl]amino}quinoxalin-2-yl)-1-methyl-1H-imidazole-4-sulfonamide Potassium Salt

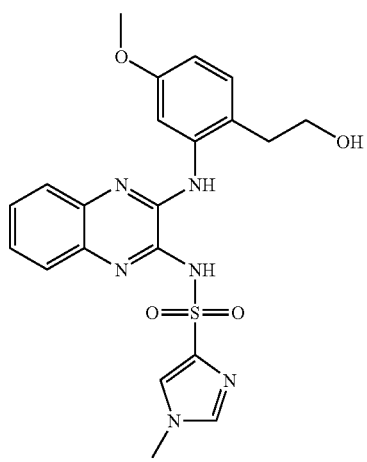 [SMILES: COc1ccc(CCO)c(Nc2nc3ccccc3nc2NS(=O)(=O)c2cn(C)cn2)c1]

Following the protocol outlined in Procedure I, Example 35 is obtained from N-(3-chloro quinoxalin-2-yl-1-methyl-1H-imidazole-4-sulfonamide (250 mg; 0.77 mmol; 1 eq) and 2-(2-amino-4-methoxyphenyl)ethanol (148.5 mg; 0.9 mmol; 1.15 eq) in EtOH (1.5 mL) and AcOH (0.14 mL) at 160° C. for 15 min using the microwave to afford 220 mg (63%) of the title compound as a parent. Treatment of the parent (120 mg; 0.26 mmol; 1 eq) with an aqueous solution of potassium hydroxide (0.53 mL; 0.5 M; 0.26 mmol; 1 eq) in water (1 mL) affords 130 mg (100%) of the title compound as a yellow solid. ¹H NMR (DMSO-d₆) δ 9.25 (m, 1H), 8.51 (dd, J=3.0 Hz, 1H), 7.64 (s, 1H), 7.35 (m, 2H), 7.10 (m, 3H), 6.53 (d, J=8.5 Hz, 1H), 5.06 (m, 1H), 3.78 (s, 3H), 3.66 (m, 5H), 2.74 (t, J=9.0 Hz, 2H). HPLC (max plot) 97%; Rt 3.37 min. LC/MS: (ES+) 455.05, (ES−) 453.1.

Example 36

4-Fluoro-N-(3-{[2-(2-hydroxyethyl)-5-methoxyphenyl]amino}quinoxalin-2-yl)benzenesulfonamide Potassium Salt

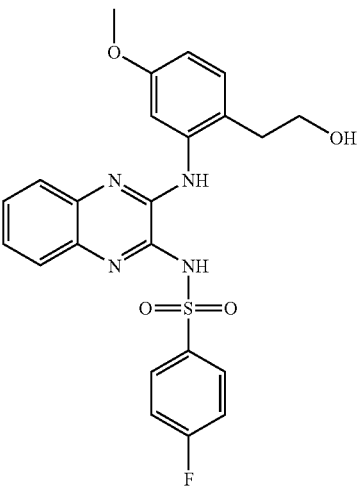 [SMILES: COc1ccc(CCO)c(Nc2nc3ccccc3nc2NS(=O)(=O)c2ccc(F)cc2)c1]

Following the protocol outlined in Procedure I, Example 36 is obtained from N-(3-chloro quinoxalin-2-yl)-4-fluorobenzenesulfonamide (300 mg; 0.89 mmol; 1 eq) and 2-(2-amino-4-methoxy-phenyl)-ethanol (163.4 mg; 0.98 mmol; 1.1 eq.) in EtOH (3 mL) and AcOH (160 µL) at 165° C. for 15 min in the microwave to afford 111 mg (27%) of the title compound as parent. Treatment of the parent (104.4 mg; 0.22 mmol; 1 eq) with an aqueous solution of potassium hydroxide (445.7 µL; 0.5 M; 0.22 mmol; 1 eq) in water (5 mL) affords 110 mg (97%) of the title compound as a yellow fluffy powder. ¹H NMR (DMSO-d₆) δ 9.05 (s, 1H), 8.50-8.30 (m, 1H), 8.15-8.00 (m, 2H), 7.45-7.00 (m, 7H), 6.52 (dd, J=7.9, 2.2 Hz, 1H), 4.70-4.58 (m, 1H), 3.76 (s, 3H), 3.68 (q, J=7.8, 3.9 Hz, 2H), 2.85-2.68 (m, 2H). HPLC (max plot) 100%; Rt 4.41 min. LC/MS; (ES+) 468.8, (ES−) 466.9.

Example 37

N-(3-{[2-(2-Hydroxyethyl)-5-methoxyphenyl]amino}quinoxalin-2-yl)methanesulfonamide Potassium Salt

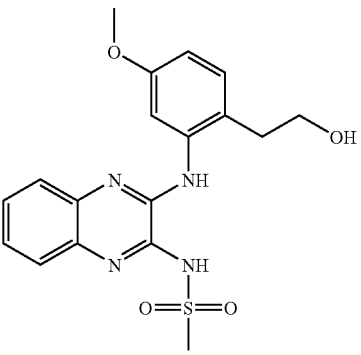 [SMILES: COc1ccc(CCO)c(Nc2nc3ccccc3nc2NS(C)(=O)=O)c1]

Following the protocol outlined in procedure I, Example 37 is obtained from N-(3-chloro quinoxaline-2-yl)methanesulphonamide (128.9 mg; 0.5 mmol, 1 eq) and 2-(2-amino-4-methoxy-phenyl)-ethanol (92 mg; 0.55 mmol; 1.1 eq) in EtOH (2 mL) and AcOH (91 µL; 1.5 mmol; 3 eq) at 165° C. for 15 min in the microwave to afford 53 mg (27%) of the title compound as a parent. Treatment of the parent (51 mg; 0.13 mmol; 1 eq) with an aqueous solution of potassium hydroxide (264.6 µL; 0.5 M; 0.13 mmol; 1 eq) in water (3 mL) affords 52 mg (92%) of the title compound as a yellow powder. $^1$H NMR (DMSO-d$_6$) δ 9.15 (s, 1H), 8.54 (d, J=2.6 Hz, 1H), 7.47-7.44 (m, 1H), 7.41-7.38 (m, 1H), 7.25-7.14 (m, 3H), 6.57 (dd, J=8.4, 2.7 Hz, 1H), 4.65 (t, J=5.3 Hz, 1H), 3.82 (s, 3H), 3.77-3.70 (m, 2H), 3.10 (s, 3H), 2.79 (t, J=6.9 Hz, 2H). HPLC (max plot) 99%; Rt 3.32 mm. LC/MS: (ES+) 388.6, (ES−) 386.9.

Example 38

N-(3-{[2-(2-Hydroxyethyl)-5-methoxyphenyl]amino}quinoxalin-2-yl)ethanesulfonamide Potassium Salt

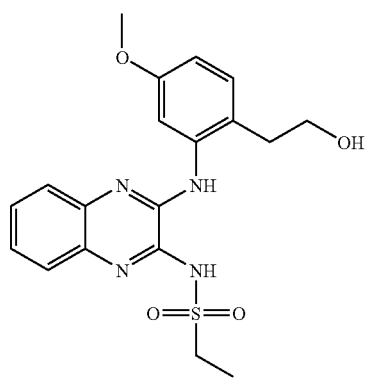 [SMILES: CCS(=O)(=O)Nc1nc2ccccc2nc1Nc1cc(OC)ccc1CCO]

Following the protocol outlined in procedure I, Example 38 is obtained from N-(3-chloro quinoxalin-2-yl)ethanesulfonamide (250 mg; 0.9 mmol; 1 eq) and 2-(2-amino-4-methoxy-phenyl)-ethanol (169.2 mg; 1 mmol; 1.1 eq) in EtOH (4 mL) and AcOH (166 µL; 2.76 mmol; 3 eq) at 165° C. for 15 min in the microwave to afford 101 mg (27%) of the title compound as parent. Treatment of the parent (99 mg; 0.25 mmol; 1 eq) with an aqueous solution of potassium hydroxide (492.5 µL; 0.5 M; 0.25 mmol; 1 eq) in water (5 mL) affords 104.3 mg (96%) of the title compound as a yellow fluffy powder. $^1$H NMR (DMSO-d$_6$) δ 9.25 (s, 1H), 8.58 (s, 1H), 7.49-7.46 (m, 1H), 7.40-7.38 (m, 1H), 7.23-7.16 (m, 3H), 6.60-6.58 (m, 1H), 4.68 (m, 1H), 3.84 (s, 3H), 3.75 (q, J=6.4 Hz, 2H), 3.36-3.31 (m, 2H), 2.82 (t, J=6.9 Hz, 2H), 1.22 (t, J=7.4 Hz, 3H). HPLC (max plot) 98.3%; Rt 3.19 min. LC/MS: (ES+) 402.9, (ES−) 400.9.

Example 39

N-(3-{[2-(2-Hydroxyethyl)-5-methoxyphenyl]amino}quinoxalin-2-yl)propane-1-sulfonamide Potassium Salt

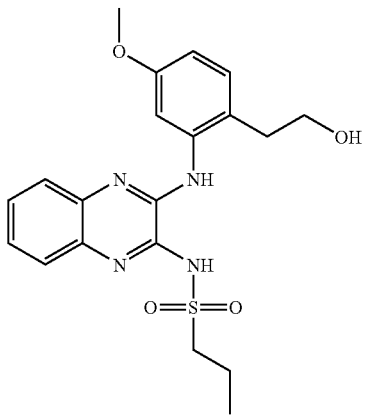 [SMILES: CCCS(=O)(=O)Nc1nc2ccccc2nc1Nc1cc(OC)ccc1CCO]

Following the protocol outlined in procedure I, Example 39 is obtained from N-(3-chloro quinoxalin-2-yl)propane-1-sulfonamide (250 mg; 0.87 mmol; 1 eq) and 2-(2-amino-4-methoxy-phenyl)-ethanol (161 mg; 0.96 mmol; 1.1 eq) were suspended in EtOH (4 mL) and AcOH (158 µL; 2.62 mmol; 3 eq) at 165° C. for 15 min the microwave to afford 130 mg (36%) of the title compound as a parent Treatment of the parent (128 mg; 0.3 mmol; 1 eq) with an aqueous solution of potassium hydroxide (613.2 µL; 0.5 M; 0.3 mmol; 1 eq) in water (5 mL) affords 134 mg (96%) of the title compound as a yellow fluffy powder. $^1$H NMR (DMSO-d$_6$) δ 9.24 (s, 1H), 8.58 (d, J=2.8 Hz, 1H), 7.47 (dd, J=7.7, 1.7 Hz, 1H), 7.39 (dd, J=7.9, 1.7, 1H), 7.26-7.15 (m, 3H), 6.58 (dd, J=8.3, 2.8 Hz, 1H), 4.66 (br s, 1H), 3.84 (s, 3H), 3.76 (m, 2H), 3.36-3.30 (m, 2H), 2.82 (t, J=6.9 Hz, 2H), 1.77-1.69 (m, 2H), 0.99 (t, J=7.2 Hz, 3H). HPLC, (max plot) 97%; Rt 3.86 min. LC/MS: (ES+) 416.9, (ES−) 414.9.

Example 40

N-[3-({5-Methoxy-2-[2-(methylsulfonyl)ethyl]phenyl}amino)quinoxalin-2-yl]-1-methyl-1H-imidazole-4-sulfonamide Potassium Salt

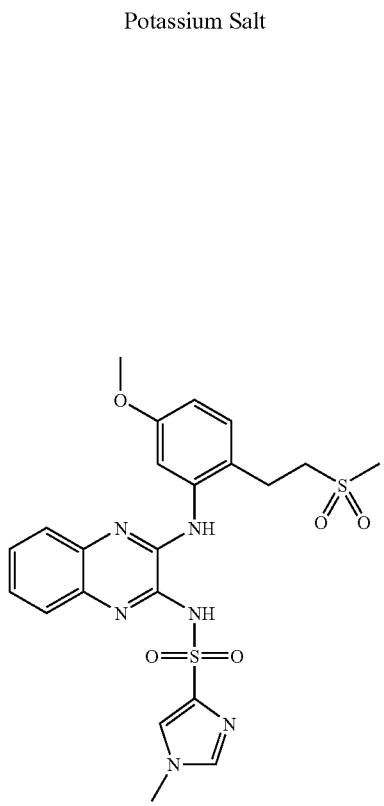

Following the protocol outlined in procedure Example 40 is obtained from 1-methyl-1H-imidazole-4-sulfonic acid (3-chloro-quinoxalin-2-yl)-amide (400 mg; 1.2 mmol; 1 eq) and 2-(2-methanesulfonyl-ethyl)-5-methoxy-phenylamine.HCl (394 mg; 1.5 mmol; 1.2 eq, desalified) in EtOH (1.5 mL) and AcOH (1 mL) at 160° C. for 15 min in the microwave to afford 380 mg (60%) of the title compound as a parent. Treatment of the parent (380 mg; 0.74 mmol, 1 eq) with an aqueous solution of potassium hydroxide (1.5 mL; 0.5 M; 0.74 mmol; 1 eq) in water (5 mL) at 0° C. affords 400 mg (98%) of the title compound as a white solid. $^1$H NMR (DMSO-d$_6$) δ 9.01 (s, 1H), 8.46 (s, 1H), 7.66 (s, 1H), 7.46-7.35 (m, 3H), 7.25-7.10 (m, 3H), 6.58 (dd, J=9.0, 3.0 Hz, 1H), 3.79 (s, 3H), 3.64 (s, 3H), 3.43-3.34 (m, 2H), 3.10-3.02 (m, 5H). HPLC (max plot) 99%; Rt 3.21 min. LC/MS: (ES+) 516.7, (ES−) 514.8.

Example 41

Methyl 3-(4-{[(3-{[2-(2-hydroxyethyl)-5-methoxyphenyl]amino}quinoxalin-2-yl)amino]sulfonyl}phenyl)propanoate

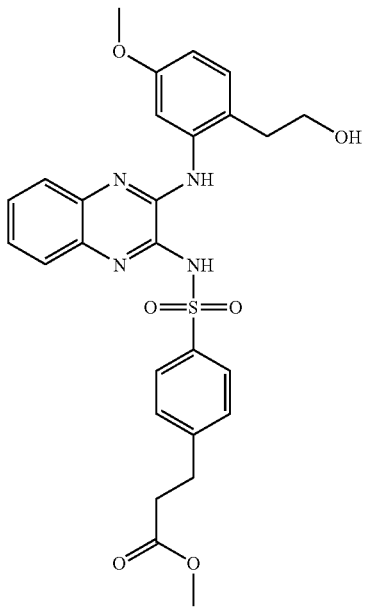 [SMILES: COC(=O)CCc1ccc(S(=O)(=O)Nc2nc3ccccc3nc2Nc2cc(OC)ccc2CCO)cc1]

Following the protocol outlined in procedure I, Example 41 is obtained from methyl 3-(4-{[(3-chloroquinoxalin-2-yl)amino]sulfonyl}phenyl)propanoate (300 mg; 0.74 mmol; 1 eq) and 2-(2-amino-4-methoxy-phenyl)-ethanol (136 mg; 0.8 mmol; 1.1 eq) in MeOH (4 mL) and AcOH (97 μL; 2.2 mmol; 3 eq) at 80° C. for 9 h to afford 161 mg (41%) of the title compound as a yellow powder. $^1$H NMR (DMSO-d$_6$) δ 12.34 (br s, 1H), 9.31 (s, 1H), 8.10-7.75 (m, 4H), 7.55-7.23 (m, 5H), 7.14 (d, J=7.4 Hz, 1H), 6.67 (dd, J=7.7, 2.2 Hz, 1H), 4.91 (br s, 1H), 3.75 (s, 3H), 3.65-3.50 (m, 5H), 2.98-2.85 (m, 2H), 2.73-2.53 (m, 4H). HPLC (max plot) 98%; Rt 4.46 min. UPLC/MS (ES+) 537.3, (ES−) 535.4.

Example 42

N-(3-{[2-(3-Hydroxpropyl)-5-methoxyphenyl]amino}quinoxalin-2-yl)-3,5-dimethylisoxazole-4-sulfonamide Potassium Salt

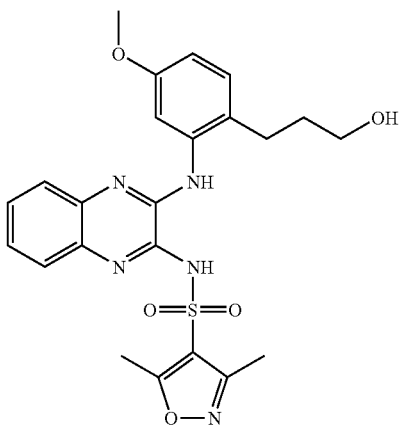 [SMILES: COc1ccc(CCCO)c(Nc2nc3ccccc3nc2NS(=O)(=O)c2c(C)noc2C)c1]

Following the protocol outlined in procedure I, Example 42 is obtained from N-(3-chloro quinoxalin-2-yl)-3,5-dimethylisoxazole-4-sulfonamide (300 mg; 0.9 mmol; 1 eq) and 3-(2-amino-4-methoxy-phenyl)-propan-1-ol (192.6 mg; 1.1 mmol; 1.2 eq) in MeOH (4 mL) at 170° C. for 15 min in the microwave to afford 170 mg (40%) of the title compound as a parent.

Treatment of the parent (167.7 mg; 0.34 mmol; 1 eq) with an aqueous solution of potassium hydroxide (680 µL; 0.50 M; 0.34 mmol; 1 eq) in water (4 mL) affords 86 mg (53%) of the title compound as a yellow powder. $^1$H NMR (DMSO-d$_6$) δ 12.64 (brs, 1H), 8.76 (brs, 1H), 8.00-7.86 (m, 2H), 7.53-7.50 (m, 1H), 7.35-7.31 (m, 2H), 7.15-7.13 (m, 1H), 6.70-6.67 (m, 1H), 3.77 (s, 3H), 3.30-3.26 (m, 2H), 2.69 (s, 3H), 2.54 (s, 2H), 2.38 (s, 3H), 1.61-1.57 (m, 2H). HPLC (max plot) 99%; Rt 3.84 min. UPLC/MS (ES+) 484.3, (ES−) 482.4,

Example 43

N-(3-{[2-2-Hydroxyethyl)-5-methoxyphenyl] amino}quinoxalin-2-yl)-3,5-dimethylisoxazole-4-sulfonamide

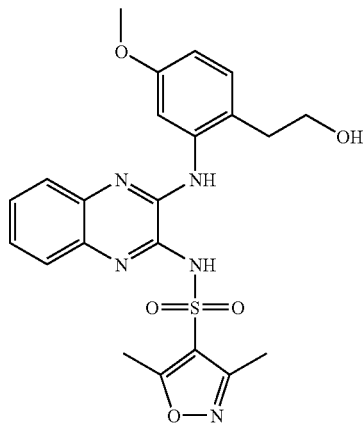 [SMILES: COc1ccc(CCO)c(Nc2nc3ccccc3nc2NS(=O)(=O)c2c(C)noc2C)c1]

Following the protocol outlined in procedure I, Example 43 is obtained from N-(3-chloro quinoxalin-2-yl)-3,5-dimethylisoxazole-4-sulfonamide (300 mg; 0.9 mmol; 1 eq) and 2-(2-amino-4-methoxy-phenyl)-ethanol (162.88 mg; 1 mmol; 1.1 eq) in MeOH (4 mL) and AcOH (116.5 µL; 2.66 mmol; 3 eq) at 80° C. overnight to afford 247 mg (59%) of the title compound as as a yellow solid. $^1$H NMR (DMSO-d$_6$) δ 12.60 (brs, 1H), 9.36 (brs, 1H), 7.90-7.78 (m, 2H), 7.48-7.45 (m, 1H), 7.33-7.31 (m, 2H), 7.17-7.14 (m, 1H), 6.71-6.68 (m, 1H), 5.76 (brs, 1H), 3.76 (s, 3H), 3.54-3.51 (m, 2H), 2.67 (s, 3H), 2.64-2.59 (m, 2H), 2.39 (s, 3H). HPLC (max plot) 98%; Rt 4.04 min. UPLC/MS (ES+) 470.2, (ES−) 468.3.

Example 44

N-[3-({5-Methoxy-2-[2-(methylsulfonyl)ethyl] phenyl}amino)quinoxalin-2-yl]methanesulfonamide Potassium Salt

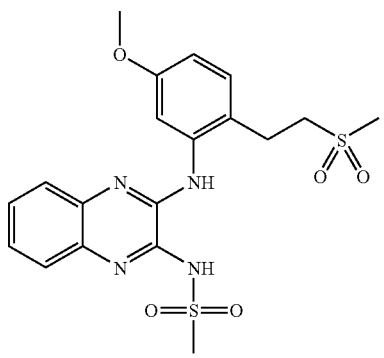 [SMILES: COc1ccc(CCS(C)(=O)=O)c(Nc2nc3ccccc3nc2NS(C)(=O)=O)c1]

Following the protocol outlined in procedure I. Example 44 is obtained from N-(3-chloroquinoxaline-2-yl)methanesulphonamide (200 mg; 0.78 mmol; 1 eq) and 5-methoxy-2-[2-(methylsulfonyl)ethyl]aniline (195.8 mg; 0.85 mmol; 1.1 eq, desalified) in EtOH (4 mL) and AcOH (140 µL; 2.33 mmol; 3 eq) at 165° C. for 15 min in the microwave to afford 27.5 mg (8%) of the title compound as a parent. Treatment of the parent (25 mg; 0.05 mmol; 1 eq) with an aqueous solution of potassium hydroxide (107.8 µL; 0.5 M; 0.05 mmol; 1 eq) in water (2 mL) affords 27 mg (100%) of the title compound as a white powder. $^1$H NMR (DMSO-d$_6$) δ 8.99 (s, 1H), 8.53 (d, J=2.7 Hz, 1H), 7.50-7.40 (m, 2H), 7.27-7.15 (m, 3H), 6.62 (dd, J=8.4, 2.7 Hz, 1H), 3.84 (s, 3H), 3.48-3.40 (m, 2H), 3.14-3.04 (m, 8H). HPLC (max plot) 99%; Rt 3.52 min. UPLC/MS (ES+) 451.3, (ES−) 449.3.

Example 45

N-(3-{[2-(2-Hydroxyethyl)-5-methoxyphenyl] amino}quinoxalin-2-yl) cyclohexanesulfonamide Potassium Salt

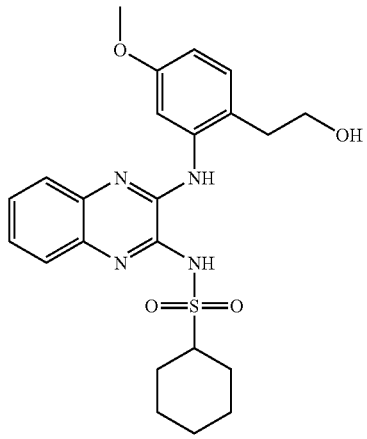 [SMILES: COc1ccc(CCO)c(Nc2nc3ccccc3nc2NS(=O)(=O)C2CCCCC2)c1]

145

Following the protocol outlined in procedure I, Example 45 is obtained from N-(3-chloro quinoxalin-2-yl)cyclohexanesulfonamide (150 mg; 0.46 mmol; 1 eq) and 2-(2-amino-4-methoxy-phenyl)-ethanol (84.7 mg; 0.5 mmol; 1.1 eq) in EtOH (4 mL) and AcOH (83 μL; 1.38 mmol; 3 eq) at 165° C. for 15 min in the microwave to afford 83 mg (39%) of the title compound as a parent. Treatment of the parent (79 mg; 0.17 mmol; 1 eq) with an aqueous solution of potassium hydroxide (347 μL; 0.5 M; 0.17 mmol; 1 eq) in water (4 mL) affords 84 mg (98%) of the title compound as a yellow powder. $^1$H NMR (DMSO-d$_6$) δ 9.23 (s, 1H), 8.59 (s, 1H), 7.47-7.13 (m, 5H), 6.60-6.56 (m, 1H), 4.67 (br s, 1H), 3.83 (s, 3H), 3.77-3.69 (m, 2H), 3.55-3.40 (m, 1H), 2.80 (t, J=6.8 Hz, 2H), 2.15-2.05 (m, 2H), 1.86-1.76 (m, 2H), 1.69-1.60 (m, 1H), 1.56-1.14 (m, 5H). HPLC (max plot) 99%; Rt 4.52 min. UPLC/MS (ES+) 457.3, (ES−) 455.5.

Example 46

N-(3-{[2-(3-Hydroxypropyl)-5-methoxyphenyl] amino}quinoxalin-2-yl)methanesulfonamide Potassium Salt

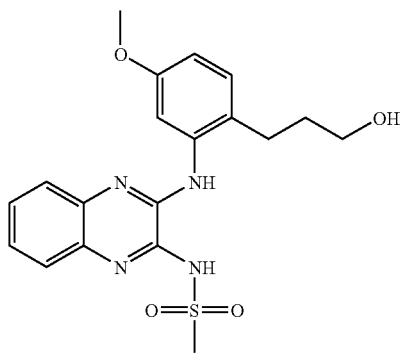 [SMILES: COc1ccc(CCCO)c(Nc2nc3ccccc3nc2NS(C)(=O)=O)c1]

Following the protocol outlined in procedure I, Example 46 is obtained from N-(3-chloro quinoxaline-2-yl)methanesulphonamide (200 mg; 0.8 mmol; 1 eq) and 3-(2-amino-4-methoxy-phenyl)-propan-1-ol (154.7 mg; 0.85 mmol; 1.1 eq) were suspended in EtOH (4 mL) and AcOH (139.8 μL; 2.33 mmol; 3 eq) at 165° C. for 15 min in the microwave to afford 128 mg (41%) of the title compound as a parent. Treatment of the parent (114.4 mg; 0.28 mmol; 1 eq) with an aqueous solution of potassium hydroxide (564.5 μL; 0.5 M; 0.28 mmol; 1 eq) in water (4 mL) affords 107 mg (86%) of the title compound as a yellow powder. $^1$H NMR (DMSO-d$_6$) δ 9.19 (s, 1H), 8.72 (d, J=2.6 Hz, 1H), 7.51-7.47 (m, 1H), 7.43-7.39 (m, 1H), 7.27-7.15 (m, 2H), 7.12 (d, J=8.3 Hz, 1H), 6.54 (dd, J=8.3, 2.6 Hz, 1H), 4.44 (t, J=5.6 Hz, 1H), 3.83 (s, 3H), 3.55 (q, J=6.1 Hz, 2H), 3.11 (s, 3H), 2.74-2.65 (m, 2H), 1.88-1.76 (m, 2H). HPLC (max plot) 98%; Rt 3.62 min, LC/MS: (ES+) 402.9, (ES−) 4009.

Example 47

2-[(Dimethylamino)methyl]-N-(3-{[2-(3-hydroxypropyl)-5-methoxyphenyl]amino}quinoxalin-2-yl)-1-methyl-1H-imidazole-4-sulfonamide HCl Salt

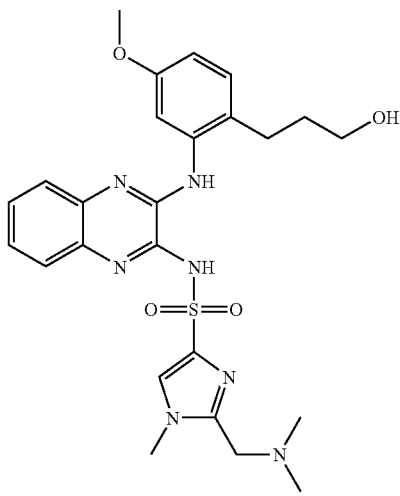 [SMILES: COc1ccc(CCCO)c(Nc2nc3ccccc3nc2NS(=O)(=O)c2cn(C)c(CN(C)C)n2)c1]

Following the protocol outlined in procedure I, Example 47 is obtained from N-(3-chloro quinoxalin-2-yl)-2-[(dimethylamino)methyl]-1-methyl-1H-imidazole-4-sulfonamide (1.2 g; 3.15 mmol; 1 eq) and 3-(2-amino-4-methoxy-phenyl)-propan-1-ol (599.58 mg; 3.31 mmol; 1.05 eq) in 1-butanol (15 mL) at 170° C. for 2×45 min to afford 750 mg (45%) of the title compound as a parent. Treatment of the parent (740 mg; 1.41 mmol; 1 eq) with an aqueous solution of hydrogen chloride (2.8 mL; 1 M; 2.82 mmol; 2 eq) in water (10 mL) affords 665 mg (84%) of the title compound as a yellow greenish powder. $^1$H NMR (DMSO-d$_6$) δ 12.42 (br s, 1H), 10.71 (br s, 1H), 8.80 (s, 1H), 8.25-8.00 (m, 2H), 7.99-7.82 (m, 1H), 7.63-7.48 (m, 1H), 7.45-7.28 (m, 2H), 7.20-7.05 (m, 1H), 6.75-6.60 (m, 1H), 4.44 (s, 2H), 3.90-3.65 (m, 6H), 3.60-3.20 (m, 3H), 2.78 (s, 6H), 2.65-2.40 (m, 2H), 1.70-1.50 (m, 2H). HPLC (max plot) 99%; Rt 3.01 min. UPLC/MS (ES+) 526.3, (ES−) 524.3.

Example 48

N-(3-{[2-(3-Hydroxypropyl)-5-methoxyphenyl] amino}quinoxalin-2-yl)ethanesulfonamide

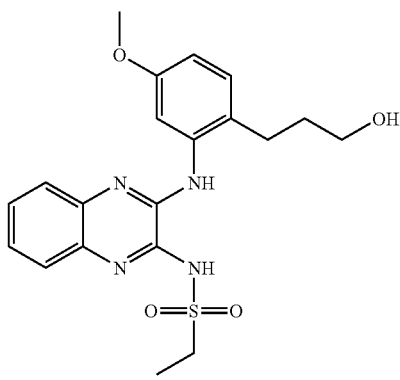 [SMILES: CCS(=O)(=O)Nc1nc2ccccc2nc1Nc1cc(OC)ccc1CCCO]

Following the protocol outlined in procedure I, Example 48 is obtained from N-(3-chloroquinoxalin-2-yl)ethanesulfonamide (200 mg; 0.74 mmol; 1 eq) and 3-(2-amino-4-methoxy-phenyl)-propan-1-ol (146.7 mg; 0.81 mmol; 1.1 eq) in EtOH (4 mL) and AcOH (133 µL, 2.2 mmol; 3 eq) at 165° C. for 15 min in the microwave to afford 88 mg (29%) of the title compound as a yellow solid. $^1$H NMR (DMSO-$d_6$) δ 12.31 (s, 1H), 8.92 (s, 1H), 8.20-8.16 (m, 1H), 7.95-7.88 (m, 1H), 7.58-7.53 (m, 1H), 7.42-7.32 (m, 2H), 7.21 (d, J=8.5 Hz, 1H), 6.73 (dd, J=8.4, 2.7 Hz, 1H), 4.58 (br s, 1H), 3.83 (s, 3H), 3.50-3.28 (m, 4H), 2.69 (t, J=7.6 Hz, 2H), 1.81-1.71 (m, 2H), 1.38 (t, J=7.3 Hz, 3H). HPLC (max plot) 100%; Rt 3.86 min. UPLC/MS: (ES+) 417.3, (ES−) 415.4.

Example 49

N-(3-{[2-(3-Hydroxypropyl)-5-methoxyphenyl]amino}quinoxalin-2-yl)propane-1-sulfonamide

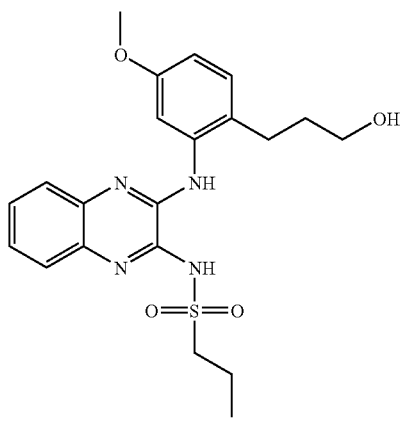 [SMILES: CCCS(=O)(=O)Nc1nc2ccccc2nc1Nc1cc(OC)ccc1CCCO]

Following the protocol outlined in procedure I, Example 49 is obtained from N-(3-chloro quinoxalin-2-yl)propane-1-sulfonamide (200 mg; 0.7 mmol; 1 eq) and 3-(2-amino-4-methoxy-phenyl)-propan-1-ol (139.5 mg; 0.77 mmol; 1.1 eq) in EtOH (4 mL) and AcOH (126.1 µL; 2.1 mmol; 3 eq) at 165° C. for 15 min in the microwave to afford 74 mg (24%) of the title compound as a yellow powder. $^1$H NMR (DMSO-$d_6$) δ 12.29 (s, 1H), 8.91 (s, 1H), 8.21-8.15 (m, 1H), 7.88-7.95 (m, 1H), 7.59-7.53 (m, 1H), 7.42-7.32 (m, 2H), 7.21 (d, J=8.4 Hz, 1H), 6.73 (dd, J=8.4, 2.6 Hz, 1H), 4.58 (br s, 1H), 3.83 (s, 3H), 3.50-3.28 (m, 4H), 2.69 (t, J=7.6 Hz, 2H), 1.95-1.70 (m, 4H), 1.07 (t, J=7.4 Hz, 3H). HPLC (max plot) 100%; Rt 4.16 min. UPLC/MS: (ES+) 431.3, (ES−) 429.4. CHN analysis: [C21H26N4O4S-0.06 CH2Cl2-0.1 H20] Corrected: C57.83%, H6.06%, N12.81%; Found: C57.78%, H5.95%, N12.67%.

Example 50

N-(3-{[2-(3-Hydroxyproxyl)-5-methoxypheyl]amino}quinoxalin-2-yl)propane-2-sulfonamide

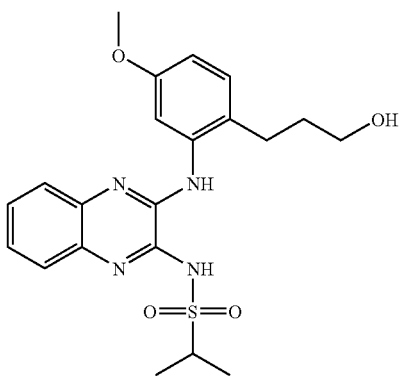 [SMILES: COc1ccc(CCCO)c(Nc2nc3ccccc3nc2NS(=O)(=O)C(C)C)c1]

Following the protocol outlined in procedure I, Example 50 is obtained from N-(3-chloro quinoxalin-2-yl)propane-2-sulfonamide (200 mg; 0.7 mmol; 1 eq) and 3-(2-amino-4-methoxy-phenyl)-propan-1-ol (139.5 mg; 0.77 mmol; 1.1 eq) in EtOH (4 mL) and AcOH (126.1 µL; 2.1 mmol; 3 eq) at 165° C. for 15 min in the microwave to afford 43 mg (14%) of the title compound as a yellow powder. $^1$H NMR (DMSO-$d_6$) δ 12.29 (s, 1H), 8.85 (s, 1H), 8.25-8.18 (m, 1H), 7.96-7.88 (m, 1H), 7.60-7.53 (m, 1H), 7.42-7.31 (m, 2H), 7.21 (d, J=8.4 Hz, 1H), 6.73 (dd, J=8.5; 2.6 Hz, 1H), 4.55 (br s, 1H), 3.83 (s, 3H), 3.53-3.36 (m, 3H), 2.69 (t, J=7.5 Hz, 2H), 1.76 (quint., J=6.9 Hz, 2H), 1.42 (d, J=6.8 Hz, 6H). HPLC (max plot) 99%; Rt 4.07 min. UPLC/MS: (ES+) 431.3, (ES−) 429.4. CHN analysis: [C21H26N4O4S-0.01 CH2Cl2-0.1 H20] Corrected: C58.26%, H6.10%, N12.93%; Found: C58.45%, H6.05%, N12.75%.

Example 51

N-[3-({5-Methoxy-2-[2-(methylsulfonyl)ethyl]phenyl}amino)quinoxalin-2-yl]ethanesulfonamide Potassium Salt

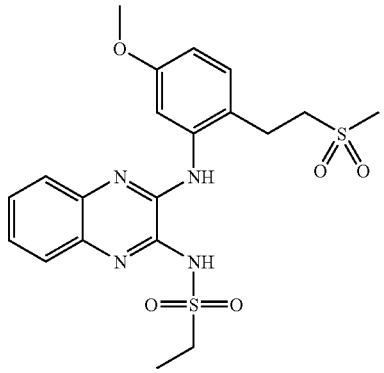 [SMILES: CCS(=O)(=O)Nc1nc2ccccc2nc1Nc1cc(OC)ccc1CCS(C)(=O)=O]

Following the protocol outlined in procedure I, Example 51 is obtained from N-(3-chloro quinoxalin-2-yl)ethanesulfonamide (200 mg; 0.74 mmol; 1 eq) and 5-methoxy-2-

[2-(methylsulfonyl)ethyl]aniline (185.65 mg; 0.81 mmol; 1.1 eq, desalified) in EtOH (4 mL) and AcOH (132.6 µL; 2.2 mmol; 3 eq) at 165° C. for 15 min in the microwave to afford 31 mg (9%) of the title compound as a parent. Treatment of the parent (239 mg; 0.05 mmol; 1 eq) with an aqueous solution of potassium hydroxide (102.2 µL; 0.5 M; 0.05 mmol; 1 eq) in water (4 mL) affords 27 mg (100%) of the title compound as a yellow powder. $^1$H NMR (DMSO-d$_6$) δ 9.08 (s, 1H), 8.54 (br s, 1H), 7.50-7.36 (m, 2H), 7.27-7.14 (m, 3H), 6.65-6.59 (m, 1H), 3.84 (s, 3H), 3.48-3.32 (m, 4H), 3.16-3.04 (m, 5H), 1.18 (t, J=7.4 Hz, 3H). HPLC (max plot) 99%; Rt 3.70 mi. UPLC/MS: (ES+) 465.3, (ES−) 463.4.

Example 52

N-[3-({5-Methoxy-2-[2-(methylsulfonyl)ethyl]phenyl}amino)quinoxalin-2-yl]propane-2-sulfonamide Potassium Salt

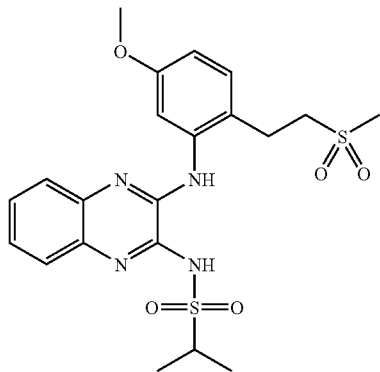 [SMILES: COc1ccc(CCS(C)(=O)=O)c(Nc2nc3ccccc3nc2NS(=O)(=O)C(C)C)c1]

Following the protocol outlined in procedure I, Example 52 is obtained from N-(3-chloro quinoxalin-2-yl)propane-2-sulfonamide (200 mg; 0.7 mmol; 1 eq) and 5-methoxy-2-[2-(methylsulfonyl)ethyl]aniline (176.5 mg; 0.77 mmol; 1.1 eq, desalified) in EtOH (4 mL) and AcOH (126 µL; 2.1 mmol; 3 eq) at 70° C. for 45 h to afford 62 mg (19%) of the title compound as a parent. Treatment of the parent (56.7 mg; 0.12 mmol; 1 eq) with an aqueous solution of potassium hydroxide (233.6 µL; 0.5 M; 0.12 mmol; 1 eq) in water (4 mL) affords 59 mg (98%) of the title compound as an off white powder. $^1$H NMR (DMSO-d$_6$) δ 9.11 (s, 1H), 8.56 (d, J=2.7 Hz, 1H), 7.49-7.44 (m, 1H), 7.40-7.35 (m, 1H), 7.26-7.13 (m, 3H), 6.61 (dd, J=2.7; 8.3 Hz, 1H), 4.06 (quint., J=6.8 Hz, 1H), 3.84 (s, 3H), 3.47-3.33 (m, 2H), 3.15-3.03 (m, 5H), 1.23 (d, J=6.8 Hz, 6H). HPLC (max plot) 99.4%; Rt 3.92 min. UPLC/MS: (ES+) 479.4, (ES−) 477.4.

Example 53

N-[3-({5-Methoxy-2-[2-(methylsulfonyl)ethyl]phenyl}amino)quinoxalin-2-yl]propane-1-sulfonamide

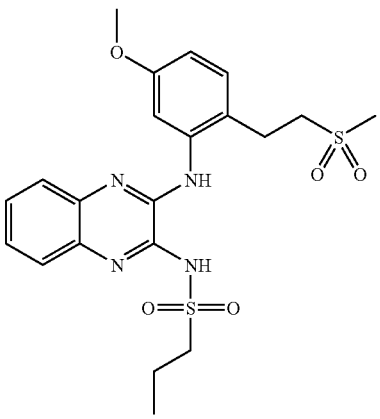 [SMILES: CCCS(=O)(=O)Nc1nc2ccccc2nc1Nc1cc(OC)ccc1CCS(C)(=O)=O]

Following the protocol outlined in procedure I, Example 53 is obtained from N-(3-chloro quinoxalin-2-yl)propane-1-sulfonamide (200 mg; 0.7 mmol; 1 eq) and 2-(2-methanesulfonyl-ethyl)-5-methoxy-phenylamine (192.6 mg; 0.84 mmol; 1.2 eq, desalified) in EtOH (1 mL) and AcOH (650 µL) at 160° C. for 15 min in the microwave to afford 51 mg (15%) of the title compound as a pale yellow solid. $^1$H NMR (DMSO-d$_6$) δ 12.19 (s, 1H), 8.87 (s, 1H), 7.89-7.80 (m, 1H), 7.66-7.58 (m, 1H), 7.46-7.39 (m, 1H), 7.33-7.24 (m, 3H), 6.82-6.78 (m, 1H), 3.85 (s, 3H), 3.50-3.20 (m, 4H), 3.08-2.90 (m, 2H), 2.90 (s, 3H), 1.86-1.74 (m, 2H), 1.01 (t, J=7.5 Hz, 3H), HPLC (max plot) 97%; Rt 3.84 min. UPLC/MS: (ES+) 479.3, (ES−) 477.3.

Example 54

N-[3-({5-Methoxy-2-[2-(methylsulfonyl)ethyl]phenyl}amino)quinoxalin-2-yl]-3,5-dimethylisoxazole-4-sulfonamide

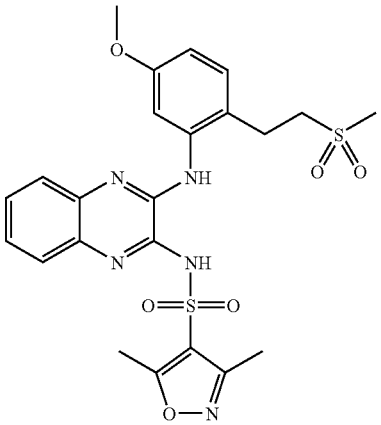 [SMILES: COc1ccc(CCS(C)(=O)=O)c(Nc2nc3ccccc3nc2NS(=O)(=O)c2c(C)noc2C)c1]

Following the protocol outlined in procedure I, Example 54 is obtained from N-(3-chloro quinoxalin-2-yl)-3,5-dimethylisoxazole-4-sulfonamide (210 mg; 0.6 mmol; 1 eq) and 2-(2-methanesulfonyl-ethyl)-5-methoxy-phenylamine. HCl (181 mg; 0.7 mmol; 1.1 eq, desalified) in EtOH (3 mL) and AcOH (112 µL) at 170° C. for 15 min in the microwave to afford 99 mg (30%) of the title compound as a yellow powder. ¹H NMR (DMSO-d₆) δ 12.43 (s, 1H), 8.85 (s, 1H), 7.90 (s, 1H), 7.41-7.38 (m, 1H), 7.32-7.27 (m, 4H), 6.83-6.80 (m, 1H), 3.75 (s, 3H), 3.34-3.30 (m, 2H), 2.93-2.88 (m, 2H), 2.82 (s, 3H), 2.69 (s, 3H), 2.39 (s, 3H). HPLC (max plot) 100%; Rt 4.01 min. UPLC/MS: (ES+) 532.3, (ES−) 530.4. CHN analysis: [C23H25N5O6S2-0.2 H2O] Corrected: C51.62%, H4.78%, N13.09%; Found: C51.21%, H4.51%, N12.87%.

Example 55

N-[3-({5-Methoxy-2-[2-(methylsulfonyl)ethyl]phenyl}amino)quinoxalin-2-yl]benzenesulfonamide

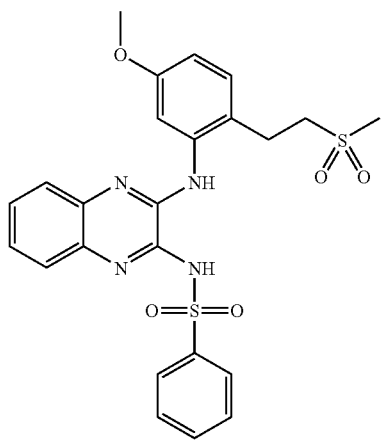 [SMILES: COc1ccc(CCS(C)(=O)=O)c(Nc2nc3ccccc3nc2NS(=O)(=O)c2ccccc2)c1]

Following the protocol outlined in procedure I, Example 55 is obtained from N-(3-chloro-2-quinoxalinyl)benzenesulfonamide (220 mg; 0.7 mmol; 1 eq) and 2-(2-methanesulfonyl-ethyl)-5-methoxy-phenylamine.HCl (201 mg; 0.76 mmol; 1.1 eq, desalified) in EtOH (2 mL) and AcOH (124 µL) at 170° C. for 16 min in the microwave to afford 94 mg (27%) of the title compound as a yellow solid. ¹H NMR (DMSO-d₆) 12.32 (s, 1H), 8.84 (s, 1H), 8.10 (d, J=7.0 Hz, 2H), 7.93 (m, 1H), 7.67-7.57 (m, 3H), 7.45-7.39 (m, 2H), 7.33-7.25 (m, 3H), 6.79 (dd, J=8.5, 2.5 Hz, 1H), 3.75 (s, 3H), 3.32-3.27 (m, 2H), 2.92-2.87 (m, 2H), 2.77 (s, 3H). HPLC (max plot) 99%; Rt 4.24 min. UPLC/MS: (ES+) 513.3, (ES−) 511.4.

Example 56

N-(3-{[2-2-Hydroxyethyl)-5-methoxyphenyl]amino}quinoxalin-2-yl)tetrahydrothiophene-3-sulfonamide 1,1-dioxide

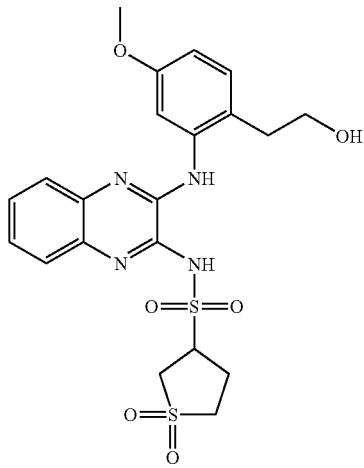 [SMILES: COc1ccc(CCO)c(Nc2nc3ccccc3nc2NS(=O)(=O)C2CCS(=O)(=O)C2)c1]

Following the protocol outlined in procedure I, Example 56 is obtained from N-(3-chloro quinoxalin-2-yl)tetrahydrothiophene-3-sulfonamide 1,1-dioxide (120 mg; 0.33 mmol; 1 eq) and 2-(2-amino-4-methoxy-phenyl)-ethanol (66.5 mg; 0.4 mmol; 1.2 eq.) in EtOH (1 mL) and AcOH (660 µL; 0.33 mmol; 1 eq) at 160° C. for 15 min in the microwave to afford 27 mg (17%) of the title compound as a yellow solid. ¹H NMR (DMSO-d₆) 12.47 (s, 1H), 8.33 (s, 1H), 7.81 (br d, J=8.4 Hz, 1H), 7.51-7.45 (m, 1H), 7.39-7.28 (m, 2H), 7.19 (d, J=8.4 Hz, 1H), 6.74 (dd, J=8.4, 2.6 Hz, 1H), 4.50 (br s, 1H), 4.35 (quint, J=7.8 Hz, 1H), 3.78 (s, 3H), 3.69 (dd, J=13.9, 9.1 Hz, 1H), 3.50-3.32 (m, 2H), 3.30-3.17 (m, 1H), 2.63 (br t, J=7.5 Hz, 2H), 2.64-2.40 (m, 2H), 1.70 (quint, J=7.2 Hz, 2H). HPLC (max plot) 96%; Rt 3.57 min. UPLC/MS: (ES+) 493.3, (ES−) 491.4.

Example 57

N-[3-({5-Methoxy-2-[2-(methylsulfonyl)ethyl]phenyl}amino)quinoxalin-2-yl]-3-(methylthio)propane-1-sulfonamide

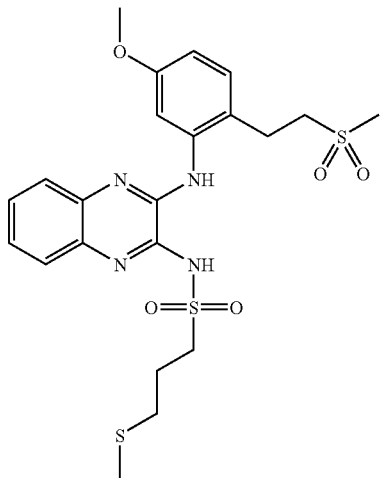 [SMILES: COc1ccc(CCS(C)(=O)=O)c(Nc2nc3ccccc3nc2NS(=O)(=O)CCCSC)c1]

Following the protocol outlined in procedure I, Example 57 is obtained from N-(3-chloro quinoxalin-2-yl)-3-(methylthio)propane-1-sulfonamide (332 mg; 1 mmol; 1 eq) and 2-(2-methanesulfonyl-ethyl)-5-methoxy-phenylamine.HCl (319 mg; 1.2 mmol; 1.2 eq, desalified) in EtOH (1.5 mL) and AcOH (1 mL) at 160° C. for 15 min in the microwave to afford 89 mg (17%) of the title compound as a yellow powder. $^1$H NMR (DMSO-d$_6$) δ 12.22 (s, 1H), 8.89 (s, 1H), 7.90-7.81 (m, 1H), 7.60-7.51 (m, 1H), 7.45-7.38 (m, 1H), 7.35-7.25 (m, 3H), 6.81 (dd, J=2.1, 8.7 Hz, 1H), 3.77 (s, 3H), 3.42-3.34 (m, 4H), 3.04-2.93 (m, 2H), 2.88 (s, 3H), 2.63 (t, J=7.2 Hz, 2H), 2.14-2.02 (m, 2H), 2.04 (s, 3H). HPLC (max plot) 98%; Rt 4.08 min. UPLC/MS: (ES+) 525.3, (ES−) 523.4. CHN analysis: [C22H28N4O5S3] corrected: C50.36%; H5.38%; N10.68%; found: C50.20%; H5.24%; N10.58%.

Example 58

N-(3-{[2-(2-Hydroxyethyl)-5-methoxyphenyl]amino}quinoxalin-2-yl)-3-(methylthio)propane-1-sulfonamide

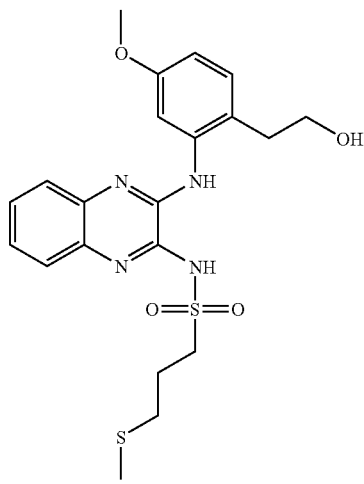 [SMILES: COc1ccc(CCO)c(Nc2nc3ccccc3nc2NS(=O)(=O)CCCSC)c1]

Following the protocol outlined in procedure I, Example 58 is obtained from N-(3-chloro quinoxalin-2-yl)-3-(methylthio)propane-1-sulfonamide (331.8 mg; 1 mmol; 1 eq) and 2-(2-amino-4-methoxy-phenyl)-ethanol (200.6 mg; 1.2 mmol; 1.2 eq) in EtOH (1.5 mL) and AcOH (1 mL) at 160° C. for 15 min in the microwave to afford 31 mg (7%) of the title compound as a yellow powder. $^1$H NMR (DMSO-d$_6$) δ 12.26 (s, 1H), 9.54 (s, 1H), 7.95-7.80 (m, 2H), 7.49-7.42 (m, 1H), 7.35-7.24 (m, 2H), 7.19 (d, J=8.1 Hz, 1H), 6.70 (dd, J=8.4, 2.7 Hz, 1H), 5.14 (s, 1H), 3.78 (s, 3H), 3.74-3.62 (m, 2H), 3.39-3.28 (m, 2H), 2.73 (t, J=5.8 Hz, 2H), 2.63 (t, J=7.2 Hz, 2H), 2.18-2.04 (m, 2H), 2.05 (s, 3H). HPLC (max plot) 97.4%; Rt 4.14 min. UPLC/MS: (ES+) 463.3, (ES−) 461.3.

Example 59

N-[3-({5-Methoxy-2-[2-(methylsulfonyl)ethyl]phenyl}amino)quinoxalin-2-yl]-3-(methylsulfonyl)propane-1-sulfonamide

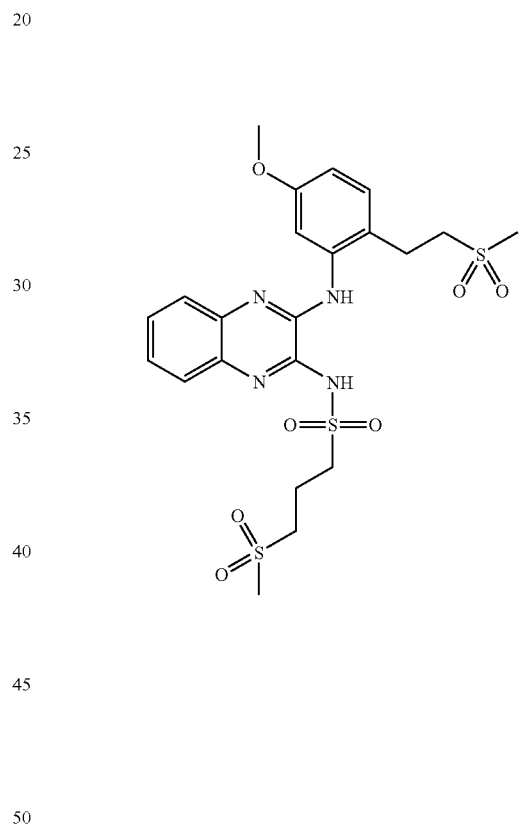

Following the protocol outlined in procedure I, Example 59 is obtained from N-(3-chloro quinoxalin-2-yl)-3-(methylthio)propane-1-sulfonamide (331.8 mg; 1 mmol; 1 eq) and 2-(2-methanesulfonyl-ethyl)-5-methoxy-phenylamine.HCl (319 mg; 1.2 mmol; 1.2 eq, desalified) in EtOH (1.5 mL) and AcOH (1 mL) at 160° C. for 15 min in the microwave to afford 155 mg (28%) of the title compound as a pale yellow powder, $^1$H NMR (DMSO-d$_6$) δ 12.28 (s, 1H) 8.89 (s, 1H), 7.86 (br s, 1H), 7.55 (br s, 1H), 7.45-7.39 (m, 1H), 7.34-7.26 (m, 3H), 6.81 (dd, J=8.4, 2.7 Hz, 1H), 3.78 (s, 3H), 3.50-3.25 (m, 6H), 3.05-2.94 (m, 2H), 3.00 (s, 3H), 2.88 (s, 3H), 2.27 (quint, J=6.9 Hz, 2H), HPLC (max plot) 98.%; Rt 3.30 min. UPLC/MS: (ES+) 557.4, (ES−) 555.4.

Example 60

N-(3-{[2-(3-Hydroxypropyl)-5-methoxyphenyl]amino}quinoxalin-2-yl)-3-(methylsulfonyl)propane-1-sulfonamide

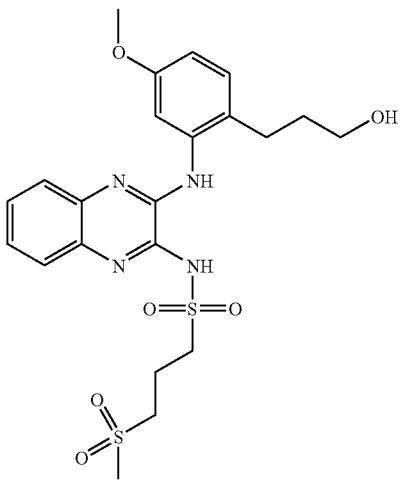 [SMILES: COc1ccc(CCCO)c(Nc2nc3ccccc3nc2NS(=O)(=O)CCCS(C)(=O)=O)c1]

Following the protocol outlined in procedure I, Example 60 is obtained from N-(3-chloro quinoxalin-2-yl)-3-(methylsulfonyl)propane-1-sulfonamide (363.8 mg; 1 mmol; 1 eq) and 3-(2-amino-4-methoxy-phenyl)-propan-1-ol (217.5 mg; 1.2 mmol; 1.2 eq) EtOH (1.5 mL) and AcOH (1 mL) at 160° C. for 15 min in the microwave to afford 140 mg (28%) of the title compound as a yellow powder. $^1$H NMR (DMSO-$d_6$) δ 12.32 (s, 1H), 8.90 (s, 1H), 8.03 (br s, 1H), 7.89 (br d, J=7.9 Hz, 1H), 7.54-7.47 (m, 1H), 7.39-7.28 (m, 2H), 7.17 (d, J=8.4 Hz, 1H), 6.70 (dd, J=8.4, 2.6 Hz, 1H) 4.55 (br s, 1H), 3.78 (s, 3H), 3.52-3.23 (m, 6H), 2.99 (s, 3H), 2.64 (t, J=7.6 Hz, 2H), 2.32-2.17 (m, 2H), 1.72 (quint, J=7.0 Hz, 2H). HPLC (max plot) 99%; Rt 3.38 min. UPLC/MS: (ES+) 509.4, (ES−) 507.5.

Example 61

N-(3-{[2-(2-Hydroxyethyl)-5-methoxyphenyl]amino}quinoxalin-2-yl)-3-(methylsulfonyl)propane-1-sulfonamide

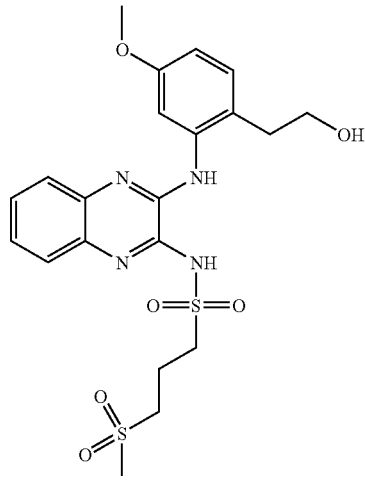 [SMILES: COc1ccc(CCO)c(Nc2nc3ccccc3nc2NS(=O)(=O)CCCS(C)(=O)=O)c1]

Following the protocol outlined in procedure I, Example 61 is obtained from N-(3-chloro quinoxalin-2-yl)-3-(methylsulfonyl)propane-1-sulfonamide (210 mg; 0.58 mmol; 1 eq) and 2-(2-amino-4-methoxy-phenyl)-ethanol (106.2 mg; 0.63 mmol; 1.1 eq) in EtOH (3 mL) and AcOH (0.1 mL) at 170° C. for 15 min in the microwave to afford 71 mg (25%) of the title compound as a yellow powder. $^1$H NMR (DMSO-$d_6$) δ 12.30 (s, 1H), 9.50 (s, 1H), 7.87-7.84 (m, 2H), 7.46 (dd, J=49, 1.2 Hz, 1H), 7.32-7.28 (m, 2H), 7.18 (d, J=8.2 Hz, 1H), 6.72-6.69 (m, 1H), 5.18-5.12 (m, 1H), 3.77 (s, 3H), 3.72-3.68 (m, 2H), 3.45-3.38 (m, 4H), 2.90 (s, 3H), 2.78-2.68 (m, 2H), 2.32-2.22 (m, 2H). HPLC (max plot) 99%; Rt 3.49 min. UPLC/MS (ES+) 495.4, (ES−) 493.5

Example 62

N-(3-{[5-Methoxy-2-(2-methoxyethyl)phenyl]amino}quinoxalin-2-yl)-1-methyl-1H-imidazole-4-sulfonamide

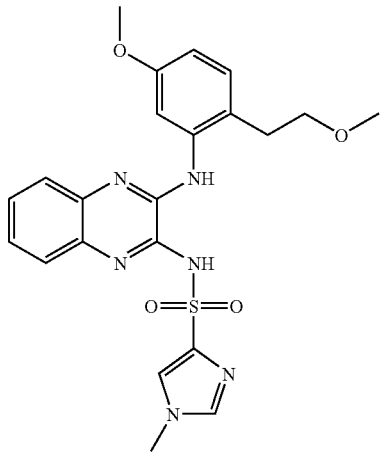 [SMILES: COCCc1ccc(OC)cc1Nc1nc2ccccc2nc1NS(=O)(=O)c1cn(C)cn1]

Following the protocol outlined in procedure I, Example 62 is obtained from 1-methyl-1H-imidazole-4-sulfonic acid (3-chloro-quinoxalin-2-yl)-amide (2 g; 6.2 mmol; 1 eq) and 5-methoxy-2-(2-methoxy-ethyl)-phenylamine (1.2 g; 6.8 mmol; 1.1 eq) iPrOH (30 mL) at 160° C. for 20 min in the microwave to afford 1.7 g (58%) of the title compound as a yellow powder. $^1$H NMR (DMSO-$d_6$) δ 12.75 (br s, 1H), 9.43 (s, 1H), 8.10-7.88 (m, 2H), 7.85-7.70 (m, 2H), 7.60-7.28 (m, 3H), 7.30-7.10 (m, 1H), 6.80-6.65 (m, 1H), 3.85-3.65 (m, 6H), 3.58-3.47 (m, 2H), 3.26 (s, 3H), 2.83-2.68 (m, 2H). HPLC (max plot) 98%; Rt 4.52 min. UPLC/MS (ES+) 469.2, (ES−) 467.3. CHN analysis: [C22H24N6O4S-0.02 C4H10O-0.15 H20] Corrected: C56.10%, H5.22%, N17.78%; Found: C56.06%, H5.16%, N17.82%.

Example 63

N-(3-{[2-(3-Hydroxypropyl)-5-methoxyphenyl]amino}quinoxalin-2-yl)tetrahydrothiophene-3-sulfonamide 1,1-dioxide

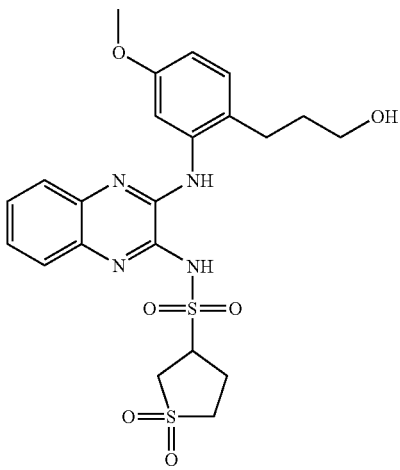 [SMILES: COc1ccc(CCCO)c(Nc2nc3ccccc3nc2NS(=O)(=O)C2CCS(=O)(=O)C2)c1]

Following the protocol outlined in procedure I, Example 63 is obtained from N-(3-chloro quinoxalin-2-yl)tetrahydrothiophene-3-sulfonamide 1,1-dioxide (300 mg; 0.83 mmol; 1 eq) and 3-(2-amino-4-methoxy-phenyl)-propan-1-ol (157.8 mg; 0.87 mmol; 1.05 eq) EtOH (2 mL) at 160° C. for 15 min in the microwave to afford 129 mg (31%) of the title compound as a yellow powder. $^1$H NMR (DMSO-$d_6$) δ 12.47 (s, 1H), 8.83 (s, 1H), 7.90-7.77 (m, 2H), 7.52-7.44 (m, 1H), 7.39-7.27 (m, 2H), 7.19 (d, J=8.4 Hz, 1H), 6.74 (dd, J=8.4, 2.6 Hz, 1H), 4.53 (br s, 1H), 4.43-4.28 (m, 1H), 3.78 (s, 3H), 3.69 (dd, J=13.9, 9.1 Hz, 1H), 3.49-3.15 (m, 5H), 2.68-2.39 (m, 4H), 1.70 (quint, J=6.9 Hz, 2H). HPLC (max plot) 97%; Rt 3.25 min. UPLC/MS (ES+) 507.2, (ES−) 505.3. CHN analysis: [C22H26N4O6S2.0.15H2O] Corrected: C51.88, H5.20, N11.00; found C51.53, H5.10, N10.91.

Example 64

N-(2-Hydroxyethyl)-4-methoxy-2-{[3-({[3-(methylsulfonyl)propyl]sulfonyl}amino)quinoxalin-2-yl]amino}benzenesulfonamide

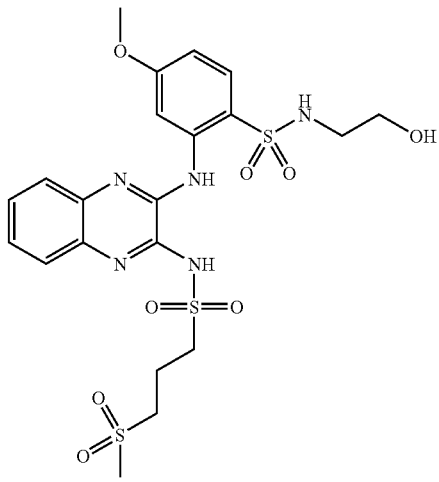 [SMILES: COc1ccc(S(=O)(=O)NCCO)c(Nc2nc3ccccc3nc2NS(=O)(=O)CCCS(C)(=O)=O)c1]

Following the protocol outlined in procedure I, Example 64 is obtained from N-(3-chloro quinoxalin-2-yl)-3-(methylsulfonyl)propane-1-sulfonamide (250 mg; 0.7 mmol; 1 eq) and 2-amino-N-(2-hydroxyethyl)-4-methoxybenzenesulfonamide (186 mg; 0.76 mmol; 1.1 eq) in EtOH (3 mL) and AcOH (0.1 mL) at 170° C. for 3 h in the microwave to afford 34 mg (9%) of the title compound as a light yellow powder. $^1$H NMR (DMSO-$d_6$) δ 12.47 (s, 1H), 10.46 (s, 1H), 8.7 (s, 1H), 7.92 (br s, 1H), 7.76 (d, J=8.8 Hz, 1H), 7.69-7.58 (m, 2H), 7.39 (br s, 2H), 6.82 (d, J=8.5 Hz, 1H), 4.67 (t, J=5.8 Hz, 1H), 3.90 (s, 3H), 3.42-3.25 (m, 6H), 2.99 (s, 3H), 2.86-2.79 (m, 2H), 2.35-2.26 (m, 2H). HPLC (max plot) 98%; Rt 3.70 min. UPLC/MS (ES+) 574.3, (ES−) 572.4.

Example 65

2-[(Dimethylamino)methyl]-N-[3-({5-methoxy-2-[2-(methylsulfonyl)ethyl]phenyl}amino)quinoxalin-2-yl]-1-methyl-1H-imidazole-4-sulfonamide

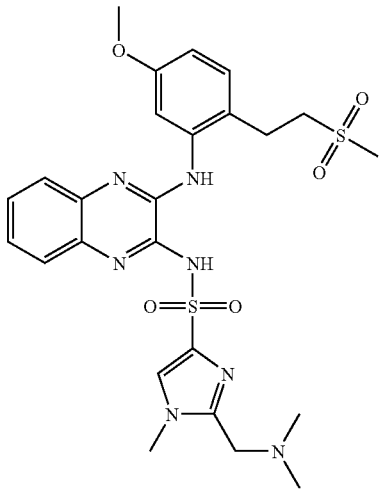 [SMILES: COc1ccc(CCS(C)(=O)=O)c(Nc2nc3ccccc3nc2NS(=O)(=O)c2cn(C)c(CN(C)C)n2)c1]

Following the protocol outlined in procedure I, Example 65 is obtained from N-(3-chloro quinoxalin-2-yl)-2-[(dimethylamino)methyl]-1-methyl-1H-imidazole-4-sulfonamide (50 mg; 0.13 mmol; 1 eq) and 2-(2-methane sulfonyl-ethyl)-5-methoxy-phenylamine.HCl (52.3 mg; 0.2 mmol; 1.5 eq, desalified) in EtOH (1 mL) at 165° C. for 2 h in the microwave to afford 10 mg (13%) of the title compound as a beige powder. ¹H NMR (DMSO-d₆) δ 12.50 (br s, 1H), 8.98-8.89 (m, 1H), 7.92 (s, 1H), 7.63-7.23 (m, 6H), 6.75 (s, 1H), 3.77 (s, 6H), 3.71 (s, 3H), 3.20-2.70 (m, 7H), 2.30-2.13 (m, 5H). HPLC (max plot) 95%; Rt 3.01 min. UPLC/MS (ES+) 574.4.

Example 66

Benzyl 4-{[(3-{[2-(3-hydroxypropyl)-5-methoxyphenyl]amino}quinoxalin-2-yl)amino]sulfonyl}piperidine-1-carboxylate

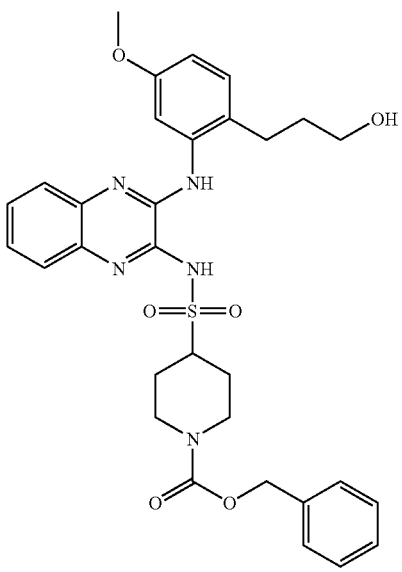 [SMILES: COc1ccc(CCCO)c(Nc2nc3ccccc3nc2NS(=O)(=O)C2CCN(C(=O)OCc3ccccc3)CC2)c1]

Following the protocol outlined in procedure I, Example 66 is obtained from benzyl 4-{[(3-chloroquinoxalin-2-yl)amino]sulfonyl}piperidine-1-carboxylate (300 mg; 0.65 mmol; 1 eq) and 3-(2-amino-4-methoxy-phenyl)-propan-1-ol (123.8 mg; 0.68 mmol; 1.05 eq) in EtOH (2 mL) at 160° C. for 15 min in the microwave to afford 245 mg (62%) of the tide compound as a yellow powder. ¹H NMR (DMSO-d₆) δ 12.29 (br s, 1H), 8.92 (br s, 1H), 8.27 (br s, 1H), 7.70 (br s, 1H), 7.50-7.47 (m, 1H), 7.36-7.27 (m, 7H), 7.13 (d, J=8.3 Hz, 1H), 6.63 (br d, J=7.3 Hz, 1H), 5.08 (s, 2H), 4.48 (br s, 1H), 4.13 (br d, J=12.6 Hz, 2H), 3.78 (s, 3H), 3.62-3.54 (m, 1H), 3.42-3.40 (m, 1H), 2.86 (m, 2H), 2.62 (t, J=7.4 Hz, 2H), 2.12-2.04 (m, 2H), 1.76-1.56 (m, 4H). HPLC (max plot) 97%; Rt 5.32 min. LC/MS: (ES+) 606.1, (ES−) 604.2.

Example 67

N-(2-Hydroxyethyl)-3-methoxy-5-[(3-{[(1-methyl-1H-imidazol-4-yl)sulfonyl]amino}quinoxalin-2-yl)amino]benzamide

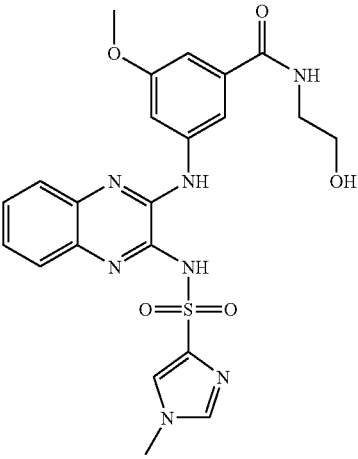 [SMILES: COc1cc(Nc2nc3ccccc3nc2NS(=O)(=O)c2cn(C)cn2)cc(C(=O)NCCO)c1]

Following the protocol outlined in procedure I, Example 67 is obtained from 1-methyl-1H-imidazole-4-sulfonic acid (3-chloro-quinoxalin-2-yl)-amide (400 mg; 1.24 mmol; 1 eq) and 3-amino-N-(2-hydroxyethyl)-5-methoxybenzamide (272.7 mg; 1.3 mmol; 1.05 eq) in iPrOH (3 mL) at 170° C. for 20 min in the microwave to afford 102 mg (17%) of the title compound as a yellow foam. ¹H NMR (DMSO-d₆) δ 12.74 (m, 1H), 9.06 (s, 1H), 8.40 (t, J=5.6 Hz, 1H), 8.06 (t, J=2.0 Hz, 1H), 7.98 (br s, 1H), 7.90 (br s, 2H), 7.80-7.77 (m, 1H), 7.63-7.58 (m, 1H), 7.45-7.37 (m, 2H), 7.13-7.12 (m, 1H), 7.13 (dd, J=2.1, 1.3 Hz, 1H), 4.74 (br s, 1H), 3.84 (s, 3H), 3.72 (s, 3H), 3.54-3.50 (t, J=5.7 Hz, 2H), 3.33 (dd, J=11.9, 5.7 Hz, 2H). HPLC (max plot) 100%; Rt 2.78 min. UPLC/MS (ES+) 498.3, (ES−) 496.3.

Example 68

N-[3-({5-Methoxy-2-[3-(methylsulfonyl)propyl]phenyl}amino)quinoxalin-2-yl]-1-methyl-1H-imidazole-4-sulfonamide

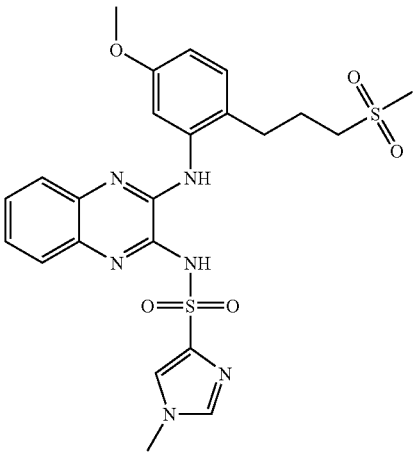 [SMILES: COc1ccc(CCCS(C)(=O)=O)c(Nc2nc3ccccc3nc2NS(=O)(=O)c2cn(C)cn2)c1]

Following the protocol outlined in procedure I, Example 68 is obtained from 1-methyl-1H-imidazole-4-sulfonic acid (3-chloro-quinoxalin-2-yl)-amide (400 mg; 1.2 mmol; 1 eq) and 5-methoxy-2-[3-(methylsulfonyl)propyl]aniline (481 mg; 2 mmol; 1.6 eq) in EtOH (8 mL) and AcOH (3.7 mg; 0.06 mmol; 0.05 eq) at 170° C. for 20 min in the microwave to 350 mg (53%) of the title compound as a beige powder. $^1$H NMR (DMSO-$d_6$) δ 8.90-8.88 (m, 1H), 8.03-7.79 (m, 4H), 7.52-7.49 (m, 1H), 7.40-7.30 (m, 2H), 7.19 (d, J=9.0 Hz, 1H), 6.72-6.69 (m, 1H), 3.80 (s, 3H), 3.72 (s, 3H), 3.15-3.05 (m, 2H), 2.93 (s, 3H), 2.66 (t, J=9.0 Hz, 2H), 1.94-1.90 (m, 2H). HPLC (max plot) 96%; Rt 3.60 min. UPLC/MS (ES+) 531.3, (ES−) 529.4.

Example 69

2-Hydroxy-N-(4-{[(3-{[2-(2-hydroxyethyl)-5-methoxyphenyl]amino}quinoxalin-2-yl)amino]sulfonyl}phenyl)acetamide

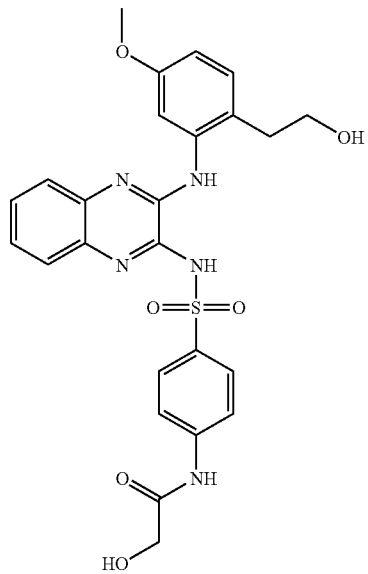 [SMILES: COc1ccc(CCO)c(Nc2nc3ccccc3nc2NS(=O)(=O)c2ccc(NC(=O)CO)cc2)c1]

Following the protocol outlined in procedure I, Example 69 is obtained from 2-[(4-{[(3-chloro quinoxalin-2-yl)amino]sulfonyl}phenyl)amino]-2-oxoethyl acetate (300 mg; 0.69 mmol; 1 eq) and 2-(2-amino-4-methoxy-phenyl)-ethanol (121 mg; 0.72 mmol; 1.05 eq) in EtOH (2 mL) at 160° C. for 15 min in the microwave to afford 45 mg (12%) of the title compound as a yellow powder. $^1$H NMR (DMSO-$d_6$) δ 12.29 (br s, 1H), 10.05 (s, 1H), 9.31 (s, 1H), 8.02 (d, J=9.0 Hz, 2H), 7.89 (m, 4H), 7.45 (m, 1H), 7.31 (m, 2H), 7.13 (d, J=9.0 Hz, 1H), 6.67 (dd, J=9.0 Hz, 1H), 5.69 (br s, 1H), 4.93 (br s, 1H), 4.01 (s, 2H), 3.74 (s, 3H), 3.56 (t, J=6.0 Hz, 2H), 2.59 (t, J=6.0 Hz, 2H). HPLC (max plot) 99.5%; Rt 3.43 min UPLC/MS (ES+) 524.3, (ES−) 522.4.

Example 70

2-Dimethylamino-N-(4-{[(3-{[2-(2-hydroxyethyl)-5-methoxyphenyl]amino}quinoxalin-2-yl)]sulfamoyl}phenyl)-acetamide. HCl Salt

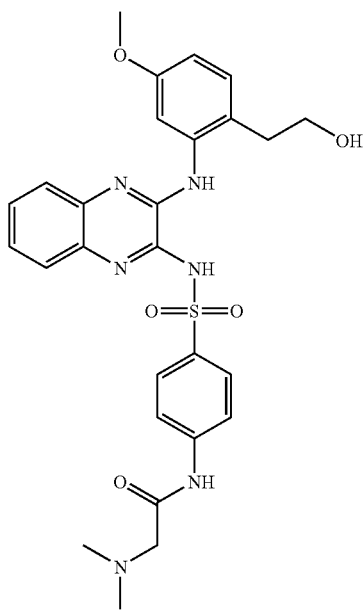 [SMILES: COc1ccc(CCO)c(Nc2nc3ccccc3nc2NS(=O)(=O)c2ccc(NC(=O)CN(C)C)cc2)c1]

Following the protocol outlined in procedure I, Example 70 is obtained from 2-dimethyamino-N-(4-{[(3-chloro quinoxalin-2-yl)]sulfamoyl}phenyl)-acetamide (215 mg; 0.51 mmol; 1 eq) and 2-(2-amino-4-methoxy-phenyl)-ethanol (94.2 mg; 0.56 mmol; 1.1 eq) in iPrOH (3 mL) at 170° C. for 20 min in the microwave to afford, after purification by preparative HPLC, the title compound as a TFA salt. The TFA salt is treated with a solution of 1N HCl then freeze dried to afford 25 mg (8%) of the title compound as an orange powder. $^1$H NMR (DMSO-$d_6$) δ 12.35 (br s, 1H), 11.22 (s, 1H), 9.96 (br s, 1H). 9.30 (s, 1H), 8.85 (d, J=9.0 Hz, 2H), 7.92 (m, 2H), 7.80 (d, J=9.0 Hz, 2H), 7.46 (m, 1H), 7.32 (m, 2H), 7.13 (d, J=6.0 Hz, 1H), 6.68 (dd, J=6.0 Hz, 1H), 4.19 (d, J=3.0 Hz, 2H), 3.75 (s, 3H), 3.56 (t, J=6.0 Hz, 2H), 2.86 (d, J=3.0 Hz, 6H), 2.59 (t, J=6.0 Hz, 2H). HPLC (max plot) 98%; Rt 3.30 min. UPLC/MS (ES+) 551.3, (ES−) 549.4.

Example 71

2-Dimethylamino-N-(4-{[(3-{[2-(3-hydroxypropyl)-5-methoxyphenyl]amino}quinoxalin-2-yl)]sulfamoyl}phenyl)-acetamide HCl Salt

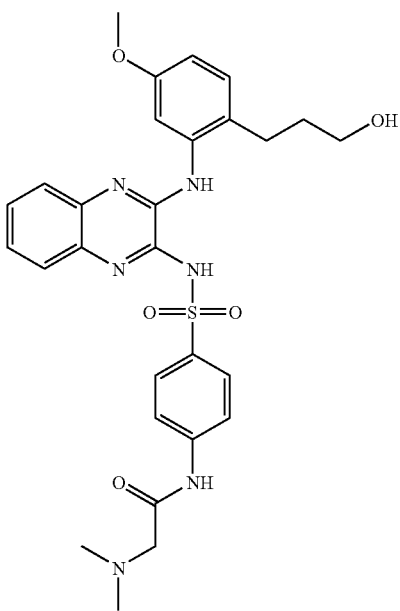 [SMILES: COc1ccc(CCCO)c(Nc2nc3ccccc3nc2NS(=O)(=O)c2ccc(NC(=O)CN(C)C)cc2)c1]

Following the protocol outlined in procedure I, Example 71 is obtained from 2-dimethylamino-N-(4-{[(3-chloro quinoxalin-2-yl)]sulfamoyl}phenyl)-acetamide (200 mg; 0.48 mmol; 1 eq) and 3-(2-amino-4-methoxy-phenyl)-propan-1-ol (95 mg; 0.52 mmol; 1.1 eq) in iPrOH (2 mL) at 170° C. for 15 min in the microwave to afford, after purification by preparative HPLC, the title compound as a TFA salt. The TFA salt is treated with a solution of 1N HCl then freeze dried to afford 37 mg (13%) of the title compound as an orange powder. $^1$H NMR (DMSO-$d_6$) δ 12.42 (br s, 1H), 11.19 (s, 1H), 9.93 (br s, 1H), 8.74 (s, 1H), 8.14 (s, 1H), 8.05 (d, J=9.0 Hz, 2H), 7.94 (br s, 1H), 7.81 (d, J=9.0 Hz, 2H), 7.54 (m, 1H), 7.37 (m, 2H), 7.11 (d, J=9.0 Hz, 1H), 6.64 (m, 1H), 4.45 (m, 2H), 4.18 (d, J=3.0 Hz, 2H), 3.76 (s, 3H), 3.25 (t, J=6.0 Hz, 2H), 3.15 (s, 1H), 2.87 (d, J=3.0 Hz, 6H), 1.54 (m, 2H). HPLC (max plot) 99%; Rt 3.52 min. UPLC/MS (ES+) 565.3, (ES−) 563.4.

Example 72

2-(Benzyloxy)-N-(3-{[(3-{[2-(3-hydroxypropyl-5-methoxyphenyl]amino}quinoxalin-2-yl)amino]sulfonyl}phenyl)acetamide

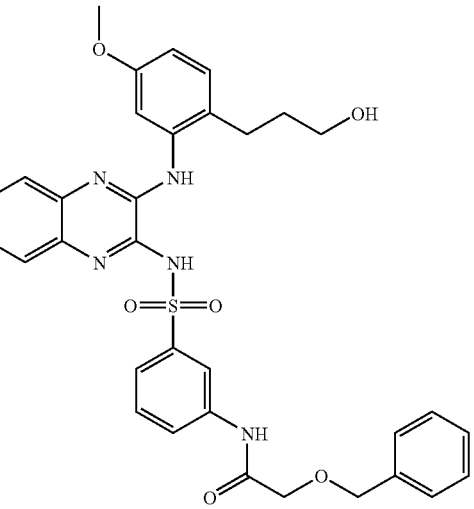

Following the protocol outlined in procedure I, Example 72 is obtained from 2-(benzyloxy)-N-(3-{[(3-chloroquinoxalin-2-yl)amino]sulfonyl}phenyl)acetamide (345 mg; 0.7 mmol; 1 eq) and 3-(2-amino-4-methoxy-phenyl)-propan-1-ol (136 mg; 0.75 mmol; 1.05 eq) in iPrOH (9 mL) at 170° C. for 20 min in the microwave to afford 100 mg (22%) of the title compound as a yellow powder. $^1$H NMR (DMSO-$d_6$) δ 12.56 (br s, 1H), 10.14 (s, 1H), 8.72 (s, 1H), 8.40 (s, 1H), 8.19 (s, 1H), 8.0-7.92 (m, 1H), 7.88 (d, J=8.2 Hz, 1H), 7.77 (d, J=8.3 Hz, 1H), 7.6-7.50 (m, 2H), 7.45-7.27 (m, 7H), 7.10 (d, J=8.3 Hz, 1H), 6.66 (dd, J=8.2, 2.7 Hz, 1H), 4.61 (s, 2H), 4.11 (s, 2H), 3.77 (s, 3H), 3.42-3.27 (m, 2H), 3.25-3.15 (m, 2H), 1.59-1.46 (m, 2H). HPLC (max plot) 98%; Rt 4.98 min, UPLC/MS (ES−) 628.3, (ES−) 626.4.

Example 73

N-(2-Hydroxyethyl)-3-methoxy-5-{[3-({[3-(methylsulfonyl)propyl]sulfonyl}amino)quinoxalin-2-yl]amino}benzamide

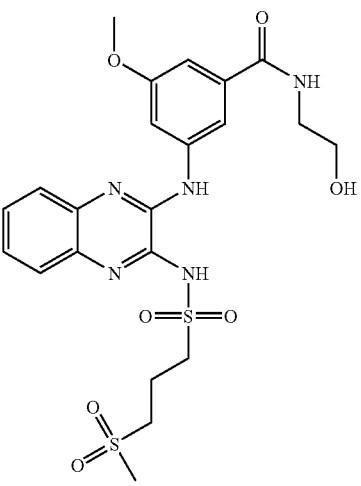 [SMILES: COc1cc(Nc2nc3ccccc3nc2NS(=O)(=O)CCCS(C)(=O)=O)cc(C(=O)NCCO)c1]

Following the protocol outlined in procedure I. Example 73 is obtained from N-(3-chloro quinoxalin-2-yl)-3-(methylsulfonyl)propane-1-sulfonamide (400 mg; 1.1 mmol; 1 eq) and 3-amino-N-(2-hydroxyethyl)-5-methoxybenzamide (242.7 mg; 1.15 mmol; 1.05 eq) in iPrOH (9 mL) at 170° C. for 20 min in the microwave to afford 30 mg (5%) of the title compound as a yellow powder. $^1$H NMR (DMSO-$d_6$) δ 12.25 (br s, 1H), 9.12 (s, 1H) 8.38 (tr, J=5.7 Hz, 1H), 8.12-8.03 (m, 1H), 8.00-7.95 (m, 1H), 7.92-7.84 (m, 1H), 7.61-7.54 (m, 1H), 7.43-7.30 (m, 2H), 7.13 (br s, 1H), 4.8-4.71 (m, 1H), 3.85 (s, 3H), 3.58-3.45 (m, 4H), 3.40-3.31 (m, 4H), 2.99 (s, 3H), 2.30-2.20 (m, 2H). HPLC (max plot) 100%; Rt 2.83 min. UPLC/MS (ES+) 538.2, (ES−) 536.3.

Example 74

2-(Hydroxymethyl)-N-(3-{[2-(3-hydroxypropyl)-5-methoxyphenyl]amino}quinoxalin-2-yl)-1-methyl-1H-imidazole-4-sulfonamide Tetrabutylammonium Salt

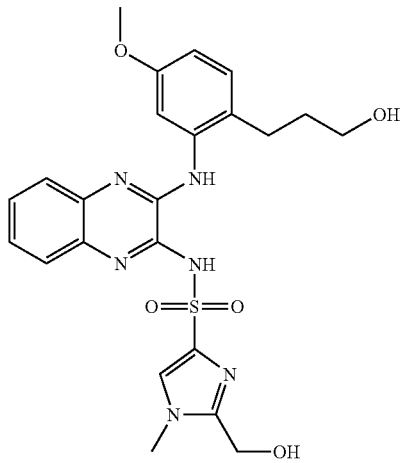 [SMILES: COc1ccc(CCCO)c(Nc2nc3ccccc3nc2NS(=O)(=O)c2cn(C)c(CO)n2)c1]

Following the protocol outlined in procedure I, Example 74 is obtained from 2-({[tert-butyl(dimethyl)silyl]oxy}methyl)-N-(3-chloroquinoxalin-2-yl)-1-methyl-1H-imidazole-4-sulfonamide (125 mg; 0.27 mmol; 1 eq) and 3-(2-amino-4-methoxy-phenyl)-propan-1-ol (72.6 mg; 0.4 mmol; 1.5 eq) in EtOH (1 mL) and AcOH (0.1 mL) at 160° C. for 20 min in the microwave to give a mixture of the title compound and the corresponding protected alcohol. To a suspension of the mixture in THF is added TBAF (500 μM, 1 M) and the reaction mixture is stirred at room temperature for 18 h to afford, after purification by preparative HPLC, 10 mg (8%) of the title compound as a yellow powder. $^1$H NMR (DMSO-$d_6$) δ 9.15 (s, 1H), 8.63 (s, 1H), 7.55 (s, 1H), 7.51-7.45 (m, 2H), 7.15-7.10 (m, 2H), 6.98 (d, J=9.0 Hz, 1H), 6.44 (dd, J=9.0, 3.0 Hz, 1H), 4.51 (s, 2H), 3.79 (s, 3H), 3.70 (t, J=9.0 Hz, 2H), 3.56 (s, 3H), 3.05-3.01 (m, 8H), 2.75-2.70 (m, 2H), 1.89-1.84 (m, 2H), 1.40-1.23 (m, 16H), 0.81 (t, J=9.0 Hz, 12H). HPLC (max plot) 97%; Rt 3.73 min. UPLC/MS (ES+) 499.3.

Example 75

3-Methoxy-N,N-dimethyl-5-[(3-{[(1-methyl-1H-imidazol-4-yl)sulfonyl]amino}quinoxalin-2-yl)amino]benzamide

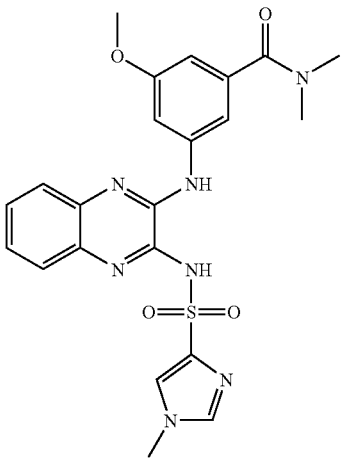 [SMILES: COc1cc(Nc2nc3ccccc3nc2NS(=O)(=O)c2cn(C)cn2)cc(C(=O)N(C)C)c1]

Following the protocol outlined in procedure I, Example 75 is obtained from N-(3-chloro quinoxalin-2-yl)-1-methyl-1H-imidazole-4-sulfonamide (300 mg; 0.93 mmol; 1 eq) and 3-amino-5-methoxy-N,N-dimethylbenzamide (198 mg; 1 mmol; 1.1 eq) in iPrOH (3 mL) at 160° C. for 20 min in the microwave to afford 220 mg (49%) of the tide compound as a white powder. $^1$H NMR (DMSO-$d_6$) δ 9.10-9.05 (m, 1H), 7.98-7.91 (m, 2H), 7.80-7.77 (m, 2H), 7.65-7.50 (m, 2H), 7.52-7.39 (m, 2H), 6.66 (d, 3.0 Hz, 1H), 3.82 (s, 3H), 3.73 (s, 3H), 3 (s, 6H). HPLC (max plot) 92%; Rt 3.18 min. UPLC/MS (ES+) 482.2, (ES−) 480.3.

Example 76

N-(3-{[2-(3-Hydroxypropyl)-5-methoxyphenyl]amino}quinoxalin-2-yl)-1-methyl-2-[(methylsulfonyl)methyl]-1H-imidazole-4-sulfonamide

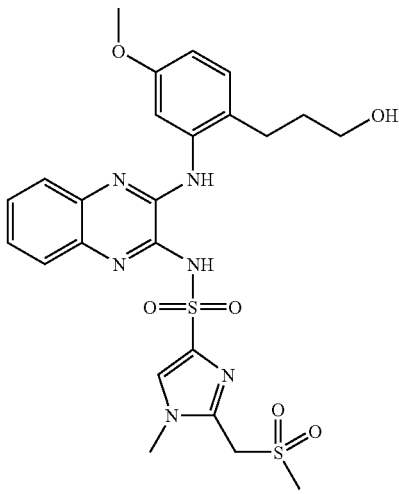 [SMILES: COc1ccc(CCCO)c(Nc2nc3ccccc3nc2NS(=O)(=O)c2cn(C)c(CS(C)(=O)=O)n2)c1]

Following the protocol outlined in procedure I, Example 76 is obtained from N-(3-chloro quinoxalin-2-yl)-1-methyl-2-[(methylsulfonyl)methyl]-1H-imidazole-4-sulfonamide (200 mg; 0.5 mmol; 1 eq) and 3-(2-amino-4-methoxy-phenyl)-propan-1-ol (104.6 mg; 0.6 mmol; 1.2 eq) in EtOH (2 mL) and AcOH (0.1 mL) at 160° C. for 15 min in the microwave to afford 50 mg (19%) of the title compound as a yellow powder. $^1$H NMR (DMSO-$d_6$) δ 12.75-12.70 (m, 1H), 8.85-8.80 (m, 1H), 8.08 (s, 2H), 7.93-7.87 (m, 1H), 7.53-7.37 (m, 3H), 7.15 (d, J=9.0 Hz, 1H), 6.70-6.66 (m, 1H), 4.92 (s, 2H), 4.42 (t, J=9.0 Hz, 1H), 3.77 (s, 6H), 2.99 (s, 3H), 2.58 (t, J=9.0 Hz, 2H), 1.66 (t, J=9.0 Hz, 2H), 1.35 (t, J=9.0 Hz, 2H). HPLC (max plot) 99%; Rt 3.65 min. UPLC/MS (ES+) 561.2, (ES−) 559.3.

Example 77

N-[3-({2-[(2R,2S)-2,3-Dihydroxypropyl]-5-methoxyphenyl}amino)quinoxalin-2-yl]-1-methyl-1H-imidazole-4-sulfonamide

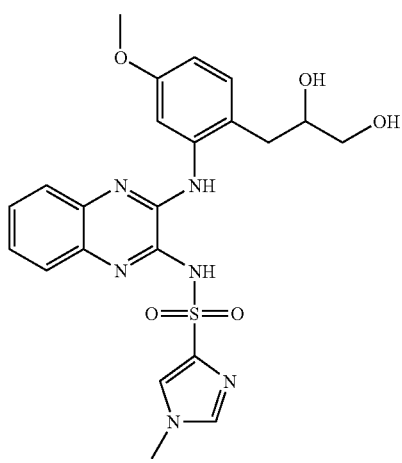 [SMILES: COc1ccc(CC(O)CO)c(Nc2nc3ccccc3nc2NS(=O)(=O)c2cn(C)cn2)c1]

Following the protocol outlined in procedure I, Example 77 is obtained from 1-methyl-1H-imidazole-4-sulfonic acid (3-chloro-quinoxalin-2-yl)-amide (323.8 mg; 1 mmol; 1 eq) and 2-(2,2-dimethyl-[1,3]dioxolan-4-ylmethyl)-5-methoxyphenylamine (284.8 mg; 1.2 mmol; 1.2 eq) in iPrOH (1.5 mL) at 160° C. for 15 min in the microwave. The reaction mixture is diluted with EtOH (10 mL) and AcOH (0.2 mL) and stirred at room temperature for 16 h to afford 72 mg (15%) of the title compound as a pale yellow solid. $^1$H NMR (DMSO-$d_6$) δ 12.66 (s, 1H), 9.60 (s, 1H), 7.96 (d, J=1.0 Hz, 1H), 7.91 (d, J=1.0 Hz, 1H), 7.85-7.76 (m, 2H), 7.51-7.44 (m, 1H), 7.39-7.30 (m, 2H), 7.16 (d, J=8.4 Hz, 1H), 6.69 (dd, J=8.4, 2.7 Hz, 1H), 3.76 (s, 3H), 3.73 (s, 3H), 3.71-3.61 (m, 1H), 3.37-3.22 (m, 2H), 2.7 (dd, J=14.1, 3.6 Hz, 1H), 2.61-2.52 (m, 1H). HPLC (max plot) 97% Rt 3.00 min. UPLC/MS (ES+) 485.2, (ES−) 483.2.

Example 78

2-Dimethylamino-N-(3-{[(3-{[2-(3-hydroxypropyl)-5-methoxyphenyl]amino}quinoxalin-2-yl)]sulfamoyl}phenyl)-acetamide

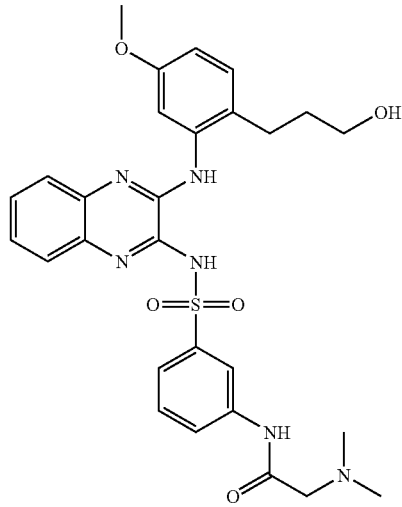 [SMILES: COc1ccc(CCCO)c(Nc2nc3ccccc3nc2NS(=O)(=O)c2cccc(NC(=O)CN(C)C)c2)c1]

Following the protocol outlined in procedure I, Example 78 is obtained from 2-dimethylamino-N-(3-{[(3-chloro quinoxalin-2-yl)]sulfamoyl}phenyl)-acetamide (462 mg; 1.1 mmol; 1 eq) and 3-(2-amino-4-methoxy-phenyl)-propan-1-ol (219.4 mg; 1.2 mmol; 1.1 eq) in iPrOH (12 mL) at 170° C. for 60 min in the microwave to afford 62 mg (10%) of the title compound as a yellow foam. $^1$H NMR (DMSO-$d_6$) δ 10.55 (br s, 1H), 10.00-9.64 (m, 1H), 9.16-9.02 (m, 1H), 8.66 (m, 1H), 8.25 (s, 1H), 7.76 (d, J=7.8 Hz, 1H), 7.70 (d, J=8.0 Hz, 1H), 7.45-7.32 (m, 3H), 7.20-7.14 (m, 2H), 7.08 (d, J=6.4 Hz, 1H), 6.52 (dd, J=8.2, 2.4 Hz, 1H), 4.44-4.42 (m, 1H), 4.01-3.90 (m, 2H), 3.77 (s, 3H), 3.53-3.45 (m, 2H), 2.77 (s, 6H), 2.70-2.60 (m, 2H), 1.85-1.70 (m, 2H). HPLC (max plot) 100%; Rt 3.61 min. UPLC/MS (ES+) 565.3, (ES−) 563.4.

Example 79

N-(3-{[5-Methoxy-2-(2-methoxyethyl)phenyl]amino}quinoxalin-2-yl)-1-methyl-2-[(methylsulfonyl)methyl]-1H-imidazole-4-sulfonamide

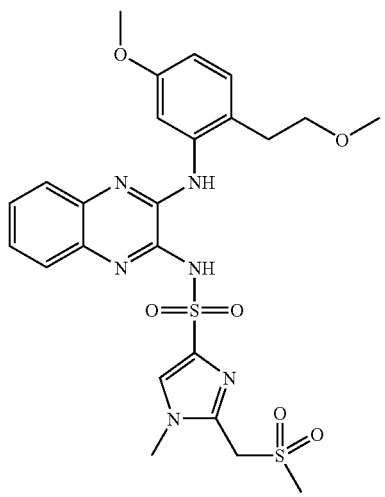 [SMILES: COCCc1ccc(OC)cc1Nc1nc2ccccc2nc1NS(=O)(=O)c1cn(C)c(CS(C)(=O)=O)n1]

Following the protocol outlined in procedure I, Example X is obtained from N-(3-chloro quinoxalin-2-yl)-1-methyl-2-[(methylsulfonyl)methyl]-1H-imidazole-4-sulfonamide (200 mg; 0.5 mmol; 1 eq) and 5-methoxy-2-(2-methoxyethyl)aniline (104.6 mg; 0.58 mmol; 1.2 eq) in EtOH (3 mL) and AcOH (50 µL) at 160° C. for 20 min in the microwave to afford 100 mg (37%) of the title compound as a yellow powder. $^1$H NMR (DMSO-$d_6$) δ 12.64 (s, 1H), 9.45-9.41 (s, 1H), 8.07 (d, J=3.0 Hz, 1H), 7.86-7.76 (m, 2H), 7.48-7.36 (m, 3H), 7.19 (d, J=9.0 Hz, 1H), 6.70 (dd, J=9.0, 3.0 Hz, 1H), 4.92 (s, 2H), 3.78 (s, 3H), 3.76 (s, 3H), 3.51 (t, J=9.0 Hz, 2H), 3.25 (s, 3H), 2.98 (s, 3H), 2.75 (t, J=9.0 Hz, 2H). HPLC (max plot) 90%; Rt 4.44 min. UPLC/MS (ES+) 561.2, (ES−) 559.2.

Example 80

3-Methoxy-N-(2-methoxyethyl)-5-[(3-{[(1-methyl-1H-imidazol-4-yl)sulfonyl]amino}quinoxalin-2-yl)amino]benzamide

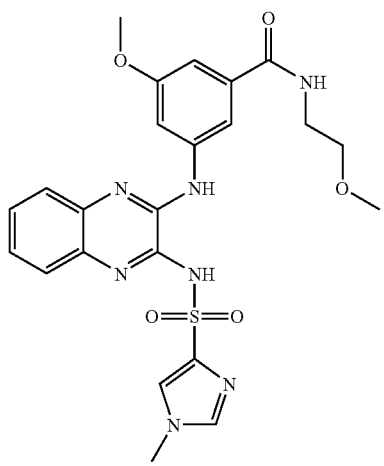 [SMILES: COCCNC(=O)c1cc(Nc2nc3ccccc3nc2NS(=O)(=O)c2cn(C)cn2)cc(OC)c1]

Following the protocol outlined in procedure I, Example 80 is obtained from N-(3-chloro quinoxalin-2-yl)-1-methyl-1H-imidazole-4-sulfonamide (240 mg; 0.74 mmol; 1 eq) and 3-amino-5-methoxy-N-(2-methoxyethyl)benzamide (220 mg; 0.89 mmol; 1.2 eq) in EtOH (1 mL) at 160° C. for 20 min in the microwave to afford 130 mg (34%) of the title compound as a yellow powder. $^1$H NMR (DMSO-$d_6$) δ 12.65 (s, 1H), 9.08 (s, 1H), 8.60-8.40 (m, 1H), 8.07-7.92 (m, 5H 7.65-7.50 (m, 1H), 7.44-7.42 (m, 2H), 7.13 (s, 1H), 3.85 (s, 3H), 3.73 (s, 3H), 3.60-3.10 (m, 7H). HPLC (max plot) 99%: Rt 3.77 min. UPLC/MS (ES+) 512.2, (ES−) 510.2.

Procedure J

Example 81

N-[3-({5-methoxy-2-[(4-methylpiperazin-1-yl)methyl]phenyl}amino)quinoxalin-2-yl]pyridine-3-sulfonamide di HCl Salt

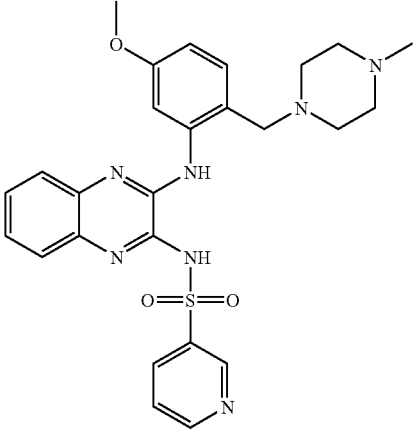

N-(3-chloroquinoxalin-2-yl)pyridine-3-sulfonamide (500 mg; 1.6 mmol; 1 eq) and 5-methoxy-2-(4-methyl-piperazin-1-ylmethyl)-phenylamine (403.5 mg; 1.7 mmol; 1.1 eq) are taken up in dry EtOH (7.5 mL) and the suspension is heated up to 50° C. for 5 days under shaking. The reaction is stopped by evaporation of EtOH. The solid residue is taken up in DMF (4 mL) and purified by preparative HPLC, affording the title compound as a di TFA salt (bright yellow powder). The product is taken up in HCl in MeOH (2.5 mL; 1.25 M; 3.1 mmol; 2 eq) and diethylether is added to the solution. After 1 h at 4° C., the precipitate formed is filtered off and washed with diethylether then dried for 2 days at 40° C. under vacuum, affording 278 mg (30%) of the title compound as a yellow powder. $^1$H NMR (DMSO-$d_6$) δ 12.42 (br s, 1H), 10.50-0.95 (m, 2H), 9.25 (d, J=1.9 Hz, 1H), 8.83 (dd, J=4.9, 1.5 Hz, 1H), 8.47 (dt, J=8.3, 1.9 Hz, 1H), 8.39-8.10 (m, 1H), 8.05-7.86 (m, 1H), 7.65 (dd, J=7.9, 4.9 Hz, 1H), 7.60-7.48 (m, 1H), 7.47-7.18 (m, 4H), 6.80-6.60 (m, 1H), 3.79 (s, 3H), 3.76-2.65 (m, 13H). HPLC (max plot) 99%; Rt 3.13 min. LC/MS: (ES+): 520.4, (ES−): 518.2. CHN analysis: [$C_{26}H_{29}N_7O_3S$-3.0 HCl-2.5 $H_2O$] Calculated: C46.33%, H5.53%, N14.55%; Found: C46.44%, H5.37%, N14.50%.

Example 82

4-fluoro-N-[3-({5-methoxy-2-[(4-methylpiperazin-1-yl)methyl]phenyl}amino)quinoxalin-2-yl]benzenesulfonamide di HCl Salt

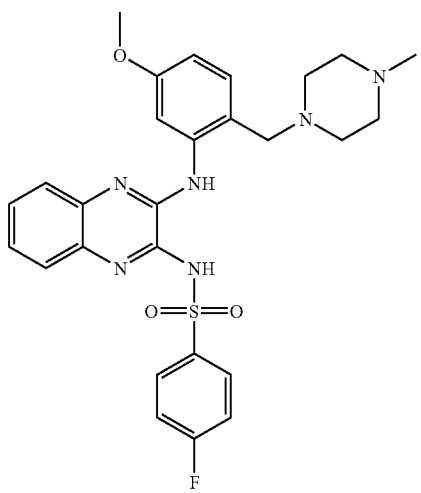 [SMILES: COc1ccc(CN2CCN(C)CC2)c(Nc2nc3ccccc3nc2NS(=O)(=O)c2ccc(F)cc2)c1]

Following the protocol outlined in Procedure J, Example 82 is obtained from N-(3-chloro quinoxalin-2-yl)-4-fluorobenzenesulfonamide (300 mg; 0.9 mmol; 1 eq) and 5-methoxy-2-(4-methyl-piperazin-1-ylmethyl)-phenylamine (229.9 mg; 0.98 mmol; 1.1 eq) in EtOH (7.5 mL) to afford the title compound as a diTFA salt. Treatment with HCl in MeOH (4.3 mL; 1.25 M; 5.3 mmol; 6 eq) affords 184 mg (34%) of the title compound as a yellow powder. $^1$H NMR (DMSO-$d_6$) δ 12.43 (br s, 1H), 11.17 (br s, 1H), 10.16 (br s, 1H), 8.37-8.32 (m, 2H), 8.14-8.12 (m, 1H), 7.67-7.49 (m, 7H), 6.91-6.89 (m, 1H), 3.96 (s, 3H), 3.94-3.85 (m, 2H), 3.60-3.56 (m, 2H), 3.40-3 (m, 4H), 2.95-2.70 (m, 2H), 2.88 (s, 3H). HPLC (max plot) 99%; Rt 3.73 min. LC/MS: (ES+): 537.2, (ES−): 535.3. CHN analysis: [$C_{27}H_{29}N_6O_3SF$-2.4 HCl-1.3 $H_2O$] Calculated: C50.08%, H5.29%, N12.98%; Found: C49.95%, H5.12%, N12.89%.

Example 83

N-(3-{[5-methoxy-2-(morpholin-4-ylmethyl)phenyl]amino}quinoxalin-2-yl)pyridine-3-sulfonamide HCl Salt

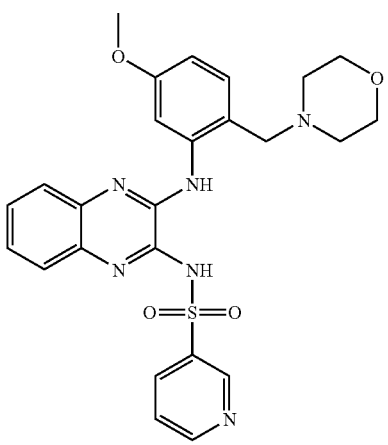

Following the protocol outlined in Procedure J, Example 83 is obtained from N-(3-chloro quinoxalin-2-yl)pyridine-3-sulfonamide (300 mg; 0.9 mmol; 1 eq) and 5-methoxy-2-morpholin-4-ylmethyl-phenylamine (270.3 mg; 1.22 mmol; 1.3 eq) in EtOH (6 mL) to afford the title compound as a TFA salt. Treatment with HCl in MeOH (243 μL; 1.25 M; 0.3 mmol; 1.2 eq) affords 46 mg (29%) of the title compound as a yellow powder. $^1$H NMR (DMSO-$d_6$) δ 12.50 (br s, 1H), 9.60-8.90 (m, 2H), 8.80 (dd, J=4.5, 1.5 Hz, 1H), 8.44 (d, J=7.9 Hz, 1H), 8.00-7.80 (m, 1H), 7.70-6.80 (m, 7H), 4.40-2.80 (m, 14H). HPLC (max plot) 98%; Rt 2.58 min. LC/MS: (ES+): 507.3, (ES−): 505.3.

Procedure K

Example 84

4-[(dimethylamino)methyl]-N-[3-({2-[(4-hydroxycyclohexyl)methyl]-5-methoxyphenyl}amino)quinoxalin-2-yl]benzenesulfonamide HCl Salt

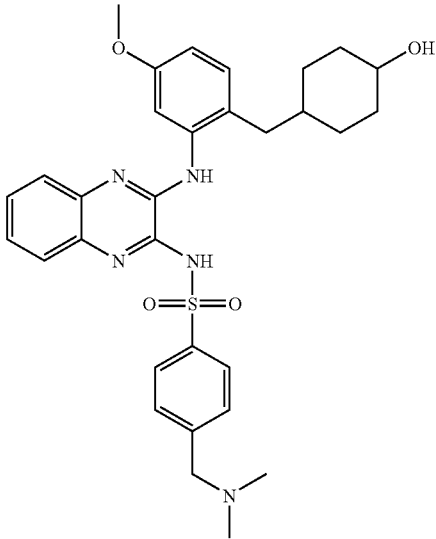 [SMILES: COc1ccc(CC2CCC(O)CC2)c(Nc2nc3ccccc3nc2NS(=O)(=O)c2ccc(CN(C)C)cc2)c1]

4-({[3-({2-[(4-hydroxycyclohexyl)methyl]-5-methoxyphenyl}amino)quinoxalin-2-yl]amino}sulfonyl)-N,N-dimethylbenzamide (228 mg; 0.39 mmol; 1 eq) is taken up in THF (5 mL) at 0° C. then lithium aluminum hydride (774 μL; 1 M; 0.77 mmol; 2 eq) is added dropwise. The reaction mixture is stirred at 0° C. for 1 h. The reaction is quenched sequentially with water (30 μL), NaOH 1N (30 μL) then water (90 μL). The suspension is filtered through a pad of celite. The celite is rinsed with THF/MeOH [1/1] and the filtrate is concentrated to dryness under reduced pressure. The residue is taken up in water (3 mL) and the resulting solution is neutralised by addition of 0.1N HCl. After one night at 4° C., the precipitate is filtered then purified by flash chromatography (eluent DCM/MeOH [8.5/1.5]) to afford 147 mg (65.5%) of the title compound as a parent. Treatment of the parent (147 mg; 0.25 mmol; 1 eq) with HCl in diethylether (248.3 μL; 1 M; 0.25 mmol; 1 eq.) in DCM (5 mL) affords 154.5 mg (75%) of the title compound as a yellow powder. $^1$H NMR (DMSO-$d_6$) δ 12.30 (br s, 1H), 10.16 (br s, 1H), 8.49 (br s, 1H), 8.11 (br s, 1H), 7.93 (d, J=7.9 Hz, 2H), 7.75 (br s, 1H), 7.55 (d, J=7.2 Hz, 2H), 7.37-7.35 (m, 1H), 7.18 (br s, 2H), 6.84 (d, J=8.3 Hz, 1H), 6.41 (d, J=6.8 Hz, 1H), 4.15 (s, 2H), 3.56-3.46 (m, 5H), 2.28 (s, 6H), 2.14-2.12 (m, 2H), 1.28-0.63 (m, 9H). HPLC (max plot) 98%; Rt 3.56 min. LC/MS: (ES+): 576.2, (ES−): 574.2. CHN analysis: [C$_{31}$H$_{37}$N$_5$O$_4$S—HCl-0.013 CH$_2$Cl$_2$] Corrected: C59.00%, H6.39%, N11.09%; Found: C59.11%, H5.99%, N10.72%.

Example 85

4-[(dimethylamino)methyl]-N-[3-({2-[(1,1-dioxidotetrahydro-2H-thiopyran-4-yl)methyl]-5-methoxyphenyl}amino)quinoxalin-2-yl]benzenesulfonamide HCl Salt

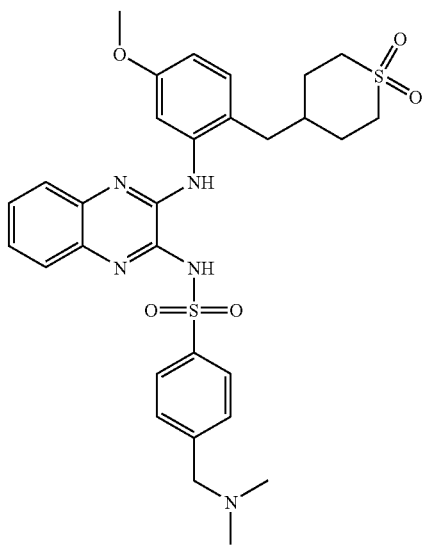 [SMILES: COc1ccc(CC2CCS(=O)(=O)CC2)c(Nc2nc3ccccc3nc2NS(=O)(=O)c2ccc(CN(C)C)cc2)c1]

Following the protocol outlined in Procedure K, Example 85 is obtained from 4-({[3-({2-[(1,1-dioxidotetrahydro-2H-thiopyran-4-yl)methyl]-5-methoxyphenyl}amino)quinoxalin-2-yl]amino}sulfonyl)-N,N-dimethylbenzamide (190 mg; 0.3 mmol; 1 eq) in THF (5 mL) at −15° C. followed by the addition of lithium aluminum hydride (609 µL; 1 M; 0.61 mmol; 2 eq) for 5 min to afford, after preparative HPLC, 82 mg (43%) of the title compound as a TFA salt. Treatment of the TFA salt (81.9 mg; 0.13 mmol; 1 eq) with HCl in diethylether (148 µL; 1 M; 0.15 mmol; 1.1 eq) in DCM (3.5 mL) affords 83 mg (99%) of the title compound as a yellow powder. $^1$H NMR (DMSO-d$_6$) δ 12.52 (br s, 1H), 10.09 (br s, 1H), 8.69 (br s, 1H), 8.27 (br s, 1H), 8.18 (d, J=8.3 Hz, 2H), 7.95 (br s, 1H), 7.72 (br s, 2H), 7.54 (br s, 1H), 7.35 (br s, 2H), 7.12 (d, J=8.7 Hz, 1H), 6.65-6.63 (m, 1H), 4.36 (s, 2H), 3.79 (s, 3H), 2.92 (br s, 4H), 2.72 (s, 6H), 2.43 (br s, 2H), 1.77 (br s, 3H), 1.53 (br s, 2H). HPLC (max plot) 99%; Rt 3.38 min. LC/MS: (ES+): 610.1, (ES−): 608.1.

Example 86

4-[(dimethylamino)methyl]-N-(3-{[methoxy-2-(tetrahydro-2H-pyran-4-ylmethyl)phenyl]amino}quinoxalin-2-yl)benzenesulfonamide HCl Salt

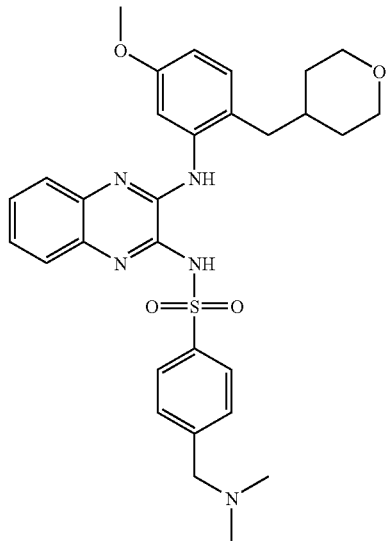 [SMILES: COc1ccc(CC2CCOCC2)c(Nc2nc3ccccc3nc2NS(=O)(=O)c2ccc(CN(C)C)cc2)c1]

Following the protocol outlined in Procedure K, Example 86 is obtained from 4-{[(3-{[5-methoxy-2-(tetrahydro-2H-pyran-4-ylmethyl)phenyl]amino}quinoxalin-2-yl)amino]sulfonyl}-N,N-dimethylbenzamide (220 mg; 0.38 mmol; 1 eq) in THF (50 mL) at 0° C. followed by the addition of lithium aluminum hydride (0.57 mL; 1 M; 0.57 mmol; 1.5 eq) for 25 min. After filtration through celite, evaporation of the solvents, the residue is taken up in DCM and HCl 1N (15 mL) is added. The precipitate formed is filtered and dried under vacuum at 40° C. to afford 150 mg (66%) of the title compound as a yellow powder. $^1$H NMR (DMSO-d$_6$) δ 12.55-12.45 (m, 1H), 10.44-10.42 (m, 1H), 8.74-8.72 (m, 1H), 8.35-8.32 (m, 1H), 8.15 (d, J=8.3 Hz, 2H), 7.96-7.94 (m, 1H), 7.75 (d, J=7.9 Hz, 2H), 7.57-7.55 (m, 1H), 7.39-7.38 (m, 2H), 7.10 (d, J=9.0 Hz, 1H), 6.64 (dd, J=9.0, 3.0 Hz, 1H), 3.78 (s, 3H), 3.74-3.71 (m, 2H), 3.08-3.05 (m, 2H), 2.71 (s, 6H), 2.39-2.37 (m, 2H), 1.59-1.57 (m, 1H), 1.26-1.24 (m, 2H), 1.03-1.01 (m, 2H). HPLC (max plot) 96%; Rt 3.78 min. LC/MS: (ES−): 560.4, (ES+): 562.5.

Example 87

N-(3-{[2-(cyclohexylmethyl)-5-methoxyphenyl]amino}quinoxalin-2-yl)-4-[(dimethylamino)methyl]benzenesulfonamide HCl Salt

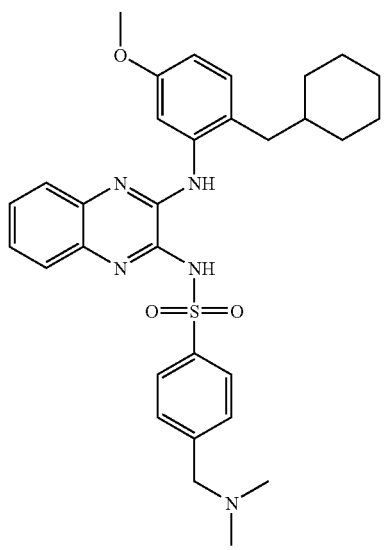 [SMILES: COc1ccc(CC2CCCCC2)c(Nc2nc3ccccc3nc2NS(=O)(=O)c2ccc(CN(C)C)cc2)c1]

Following the protocol outlined in Procedure K, Example 87 is obtained from 4-{[(3-{[2-(cyclohexylmethyl)-5-methoxyphenyl]amino}quinoxalin-2-yl)amino]sulfonyl}-N,N-dimethyl benzamide (380 mg; 0.66 mmol; 1 eq) in THF (70 mL) at −15° C. followed by the addition of lithium aluminum hydride (1.32 mL; 1 M; 1.32 mmol; 2 eq) for 2 h to afford, after purification by flash chromatography (Eluent Cyclohexane/EtOAc [1/1]), 101 mg (27%) of the title compound as a parent. Treatment of the parent (101 mg; 0.18 mmol; 1 eq) with HCl in MeOH (173.2 μL; 1.25 M; 0.22 mmol; 1.2 eq) in DCM (1.5 mL) affords 34 mg (34%) of the title compound as a yellow powder. $^1$H NMR (DMSO-$d_6$) δ 12.47 (br s, 1H), 9.98 (br s, 1H), 8.87 (br s, 1H), 8.46 (s, 1H), 8.13 (d, J=8.3 Hz, 2H), 7.67-7.29 (m, 6H), 7.03 (d, J=8.3 Hz, 1H), 6.58-6.56 (m, 1H), 4.31 (s, 2H), 3.78 (s, 3H), 2.70 (s, 6H), 2.44-2.34 (m, 2H), 1.56-1.40 (m, 6H), 1.05-0.85 (m, 5H). HPLC (max plot) 98%; Rt 4.52 min. LC/MS: (ES+): 560.1, (ES−): 558.0.

Example 88

4-[(dimethylamino)methyl]-N-(3-{[5-methoxy-2-(tetrahydro-2H-thiopyran-4-ylmethyl)phenyl]amino}quinoxalin-2-yl)benzenesulfonamide HCl Salt

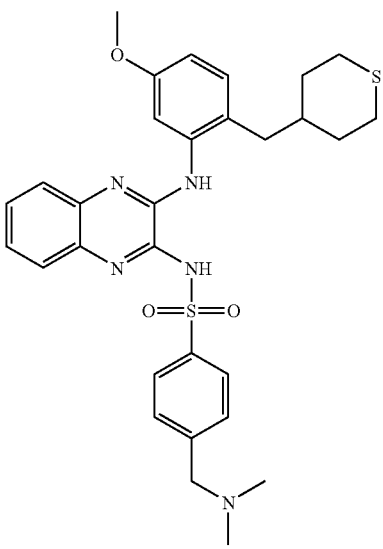 [SMILES: COc1ccc(CC2CCSCC2)c(Nc2nc3ccccc3nc2NS(=O)(=O)c2ccc(CN(C)C)cc2)c1]

Following the protocol outlined in Procedure K, Example 88 is obtained from 4-{[(3-{[5-methoxy-2-(tetrahydro-2H-thiopyran-4-ylmethyl)phenyl]amino}quinoxalin-2-yl)amino]sulfonyl}-N,N-dimethylbenzamide (200 mg; 0.34 mmol; 1 eq) in THF (5 mL) at −15° C. followed by the addition of lithium aluminum hydride (675.96 μL; 1 M; 0.68 mmol; 2 eq) at −15° C. for 5 min then 10 min at room temperature to afford, after recrystallization in EtOH, 45.5 mg (23%) of the title compound as a parent. Treatment of the parent (45.5 mg; 0.079 mmol; 1 eq) with HCl in diethylether (86 μL; 1 M; 0.087 mmol; 1.1 eq) in EtOH (3 mL) affords 445 mg (92%) of the title compound as a yellow powder. $^1$H NMR (DMSO-$d_6$) δ 12.52 (br s, 1H), 10.40 (br s, 1H), 8.69 (br s, 1H), 8.30 (br s, 1H), 8.17 (d, J=8.3 Hz, 2H), 7.96 (br s, 1H), 7.78 (d, J=7.9 Hz, 2H), 7.59-7.56 (m, 1H), 7.39-7.37 (m, 2H), 7.07 (d, J=8.3 Hz, 1H), 6.64 (dd, J=8.7, 2.6 Hz, 1H), 4.37 (br s, 2H), 3.78 (s, 3H), 2.72 (br s, 6H), 2.41-2.35 (m, 6H), 1.69-1.65 (m, 2H), 1.41 (br s, 1H), 1.16-1.08 (m, 2H). HPLC (max plot) 96%; Rt 4.15 min. LC/MS: (ES+): 578.1, (ES−): 576.1.

Example 89

4-[(Dimethylamino)methyl]-N-(3-{[2-(2-hydroxy-ethyl)-5-methoxyphenyl]amino}quinoxalin-2-yl)benzenesulfonamide HCl Salt

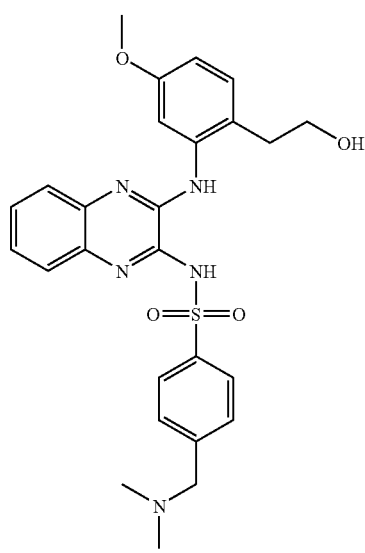 [SMILES: COc1ccc(CCO)c(Nc2nc3ccccc3nc2NS(=O)(=O)c2ccc(CN(C)C)cc2)c1]

Example 90

4-[(4-Fluoropiperidin-1-yl)methyl]-N-(3-{[2-(2-hydroxyethyl-5-methoxy phenyl]amino}quinoxalin-2-yl)benzenesulfonamide HCl Salt

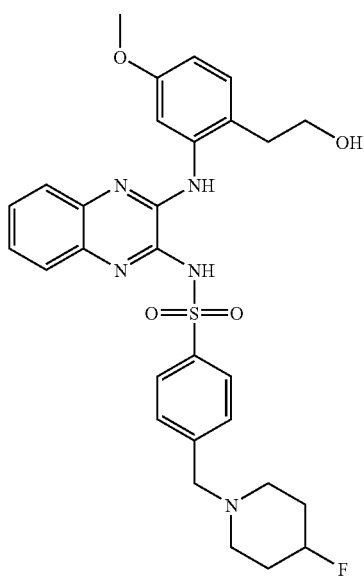 [SMILES: COc1ccc(CCO)c(Nc2nc3ccccc3nc2NS(=O)(=O)c2ccc(CN3CCC(F)CC3)cc2)c1]

Following the protocol outlined in Procedure K, Example 89 is obtained from 4-{[(3-{[2-(2-hydroxyethyl)-5-methoxyphenyl]amino}quinoxalin-2-yl)amino]sulfonyl}-N,N-dimethyl benzamide (160 mg; 0.31 mmol; 1 eq) in THF (20 mL) at 0° C. followed by the addition of lithium aluminum hydride (0.46 mL; 1 M; 0.46 mmol; 1.5 eq) for 1 h to afford 80 mg (51%) of the title compound as parent. Treatment of the parent (80 mg; 0.16 mmol; 1 eq) with a solution of HCl (0.13 mL; 1.25 M; 0.16 mmol; 1 eq) in MeOH (5 mL) affords 61 mg (71%) of the title compound as a yellow powder. $^1$H NMR (DMSO-$d_6$) δ 12.54 (s, 1H), 10.18 (s, 1H), 9.29 (s, 1H), 8.17 (d, J=9.0 Hz, 2H), 7.92-7.72 (m, 4H), 7.46-7.33 (m, 3H), 7.15 (d, J=9.0 Hz, 1H), 6.67 (dd, J=9.0, 3.0 Hz, 1H), 4.95-4.85 (m, 1H), 4.34 (s, 2H), 3.76 (s, 3H), 3.60-3.55 (m, 2H), 2.71 (s, 6H), 2.65-2.55 (m, 2H). HPLC (max plot) 99%; Rt 3.08 min. LC/MS (ES+) 508.0, (ES−) 506.0.

Following the protocol outlined in Procedure K, Example 90 is obtained from 4-[(4-fluoro piperidin-1-yl)carbonyl]-N-(3-{[2-(2-hydroxyethyl)-5-methoxyphenyl]amino}quinoxalin-2-yl)benzenesulfonamide (270 mg; 0.47 mmol; 1 eq) in THF (7 mL) at 0° C. followed by the addition of lithium aluminum hydride (0.93 mL; 1 M; 0.93 mmol; 2 eq) for 1 h to afford, after 2 purifications by preparative HPLC and treatment of the TFA salt with HCl in Et$_2$O, 61 mg (23%) of the title compound as a yellow powder. $^1$H NMR (DMSO-$d_6$) δ 12.49 (br s, 1H), 10.81 (br s, 1H), 9.32 (s, 1H), 8.17 (d, J=8.0 Hz, 2H), 8.03-7.70 (m, 4H), 7.57-7.47 (m, 1H), 7.43-7.27 (m, 2H), 7.22-7.10 (d, J=8.3 Hz, 1H), 6.69 (dd, J=8.0, 2.6 Hz, 1H), 5.15-4.80 (m, 1H), 4.55-4.30 (m, 2H), 3.76 (s, 3H), 3.65-3.49 (m, 2H), 3.45-2.75 (m, 4H), 2.70-2.45 (m, 2H), 2.35-1.85 (m, 4H). HPLC (max plot) 99%; Rt 3.28 min. LC/MS: (ES+) 566.1, (ES−) 563.9.

Example 91

N-(3-{[2-(hydroxymethyl)-5-methoxyphenyl]amino}quinoxalin-2-yl)-1-methyl-1H-imidazole-4-sulfonamide

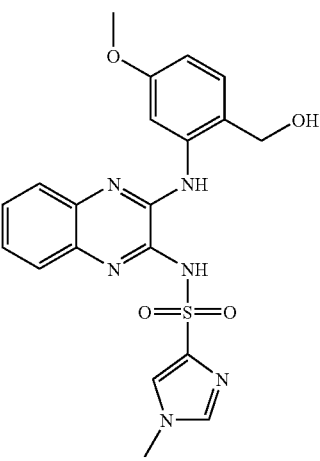 [SMILES: COc1ccc(CO)c(Nc2nc3ccccc3nc2NS(=O)(=O)c2cn(C)cn2)c1]

Following the protocol outlined in Procedure K, Example 91 is obtained from methyl 4-methoxy-2-[(3-{[(1-methyl-1H-imidazol-4-yl)sulfonyl]amino}quinoxalin-2-yl)amino]benzoate (150 mg; 0.32 mmol; 1 eq) in THF (4 mL) at 0° C. followed by the addition of lithium aluminum hydride (0.64 mL; 1 M; 0.64 mmol; 2 eq) for 1 h to afford, after recrystallization in EtOH then ACN, 36.7 mg (26%) of the title compound as a yellow powder. $^1$H NMR (DMSO-$d_6$) δ 12.70 (br s, 1H), 9.84 (s, 1H), 8.28 (s, 1H), 8.10-7.70 (m, 3H), 7.65-7.10 (m, 4H), 6.70-6.54 (m, 1H), 5.68-5.45 (m, 1H), 4.65-4.42 (m, 2H), 3.90-3.60 (m, 6H). HPLC (max plot) 94%; Rt 3.39 min. LC/MS: (ES+): 441.1, (ES−): 439.1.

Example 92

N-[3-({3-methoxy-5-[(4-methylpiperazin-1-yl)methyl]phenyl}amino)quinoxalin-2-yl]pyridine-3-sulfonamide

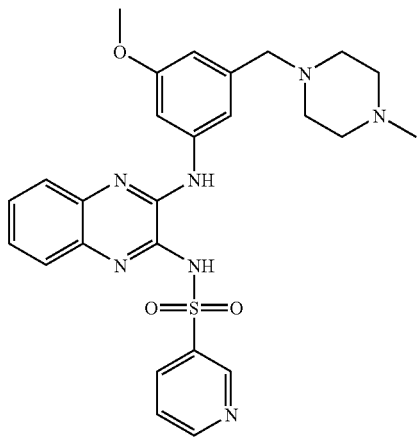 [SMILES: COc1cc(CN2CCN(C)CC2)cc(Nc2nc3ccccc3nc2NS(=O)(=O)c2cccnc2)c1]

Following the protocol outlined in Procedure K, Example 92 is obtained from N-[3-({3-methoxy-5-[(4-methylpiperazin-1-yl)carbonyl]phenyl}amino)quinoxalin-2-yl]pyridine-3-sulfonamide (180 mg; 0.34 mmol; 1 eq) in THF (200 mL) at 0° C. followed by the addition of lithium aluminum hydride (0.67 mL; 1 M; 0.67 mmol; 2 eq) for 1 h to afford 40 mg (16%) of the title compound as a yellow powder. $^1$H NMR (DMSO-$d_6$) δ 9.22 (d, J=3.0 Hz, 1H), 9.02-8.99 (m, 1H), 8.76 (dd, J=6.0, 1.5 Hz, 1H), 8.55-8.40 (m, 1H), 7.90-7.75 (m, 2H), 7.65-7.50 (m, 2H), 7.54-7.35 (m, 3H), 6.67-6.64 (m, 1H), 4.70-4.05 (m, 4H), 3.75 (s, 5H), 3.40-3.06 (m, 4H), 2.75 (s, 3H). HPLC (max plot) 95.5%; Rt 2.46 min. LC/MS: (ES+): 520.4, (ES−): 518.3.

Example 93

N-(3-{[2-(2Hydroxyethyl)-5-methoxyphenyl]amino}quinoxalin-2-yl)-4-(3-hydroxypropyl)benzenesulfonamide Potassium Salt

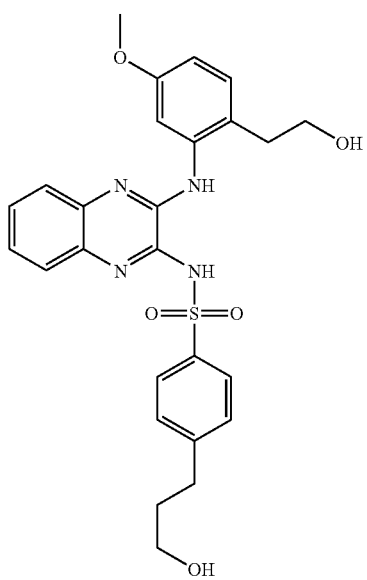 [SMILES: COc1ccc(CCO)c(Nc2nc3ccccc3nc2NS(=O)(=O)c2ccc(CCCO)cc2)c1]

Following the protocol outlined in Procedure K, Example 93 is obtained from methyl 3-(4-{[(3-{[2-(2-hydroxyethyl)-5-methoxyphenyl]amino}quinoxalin-2-yl)amino]sulfonyl}phenyl)propanoate (155 mg; 0.29 mmol; 1 eq) in THF (9 mL) at 0° C. followed by the addition of lithium aluminum hydride (578 μL; 1 M; 0.58 mmol; 2 eq) for 3 h to afford 93.5 mg (64%) of the title compound as parent. Treatment of the parent (85.7 mg; 0.17 mmol; 1 eq) with an aqueous solution of potassium hydroxide (337 µL; 0.5 M; 0.17 mmol; 1 eq) in water (3 mL) affords 88.6 mg (96%) of the title compound as a yellow powder. ¹H NMR (DMSO-d₆) δ 9.12 (s, 1H), 8.44 (s, 1H), 8.05-7.85 (m, 2H), 7.50-7.00 (m, 7H), 6.65-6.55 (m, 1H), 4.70-4.55 (m, 1H), 4.52-4.40 (m, 1H), 3.85-3.60 (m, 5H), 3.45-3.30 (m, 2H), 2.85-2.70 (m, 2H), 2.68-2.55 (m, 2H), 1.78-1.60 (m, 2H). HPLC (max plot) 99%; Rt 3.84 min. LC/MS: (ES+) 508.9, (ES−) 506.9.

Example 94

4-(2-Hydroxyethoxy)-N-(3-{[2-(2-hydroxyethyl)-5-methoxyphenyl]amino}quinoxalin-2-benzenesulfonamide Potassium Salt

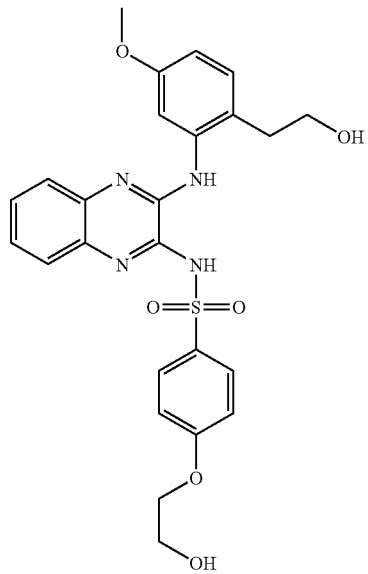 [SMILES: COc1ccc(CCO)c(Nc2nc3ccccc3nc2NS(=O)(=O)c2ccc(OCCO)cc2)c1]

Following the protocol outlined in Procedure K, Example 94 is obtained from methyl (4-{[(3-{[2-(2-hydroxyethyl)-5-methoxyphenyl]amino}quinoxalin-2-yl)amino]sulfonyl}phenoxy)acetate (111.2 mg; 0.2 mmol; 1 eq) in THF (4 mL) at 0° C. followed by the addition of lithium aluminum hydride (413 µL; 1 M; 0.4 mmol; 2 eq) for 3 h to afford 45.5 mg (43%) of the title compound as a parent. Treatment of the parent (45.5 mg; 0.09 mmol; 1 eq) with an aqueous solution of potassium hydroxide (178.2 µL; 0.5 M; 0.09 mmol; 1 eq) in water (3 mL) affords 48.8 mg (100%) of the title compound as a light yellow powder. ¹H NMR (DMSO-d₆) δ 9.11 (s, 1H), 8.45 (s, 1H), 7.97 (d, J=8.4 Hz, 2H), 7.45-7.25 (m, 2H), 7.23-7.04 (m, 3H), 6.91 (d, J=9.0 Hz, 2H), 6.53 (dd, J=8.4, 2.1 Hz, 1H), 4.85 (t, J=5.7 Hz, 1H), 4.70-4.58 (m, 1H), 4.05-3.92 (m, 2H), 3.85-3.60 (m, 7H), 2.85-2.68 (m, 2H). HPLC (max plot) 99%; Rt 3.64 min. UPLC/MS (ES+): 511.3, (ES−): 509.4.

Example 95

N-[3-({3-[(Dimethylamino)methyl]-5-methoxyphenyl}amino)quinoxalin-2-yl]-1-methyl-1H-imidazole-4-sulfonamide

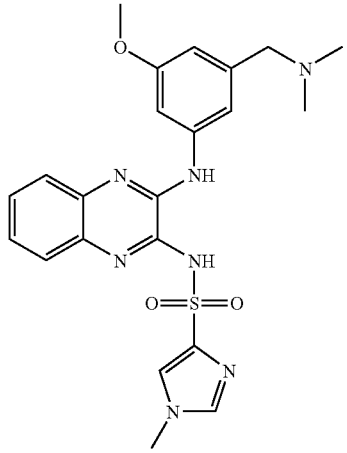 [SMILES: COc1cc(CN(C)C)cc(Nc2nc3ccccc3nc2NS(=O)(=O)c2cn(C)cn2)c1]

Following the protocol outlined in Procedure K, Example 95 is obtained from 3-methoxy-N,N-dimethyl-5-[(3-{[(1-methyl-1H-imidazol-4-yl)sulfonyl]amino}quinoxalin-2-yl)amino]benzamide (350 mg; 0.73 mmol; 1 eq) in THF (50 mL) at 0° C. followed by the addition of lithium aluminum hydride (1.45 mL; 1 M; 1.45 mmol; 2 eq.) for 4 h to afford 350 mg (96%) of the title compound as a yellow solid. ¹H NMR (DMSO-d₆) δ 10.50 (s, 1H), 9.07 (s, 1H), 7.97-7.36 (m, 8H), 6.91 (s, 1H), 4.21 (s, 2H), 3.82 (s, 3H), 3.71 (s, 3H), 2.72 (s, 6H). HPLC (max plot) 96.7%; Rt 2.70 min. UPLC/MS: (ES−): 468.2, (ES−): 466.3.

Example 96

N-{3-[(2-{[1-(N,N-dimethylglycyl)piperidin-4-yl]methyl}-5-methoxyphenyl)amino]quinoxalin-2-yl}-1-methyl-1H-imidazole-4-sulfonamide HCl Salt

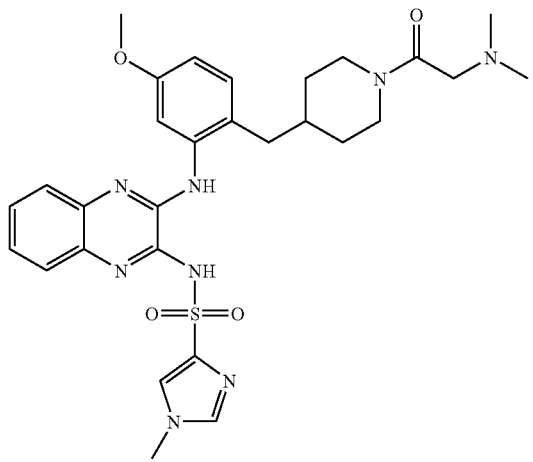 [SMILES: COc1ccc(CC2CCN(C(=O)CN(C)C)CC2)c(Nc2nc3ccccc3nc2NS(=O)(=O)c2cn(C)cn2)c1]

To a suspension of N-(3-{[5-methoxy-2-(piperidin-4-ylmethyl)phenyl]amino}quinoxalin-2-yl)-1-methyl-1H-imidazole-4-sulfonamide (175 mg; 0.34 mmol; 1 eq), 4-dimethylamino pyridine (50.5 mg; 0.41 mmol; 1.2 eq), N,N-dimethylglycine (42.7 mg; 0.41 mmol; 1.2 eq) in DCM (2.5 mL) and DMF (2.5 mL) is added N-(3-dimethylaminopropyl)-N'-ethylcarbodiimide HCl (72.7 mg; 0.38 mmol; 1.1 eq). The reaction mixture is stirred at room temperature overnight to give a dark brown solution. It is concentrated to dryness and the residue is taken up in DCM and the product is extracted with 5N HCl (25 mL). The acidic phase is washed 3 times with DCM then basified (pH 14) with 5N NaOH. The product is extracted twice with DCM. The organic phase is dried over MgSO$_4$ and the solvent is removed under reduced pressure. The residue obtained is purified by preparative HPLC, affording 105.8 mg (44%) of the title compound as a TFA salt. Treatment of the TFA salt with HCl in diethylether (165 µM, 0.15 mmol, 1.1 Eq) in EtOH (3 mL) affords 98 mg (100%) of the title compound as a yellow powder. $^1$H NMR (DMSO-d$_6$) δ 12.76 (br s, 1H), 9.49 (br s, 1H), 8.85 (br s, 1H), 8.31 (br s, 1H), 7.98 (d, J=1.1 Hz, 1H), 7.92 (d, J=1.1 Hz, 1H), 7.87-7.84 (m, 1H), 7.63-7.60 (m, 1H), 7.45-7.40 (m, 2H), 7.12 (d, J=8.3 Hz, 1H), 6.66 (dd, J=8.3, 2.6 Hz, 1H), 4.31-4.23 (m, 3H), 3.80 (s, 3H), 3.73 (s, 3H), 3.58-3.53 (m, 1H), 2.97-2.89 (m, 1H), 2.79 (t, J=5.3 Hz, 6H), 2.54 (br s, 4H), 1.79-1.66 (m, 3H), 1.26-1.16 (m, 1H). HPLC (max plot) 100%; Rt 3.27 min. LC/MS: (ES+): 593.1, (ES−): 591.1.

Example 97

N-{3-[(5-methoxy-2-{[1-(methylsulfonyl)piperidin-4-yl]methyl}phenyl)amino]quinoxalin-2-yl}-1-methyl-1H-imidazole-4-sulfonamide Potassium Salt

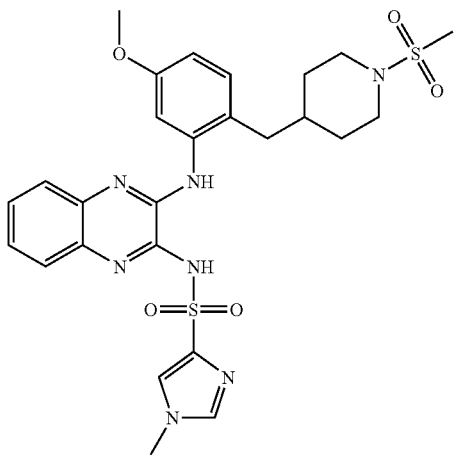 [SMILES: COc1ccc(CC2CCN(S(C)(=O)=O)CC2)c(Nc2nc3ccccc3nc2NS(=O)(=O)c2cn(C)cn2)c1]

N-(3-{[5-methoxy-2-(piperidin-4-ylmethyl)phenyl]amino}quinoxalin-2-yl)-1-methyl-1H-imidazole-4-sulfonamide (120 mg; 0.24 mmol; 1 eq) is suspended in DCM (3 mL) and the suspension is cooled to −15° C. N,N-diisopropylethylamine (141.02 µL; 0.85 mmol; 3.6 eq) is added followed by the dropwise addition of a solution of methanesulfonyl chloride (64.04 µL; 0.83 mmol; 3.5 eq) in DCM (1 mL). The conversion is not complete. N,N-diisopropylethyl amine (137.1 µL; 0.83 mmol; 3.5 eq) and methanesulfonyl chloride (64.04 µL; 0.83 mmol; 3.5 eq) are added again at 0° C. and the reaction mixture is stirred overnight at room temperature. The reaction is quenched by addition of water and the organic phase is washed twice with water then dried over MgSO$_4$. The solvent is removed under reduced pressure and the residue obtained is purified by flash chromatography (Eluent Cyclohexane/EtOAc [1/1]) to afford 114.2 mg (82.5%) of the title compound as a parent. Treatment of the parent (114 mg; 0.19 mmol; 1 eq) with an aqueous solution of potassium hydroxide (389.3 µL; 0.5 M; 0.19 mmol; 1 eq) in water (10 mL) affords 120 mg (99%) of the title compound as a yellow powder. $^1$H NMR (DMSO-d$_6$) δ 9.17 (br s, 1H), 8.62 (br s, 1H), 7.72 (br s, 1H), 7.57 (br s, 1H), 7.48-7.46 (m, 2H), 7.21 (br s, 2H), 7.06 (d, J=8.3 Hz, 1H), 6.53 (d, J=7.2 Hz, 1H), 3.79 (s, 3H), 3.65 (s, 3H), 2.80 (s, 3H), 2.68-2.60 (m, 2H), 2.57-2.55 (m, 2H), 1.80-1.76 (m, 3H), 1.23-1.19 (m, 3H). HPLC (max plot) 99%; Rt 4.08 min. LC/MS: (ES+): 586.1, (ES−): 584.0.

Comparative Example 98

4-methoxy-2-({3-[(pyridin-3-ylsulfonyl)amino]quinoxalin-2-yl}amino)benzoic acid

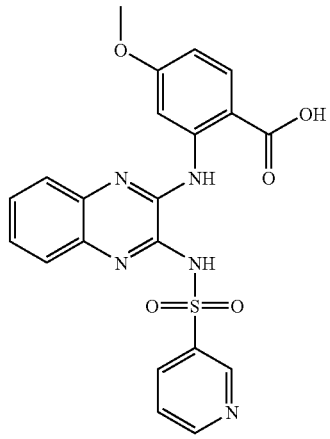 [SMILES: COc1ccc(C(=O)O)c(Nc2nc3ccccc3nc2NS(=O)(=O)c2cccnc2)c1]

Methyl-4-methoxy-2-({3-[(pyridin-3-ylsulfonyl)amino]quinoxalin-2-yl}amino)benzoate (2200 mg; 4.73 mmol; 1 eq) and K$_2$CO$_3$ (8.5 g; 61.44 mmol; 13 eq) are taken up in MeOH (100 mL) and water (25 mL) and heated up to 60° C. overnight. The reaction mixture is concentrated to half the volume and some black residue is removed by filtration. The clear solution is neutralised with aqueous citric acid 10%. After 1 h at 4° C., the precipitate formed is filtered off and washed with water. After drying under vacuum at 40° C. overnight, it affords 2.01 g (94%) of the title compound as a yellow powder. $^1$H NMR (DMSO-d$_6$) δ 13.17 (s, 1H), 12.49 (br s, 1H), 12.27 (s, 1H), 9.25 (d, J=1.9 Hz, 1H), 9.08 (d, J=2.6 Hz, 1H), 8.81-8.79 (m, 1H), 8.47-8.43 (m, 1H), 7.98 (d, J=9.0 Hz, 1H), 7.93 (br s, 1H), 7.68-7.60 (m, 2H), 7.44-7.40 (m, 2H), 6.70 (dd, J=8.7, 2.6 Hz, 1H), 3.91 (s, 3H). HPLC (max plot) 99%; Rt 4.04 min. LC/MS: (ES+): 452.3, (ES−): 450.3.

Example 99

N-(3-{[2-(3-Hydroxypropyl)-5-methoxyphenyl]amino}quinoxalin-2-yl)piperidine-4-sulfonamide HCl Salt

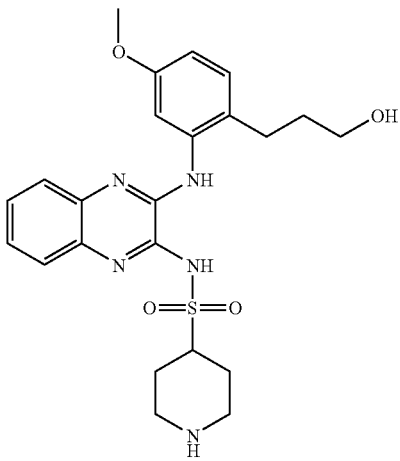 [SMILES: COc1ccc(CCCO)c(Nc2nc3ccccc3nc2NS(=O)(=O)C2CCNCC2)c1]

To as solution of 3-[4-methoxy-2-({3-[(piperidine-4-ylsulfonyl)amino]quinoxalin-2-yl}amino)phenyl]propyl trifluoroacetate (100 mg; 0.2 mmol; 1 eq) in THF (3 mL) is added dropwise an aqueous solution of KOH (1.8 mL; 0.5 M; 0.9 mmol; 5 eq) and the reaction mixture is stirred at room temperature. EtOAc is added then water and the aqueous phase is acidified with 0.1 N HCl until pH 6.5. The product is extracted with EtOAc and the organic phase is dried over MgSO$_4$. The solvent is removed under reduced pressure to afford a yellow residue. It is taken up in Et$_2$O and 1 N HCl (3 mL) in Et$_2$O is added. The yellow precipitate is filtered off and dried in vacuo to give 11 mg (12%) of the title compound as a yellow solid. $^1$H NMR (DMSO-d$_6$) δ 12.39 (s, 1H), 8.77 (br s, 2H), 8.48-8.31 (m, 1H), 8.02 (br s, 1H), 7.90-7.84 (m, 1H), 7.55-7.49 (m, 1H), 7.38-7.30 (m, 2H), 7.19 (d, J=8.5 Hz, 1H), 6.72 (dd, J=8.4, 2.5 Hz, 1H), 4.65-4.55 (m, 1H), 3.78 (s, 3H), 3.66-3.50 (m, 1H), 3.47-3.40 (m, 4H) 3.04-2.85 (m, 2H), 2.64 (t, J=7.6 Hz, 2H), 2.39-2.24 (m, 2H), 2.02-1.85 (m, 2H), 1.77-1.67 (m, 2H). HPLC (max plot) 98%; Rt 2.98 min. LC/MS: (ES+) 471.9, (ES−) 470.0.

Example 100

N-(3-{[5-Methoxy-2-(2-methoxyethyl)phenyl]amino}quinoxalin-2-yl)piperidine-4-sulfonamide HCl Salt

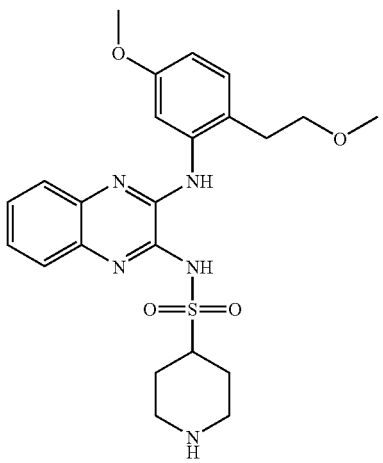 [SMILES: COCCc1ccc(OC)cc1Nc1nc2ccccc2nc1NS(=O)(=O)C1CCNCC1]

A solution of benzyl 4-{[(3-{[5-methoxy-2-(2-methoxyethyl)phenyl]amino}quinoxalin-2-yl)amino]sulfonyl}piperidine-1-carboxylate (478 mg; 0.8 mmol; 1 eq) TEA (5 mL) and DCE (5 mL) is stirred at room temperature for 4 h then at 60° C. for another 20 h. The dark yellow solution is evaporated to dryness and the residue is triturated in Et$_2$O. The precipitate is filtered off, washed with Et$_2$O then n-pentane to give a yellow solid. It is refluxed ACN (25 mL) then cooled down to room temperature. The precipitate formed is filtered off then suspended in 0.5 N HCl, stirred for 10 min and freeze dried. The residue is recrystallized from AGN to afford 76 mg (19%) of the title compound as a pale yellow powder. $^1$H NMR (DMSO-d$_6$) δ 12.31 (s, 1H), 9.16 (s, 1H), 9.07 (br s, 1H), 8.63 (br s, 1H), 7.91-7.80 (m, 2H), 7.51-7.44 (m, 1H), 7.39-7.28 (m, 2H), 7.22 (d, J=8.4 Hz, 1H), 6.73 (dd, J=2.6, 8.4 Hz, 1H), 3.78 (s, 3H), 3.60-3.47 (m, 3H), 3.47-3.37 (m, 2H), 3.26 (s, 3H), 2.94 (br q, 11.8 Hz, 2H), 2.81 (t, J=6.0 Hz, 2H), 2.34 (d, J=12.8 Hz, 2H), 1.96 (q, J=11.7 Hz, 2H). HPLC (max plot) 99%; Rt 3.23 min UPLC/MS (ES+) 472.3, (ES−) 470.3.

Example 101

1-Acetyl-N-(3-{[5-methoxy-2-(2-methoxyethyl)phenyl]amino}quinoxalin-2-yl)piperidine-4-sulfonamide

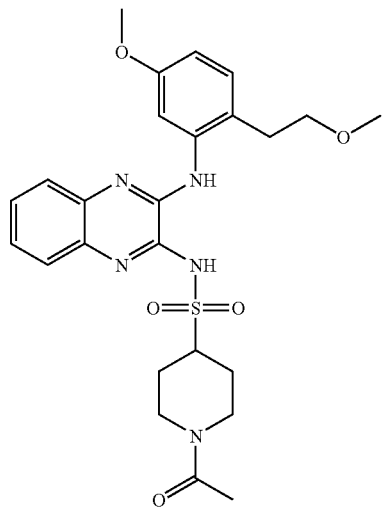 [SMILES: COCCc1ccc(OC)cc1Nc1nc2ccccc2nc1NS(=O)(=O)C1CCN(C(C)=O)CC1]

Acetic anhydride (21 mg; 0.2 mmol; 1.2 eq) is added to a suspension of N-(3-{[5-methoxy-2-(2-methoxyethyl)phenyl]amino}quinoxalin-2-yl)piperidine-4-sulfonamide (100 mg; 0.17 mmol; 1 eq) in DCM (10 mL), followed by Et$_3$N (0.06 mL; 0.43 mmol; 2.5 eq) and the reaction mixture is stirred at room temperature for 2 h. The solution is diluted to 30 mL with DCM, washed successively with 0.1 M HCl and brine, dried over MgSO$_4$ and concentrated in vacuo to give a yellow solid. The residue is recrystallised from a mixture of DCM/n-pentane to afford 59 mg (67%) of the title compound as a pale yellow solid. $^1$H NMR (DMSO-d$_6$) δ 12.25 (s, 1H), 9.15 (s, 1H), 7.95-7.81 (m, 2H), 7.50-7.44 (m, 1H), 7.37-7.26 (m, 2H), 7.22 (d, J=8.4 Hz, 1H), 6.71 (dd, J=8.4, 2.6 Hz, 1H), 4.53 (br d, J=12.8 Hz, 1H), 3.97 (br d, J=13.3 Hz, 1H), 3.78 (s, 3H), 3.60-3.36 (m, 3H), 3.25 (s, 3H), 3.10 (br t, J=12.0 Hz, 1H), 2.78 (t, J=6.0 Hz, 2H), 2.58 (br t, J=12.7 Hz, 1H), 2.19 (br d, J=12.7 Hz, 2H), 2.02 (s, 3H), 1.80-1.50 (m, 2H). HPLC (max plot) 99%; Rt 3.85 min. UPLC/MS (ES+) 512.2, (ES−) 512.3.

Example 102

2-Hydroxy-N-(3-{[(3-{[2-(3-hydroxypropyl)-5-methoxyphenyl]amino}quinoxalin-2-yl)amino]sulfonyl}phenyl)acetamide

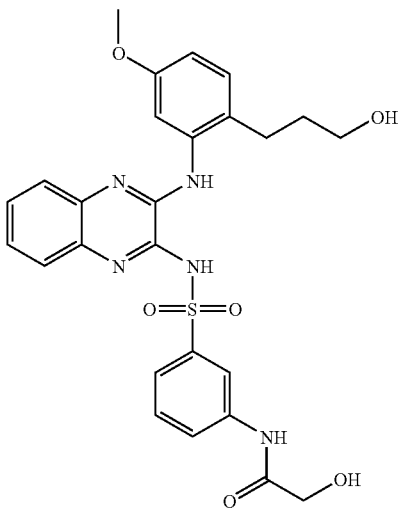 [SMILES: COc1ccc(CCCO)c(Nc2nc3ccccc3nc2NS(=O)(=O)c2cccc(NC(=O)CO)c2)c1]

To a mixture of 2-(benzyloxy)-N-(3-{[(3-{[2-(3-hydroxypropyl)-5-methoxyphenyl]amino}quinoxalin-2-yl)amino]sulfonyl}phenyl)acetamide (69 mg; 0.1 mmol; 1 eq) in EtOH (12 mL) are added ammonium formate (69.3 mg; 1.1 mmol; 10 eq) and palladium on charcoal (10 mg, 10%). The reaction mixture is stirred at reflux for 2 h. The catalyst is filtered through celite, washed with EtOH and the filtrate is concentrated under reduced pressure to give a yellow residue. It is suspended in EtOH (2 mL), sonicated, filtered off and washed with EtOH (400 µL). The solid is dried in vacuo to give 41 mg (70%) of the title compound as a yellow solid $^1$H NMR (DMSO-$d_6$) δ 12.53 (br s, 1H), 10.00 (s, 1H), 8.73 (s, 1H), 8.45 (s, 1H), 8.19 (br s, 1H), 7.99-7.91 (m, 2H), 7.75 (d, J=7.4 Hz, 1H), 7.57-7.48 (m, 2H), 7.42-7.32 (m, 2H), 7.09 (d, J=8.3 Hz, 1H), 6.68-6.61 (m, 1H), 5.75-5.62 (m, 1H), 4.45-4.30 (m, 1H), 4.00 (s, 2H), 3.70 (s, 3H), 3.28-3.15 (m, 4H), 1.58-1.45 (m, 2H). HPLC (max plot) 99%; Rt 3.71 min. UPLC/MS (ES−) 538.2, (ES−) 536.3.

Example 103

2-{4-Methoxy-2-[(3-{[(1-methyl-1H-imidazol-4-yl)sulfonyl]amino}quinoxalin-2-yl)amino]phenyl}ethyl N-[(9H-fluoren-9-ylmethoxy)carbonyl]-L-valinate

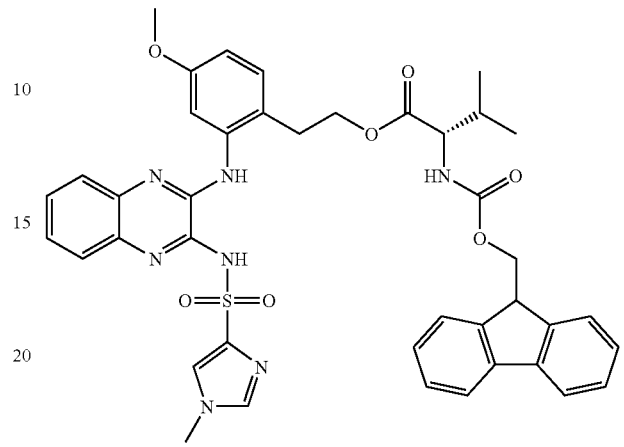

To a suspension of N-(3-{[2-(2-hydroxyethyl)-5-methoxyphenyl]amino}quinoxalin-2-yl)-1-methyl-1H-imidazole-4-sulfonamide (200 mg; 0.44 mmol; 1 eq), 1-(3-dimethylaminopropyl)-3-ethylcarbodiimide hydrochloride (92.8 mg; 0.48 mmol; 1.1 eq) and N,N-dimethylpyridin-4-amine (59 mg; 0.48 mmol; 1.1 eq) in a mixture of DCM (10 mL) and DMF (1 mL) is added fmoc-l-valine (164 mg; 0.48 mmol; 1.1 eq). The reaction mixture is stirred for 18 h at room temperature. Water is added and organic phase is washed several times with 10% citric acid then dried under MgSO$_4$. The solvent is removed under reduced pressure and residue purified by flash chromatography using EtOAc as eluent to afford 200 mg (59%) of the title compound as a yellow gum. HPLC (max plot) 98%; Rt 5.46 min. LC/MS: (ES+): 775.7, (ES−): 773.9.

Example 104

2-{4-Methoxy-2-[(3-{[1-methyl-1H-imidazol-4-yl)sulfonyl]amino}quinoxalin-2-yl)amino]phenyl}ethyl-L-valinate

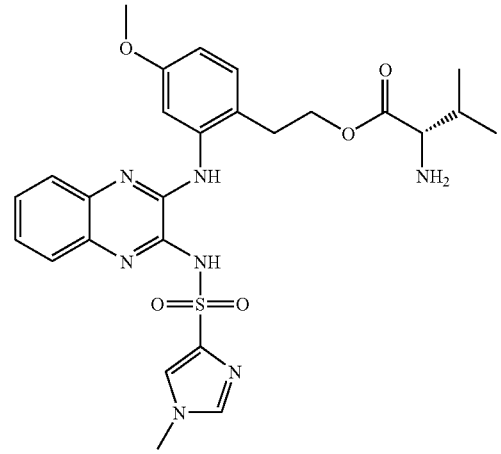 [SMILES: COc1ccc(CCOC(=O)[C@@H](N)C(C)C)c(Nc2nc3ccccc3nc2NS(=O)(=O)c2cn(C)cn2)c1]

To a suspension of 2-{4-methoxy-2-[(3-{[(1-methyl-1H-imidazol-4yl)sulfonyl]amino}quinoxalin-2-yl)amino]phenyl}ethyl N-[(9H-fluoren-9-ylmethoxy)carbonyl]-L- valinate (300 mg; 0.4 mmol; 1 eq) in DCM (2 mL) is added diethylamine (2 mL; 27.4 mmol; 71 eq) and the mixture is stirred at room temperature for 18 h. The solvents are removed under reduced pressure and the residue is purified by flash chromatography using EtOAc/EtOH/NH$_4$OH (70/30/1) as eluent to afford 185 mg (86%) of the title compound as a yellow gum. $^1$H NMR (DMSO-d$_6$) δ 8.33 (d, J=3.0 Hz, 1H), 7.81 (s, 1H), 7.71 (m, 1H), 7.57 (s, 1H), 7.50-7.46 (m, 1H), 7.41-7.37 (m, 1H), 7.21-7.15 (m, 3H), 6.58 (dd, J=9.0, 3.0 Hz, 1H), 4.70-4.40 (m, 1H), 4.25-4.18 (m, 2H), 3.83 (s, 3H), 3.65 (s, 3H), 3.15-3.02 (m, 2H), 0.85-0.60 (m, 7H). HPLC (max plot) 94%; Rt 3.23 min. LC/MS: (ES+): 554.0, (ES−): 552.0.

The following additional examples could be obtained according to the experimental described in the above examples.

N-(3-{[5-methoxy-2-(2-methoxyethenyl)phenyl]amino}quinoxalin-2-yl)-1-methylsulfonyl)piperidine-4-sulfonamide

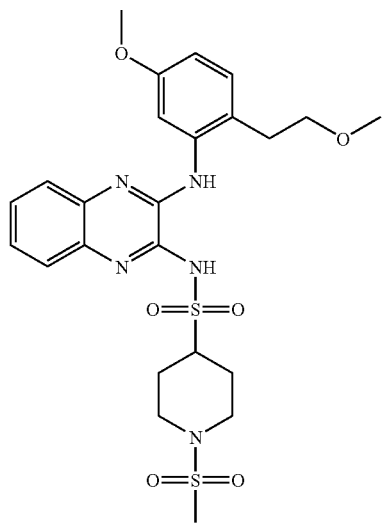 [SMILES: COCCc1ccc(OC)cc1Nc1nc2ccccc2nc1NS(=O)(=O)C1CCN(S(C)(=O)=O)CC1]

N-(3-{[3-(3-hydroxypropyl)-5-methoxyphenyl]amino}quinoxalin-2-yl)-1-methyl-1H-imidazole-4-sulfonamide

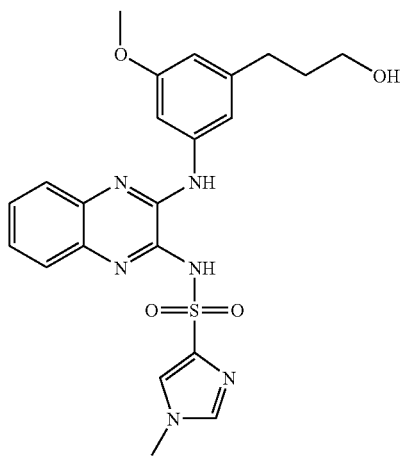 [SMILES: COc1cc(CCCO)cc(Nc2nc3ccccc3nc2NS(=O)(=O)c2cn(C)cn2)c1]

2-[(dimethylamino)methyl]-N-(3-{[5-methoxy-2-(2-methoxyethyl)phenyl]amino}quinoxalin-2-yl)-1-methyl-1H-imidazole-4-sulfonamide

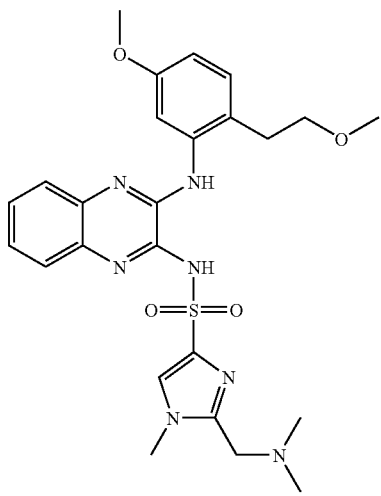 [SMILES: COCCc1ccc(OC)cc1Nc1nc2ccccc2nc1NS(=O)(=O)c1cn(C)c(CN(C)C)n1]

1-glycoloyl-N-(3-{[5-methoxy-2-(2-methoxyethyl)phenyl]amino}quinoxalin-2-yl)piperidine-4-sulfonamide

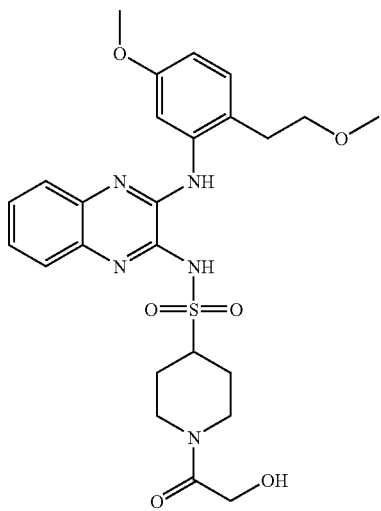 [SMILES: COCCc1ccc(OC)cc1Nc1nc2ccccc2nc1NS(=O)(=O)C1CCN(C(=O)CO)CC1]

191

1-(N,N-dimethylglycyl)-N-(3-{[5-methoxy-2-(2-methoxyethyl)phenyl]amino}quinoxalin-2-yl)piperidine-4-sulfonamide

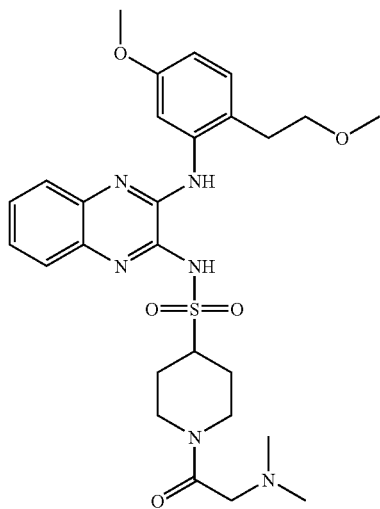 [SMILES: COCCc1ccc(OC)cc1Nc1nc2ccccc2nc1NS(=O)(=O)C1CCN(C(=O)CN(C)C)CC1]

192

N-(3-{[2-(3-hydroxypropyl)-5-methoxyphenyl]amino}quinoxalin-2-yl)-1-(methoxyacetyl)piperidine-4-sulfonamide

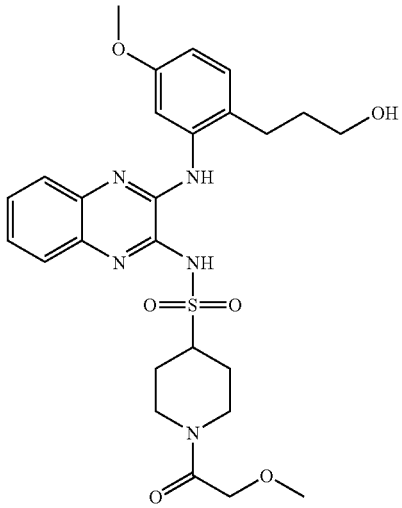

1-(N,N-dimethylglycyl)-N-(3-{[2-hydroxypropyl)-5-methoxyphenyl]amino}quinoxalin-2-yl)piperidine-4-sulfonamide

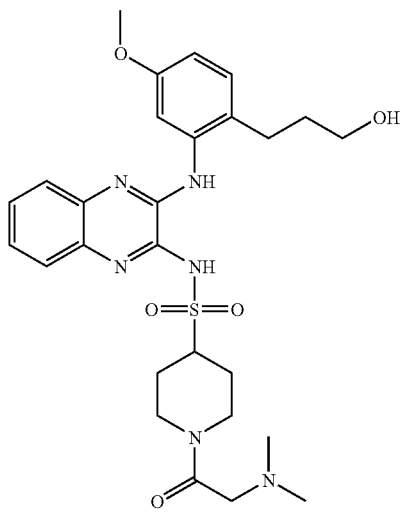 [SMILES: COc1ccc(CCCO)c(Nc2nc3ccccc3nc2NS(=O)(=O)C2CCN(C(=O)CN(C)C)CC2)c1]

1-(methoxyacetyl)-N-(3-{[5-methoxy-2-(2-methoxyethyl)phenyl]amino}quinoxalin-2-yl)piperidine-4-sulfonamide

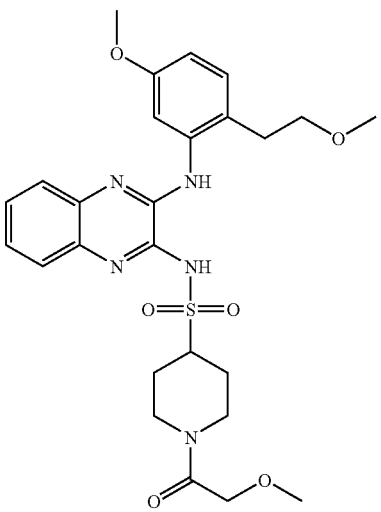 [SMILES: COCCc1ccc(OC)cc1Nc1nc2ccccc2nc1NS(=O)(=O)C1CCN(C(=O)COC)CC1]

193
4-{[(3-{[5-methoxy-2-(2-methoxyethyl)phenyl]amino}quinoxalin-2-yl)amino]sulfonyl}-N-methylpiperidine-1-carboxamide

194
N-{3-[(3-methoxy-5-{[(methylsulfonyl)amino]methyl}phenyl)amino]quinoxalin-2-yl}-1-methyl-1H-imidazole-4-sulfonamide

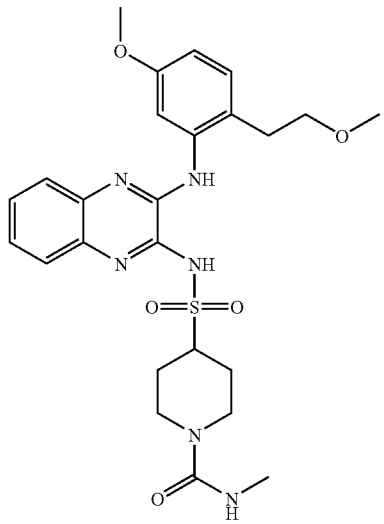 [SMILES: CNC(=O)N1CCC(S(=O)(=O)Nc2nc3ccccc3nc2Nc2cc(OC)ccc2CCOC)CC1]

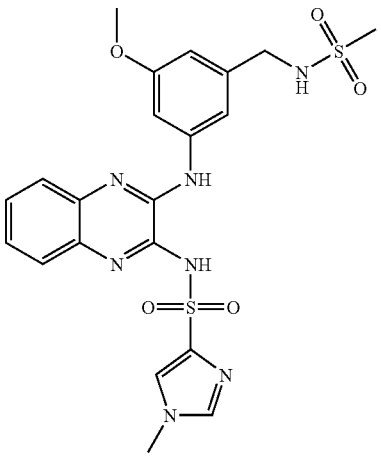

N-{3-methoxy-5[(3-{[(1-methyl-1H-imidazol-4-yl)sulfonyl]amino}quinoxalin-2-yl)amino]benzyl}acetamide N-(3-{[3-methoxy-5-(methoxymethyl)phenyl]amino}quinoxalin-2-yl)-1-methyl-1H-imidazole-4-sulfonamide

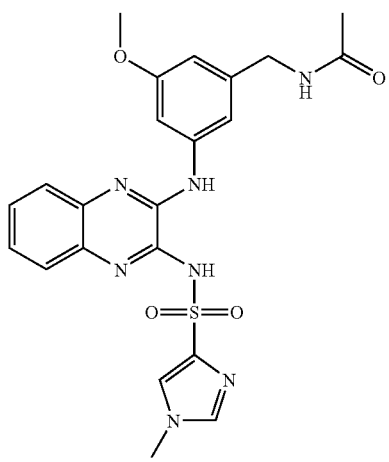 [SMILES: COc1cc(CNC(C)=O)cc(Nc2nc3ccccc3nc2NS(=O)(=O)c2cn(C)cn2)c1]

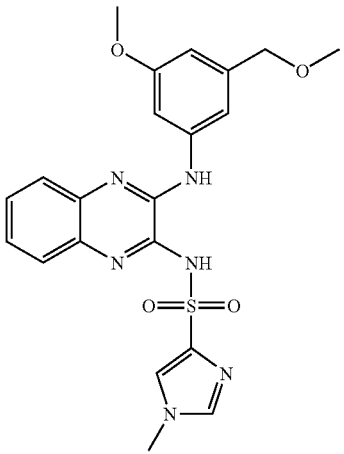 [SMILES: COCc1cc(Nc2nc3ccccc3nc2NS(=O)(=O)c2cn(C)cn2)cc(OC)c1]

| 195 | 196 |
|---|---|
| N-(3-{[3-(hydroxymethyl)-5-methoxyphenyl]amino}quinoxalin-2-yl)-1-methyl-1H-imidazole-4-sulfonamide | N-(3-{[3-(2-hydroxyethyl)-5-methoxyphenyl]amino}quinoxalin-2-yl-1-methyl-1H-imidazole-4-sulfonamide |

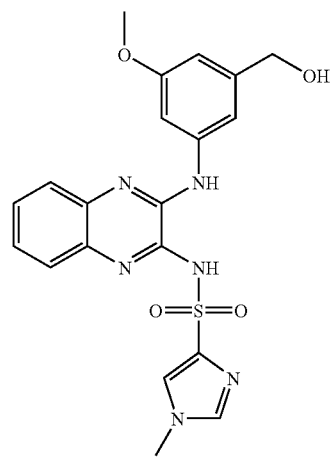 [SMILES: COc1cc(CO)cc(Nc2nc3ccccc3nc2NS(=O)(=O)c2cn(C)cn2)c1]

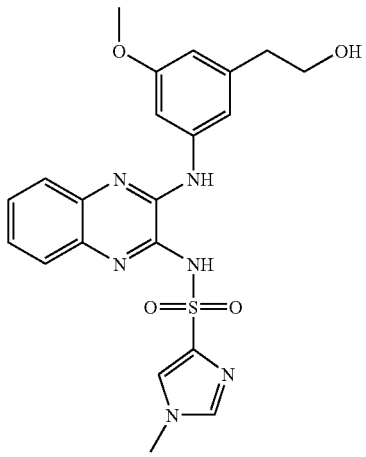

N-(3-{[3-methoxy-5-(2-methoxyethyl)phenyl]amino}quinoxalin-2-yl)-1-methyl-1H-imidazole-4-sulfonamide 2-[(dimethylamino)methyl]-N-(3-{[3-(2-hydroxyethyl)-5-methoxyphenyl]amino}quinoxalin-2-yl)-1-methyl-1H-imidazole-4-sulfonamide

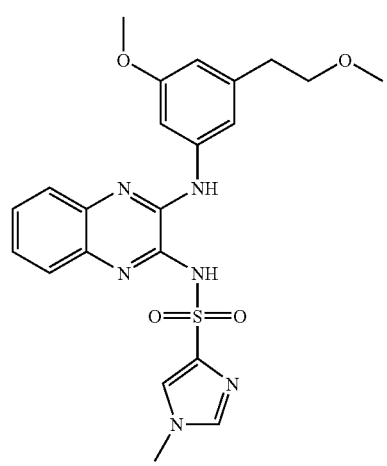 [SMILES: COCCc1cc(Nc2nc3ccccc3nc2NS(=O)(=O)c2cn(C)cn2)cc(OC)c1]

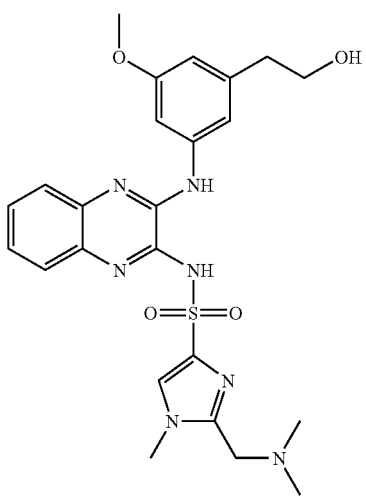 [SMILES: COc1cc(CCO)cc(Nc2nc3ccccc3nc2NS(=O)(=O)c2cn(C)c(CN(C)C)n2)c1]

N-(2-hydroxyethyl)-3-methoxy-N-methyl-5-[(3-{[(1-methyl-1H-imidazol-4-yl)sulfonyl]amino}quinoxalin-2-yl)amino]benzamide

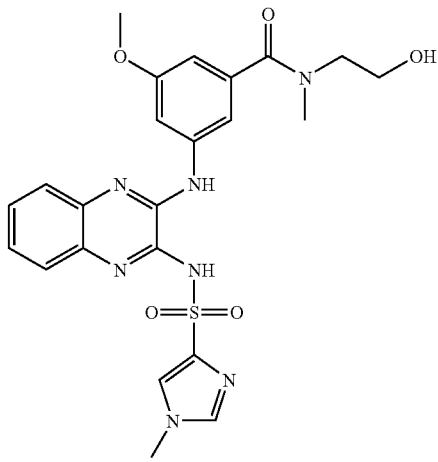 [SMILES: COc1cc(Nc2nc3ccccc3nc2NS(=O)(=O)c2cn(C)cn2)cc(C(=O)N(C)CCO)c1]

N-{3-[(3-methoxy-5-{[(2-methoxyethyl)amino]methyl}phenyl)amino]quinoxalin-2-yl}-1-methyl-1H-imidazole-4-sulfonamide

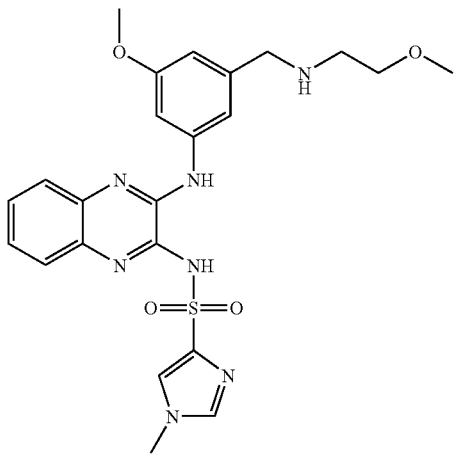 [SMILES: COCCNCc1cc(Nc2nc3ccccc3nc2NS(=O)(=O)c2cn(C)cn2)cc(OC)c1]

Example A

Biological Assays

The efficacy of compounds of the invention in inhibiting the PI3K induced-lipid phosphorylation may be tested in the following binding assay. The assay combines the scintillation proximity assay technology (SPA, Amersham) with the capacity of neomycin (a polycationic antibiotic) to bind phospholipids with high affinity and specificity. The Scintillation Proximity Assay is based on the properties of weakly emitting isotopes (such as $^3$H, $^{125}$I, $^{33}$P). Coating SPA beads with neomycin allows the detection of phosphorylated lipid substrates after incubation with recombinant PI3K and radioactive ATP in the same well, by capturing the radioactive phospholipids to the SPA beads through their specific binding to neomycin.

To a 96 wells MTP containing 10 μL of the test compound of Formula (I) (solubilized in 10% DMSO; to yield a concentration of 100, 25, 5.0, 1.25, 0.312, 0.078, 0.0195, 0.00488, 0.00122 and 0.0003 μM of the test compound), the following assay components are added: 1) 10 μL of lipid micelles 2) 20 μL of Kinase buffer ([$^{33}$P]γATP162 μM/300 nCi, MgCl$_2$ 2.5 mM, DTT 2.5 mM, Na$_3$VO$_4$ 25 uM in Hepes 40 mM, pH 7.4) and 3) 10 μL (100 ng) of Human recombinant GST-PI3K (in Hepes 40 mM, pH 7.4, ethylenglycol 4%). After incubation at room temperature for 120 minutes, with gentle agitation, the reaction is stopped by addition of 200 μL of a solution containing 250 μg of neomycin-coated PVT SPA beads, ATP 60 mM and EDTA 6.2 mM in PBS. The assay is further incubated at room temperature for 60 minutes with gentle agitation to allow binding of phospholipids to neomycin-SPA beads. After precipitation of the neomycin-coated PVT SPA beads for 5 minutes at 1500×g, radioactive PtdIns(3)P is quantified by scintillation counting in a Wallac MicroBeta™ plate counter.

The values indicated in Table I below refer to the IC$_{50}$ (μM) with respect to PI3K, i.e. the amount necessary to achieve 50% inhibition of said target. Said values show a considerable inhibitory potency of quinoxaline compounds with regard to PI3K.

Examples of inhibitory activities for compounds according to the invention are set out in Table I below.

TABLE I

IC$_{50}$ values of quinoxaline compounds according to the invention against PI3K

| Example No | PI3K IC$_{50}$ (μM) |
|---|---|
| 1 | 0.021 |
| 2 | 0.088 |
| 3 | 1.650 |
| 4 | 3.340 |
| 5 | 3.100 |
| 6 | 5.620 |
| 7 | 0.049 |
| 8 | 0.130 |
| 9 | 0.027 |
| 10 | 0.150 |
| 11 | 0.043 |
| 12 | 0.045 |
| 13 | 0.110 |
| 14 | 0.420 |
| 15 | 0.110 |
| 16 | 0.089 |
| 17 | 0.051 |
| 18 | 0.170 |
| 19 | 0.490 |
| 20 | 0.450 |
| 21 | 68% at 20 μM |
| 22 | 0.018 |
| 23 | 0.020 |
| 24 | 0.180 |
| 25 | 0.100 |
| 26 | 0.030 |
| 27 | 0.040 |
| 28 | 0.021 |
| 29 | 0.550 |
| 30 | 0.200 |
| 31 | 0.011 |
| 32 | 0.250 |
| 33 | 0.106 |
| 34 | 0.022 |
| 35 | 0.048 |
| 36 | 0.023 |
| 37 | 0.095 |

TABLE I-continued

IC$_{50}$ values of quinoxaline compounds according to the invention against PI3K

| Example No | PI3K IC$_{50}$ (µM) |
|---|---|
| 38 | 0.06 |
| 39 | 0.044 |
| 40 | 0.084 |
| 41 | 0.07 |
| 42 | 0.13 |
| 43 | 0.286 |
| 44 | 0.2 |
| 45 | 0.057 |
| 46 | 0.064 |
| 47 | 0.028 |
| 48 | 0.059 |
| 49 | 0.049 |
| 50 | 0.072 |
| 51 | 0.088 |
| 52 | 0.16 |
| 53 | 0.087 |
| 54 | 0.19 |
| 55 | 0.042 |
| 56 | 0.086 |
| 57 | 0.14 |
| 58 | 0.075 |
| 59 | 0.35 |
| 60 | 0.12 |
| 61 | 0.12 |
| 62 | 0.083 |
| 63 | 0.13 |
| 64 | 0.3 |
| 65 | 0.087 |
| 66 | 0.72 |
| 67 | 0.1 |
| 68 | 0.05 |
| 69 | 0.065 |
| 70 | 0.027 |
| 71 | 0.032 |
| 72 | 0.48 |
| 73 | 0.35 |
| 74 | 0.084 |
| 75 | 0.76 |
| 76 | 0.087 |
| 77 | 0.12 |
| 78 | 0.03 |
| 79 | 0.2 |
| 80 | 0.4 |
| 81 | 0.049 |
| 82 | 0.110 |
| 83 | 0.072 |
| 84 | 0.026 |
| 85 | 0.010 |
| 86 | 0.030 |
| 87 | 0.760 |
| 88 | 0.035 |
| 89 | 0.026 |
| 90 | 0.043 |
| 91 | 0.470 |
| 92 | 0.970 |
| 93 | 0.036 |
| 94 | 0.034 |
| 95 | 1.1 |
| 96 | 0.100 |
| 97 | 0.160 |
| 98 | 4.680 |
| 99 | 0.026 |
| 100 | 0.098 |
| 101 | 0.3 |
| 102 | 0.012 |
| 103 | 1.84 |
| 104 | 0.1 |

Example B

IgM-Induced Akt Phosphorylation in B Cell

Protocol:

In Vitro Stimulation:

Human PBMC were prepared from a Buffy coat (Geneve Hospital) after a Ficoll gradient (Ficoll-Paque™ Plus PHARMACIA ref: 17-1440-03).

Cell concentration was adjusted to $10^6$ cells per mL in RPMI (GIBCO Ref: 72400-21) without serum. Before stimulation, 90 µl of PBMC suspension was incubated with 10 µl of diluted compound in a 96 well round bottom plate for 20 minutes at 37° C.

For B cell activation, 30 µl of Fab'2 Goat anti IgM (Jackson Immuno-research) at 10 µg/mL was added to each well. After 5 minutes, cell activation was stopped with 4% paraformaldehyde (10 minutes at room temperature).

Fixed PBMC were then treated for 20 minutes with 0.15% Triton, washed twice with PBS and permeabilized with 50% methanol for 15 minutes.

Surface Staining:

PBMC were washed twice in PBS, resuspended in: PBS-4% FCS and incubated with anti P-Akt ($1/100$ dilution) for one h at room temperature.

After one wash, PBMC were further stained for 30 minutes with a mixture of anti-CD19-PE (BD Biosciences), anti-IgM-FITC (BD Biosciences) and goat anti rabbit IgG-Alexa 647 (Molecular probe).

Flow Cytometry Analysis

After washing, PBMC (Peripheral Blood Mononuclear Cells) were analysed on a FACSCalibur instrument (BD Biosciences) equipped with a 633 helium-neon laser, or stored at 4° C. for further analysis. $5 10^3$ B cells events were gathered per sample in the CD19 positive region.

For the analysis, a threshold was applied on P-Akt histogram of CD19+ IgM+ lymphocytes cells from the non stimulated samples and the percentage of cells above this threshold was determined for each sample.

Result:

Inhibition of IgM-induced Akt phosphorylation.

Examples of inhibitory activities for compounds according to the invention are set out in Table II below.

TABLE II

| Example n° | IC$_{50}$ µM |
|---|---|
| 9 | 0.010 |
| 7 | 0.020 |
| 8 | 0.070 |
| 11 | 0.070 |
| 13 | 0.070 |
| 2 | 0.040 |
| 1 | 0.070 |
| 81 | 0.030 |
| 16 | 0.076 |
| 86 | 0.013 |
| 17 | 0.037 |
| 23 | 0.017 |

Example C

IgM-Induced Akt Phosphorylation in B Cell in the Presence of Whole Blood

Protocol:

Cell Activation:

100 μl of blood are pre-incubated in falcon tube (352063) for 20 minutes at 37° C.

For B cell activation 100 μl of Fab'2 Goat anti Human IgM (30 ug/mL final) is added to each tube and cells are maintained at 37° C.

After 5 minutes, cell activation is stopped with 130 μl Formaldehyde 10% (4% final) and cells are left 10 minutes at room temperature.

Fixed cells are then treated 30 minutes with Triton 0.1% final (add 1 mL of 0.15% Triton)

After several washes with PBS (red cells lysed progressively during washes, 3-4 washes are necessary), cells are transferred in 96 well plate and permeabilized with 50% ice cold Methanol (resuspend first the cells with 80 μl PBBS and then with 80 μl 100% ice cold Methanol) and put on ice for 15 minutes. Plate can be stored in −20° C. in methanol and surface staining performed another day).

Surface Staining:

Cells are washed twice with PBS and once with the staining buffer-PBS-4% FCS.

Cells are incubated with anti P-Akt (1/70 dilution) In staining buffer for one h.

After a wash with staining buffer, cells are stained with a mixture of anti CD19-PE (3 ul/well), anti-IGM-FITC (3 ul/well), Goat anti rabbit IgG-Alexa 647 (1/500), goat IgG (1/200) for 30 minutes.

After a wash, cells are resuspended in staining buffer or PBS, kept in fridge or immediately passed on a FACSCalibur instrument (BD Biosciences) equipped with a 633 helium-neon laser (red laser).

Facs Analysis:

P-akt histogram of CD19+IGM+ cells is represented and a threshold is set with the non stimulated sample. The parameter reported for each sample is the % of positive cells above this cursor. A representative example is set out in FIG. 1.

Result:

Inhibition of IgM-induced Akt phosphorylation in the presence of whole blood.

Examples of inhibitory activities for compounds of the invention are set out in Table III below.

TABLE III

| Example n° | IC$_{50}$ μM |
|---|---|
| 11 | 0.3 |
| 13 | 1.0 |
| 81 | 1.9 |

Example D

Ex-Vivo IgM-Induced Akt Phosphorylation in Mouse After Oral Administration

Protocol:

Mouse Administration and Blood Collection:

Compounds are dissolved in 0.5% Carboxymethylcellulose containing 0.25% Tween 20 in water and administered orally to each mouse (6-8 weeks old C57B1/6 males from janvier) in a volume of 10 mL/kg. Half an hour before blood collection, heparin at 100 U/kg is injected intraperitonealy to each mouse. At appropriate Tm (maximum exposure) mice are sacrificed and blood collected by intra-cardiac puncture in heparinised tubes.

B Cell Activation by BCR Cross Linking:

Blood is pre-incubated at 37° C. for 20 minutes, then an equal volume of Fab'2 Goat anti-Mouse IgM (μspecific, Jackson ImmunoResearch) at 60 μg/mL is added to each tube. B cell activation is terminated after 3 minutes using formaldehyde 4% final and red blood cells are lysed with another 30 minutes Triton X-100 0.1% treatment. Further to several washes with PBS, cells are transferred in a 96 well plate, permeabilized with 50% ice cold Methanol and put on ice for 15 minutes.

Intracellular P-Akt and Surface Staining:

Cells were washed PBS before being incubated for one hour with a Rabbit anti Phospho-Akt antibody (4058 from Cell Signaling) in PBS-4% FCS. After a wash, cells are labelled with a mixture of anti B220-PE, anti-IGM-FITC (Pharmingen), Goat anti rabbit IgG-Alexa 647, goat IgG (Invitrogen).

Facs Analysis:

Cells were analysed on a FACSCalibur instrument (BD Biosciences) equipped with a 633 helium-neon laser (red laser) and 5.10$^3$ B cells are collected. A threshold was applied on P-Akt histogram of B220$^+$ IgM+ lymphocytes from the non stimulated tube and the percentage of cells above this threshold is determined for each sample.

Result:

ex-vivo IgM-induced Akt phosphorylation in mouse after oral administration. FIG. 2 shows the inhibitory activity for a representative compound of the invention (compound of example 81): Vehicle (n=4), compound (n=6), IC$_{50}$ WB=1.9 μM, Tmax 15 min.

Example E

Preparation of a Pharmaceutical Formulation

Formulation 1—Tablets

A compound of Formula (I) is admixed as a dry powder with a dry gelatin binder in an approximate 1:2 weight ratio. A minor amount of magnesium stearate is added as a lubricant. The mixture is formed into 240-270 mg tablets (80-90 mg of active quinoxaline compound per tablet) in a tablet press.

Formulation 2—Capsules

A compound of Formula (I) is admixed as a dry powder with a starch diluent in an approximate 1:1 weight ratio. The mixture is filled into 250 mg capsules (125 mg of active quinoxaline compound per capsule).

Formulation 3—Liquid

A compound of Formula (I) (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A compound of Formula (I) is admixed as a dry powder with a dry gelatin binder in an approximate 1:2 weight ratio. A minor amount of magnesium stearate is added as a lubricant. The mixture is formed into 450-900 mg tablets (150-300 mg of active quinoxaline compound) in a tablet press.

Formulation 5—Injection

A compound of Formula (I) is dissolved in a buffered sterile saline injectable aqueous medium to a concentration of approximately 5 mg/mL.

REFERENCE LIST

1—S. Imamura, Y. Nishikawa, T. Ichikawa, T. Hattori, Y. Matsushita, S. Hashigushi, N. Kanzaki, Y. Iizawa, M. Baba and Y. Sugihara, Bioorg. Med. Chem, 2005, 13, 397-416.
2—S. Han, R. A. Moore and R. E. Viola, Bioorg. Chem, 2002, 30, 81-94.
3—S. Kuchinski, S. Centioni, T Howard, J. Trzupek, S. Roller, V. Carnahan, H. Townes, B. Purnell, C. Price, H. Handl, K. Summerville, K. Johnson, J. Toth, S. Hudson, K, Kiakos, J. A. Hartley and M. Lee, Bioorg. Med. Chem, 2004, 12, 6221-6236.

The invention claimed is:

1. A quinoxaline compound according to the following Formula (I)

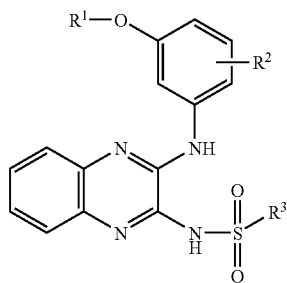

wherein:
$R^1$ is selected from H; or $C_1$-$C_6$alkyl;
$R^2$ is selected from $(CH_2)_m$—$R^4$ or CO—$R^{4'}$;
$R^3$ is selected from a $C_1$-$C_6$ alkyl; $C_6$-$C_{18}$ aryl; or $C_3$-$C_{18}$ heteroaryl group; wherein aryl and heteroaryl groups may also be substituted with one to five of the following groups: $C_1$-$C_6$ alkyl; $C_1$-$C_6$ alkoxy; $NH_2$; NH—($C_1$-$C_6$ alkyl); $N(C_1$-$C_6$ alkyl)$_2$; amino ($C_1$-$C_6$)alkyl; halogen; CN; or $C_3$-$C_8$ heterocycloalkyl;
$R^4$ is selected from hydroxy; $C_1$-$C_6$ alkoxy; $C_3$-$C_8$ cycloalkyl; or $C_3$-$C_8$ heterocycloalkyl in which up to 3 carbon atoms are replaced by heteroatoms selected from O, S, $SO_2$ or NR, R being selected from a bond to said $(CH_2)_m$ group, hydrogen, methyl, acetyl, acyl or sulfone;
$R^{4'}$ is selected from $C_1$-$C_6$ alkoxy; cycloalkyl; or $C_3$-$C_8$ heterocycloalkyl;
m is 1, 2, 3, 4, 5, or 6;
or geometrical isomers, enantiomers, diastereomers, tautomers, racemates thereof, and pharmaceutically acceptable salts thereof.

2. The quinoxaline compound according to claim 1, wherein $R^2$ is $(CH_2)_m$—$R^4$, in which m is 1 or 2.

3. The quinoxaline compound according to claim 2, wherein $R^4$ is a hydroxy, a $C_3$-$C_8$ cycloalkyl or $C_3$-$C_8$ heterocycloalkyl group.

4. The quinoxaline compound according to claim 2, wherein $R^4$ is a cyclohexyl or cyclopentyl group.

5. The quinoxaline compound according to claim 2, wherein $R^4$ is selected from piperazine, morpholine, tetrahydropyran, tetrahydrothiopyran, piperidine, and 8-methyl-8-aza-bicyclo[3.2.1]octane.

6. The quinoxaline compound according to claim 1, wherein $R^2$ is CO—$R^4$, in which $R^4$ is a hydroxy group; $C_1$-$C_6$ alkoxy; or a $C_3$-$C_8$ heterocycloalkyl group.

7. The quinoxaline compound according to claim 6, wherein $R^4$ is a methoxy or ethoxy group.

8. The quinoxaline compound according to claim 6, wherein $R^4$ is selected from piperazine, morpholine, tetrahydropyran, or piperidine.

9. The quinoxaline compound according to claim 1, wherein $R^3$ is selected from $C_1$-$C_4$ alkyl; phenyl; and $C_3$-$C_{18}$ heteroaryl group.

10. The quinoxaline compound according to claim 9, wherein $R^3$ is a methyl, ethyl, butyl, or propyl group.

11. The quinoxaline compound according to claim 1, wherein $R^1$ is methyl.

12. The quinoxaline compound according to claim 1, wherein $R^3$ is an imidazole or a pyridine group, optionally substituted by a $C_1$-$C_4$ alkyl group.

13. The quinoxaline compound according to claim 1, wherein $R^3$ is a phenyl, optionally substituted by at least one halogen atom or amino($C_1$-$C_6$)alkyl group.

14. The quinoxaline compound according to claim 1, wherein $R^4$ selected from the following groups:

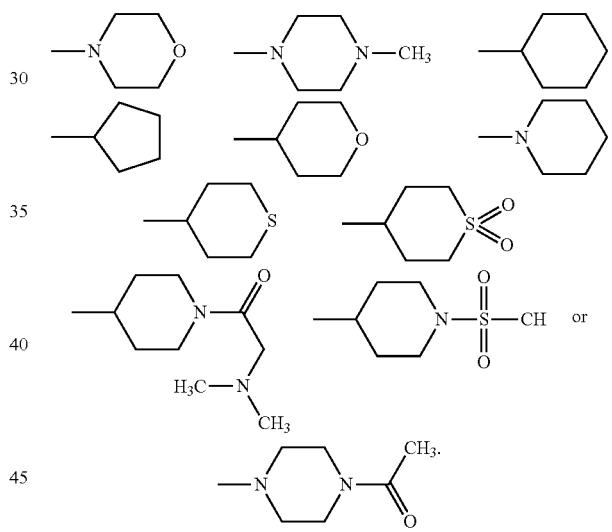

15. The quinoxaline compound according to claim 1, wherein $R^3$ is selected from the following groups:

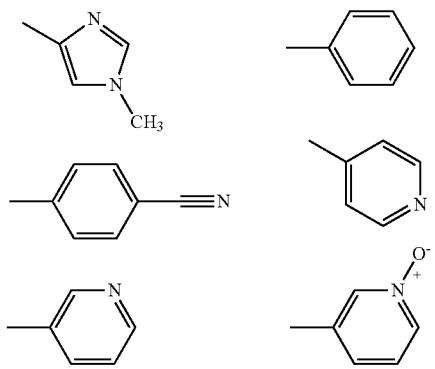

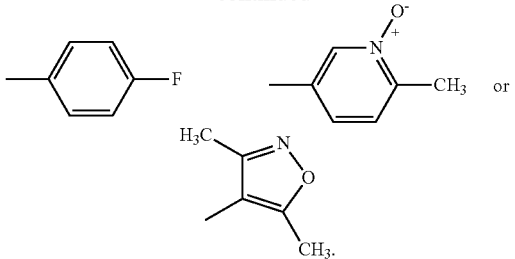 or

16. The quinoxaline compound according to claim 1, wherein said amino (C$_1$-C$_6$) alkyl is dimethylamino methyl.

17. The quinoxaline compound according to claim 1, wherein said compound is selected from:

methyl 4-methoxy-2-[(3-{[(1-methyl-1H-imidazol-4-yl)sulfonyl]amino}quinoxalin-2-yl)amino]benzoate;
methyl 4-methoxy-2-({3-[(pyridin-3-ylsulfonyl)amino]quinoxalin-2-yl}amino)benzoate;
methyl 4-methoxy-2-({3-[(methylsulfonyl)amino]quinoxalin-2-yl}amino)benzoate;
N-[3-({3-methoxy-5-[(4-methylpiperazin-1-yl)carbonyl]phenyl}amino)quinoxalin-2-yl]pyridine-3-sulfonamide;
N-(3-{[3-methoxy-5-(morpholin-4-ylcarbonyl)phenyl]amino}quinoxalin-2-yl)pyridine-3-sulfonamide;
N-(3-{[3-methoxy-5-(morpholin-4-ylcarbonyl)phenyl]amino}quinoxalin-2-yl)methanesulfonamide;
N-(3-{[5-methoxy-2-(tetrahydro-2H-pyran-4-ylmethyl)phenyl]amino}quinoxalin-2-yl)-1-methyl-1H-imidazole-4-sulfonamide;
N-(3-{[5-methoxy-2-(tetrahydro-2H-pyran-4-ylmethyl)phenyl]amino}quinoxalin-2-yl)methanesulfonamide;
N-(3-{[5-methoxy-2-(tetrahydro-2H-pyran-4-ylmethyl)phenyl]amino}quinoxalin-2-yl)pyridine-3-sulfonamide;
4-fluoro-N-(3-{[5-methoxy-2-(tetrahydro-2H-pyran-4-ylmethyl)phenyl]amino}quinoxalin-2-yl)benzenesulfonamide;
N-[3-({5-methoxy-2-[(1-methylpiperidin-4-yl)methyl]phenyl}amino)quinoxalin-2-yl]-1-methyl-1H-imidazole-4-sulfonamide;
N-[3-({5-methoxy-2-[(1-methylpiperidin-4-yl)methyl]phenyl}amino)quinoxalin-2-yl]pyridine-3-sulfonamide;
N-[3-({5-methoxy-2-[(1-methylpiperidin-4-yemethyl]phenyl}amino)quinoxalin-2-yl]methanesulfonamide;
N-[3-({5-methoxy-2-[(1,2,2,6,6-pentamethylpiperidin-4-yl)methyl]phenyl}amino)quinoxalin-2-yl]-1-methyl-1H-imidazole-4-sulfonamide;
N-{3-[(5-methoxy-2-{[(1R,5S)-8-methyl-8-azabicyclo[3.2.1]oct-3-yl]methyl}phenyl)amino]quinoxalin-2-yl}-1-methyl-1H-imidazole-4-sulfonamide;
N-(3-{[2-(cyclohexylmethyl)-5-methoxyphenyl]amino}quinoxalin-2-yl)pyridine-3-sulfonamide;
N-(3-{[2-(cyclohexylmethyl)-5-methoxyphenyl]amino}quinoxalin-2-yl)-1-methyl-1H-imidazole-4-sulfonamide;
N-(3-{[2-(cyclohexylmethyl)-5-methoxyphenyl]amino}quinoxalin-2-yl)methanesulfonamide;
N-[3-({2-[(4-hydroxycyclohexyl)methyl]-5-methoxyphenyl}amino)quinoxalin-2-yl]-1-methyl-1H-imidazole-4-sulfonamide;
N-[3-({2-[(4-hydroxycyclohexyl)methyl]-5-methoxyphenyl}amino)quinoxalin-2-yl]pyridine-3-sulfonamide;
N-(3-{[2-(cyclopentylmethyl)-5-methoxyphenyl]amino}quinoxalin-2-yl)-1-methyl-1H-imidazole-4-sulfonamide;
N-(3-{[5-methoxy-2-(tetrahydro-2H-thiopyran-4-ylmethyl)phenyl]amino}quinoxalin-2-yl)-1-methyl-1H-imidazole-4-sulfonamide;
N-[3-({2-[(1,1-dioxidotetrahydro-2H-thiopyran-4-yl)methyl]-5-methoxyphenyl}amino)quinoxalin-2-yl]-1-methyl-1H-imidazole-4-sulfonamide;
N-(3-{[2-(2-hydroxyethyl)-5-methoxyphenyl]amino}quinoxalin-2-yl)pyridine-3-sulfonamide;
N-(3-{[2-(3-Hydroxypropyl)-5-methoxyphenyl]amino}quinoxalin-2-yl)-1-methyl-1H-imidazole-4-sulfonamide;
N-[3-({2-[2-Hydroxy-1-(hydroxymethyl)ethyl]-5-methoxyphenyl}amino)quinoxalin-2-yl]-1-methyl-1H-imidazole-4-sulfonamide;
N-{3-[(2-Isopropyl-5-methoxyphenyl)amino]quinoxalin-2-yl}-1-methyl-1H-imidazole-4-sulfonamide;
N-[3-({2-[3-(Dimethylamino)propyl]-5-methoxyphenyl}amino)quinoxalin-2-yl]-1-methyl-1H-imidazole-4-sulfonamide;
4-{[(3-{[2-(2-Hydroxyethyl)-5-methoxyphenyl]amino}quinoxalin-2-yl)amino]sulfonyl}-N,N-dimethylbenzamide;
N-(3-{[2-(2-Hydroxyethyl)-5-methoxyphenyl]amino}quinoxalin-2-yl)-6-methylpyridine-3-sulfonamide 1-oxide;
4-cyano-N-(3-{[2-(2-Hydroxyethyl)-5-methoxyphenyl]amino}quinoxalin-2-yl)benzenesulfonamide;
N-(3-{[2-(2-Hydroxyethyl)-5-methoxyphenyl]amino}quinoxalin-2-yl)-1-methyl-1H-imidazole-4-sulfonamide;
4-Fluoro-N-(3-{[2-(2-hydroxyethyl)-5-methoxyphenyl]amino}quinoxalin-2-yl)benzenesulfonamide;
N-(3-{[2-(2-Hydroxyethyl)-5-methoxyphenyl]amino}quinoxalin-2-yl)methanesulfonamide;
N-(3-{[2-(2-Hydroxyethyl)-5-methoxyphenyl]amino}quinoxalin-2-yl)ethanesulfonamide;
N-(3-{[2-(2-Hydroxyethyl)-5-methoxyphenyl]amino}quinoxalin-2-yl)propane-1-sulfonamide;
N-[3-({5-Methoxy-2-[2-(methylsulfonyl)ethyl]phenyl}amino)quinoxalin-2-yl]-1-methyl-1H-imidazole-4-sulfonamide;
Methyl 3-(4-{[(3-{[2-(2-hydroxyethyl)-5-methoxyphenyl]amino}quinoxalin-2-yl)amino]sulfonyl}phenyl)propanoate;
N-(3-{[2-(3-Hydroxypropyl)-5-methoxyphenyl]amino}quinoxalin-2-yl)-3,5-dimethylisoxazole-4-sulfonamide;
N-(3-{[2-(2-Hydroxyethyl)-5-methoxyphenyl]amino}quinoxalin-2-yl)-3,5-dimethylisoxazole-4-sulfonamide;
N-[3-({5-Methoxy-2-[2-(methylsulfonyl)ethyl]phenyl}amino)quinoxalin-2-yl]methanesulfonamide;
N-(3-{[2-(2-Hydroxyethyl)-5-methoxyphenyl]amino}quinoxalin-2-yl)cyclohexanesulfonamide;
N-(3-{[2-(3-Hydroxypropyl)-5-methoxyphenyl]amino}quinoxalin-2-yl)methanesulfonamide;
2-[(Dimethylamino)methyl]-N-(3-{[2-(3-hydroxypropyl)-5-methoxyphenyl]amino}quinoxalin-2-yl)-1-methyl-1H-imidazole-4-sulfonamide;
N-(3-{[2-(3-Hydroxypropyl)-5-methoxyphenyl]amino}quinoxalin-2-yl)ethanesulfonamide;

N-(3-{[2-(3-Hydroxypropyl)-5-methoxyphenyl]amino}quinoxalin-2-yl)propane-1-sulfonamide;
N-(3-{[2-(3-Hydroxypropyl)-5-methoxyphenyl]amino}quinoxalin-2-yl)propane-2-sulfonamide;
N-[3-({5-Methoxy-2-[2-(methylsulfonyl)ethyl]phenyl}amino)quinoxalin-2-yl]ethanesulfonamide;
N-[3-({5-Methoxy-2-[2-(methylsulfonyl)ethyl]phenyl}amino)quinoxalin-2-yl]propane-2-sulfonamide;
N-[3-({5-Methoxy-2-[2-(methylsulfonyl)ethyl]phenyl}amino)quinoxalin-2-yl]propane-1-sulfonamide;
N-[3-({5-Methoxy-2-[2-(methylsulfonyl)ethyl]phenyl}amino)quinoxalin-2-yl]-3,5-dimethylisoxazole-4-sulfonamide;
N-[3-({5-Methoxy-2-[2-(methylsulfonyl)ethyl]phenyl}amino)quinoxalin-2-yl]benzenesulfonamide;
N-(3-{[2-(2-Hydroxyethyl)-5-methoxyphenyl]amino}quinoxalin-2-yl) tetrahydrothiophene-3-sulfonamide 1,1-dioxide;
N-[3-({5-Methoxy-2-[2-(methylsulfonyl)ethyl]phenyl}amino)quinoxalin-2-yl]-3-(methylthio)propane-1-sulfonamide;
N-(3-{[2-(2-Hydroxyethyl)-5-methoxyphenyl]amino}quinoxalin-2-yl)-3-(methylthio)propane-1-sulfonamide;
N-[3-({5-Methoxy-2-[2-(methylsulfonyl)ethyl]phenyl}amino)quinoxalin-2-yl]-3-(methylsulfonyl)propane-1-sulfonamide;
N-(3-{[2-(3-Hydroxypropyl)-5-methoxyphenyl]amino}quinoxalin-2-yl)-3-(methylsulfonyl)propane-1-sulfonamide;
N-(3-{[2-(2-Hydroxyethyl)-5-methoxyphenyl]amino}quinoxalin-2-yl)-3-(methylsulfonyl)propane-1-sulfonamide;
N-(3-{[5-Methoxy-2-(2-methoxyethyl)phenyl]amino}quinoxalin-2-yl)-1-methyl-1H-imidazole-4-sulfonamide;
N-(3-{[2-(3-Hydroxypropyl)-5-methoxyphenyl]amino}quinoxalin-2-yl)tetrahydrothiophene-3-sulfonamide 1,1-dioxide;
2-[(Dimethylamino)methyl]-N-[3-({5-methoxy-2-[2-(methylsulfonyl)ethyl]phenyl}amino)quinoxalin-2-yl]-1-methyl-1H-imidazole-4-sulfonamide;
Benzyl 4-{[(3-{[2-(3-hydroxypropyl)-5-methoxyphenyl]amino}quinoxalin-2-yl)amino]sulfonyl}piperidine-1-carboxylate;
N-[3-({5-Methoxy-2-[3-(methylsulfonyl)propyl]phenyl}amino)quinoxalin-2-yl]-1-methyl-1H-imidazole-4-sulfonamide;
N-(2-Hydroxyethyl)-3-methoxy-5-{[3-({[3-(methylsulfonyl)propyl]sulfonyl}amino)quinoxalin-2-yl]amino}benzamide;
2-(Hydroxymethyl)-N-(3-{[2-(3-hydroxypropyl)-5-methoxyphenyl]amino}quinoxalin-2-yl)-1-methyl-1H-imidazole-4-sulfonamide;
N-(3-{[2-(3-Hydroxypropyl)-5-methoxyphenyl]amino}quinoxalin-2-yl)-1-methyl-2-[(methylsulfonyl)methyl]-1H-imidazole-4-sulfonamide;
N-[3-({2-[(2R,2S)-2,3-Dihydroxypropyl]-5-methoxyphenyl}amino)quinoxalin-2-yl]-1-methyl-1H-imidazole-4-sulfonamide;
N-(3-{[5-Methoxy-2-(2-methoxyethyl)phenyl]amino}quinoxalin-2-yl)-1-methyl-2-[(methylsulfonyl)methyl]-1H-imidazole-4-sulfonamide;

N-[3-({5-methoxy-2-[(4-methylpiperazin-1-yl)methyl]phenyl}amino)quinoxalin-2-yl]pyridine-3-sulfonamide;
4-fluoro-N-[3-({5-methoxy-2-[(4-methylpiperazin-1-yl)methyl]phenyl}amino)quinoxalin-2-yl]benzenesulfonamide;
N-(3-{[5-methoxy-2-(morpholin-4-ylmethyl)phenyl]amino}quinoxalin-2-yl)pyridine-3-sulfonamide;
4-[(dimethylamino)methyl]-N-[3-({2-[(4-hydroxycyclohexyl)methyl]-5-methoxyphenyl}amino)quinoxalin-2-yl]benzenesulfonamide;
4-[(dimethylamino)methyl]-N-[3-({2-[(1,1-dioxidotetrahydro-2H-thiopyran-4-yl)methyl]-5-methoxyphenyl}amino)quinoxalin-2-yl]benzenesulfonamide;
4-[(dimethylamino)methyl]-N-(3-{[5-methoxy-2-(tetrahydro-2H-pyran-4-ylmethyl)phenyl]amino}quinoxalin-2-yl)benzenesulfonamide;
N-(3-{[2-(cyclohexylmethyl)-5-methoxyphenyl]amino}quinoxalin-2-yl)-4-[(dimethylamino)methyl]benzene sulfonamide;
4-[(dimethylamino)methyl]-N-(3-{[5-methoxy-2-(tetrahydro-2H-thiopyran-4-ylmethyl)phenyl]amino}quinoxalin-2-yl)benzenesulfonamide;
4-[(Dimethylamino)methyl]-N-(3-{[2-(2-hydroxyethyl)-5-methoxyphenyl]amino}quinoxalin-2-yl)benzenesulfonamide;
4-[(4-Fluoropiperidin-1-yl)methyl]-N-(3-{[2-(2-hydroxyethyl)-5-methoxy phenyl]amino}quinoxalin-2-yl)benzenesulfonamide;
N-(3-{[2-(hydroxymethyl)-5-methoxyphenyl]amino}quinoxalin-2-yl)-1-methyl-1H-imidazole-4-sulfonamide;
N-[3-({3-methoxy-5-[(4-methylpiperazin-1-yl)methyl]phenyl}amino)quinoxalin-2-yl]pyridine-3-sulfonamide;
N-(3-{[2-(2-Hydroxyethyl)-5-methoxyphenyl]amino}quinoxalin-2-yl)-4-(3-hydroxypropyl)benzenesulfonamide;
4-(2-Hydroxyethoxy)-N-(3-{[2-(2-hydroxyethyl)-5-methoxyphenyl]amino}quinoxalin-2-yl)benzenesulfonamide;
N-[3-({3-[(Dimethylamino)methyl]-5-methoxyphenyl}amino)quinoxalin-2-yl]-1-methyl-1H-imidazole-4-sulfonamide;
N-{3-[(5-methoxy-2-{[1-(methylsulfonyl)piperidin-4-yl]methyl}phenyl)amino]quinoxalin-2-yl}-1-methyl-1H-imidazole-4-sulfonamide;
N-(3-{[2-(3-Hydroxypropyl)-5-methoxyphenyl]amino}quinoxalin-2-yl)piperidine-4-sulfonamide;
N-(3-{[5-Methoxy-2-(2-methoxyethyl)phenyl]amino}quinoxalin-2-yl)piperidine-4-sulfonamide;
N-(3-{[5-methoxy-2-(2-methoxyethyl)phenyl]amino}quinoxalin-2-yl)-1-(methylsulfonyl)piperidine-4-sulfonamide;
N-(3-{[3-(3-hydroxypropyl)-5-methoxyphenyl]amino}quinoxalin-2-yl)-1-methyl-1H-imidazole-4-sulfonamide;
2-[(dimethylamino)methyl]-N-(3-{[5-methoxy-2-(2-methoxyethyl)phenyl]amino}quinoxalin-2-yl)-1-methyl-1H-imidazole-4-sulfonamide;
N-(3-{[3-methoxy-5-(methoxymethyl)phenyl]amino}quinoxalin-2-yl)-1-methyl-1H-imidazole-4-sulfonamide;
N-(3-{[3-(hydroxymethyl)-5-methoxyphenyl]amino}quinoxalin-2-yl)-1-methyl-1H-imidazole-4-sulfonamide;

N-(3-{[3-methoxy-5-(2-methoxyethyl)phenyl]amino}quinoxalin-2-yl)-1-methyl-1H-imidazole-4-sulfonamide;

N-(3-{[3-(2-hydroxyethyl)-5-methoxyphenyl]amino}quinoxalin-2-yl)-1-methyl-1H-imidazole-4-sulfonamide;

2-[(dimethylamino)methyl]-N-(3-{[3-(2-hydroxyethyl)-5-methoxyphenyl]amino}quinoxalin-2-yl)-1-methyl-1H-imidazole-4-sulfonamide.

18. A pharmaceutical composition containing at least one quinoxaline compound according to claim 1 and a pharmaceutically acceptable carrier, diluent or excipient thereof.

* * * * *

UNITED STATES PATENT AND TRADEMARK OFFICE
CERTIFICATE OF CORRECTION

PATENT NO. : 8,614,215 B2
APPLICATION NO. : 12/525095
DATED : December 24, 2013
INVENTOR(S) : Pascale Gaillard et al.

It is certified that error appears in the above-identified patent and that said Letters Patent is hereby corrected as shown below:

In the Specification

Column 4,
Line 29, "it can longer" should read --it can no longer--.

Column 5,
Line 56, "the 8 isoform" should read --the δ isoform--.

Column 7,
Line 64, "text-butyl," should read --*tert*-butyl,--.

Column 8,
Line 27, "tetrahydropyrane," should read --tetrahydrofurane,--.
Line 66, "-C1-C6alkyl" should read -- -$C_1$-$C_6$ alkyl--.

Column 10,
Lines 33-34, "Phosphatoinositides" should read --phosphoinositides--.
Line 34, "γ δ or" should read --γ, δ or--.
Line 35, "phosphatoinositides" should read --phosphoinositides--.
Lines 58-59, "phosphatoinositides" should read --phosphoinositides--.
Line 65, "phosphatoinositides" should read --phosphoinositides--.

Column 11,
Line 1, "Phosphatoinositides" should read --phosphoinositides--.
Line 5, "thus cancers" should read --these cancers--.
Line 57, "p and p' and" should read --p and p' are--.

Column 27,
Lines 29-30, "compositions is typically" should read --compositions are typically--.

Signed and Sealed this
Fourteenth Day of April, 2015

Michelle K. Lee
*Director of the United States Patent and Trademark Office*

Column 28,
Line 23, "and R₄" should read --and $R^4$--.

Column 34,
Lines 6-7, "N-(3-{[(3-Chloroquinoxalin-2-yl)]sulfamoyl}phenyl)-2-ditriethylamino-amide" should read
--N-(3-{[(3-Chloroquinoxalin-2-yl)]sulfamoyl}phenyl)-2-dimethylamino-amide--.

Column 35,
Line 23, "3-(4-methoxy-2-nitrophertyl)propyl" should read --3-(4-methoxy-2-nitrophenyl)propyl--.

Column 40,
Line 47, "one skill in" should read --one skilled in--.

Column 57,
Line 64, "EtOH (1.5 mL)" should read --EtOH (15 mL)--.

Column 58,
Lines 24-25, "(m, 1 ED, 6.18 (s, 1.14)," should read --(m, 1H), 6.18 (s, 1H),--.
Line 42, "at CFC" should read --at 0°C--.
Lines 57-58, "Procedure 1)," should read --Procedure D.--.

Column 59,
Line 21, "(m, 11-1)," should read --(m, 1H),--.

Column 60,
Line 4, "(s, 314)," should read --(s, 3H),--.
Lines 30-31, "of atmosphere," should read --of 1 atmosphere,--.
Line 35, "3.71 s, 3H)," should read --3.71 (s, 3H),--.
Line 60, "(600 trig," should read --(600 mg,--.

Column 63,
Line 64, "(d, *j*=2.6" should read --(d, *J* = 2.6--.

Column 69,
Line 66, "3.24 (s, 314)," should read --3.24 (s, 3H),--.

Column 70,
Lines 1-2, "Intermediate 52: 2-(4-Methoxy-2-nitrophenyl)propane-1-diol" should read
--Intermediate 52: 2-(4-Methoxy-2-nitrophenyl)propane-1,3-diol--.

Column 72,
Lines 50-51, "(2*E*)-3-(4-methoxy-2-nirophertyl) acrylate" should read
--(2*E*)-3-(4-methoxy-2-nitrophenyl)acrylate--.
Line 51, "(30 nit)" should read --(30 mL)--.

Column 73,
Line 55, "To stirred" should read --To a stirred--.

Column 75,
Line 9, "(m, 214)," should read --(m, 2H),--.

Column 76,
Line 32, "2% EtaAc" should read --2% EtOAc--.

Column 77,
Line 30, "crystalline $^1$H NMR" should read --crystalline solid. $^1$H NMR--.
Line 65, "(m, 1)," should read --(m, 1H),--.

Column 78,
Line 29, "brown $^1$H NMR" should read --brown liquid. $^1$H NMR--.

Column 79,
Line 30, "Rt 220 min. UPLCIMS:" should read --Rt 2.28 min. UPLC/MS:--.
Line 67, "Rt 1.73 mm." should read --Rt 1.73 min.--.

Column 80,
Line 24, "afford (1.3 g" should read --afford 1.3 g--.

Column 81,
Line 30, "5 N (1 mL)" should read --5 N HCl (1 mL)--.

Column 83,
Line 15, "1.87 (m, HPLC" should read --1.87 (m, 4H). HPLC--.

Column 84,
Line 20, "DCM lien" should read --DCM then--.

Column 85,
Lines 29-30, "3-(Methylthio)propane-1-sulfonyl" should read
--3-(methylthio)propane-1-sulfonyl--.
Lines 37-38, "as pale a yellow solid." should read --as a pale yellow solid.--.

Column 87,
Lines 37-38, "Intermediate 92: 2-Dimethylamino-N-[3-sulfamoyl)phenyl]-acetamide" should read
--Intermediate 92: 2-Dimethylamino-N-[3-(sulfamoyl)phenyl]-acetamide--.

CERTIFICATE OF CORRECTION (continued)
U.S. Pat. No. 8,614,215 B2

Column 89,
Line 67, "tert-butyldimethylehlorosilane" should read --*tert*-butyldimethylchlorosilane--.

Column 90,
Lines 15-16, "Intermediate 98: 1-Methyl-2-[(methylthio) methyl]-1-imidazole-4-sulfonamide" should read
--Intermediate 98: 1-Methyl-2-[(methylthio) methyl]-1*H*-imidazole-4-sulfonamide--.
Line 66, "1.78 (s, 2H)" should read --4.78 (s, 2H)--.

Column 92,
Lines 26-27, "intermediate 102" should read --Intermediate 102--.

Column 93,
Line 66, "(m, HPLC" should read --(m, 1H). HPLC--.

Column 95,
Line 31, "348.9" should read --348.9.--.

Column 97,
Lines 58-59, "intermediate 113" should read --Intermediate 113--.

Column 98,
Line 30, "(hr s, 1H)," should read --(br s, 1H),--.
Line 33, "379.2," should read --379.2.--.

Column 99,
Line 25, "methanesulfanylmethyl" should read --methanesulfonylmethyl--.

Column 103,
Lines 22-23, "intermediate 134" should read --Intermediate 134--.

Column 111,
Lines 59-60, "procedure intermediate 147" should read --procedure H, intermediate 147--.

Column 126,
Line 40, "7.41-7.31 (2H)," should read --7.41-7.31 (m, 2H),--.

Column 130,
Lines 18-22, "Example 26: N-[3-({2-[(1,1-dioxidotetrahydro-2H-thiopyran-4-yl)methyl]-5-methoxy phenyl}amino)auinoxalin-2-yl]-1-methyl-1H-imidazole-4-sulfonamide" should read --Example 26: N-[3-({2-[(1,1-dioxidotetrahydro-2H-thiopyran-4-yl)methyl]-5-methoxy phenyl}amino)quinoxalin-2-yl]-1-methyl-1H-imidazole-4-sulfonamide--.

CERTIFICATE OF CORRECTION (continued)
U.S. Pat. No. 8,614,215 B2

Column 132,
Line 65, "CHIN" should read --CHN--.

Column 137,
Line 63, "7.64 (s, 1H), 7.35 (m, 2H)," should read --7.64 (s, 1H), 7.54 (s, 1H), 7.35 (m, 2H),--.

Column 145,
Line 67, "4009." should read --400.9.--.

Column 149,
Line 5, "(239 mg;" should read --(23.9 mg;--.
Line 12, "3.70 mi." should read --3.70 min.--.

Column 165,
Line 56, "(500 μM," should read --(500 μL,--.

Column 174,
Lines 10-15, "Example 86: 4-[(dimethylamino)methyl]-N-(3-{[methoxy-2-(tetrahydro-2H-pyran-4-ylmethyl)phenyl]amino}quinoxalin-2-yl)benzenesulfonamide" should read --Example 86: 4-[(dimethylamino)methyl]-N-(3-{[5-methoxy-2-(tetrahydro-2H-pyran-4-ylmethyl)phenyl]amino}quinoxalin-2-yl)benzenesulfonamide--.

Column 177,
Line 54, "in THE" should read --in THF--.

Column 180,
Line 63, "THE (9 mL)" should read --THF (9 mL)--.

Column 181,
Line 55, "in THE" should read --in THF--.

Column 183,
Lines 15-16, "(165 μM, 0.15 mmol," should read --(165 μM, 1M, 0.15 mmol,--.

Column 185,
Line 25, "To as solution" should read --To a solution--.
Line 27, "in THE" should read --in THF--.

Column 186,
Lines 3-4, "1 eq) TEA" should read --1 eq) in TFA--.
Line 12, "AGN to" should read --ACN to--.

Column 189,
Lines 17-19, "N-(3-{[5-methoxy-2-(2-methoxyethenyl)phenyl]amino}quinoxalin-2-yl)-1-methylsulfonyl) piperidine-4-sulfonamide)"
  should read --N-(3-{[5-methoxy-2-(2-methoxyethyl)phenyl]amino}quinoxalin-2-yl)-1-methylsulfonyl) piperidine-4-sulfonamide--.

Column 198,
Line 7, "25 uM" should read --25 µM--.

Column 201,
Line 22, "PBBS" should read --PBS--.

Column 202,
Line 8, "(µspecific," should read --(µ specific,--.
Lines 11-12, "with another 30 minutes Triton" should read --for another 30 minutes with Triton--.

In the Claims

Column 205, Claim 17,
Lines 49-50, "N-[3-({5-methoxy-2-[(1-methylpiperidin-4-yemethyl]phenyl}amino) quinoxalin-2-yl]methanesulfonamide;"
  should read --N-[3-({5-methoxy-2-[(1-methylpiperidin-4-yl)methyl]phenyl}amino) quinoxalin-2-yl]methanesulfonamide;--.

Column 208, Claim 17,
Lines 19-21, "N-(3-{[2-(cyclohexylmethyl)-5-methoxyphenyl]amino}quinoxalin-2-yl)-4-[(dimethylamino)methyl]benzene sulfonamide;"
  should read --N-(3-{[2-(cyclohexylmethyl)-5-methoxyphenyl]amino}quinoxalin-2-yl)-4-[(dimethylamino)methyl]benzenesulfonamide;--.